US007671010B2

(12) United States Patent
Arap et al.

(10) Patent No.: US 7,671,010 B2
(45) Date of Patent: Mar. 2, 2010

(54) COMPOSITIONS AND METHODS OF USE OF TARGETING PEPTIDES FOR DIAGNOSIS AND THERAPY OF HUMAN CANCER

(75) Inventors: Wadih Arap, Houston, TX (US);
Mikhail G. Kolonin, Houston, TX (US);
Paul J. Mintz, Houston, TX (US);
Renata Pasqualini, Houston, TX (US);
Amado J. Zurita, Houston, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 446 days.

(21) Appl. No.: 10/530,168

(22) PCT Filed: Oct. 30, 2002

(86) PCT No.: PCT/US02/34987

§ 371 (c)(1),
(2), (4) Date: Feb. 23, 2006

(87) PCT Pub. No.: WO2004/020999

PCT Pub. Date: Mar. 11, 2004

(65) Prior Publication Data

US 2006/0239968 A1    Oct. 26, 2006

(51) Int. Cl.
*A61K 38/00* (2006.01)
(52) U.S. Cl. .......................................... 514/2; 530/300
(58) Field of Classification Search ........................ None
See application file for complete search history.

(56) References Cited

U.S. PATENT DOCUMENTS

| 4,472,509 | A | 9/1984 | Gansow et al. ............... 436/548 |
|---|---|---|---|
| 4,912,040 | A | 3/1990 | Kaufman et al. ............ 435/69.6 |
| 4,931,053 | A | 6/1990 | L'Esperance, Jr. .............. 606/2 |
| 5,021,236 | A | 6/1991 | Gries et al. ...................... 424/9 |
| 5,081,034 | A | 1/1992 | Bevilasqua et al. ..... 435/252.33 |
| 5,098,833 | A | 3/1992 | Lasky et al. ................. 435/69.1 |
| 5,188,964 | A | 2/1993 | McGuire et al. .............. 436/64 |
| 5,196,523 | A | 3/1993 | Lee ........................... 536/23.5 |
| 5,206,347 | A | 4/1993 | Ruoslahti et al. ............ 530/413 |
| 5,216,131 | A | 6/1993 | Lasky et al. ................. 435/69.1 |
| 5,223,409 | A | 6/1993 | Ladner et al. .............. 435/69.7 |
| 5,225,538 | A | 7/1993 | Capon et al. .............. 530/387.3 |
| 5,259,380 | A | 11/1993 | Mendes et al. .............. 607/115 |
| 5,270,163 | A | 12/1993 | Gold et al. ....................... 435/6 |
| 5,288,846 | A | 2/1994 | Quertermous et al. ..... 435/172.3 |
| 5,304,640 | A | 4/1994 | Lasky et al. ................. 536/23.5 |
| 5,415,874 | A | 5/1995 | Bender et al. ................ 424/520 |
| 5,428,130 | A | 6/1995 | Capon et al. ................ 530/350 |
| 5,453,362 | A | 9/1995 | Lamarco et al. ............ 435/69.1 |
| 5,463,026 | A | 10/1995 | Nakamura et al. ....... 530/387.3 |
| 5,464,436 | A | 11/1995 | Smith ........................... 607/89 |
| 5,492,807 | A | 2/1996 | Santi ............................... 435/5 |
| 5,506,126 | A | 4/1996 | Seed et al. ................ 435/172.3 |
| 5,536,814 | A | 7/1996 | Ruoslahti et al. ............ 530/329 |
| 5,585,277 | A | 12/1996 | Bowie et al. ................ 436/518 |
| 5,622,699 | A | 4/1997 | Ruoslahti et al. ............ 424/93.6 |
| 5,670,312 | A | 9/1997 | Santi ............................... 435/5 |
| 5,688,692 | A | 11/1997 | Jat et al. ...................... 435/354 |
| 5,688,935 | A | 11/1997 | Stephens et al. ............. 536/23.1 |
| 5,705,610 | A | 1/1998 | Zuckermann et al. ........ 530/338 |
| 5,750,344 | A | 5/1998 | Doyle ............................. 435/6 |
| 5,840,841 | A | 11/1998 | Zuckermann et al. ........ 530/338 |
| 5,866,759 | A | 2/1999 | Jat et al. ......................... 800/3 |
| 5,902,598 | A | 5/1999 | Chen et al. .................. 424/423 |
| 5,955,572 | A | 9/1999 | Ruoslahti et al. ............ 530/317 |
| 6,057,098 | A | 5/2000 | Buechler et al. ............... 435/6 |
| 6,057,116 | A | * 5/2000 | Vielkind ..................... 435/7.23 |
| 6,068,829 | A | 5/2000 | Ruoslahti et al. ............ 242/9.1 |
| 6,093,800 | A | 7/2000 | Reiter et al. ................. 530/350 |
| 6,174,861 | B1 | 1/2001 | O'Reilly et al. ............... 514/12 |
| 6,184,973 | B1 | 2/2001 | Baer et al. ..................... 356/36 |

(Continued)

FOREIGN PATENT DOCUMENTS

| WO | WO 99/47554 | | 9/1999 |
|---|---|---|---|
| WO | WO/00/42973 | * | 7/2000 |
| WO | WO 02/20722 | | 3/2002 |
| WO | WO 02/20723 | | 3/2002 |
| WO | WO/02/20723 | * | 3/2002 |
| WO | WO 02/20724 | | 3/2002 |
| WO | WO 02/20769 | | 3/2002 |
| WO | WO 02/20822 | | 3/2002 |
| WO | WO 03/022991 | | 3/2003 |

OTHER PUBLICATIONS

Campbell et al. (American J. of Pathol. vol. 158, pp. 25-32, 2001).*
Schally et al. (The Prostate vol. 45, pp. 158-166, 2000).*
Arap et al., "Cancer Treatment by Targeted Drug Delivery to Tumor Vasculature in a Mouse Model," *Science*, 279:377-380, 1998.
Arap et al., "Chemotherapy targeted to tumor vasculature," *Curr. Opin. Onocol.*, 10:560-565, 1998.
Arap et al., "Steps toward mapping the human vasculature by phage display." *Nature Med.*, 8:121-127, 2002.

(Continued)

*Primary Examiner*—Larry R. Helms
*Assistant Examiner*—Meera Natarajan
(74) *Attorney, Agent, or Firm*—Fulbright & Jaworski LLP

(57) ABSTRACT

The present invention concerns compositions comprising and methods of identification and use of targeting peptides selective for cancer tissue, particularly prostate or ovarian cancer tissue. The method may comprise identifying endogenous mimeotopes of such peptides, such as GRP78, IL-11Rα and hsp90. Antibodies against such targeting peptides or their mimeotopes may be used for detection, diagnosis and/or staging of prostate or ovarian cancer. In other embodiments, the compositions and methods concern novel type of gene therapy vector, known as adeno-associated phage (AAP). AAP are of use for targeted delivery of therapeutic agents to particular tissues, organs or cell types, such as prostate or ovarian cancer. In still other embodiments, targeting peptides selective for low-grade lipomas may be used for detection, diagnosis and targeted delivery of therapeutic agents.

29 Claims, 37 Drawing Sheets

U.S. PATENT DOCUMENTS

| | | | |
|---|---|---|---|
| 6,215,550 B1 | 4/2001 | Baer et al. | 356/36 |
| 6,232,440 B1 | 5/2001 | Hillman et al. | 530/350 |
| 6,261,789 B1 | 7/2001 | Reiter et al. | 435/7.23 |
| 6,271,196 B1 | 8/2001 | O'Brien | 514/2 |
| 6,350,855 B1 | 2/2002 | Tobin | 530/350 |
| 6,372,720 B1 | 4/2002 | Longmuir et al. | 514/44 |
| 6,395,255 B1 * | 5/2002 | Thakur | 424/1.69 |
| 6,399,384 B1 | 6/2002 | Jat | 435/456 |
| 6,458,381 B1 | 10/2002 | Sourovoi et al. | 424/450 |
| 6,528,281 B1 | 3/2003 | Tobin | 435/69.1 |
| 2001/0046498 A1 | 11/2001 | Rouslahti et al. | 424/178.1 |
| 2003/0113320 A1 | 6/2003 | Ruoslahti et al. | 424/143.1 |

OTHER PUBLICATIONS

Barrow and Soothill, "Bacteriophage therapy and prophylaxis: rediscovery and renewed assessment of potential," *Trends Microbiol.*, 5:268-271, 1997.

Bergelson et al., "Isolation of a Common Receptor for Coxsackie B Viruses and Adenoviruses 2 and 5," *Science*, 275:1320-1323, 1997.

Brawn et al., "Prostatic Acid Phosphatase Levels (Enzymatic Method) From Completely Sectioned, Clinically Benign, Whole Prostates," *The Prostate*, 28:295-299, 1996.

Burg et al., "NG2 Proteoglycan-binding Peptides Target Tumor Neovasculature," *Cancer Res*, 59:2869-2874, 1999.

Campbell et al., "Increased Expression of the Interleukin-11 Receptor and Evidence of STAT3 Activation in Prostate Carcinoma." *Am. J. Pathol.*, 158:25-32, 2001.

Chen et al., "Thapsigargin-induced grp78 expression is mediated by the increase of cytosolic free calcium in 9L rat brain tumor cells," *J. Cell. Biochem.*, 78:404-416, 2000.

Choongkittaworn et al., "Expression of prohibitin in rat seminiferous epithelium," *Biol. Reprod.*, 49(2):300-310, 1993.

Curnis et al., "Enhancement of tumor necrosis factor alpha antitumor immunotherapeutic properties by targeted delivery to aminopeptidase N (CD13)," *Nat Biotechnol.*, (11):1185-90, 2000.

Database NCBI on STN, Accession No. G69514, Klenk et al., "The Complete Genome Sequence of the Hyperthermophilic, Sulphate-reducing Archaeon Archaeoglobus Fulgidus," *Nature*, 390:364-370, 1997.

Database NCBI on STN, Accession No. T21276, Matthews et al., "Direct Submission," 1999.

Delpino et al., "Cell surface localization of the 78 kD glucose regulated protein (GRP 78) induced by thapsigargin," *Mol. Membr. Biol.*, 15(1):21-26, 1998.

Ellerby et al., "Anti- cancer activity of targeted pro-apoptotic peptides," *Nature Med.*, 5:1032-1038, 1999.

Giannakouros et al., "Post-translational Processing of Schizosaccharomyces pombe YPT5 Protein: In Vitro and In Vivo Analysis of Processing Mutants," *Journal of Biological Chemistry*, 268:24467-24474, 1993.

Grifman et al., "Incorporation of Tumor-Targeting Peptides into Recombinant Adeno-associated Virus Capsids," *Mol. Ther.*, 3(6):964-975, 2001.

Harrington et al., "Gene Therapy for prostate cancer: current status and future prospects," *J. Urol.*, 166:1220-1233, 2001.

Hong et al., "Adenovirus type 5 fiber knob binds to MHC class I alpha-2 domain at the surface of human epithelial and B lymphoblastoid cells," *EMBO J.*, 16:2294-2306, 1997.

Huang et al., "Comparison of Prostate Secretory Protein With Prostate Specific Antigen and Prostatic Acid Phosphatase as a Serum Biomarker for Diagnosis and Monitoring Patients With Prostate Carcinoma." *Prostate*, 23:201-212, 1993.

Ikonen et al., "Prohibitin, an antiproliferative protein, is localized to mitochondria," *FEBS Letters*, 358(3):273-277, 1995.

Ino et al., "Expression of aminopeptidase A in human gestational choriocarcinoma cell lines and tissues," *Placenta*, 21:63-72, 2000.

Koivunen et al., "Inhibition of Beta(2) Integrin-mediated Leukocyte Cell Adhesion by Leucine-Leucine-Glycine Motif-containing Peptides." *J. Cell Biol.*, 153:905-915, 2001.

Koivunen et al., "Tumor targeting with a selective gelatinase inhibitor," *Nature Biotechnol*, 17:768-774, 1999a.

Larocca et al., "Gene transfer to mammalian cells using genetically targeted filamentous bacteriophage," *FASEB J*, 13:727-734, 1999.

Mahboubi et al., "IL-11 Activates Human Endothelial Cells to Resist Immune-Mediated Injury," *J. Immunol.*, 164:3837-3846, 2000.

Melnick and Argon, "Molecular chaperones and the biosynthesis of antigen receptors." *Immunol. Today*, 16:243-250, 1995.

Misra et al., "The role of Grp 78 in alpha 2-macroglobulin-induced signal transduction. Evidence from RNA interference that the low density lipoprotein receptor-related protein is associated with, but not necessary for, GRP 78-mediated signal transduction," *J Biol Chem.*, 277(44):42082-7, 2002.

Murphy et al., "Evaluation and Comparison of Two New Prostate Carcinoma Markers. Free-Prostate Specific Antigen and Prostate Specific Membrane Antigen." *Cancer*, 78:809-818, 1996.

O'Dowd et al., "Update on the Appropriate Staging Evaluation for Newly Diagnosed Prostate Cancer," *J. Urol.*, 158:687-698, 1997.

Pasqualini and Ruoslahti, "Organ targeting in vivo using phage display peptide libraries," *Nature* 380:364-366, 1996.

Pasqualini et al., "Aminopeptidase N I a Receptor for Tumor-homing Peptides and a Target for Inhibiting Angiogenesis," *Cancer Res.*, 60:722-727, 2000.

Pasqualini, "Vascular targeting with phage peptide libraries," *The Quart. J. Nucl. Med.*, 43:159-162, 1999.

Piironen et al., "Immunofluorometric assay for sensitive and specific measurement of human prostatic glandular kallikrein (hK2) in serum." *Clin. Chem.*, 42:1034-1041, 1996.

Poul and Marks, "Targeted Gene Delivery to Mammalian Cells by Filamentous Bacteriophage," *J. Mol. Biol.*, 288:203-211, 1999.

Raisler et al., "Adeno-associated virus type-2 expression of pigmented epithelium-derived factor or Kringles I-3 of angiostatin reduce retinal neovascularization," *Proc. Natl. Acad Sci.*, 99:8909-8914, 2002.

Rajotte and Ruoslahti, "Membrane Dipeptidase Is the Receptor for a Lung-targeting Peptide Identified by in Vivo Phage Display," *J Biol Chem.*, 274:11593-11598, 1999.

Rajotte et al., "Molecular Heterogeneity of the Vascular Endothelium Revealed by In Vivo Phage Display," *J Clin. Invest.*, 102:430-437, 1998.

Ruoslahti, "RGD And Other Recognition Sequences For Integrins," *Annu. Rev. Cell Dev. Biol.*, 12:697-715, 1996.

Shi et al., "Adeno-associated virus-mediated gene transfer of endostatin inhibits angiogenesis and tumor growth in vivo," *Cancer Gene Therapy*, 9:513-521 (2002).

Smith and Scott, "Libraries of Peptides and Proteins Displayed on Filamentous Phage," *Meth. Enzymol*, 217:228-257, 1993.

Trepel et al., "Molecular Adaptors for Vascular-Targeted Adenoviral Gene Delivery," *Hum. Gene. Ther.*, 11:1971-1981, 2000.

Tsimanis et al., "Over-expression of the functional interleukin-11 alpha receptor in the development of B-cell chronic lymphocytic leukemia," *Leuk. Lymphoma*, 42(1-2):195-205, 2001.

Veltri et al., "Interleukin-8 Serum Levels in Patients With Benign Prostatic Hyperplasia and Prostate Cancer," *Urology*, 53:139-147, 1999.

Vendruscolo et al., "Three key residues form a critical contact network in a protein folding transition state," *Nature*, 409:641-45, 2001.

Wang et al., "Prohibitin, a potential tumor suppressor, interacts with RB and regulates E2F function," *Oncogene*, 18(23):3501-3510, 1999.

Weitzman et al., "Adenovirus Vectors in Cancer Gene Therapy," *In: Gene Therapy Technology and Vector Systems*, 2:17-25, 1997.

Wickham, "Targeting adenovirus," *Gene Ther*, 7:110-114, 2000.

Zhang, "Development and application of adenoviral vectors for gene therapy of cancer," *Cancer Gene Ther.*, 6:113-138, 1999.

PCT International Search Report and Written Opinion, issued in International Application No. PCT/US0234987, dated Nov. 5, 2007.

\* cited by examiner

FIG. 4
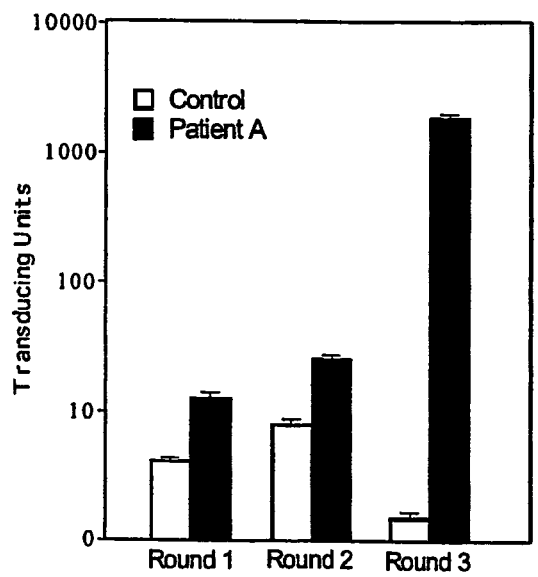
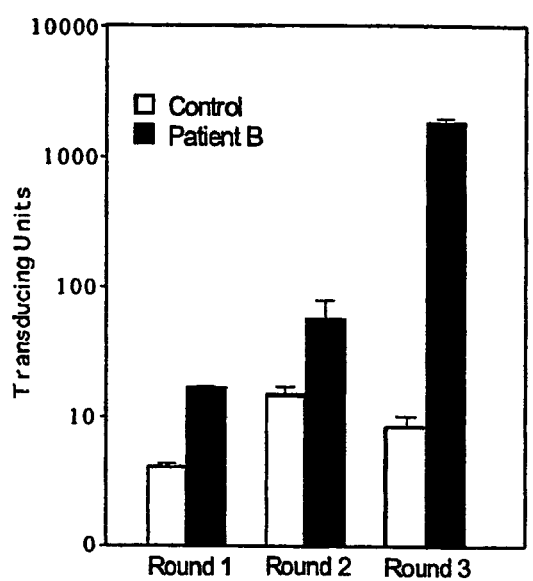
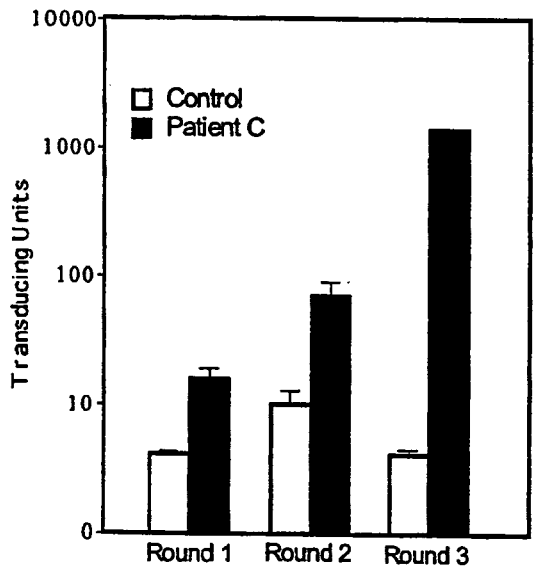
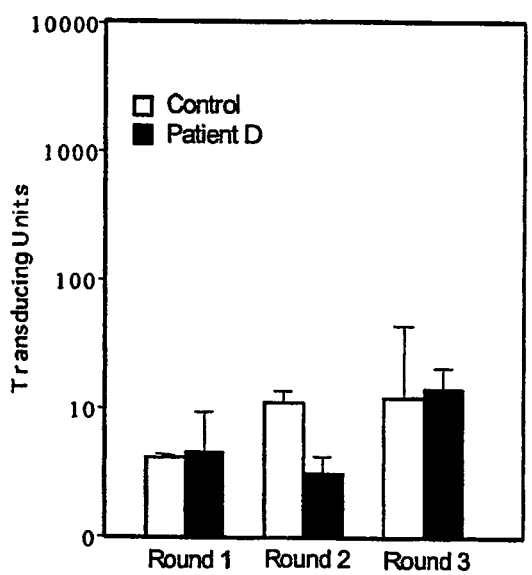

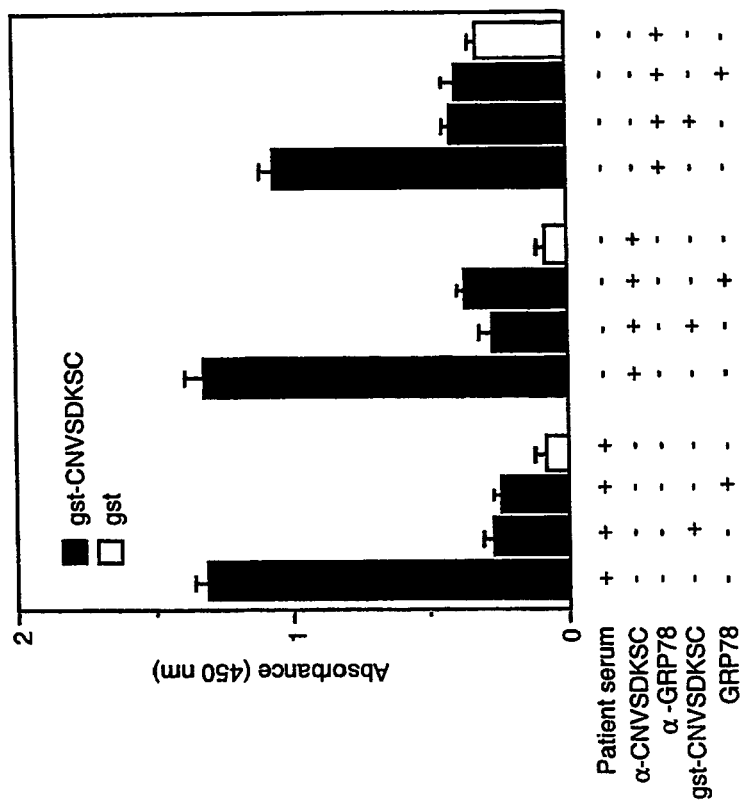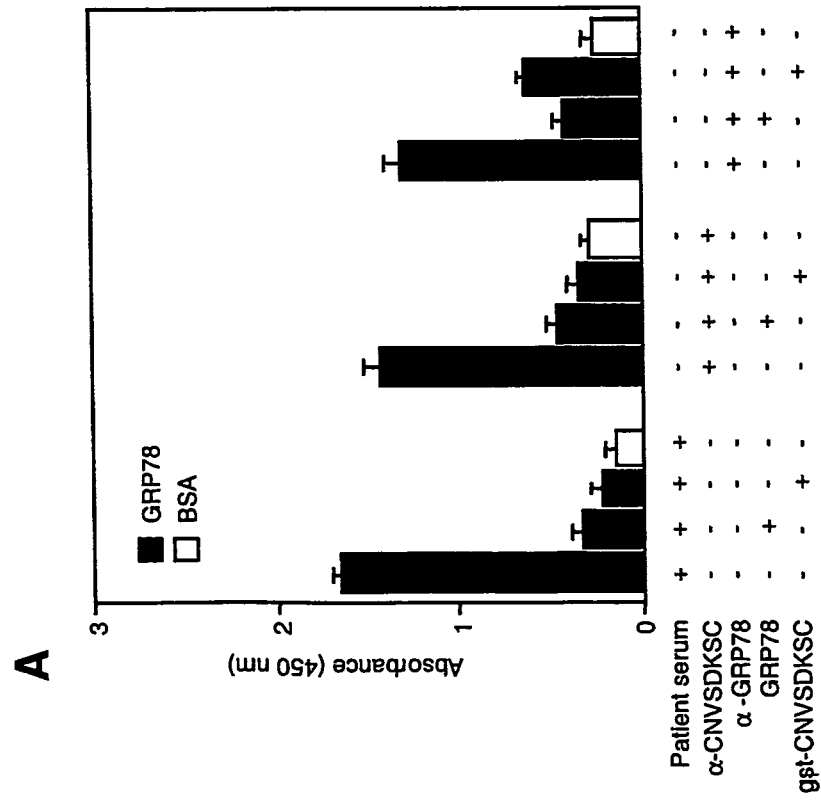
FIG. 8

FIG. 13
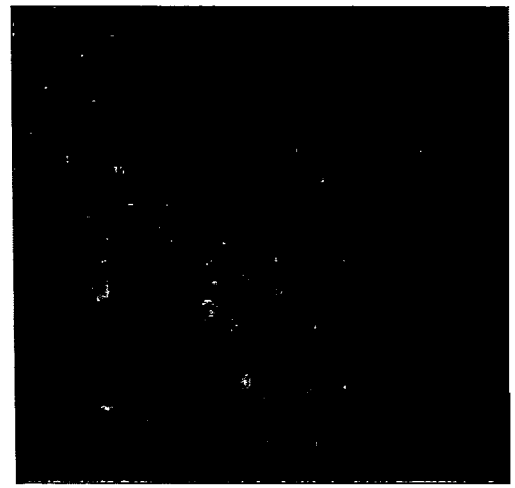
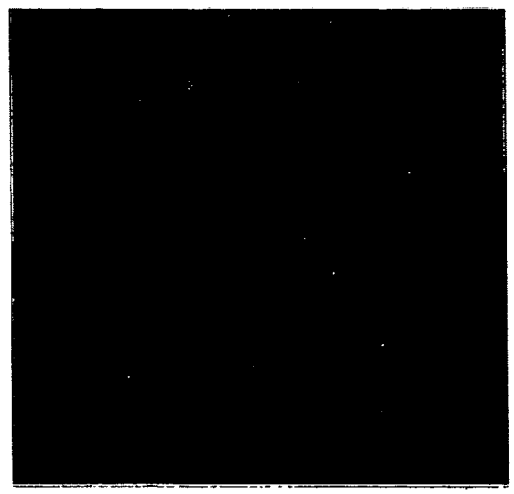

FIG. 14
(A)
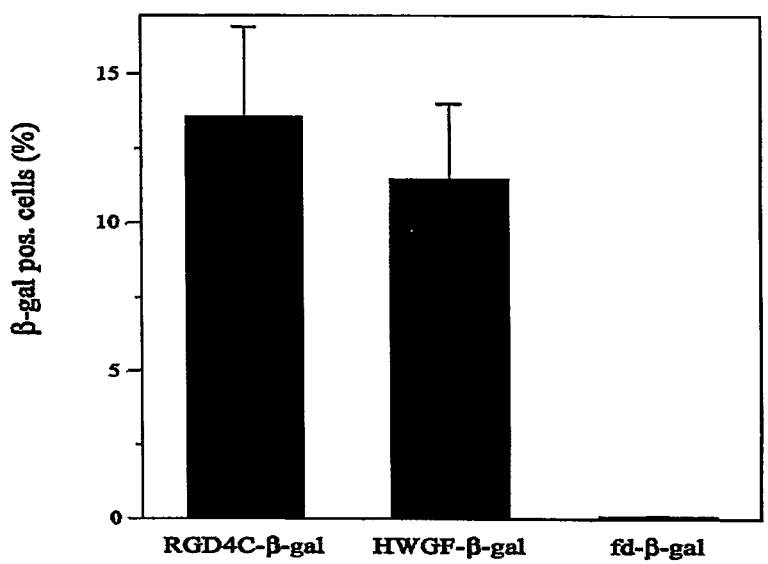
(B)
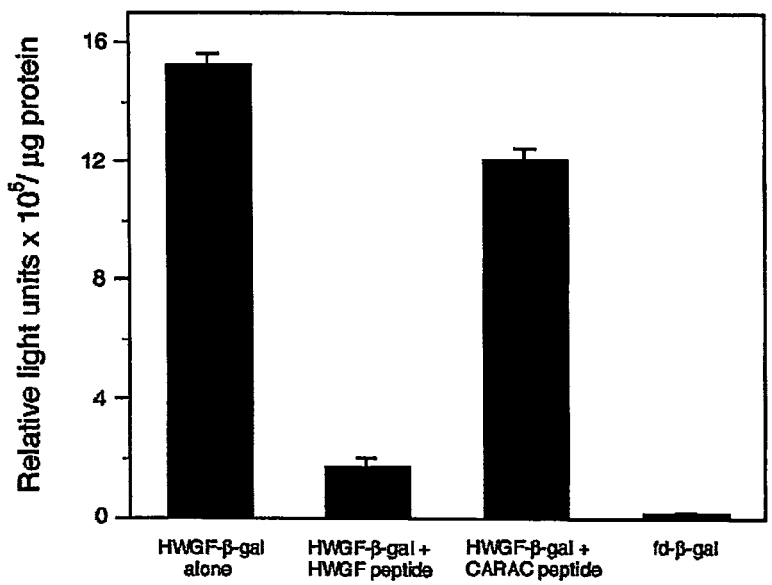
(C)
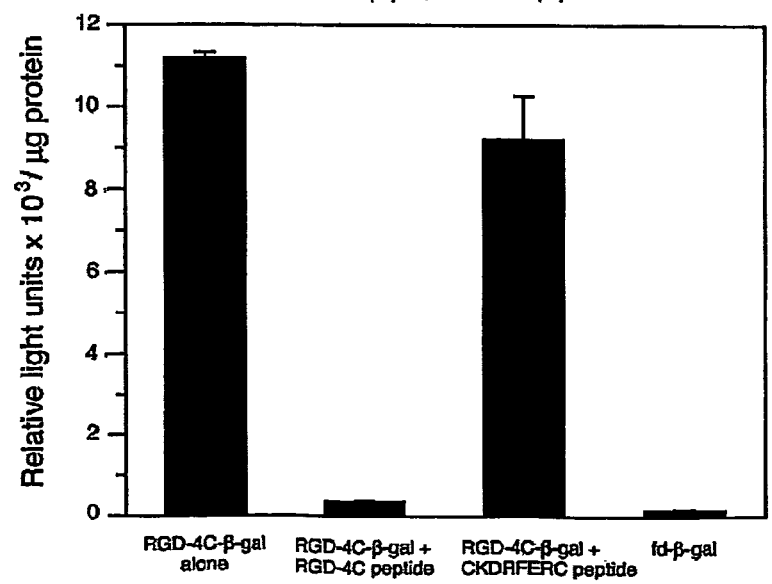

Day 0
Day 15
Day 30
Day 45
*FIG. 21*

FIG. 22
Uninfected
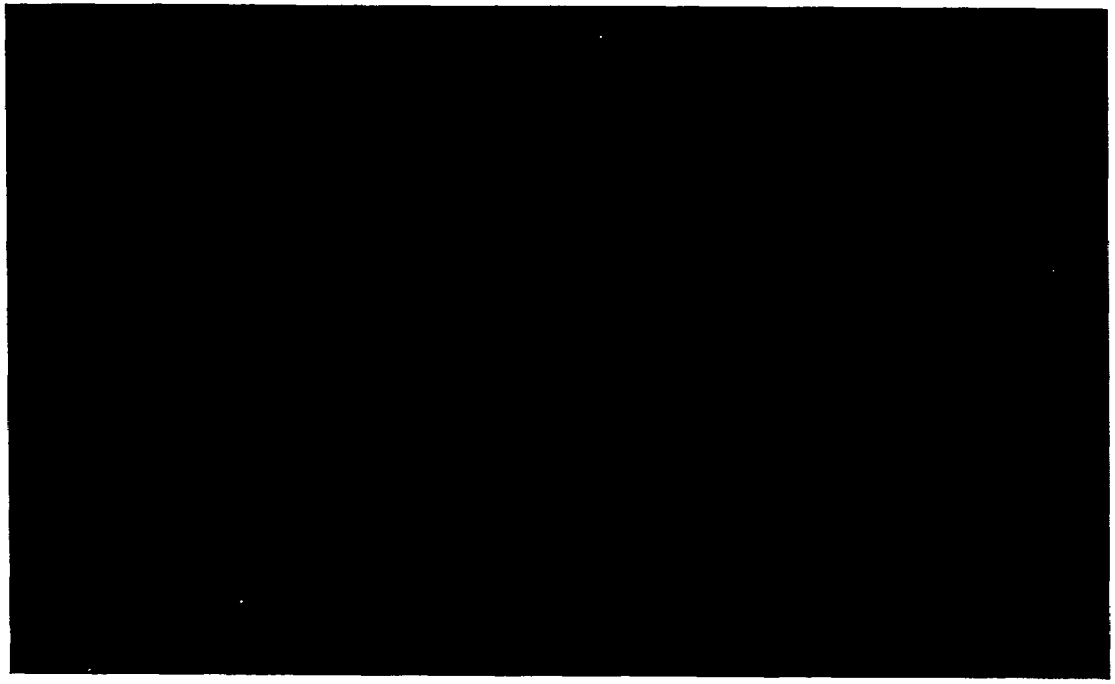
Rescued
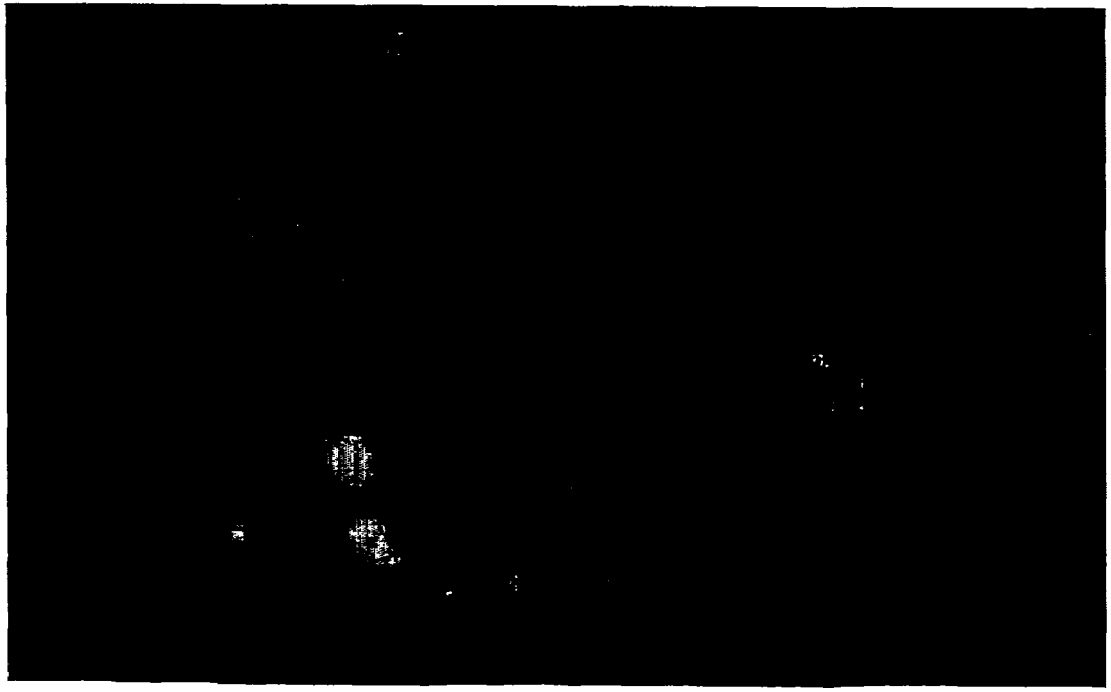

FIG. 27
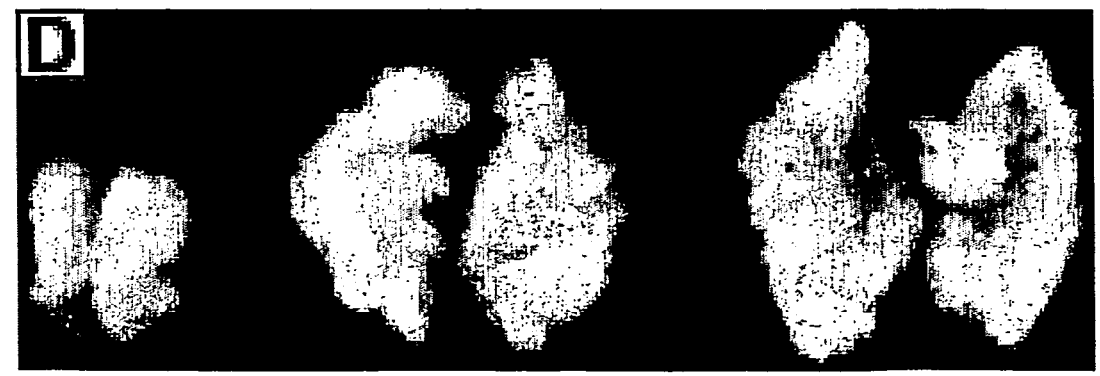

Horizontal line in box=median value; "x" in box=mean value; upper and lower limits of the box=$25^{th}$-$75^{th}$ percentiles; whiskers=range.

COMPOSITIONS AND METHODS OF USE OF TARGETING PEPTIDES FOR DIAGNOSIS AND THERAPY OF HUMAN CANCER

This invention was made with U.S. government support under grants CA90270, 1R1CA90810-01 and 1R01CA82976-01 awarded by the National Institutes of Health. The U.S. government has certain rights in this invention.

This application is a national phase application under 35 U.S.C. §371 of International Application No. PCT/US2002/034987 filed 30 Oct. 2002, which claims priority to International Application No. PCT/US2002/27836 filed 30 Aug. 2002. The entire texts of all the above-cited applications are incorporated herein by reference.

BACKGROUND OF THE INVENTION

1. Field of the Invention

The present invention concerns the fields of cancer diagnostics and targeted delivery of therapeutic agents to cancer cells. More specifically, the present invention relates to compositions and methods for identification and use of peptides that selectively target cancer cell receptors, such as the IL-11 receptor and/or the GRP78 receptor. In particular embodiments, the targeted receptors are preferentially expressed in prostate cancer, especially in metastatic prostate cancer. In certain embodiments, the invention concerns compositions and methods of use of novel phage-based gene delivery vectors.

2. Description of Related Art

Therapeutic treatment of many disease states is limited by the systemic toxicity of the therapeutic agents used. Cancer therapeutic agents in particular exhibit a very low therapeutic index, with rapidly growing normal tissues such as skin and bone marrow affected at concentrations of agent that are not much higher than the concentrations used to kill tumor cells. Treatment of cancer and other organ, tissue or cell type confined disease states would be greatly facilitated by the development of compositions and methods for targeted delivery to a desired organ, tissue or cell type of a therapeutic agent.

Recently, an in vivo selection system was developed using phage display libraries to identify targeting peptides for various organs, tissues or cell types in a mouse model system. Phage display libraries expressing transgenic peptides on the surface of bacteriophage were initially developed to map epitope binding sites of immunoglobulins (Smith and Scott, 1986, 1993). Such libraries can be generated by inserting random oligonucleotides into cDNAs encoding a phage surface protein, generating collections of phage particles displaying unique peptides in as many as $10^9$ permutations. (Pasqualini and Ruoslahti, 1996, Arap et al, 1998a; Arap et al 1998b).

Intravenous administration of phage display libraries to mice was followed by the recovery of phage from individual organs (Pasqualini and Ruoslahti, 1996). Phage were recovered that were capable of selective homing to the vascular beds of different mouse organs, tissues or cell types, based on the specific targeting peptide sequences expressed on the outer surface of the phage (Pasqualini and Ruoslahti, 1996). A variety of organ and tumor-homing peptides have been identified by this method (Rajotte et al., 1998, 1999; Koivunen et al., 1999a; Burg et al., 1999; Pasqualini, 1999). Each of those targeting peptides bound to different receptors that were selectively expressed on the vasculature of the mouse target tissue (Pasqualini, 1999; Pasqualini et al., 2000; Folkman, 1995; Folkman 1997). Tumor-homing peptides bound to receptors that were upregulated in the tumor angiogenic vasculature of mice (Brooks et al., 1994b; Pasqualini et al., 2000). In addition to identifying individual targeting peptides selective for an organ, tissue or cell type (Pasqualini and Ruoslahti, 1996; Arap et al, 1998a; Koivunen et al., 1999b), this system has been used to identify endothelial cell surface markers that are expressed in mice in vivo (Rajotte and Ruoslahti, 1999).

This relative success notwithstanding, cell surface selection of phage libraries has been plagued by technical difficulties. A high number of non-binder and non-specific binder clones are recovered using previous in vivo methods, particularly with components of the reticuloendothelial system such as spleen and liver. Removal of this background phage binding by repeated washes is both labor-intensive and inefficient. Cells and potential ligands are frequently lost during the many washing steps required. Methods that have been successful with animal model systems are unsatisfactory for identifying human targeting peptides, which may differ from those obtained in mouse or other animal model systems.

Attachment of therapeutic agents to targeting peptides has resulted in the selective delivery of the agent to a desired organ, tissue or cell type in the mouse model system. Targeted delivery of chemotherapeutic agents and proapoptotic peptides to receptors located in tumor angiogenic vasculature resulted in a marked increase in therapeutic efficacy and a decrease in systemic toxicity in tumor-bearing mouse models (Arap et al., 1998a, 1998b; Ellerby et al., 1999). However, the targeted delivery of anti-cancer agents in humans has not yet been demonstrated. The targeted receptors reported in previous studies may be present in angiogenic normal tissues as well as in tumor tissues and may or may not be of use in distinguishing between normal tissues, non-metastatic cancers and metastatic cancer. A need exists for tumor targeting peptides that are selective against human cancers, as well as for targeting peptides that can distinguish between metastatic and non-metastatic human cancers.

Attempts have been made to target delivery of gene therapy vectors to specific organs, tissues or cell types in vivo. Directing such vectors to the site of interest would enhance therapeutic effects and diminish adverse systemic immunologic responses. Adenovirus type 5 (Ad5)-based vectors have been commonly used for gene transfer studies (Weitzman et al., 1997; Zhang, 1999). The attachment of Ad5 to the target cell is mediated by the capsid's fiber knob region, which interacts with cell surface receptors, including the coxsackie adenovirus receptor (CAR) and possibly with MHC class I (Bergelson et al., 1997; Hong et al., 1997). Upon systemic administration in vivo, binding of virus to CAR can result in unintended enrichment of vectors in non-targeted but CAR-expressing tissues. Conversely, target cells that express little or no CAR are inefficiently transduced. A need exists to develop novel gene therapy vectors to allow more selective delivery of gene therapy agents.

A need also exists to identify receptor-ligand pairs in organs, tissues or cell types. Previous attempts to identify targeted receptors and ligands binding to receptors have largely targeted a single ligand at a time for investigation. Identification of previously unknown receptors and previously uncharacterized ligands has been a very slow and laborious process. Such novel receptors and ligands may provide the basis for new therapies for a variety of disease states, such as cancer and/or metastatic prostate cancer.

SUMMARY OF THE INVENTION

The present invention solves a long-standing need in the art by providing compositions and methods of preparation and use of targeting peptides that are selective and/or specific for human cancer tissues, such as metastatic prostate cancer. In some embodiments, the invention concerns particular targeting peptides selective or specific for prostate cancer, including but not limited to SEQ ID NO:5-35, SEQ ID NO:37, SEQ ID NO:39-67 and SEQ ID NO:83-129. Other embodiments concern such targeting peptides attached to therapeutic agents. In other embodiments, cancer targeting peptides may be used to selectively or specifically deliver therapeutic agents to target tissues, such as prostate cancer and/or metastatic prostate cancer. In certain embodiments, the subject methods concern the preparation and identification of targeting peptides selective or specific for a given target cell, tissue or organ, such as prostate cancer.

One embodiment of the invention concerns isolated peptides of 100 amino acids or less in size, comprising at least 3 contiguous amino acids of a targeting peptide sequence, selected from any of SEQ ID NO:5-35, SEQ ID NO:37, SEQ ID NO:39-67 and SEQ ID NO:83-129. In a preferred embodiment, the isolated peptide is 50 amino acids or less, more preferably 30 amino acids or less, more preferably 20 amino acids or less, more preferably 10 amino acids or less, or even more preferably 5 amino acids or less in size. In other preferred embodiments, the isolated peptide may comprise at least 4, 5, 6, 7, 8 or 9 contiguous amino acids of a targeting peptide sequence, selected from any of SEQ ID NO:5-35, SEQ ID NO:37, SEQ ID NO:39-67 and SEQ ID NO:83-129.

In certain embodiments, the isolated peptide may be attached to a molecule. In preferred embodiments, the attachment is a covalent attachment. In various embodiments, the molecule is a drug, a chemotherapeutic agent, a radioisotope, a pro-apoptosis agent, an anti-angiogenic agent, a hormone, a cytokine, a growth factor, a cytotoxic agent, a peptide, a protein, an antibiotic, an antibody, a Fab fragment of an antibody, a survival factor, an anti-apoptotic factor, a hormone antagonist, an imaging agent, a nucleic acid or an antigen. Those molecules are representative only and virtually any molecule may be attached to a targeting peptide and/or administered to a subject within the scope of the invention. In preferred embodiments, the pro-aptoptosis agent is gramicidin, magainin, mellitin, defensin, cecropin, (KLAKLAK)$_2$ (SEQ ID NO:1), (KLAKKLA)$_2$ (SEQ ID NO:2), (KAAKKAA)$_2$ (SEQ ID NO:3) or (KLGKKLG)$_3$ (SEQ ID NO:4). In other preferred embodiments, the anti-angiogenic agent is angiostatin5, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, docetaxel, polyamines, a proteasome inhibitor, a kinase inhibitor, a signaling inhibitor (SU5416, SU6668, Sugen, South San Francisco, Calif.), accutin, cidofovir, vincristine, bleomycin, AGM-1470, platelet factor 4 or minocycline. In further preferred embodiments, the cytokine is interleukin 1 (IL-1), IL-2, IL-5, IL-10, IL-11, IL-12, IL-18, interferon-γ (IF-γ), IF-α, IF-β, tumor necrosis factor-α (TNF-α), or GM-CSF (granulocyte macrophage colony stimulating factor). Such examples are representative only and are not intended to exclude other pro-apoptosis agents, anti-angiogenic agents or cytokines known in the art.

In various embodiments, targeting peptides attached to one or more therapeutic agents may be administered to a subject, such as a human subject. Such administration may be of use for the treatment of various disease states, such as prostate cancer. In certain embodiments, cancer-targeting peptides attached to a cytocidal, pro-apoptotic, anti-angiogenic or other therapeutic agent may be of use in methods to treat human cancer.

In other embodiments of the invention, the isolated peptide may be attached to a macromolecular complex. In preferred embodiments, the macromolecular complex is a virus, a bacteriophage, a bacterium, a liposome, a microparticle, a magnetic bead, a yeast cell, a mammalian cell, a cell or a microdevice. These are representative examples only and macromolecular complexes within the scope of the present invention may include virtually any complex that may be attached to a targeting peptide and administered to a subject. In other preferred embodiments, the isolated peptide may be attached to a eukaryotic expression vector, more preferably a gene therapy vector.

Various embodiments concern novel targeted gene therapy vectors, comprising targeting peptides expressed on the surface of a gene therapy vector. In particular embodiments, the targeted gene therapy vector is a chimeric phage-based vector containing elements from adeno-associated virus (AAV), the modified vector being referred to as an adeno-associated phage (AAP) vector.

In another embodiment, the targeting peptides may be attached to a solid support, preferably magnetic beads, Sepharose beads, agarose beads, a nitrocellulose membrane, a nylon membrane, a column chromatography matrix, a high performance liquid chromatography (HPLC) matrix or a fast performance liquid chromatography (FPLC) matrix. Such immobilized peptides may be used, for example, for affinity purification of various components, such as receptor proteins or circulating antibodies that bind to the peptides.

Additional embodiments of the present invention concern fusion proteins comprising at least 3 contiguous amino acids of a sequence selected from any of SEQ ID NO:5-35, SEQ ID NO:37, SEQ ID NO:39-67 and SEQ ID NO:83-129. In some embodiments, larger contiguous sequences, up to a full-length sequence selected from any of SEQ ID NO:5-35, SEQ ID NO:37, SEQ ID NO:39-67 and SEQ ID NO:83-129 may be used.

Certain other embodiments concern compositions comprising the claimed isolated peptides or fusion proteins in a pharmaceutically acceptable carrier. Further embodiments concern kits comprising the claimed isolated peptides or fusion proteins in one or more containers.

Other embodiments concern methods of targeted delivery comprising selecting a targeting peptide for a desired organ, tissue or cell type, such as prostate cancer, attaching said targeting peptide to a molecule, macromolecular complex or gene therapy vector, and providing said peptide attached to said molecule, complex or vector to a subject. Preferably, the targeting peptide is selected to include at least 3 contiguous amino acids from any of selected from any of SEQ ID NO:5-35, SEQ ID NO:37 and SEQ ID NO:83-129. In other preferred embodiments, the molecule attached to the targeting peptide is a chemotherapeutic agent, an antigen or an imaging agent. In various embodiments, methods of targeted delivery may utilize antibodies against particular peptide sequences, such as SEQ ID NO:39-67. Such antibodies may be attached to a molecule, macromolecular complex or gene therapy vector and administered to a subject. The skilled artisan will realize that the targeting moiety is not limited to antibodies, but may comprise any molecule or complex that binds to a receptor located in a target tissue, including but not limited to antibodies, genetically engineered antibodies, antibody fragments, single-chain antibodies, humanized antibodies, chimeric antibodies, binding proteins and native ligands or homologs thereof. In preferred embodiments of the invention, the targeted receptor is GRP78 or IL-11Rα.

In certain embodiments, the cancer targeting peptides and/or antibodies disclosed herein may be of use for the detection, diagnosis and/or prognosis of human cancer, such as prostate cancer. In preferred embodiments, the cancer targeting peptides may be used to differentially diagnose metastatic and non-metastatic prostate cancer.

Other embodiments of the present invention concern isolated nucleic acids of 300 nucleotides or less in size, encoding a targeting peptide. In preferred embodiments, the isolated nucleic acid is 250, 225, 200, 175, 150, 125, 100, 75, 50, 40, 30, 20 or even 10 nucleotides or less in size. In other preferred embodiments, the isolated nucleic acid is incorporated into a eukaryotic or a prokaryotic expression vector. In even more preferred embodiments, the vector is a plasmid, a cosmid, a yeast artificial chromosome (YAC), a bacterial artificial chromosome (BAC), a virus or a bacteriophage. In other preferred embodiments, the isolated nucleic acid is operatively linked to a leader sequence that localizes the expressed peptide to the extracellular surface of a host cell.

Additional embodiments of the present invention concern methods of treating a disease state, such as cancer, comprising selecting a targeting peptide and/or antibody against a selected peptide that targets cells associated with the disease state, attaching one or more molecules effective to treat the disease state to the peptide, and administering the peptide to a subject with the disease state. Preferably, the peptide includes at least three contiguous amino acids selected from any of selected from any of SEQ ID NO:5-35, SEQ ID NO:37, SEQ ID NO:39-67 and SEQ ID NO:83-129.

In certain embodiments, the methods concern Biopanning and Rapid Analysis of Selective Interactive Ligands (BRASIL), a novel method for phage display that results in decreased background of non-specific phage binding, while retaining selective binding of phage to cell receptors. In preferred embodiments, targeting peptides are identified by exposing a subject to a phage display library, collecting samples of one or more organs, tissues or cell types, separating the samples into isolated cells or small clumps of cells suspended in an aqueous phase, layering the aqueous phase over an organic phase, centrifuging the two phases so that the cells are pelleted at the bottom of a centrifuge tube and collecting phage from the pellet. In an even more preferred embodiment, the organic phase is dibutylphtalate.

In other embodiments, phage that bind to a target organ, tissue or cell type, for example to prostate cancer, may be pre-screened or post-screened against a subject lacking that organ, tissue or cell type, such as a female subject. Phage that bind to a control subject are removed from the library prior to screening in subjects possessing the organ, tissue or cell type.

In preferred embodiments, targeting phage may be recovered from specific cell types or sub-types present in an organ or tissue after selection of the cell type by PALM (Positioning and Ablation with Laser Microbeams). PALM allows specific cell types to be selected from, for example, a thin section of an organ or tissue. Phage may be recovered from the selected sample.

In another embodiment, a phage display library displaying the antigen binding portions of antibodies from a subject is prepared, the library is screened against one or more antigens and phage that bind to the antibodies are collected. In more preferred embodiments, the antigen is a targeting peptide.

In certain embodiments, the methods and compositions may be used to identify one or more receptors for a targeting peptide. In alternative embodiments, the compositions and methods may be used to identify naturally occurring ligands for known or newly identified receptors. In preferred embodiments, the receptor may be selectively or specifically expressed in prostate cancer. In some embodiments, expression of the receptor may be up regulated in prostate cancer compared to normal prostate, and/or in metastatic compared to non-metastatic prostate cancer. Methods of diagnosis and/or prognosis of cancer, such as prostate cancer, may comprise detection and/or quantification of such disease-state selective or specific receptors in tissue samples. In some embodiments, detection and/or quantification may take place in situ within an intact subject, for example by attaching an imaging agent to an antibody or equivalent molecule that binds to the receptor.

In some embodiments, the methods may comprise contacting a targeting peptide to an organ, tissue or cell containing a receptor of interest, allowing the peptide to bind to the receptor, and identifying the receptor by its binding to the peptide. In preferred embodiments, the targeting peptide contains at least three contiguous amino acids selected from any of selected from any of SEQ ID NO:5-35, SEQ ID NO:37 and SEQ ID NO:83-129. In other preferred embodiments, the targeting peptide may comprise a portion of an antibody against the receptor. In more preferred embodiments, the antibody or antibody portion may bind to SEQ ID NO:39-67.

In alternative embodiments, the targeting peptide may contain a random amino acid sequence. The skilled artisan will realize that the contacting step can utilize intact organs, tissues or cells, or may alternatively utilize homogenates or detergent extracts of the organs, tissues or cells. In certain embodiments, the cells to be contacted may be genetically engineered to express a suspected receptor for the targeting peptide. In a preferred embodiment, the targeting peptide is modified with a reactive moiety that allows its covalent attachment to the receptor. In a more preferred embodiment, the reactive moiety is a photoreactive group that becomes covalently attached to the receptor when activated by light. In another preferred embodiment, the peptide is attached to a solid support and the receptor is purified by affinity chromatography. In other preferred embodiments, the solid support comprises magnetic beads, Sepharose beads, agarose beads, a nitrocellulose membrane, a nylon membrane, a column chromatography matrix, a high performance liquid chromatography (HPLC) matrix or a fast performance liquid chromatography (FPLC) matrix.

In certain embodiments, the targeting peptide may inhibit the activity of a receptor upon binding to the receptor. The skilled artisan will realize that receptor activity can be assayed by a variety of methods known in the art, including but not limited to catalytic activity and binding activity. In other embodiments, binding of a targeting peptide to a receptor may inhibit a transport activity of the receptor.

In alternative embodiments, one or more ligands for a receptor of interest may be identified by the disclosed methods and compositions. One or more targeting peptides that mimic part or all of a naturally occurring ligand may be identified by phage display and biopanning in vivo or in vitro. A naturally occurring ligand may be identified by homology with a single targeting peptide that binds to the receptor, or a consensus motif of sequences that bind to the receptor. In other alternative embodiments, an antibody may be prepared against one or more targeting peptides that bind to a receptor of interest. Such antibodies may be used for identification or immunoaffinity purification of the native ligand.

In certain embodiments, the targeting peptides of the present invention are of use for the selective delivery of therapeutic agents, including but not limited to gene therapy vectors and fusion proteins, to specific organs, tissues or cell types. The skilled artisan will realize that the scope of the claimed methods of use include any disease state that can be treated by targeted delivery of a therapeutic agent to a desired organ, tissue or cell type. Although such disease states include those where the diseased cells are confined to a specific organ, tissue or cell type, other disease states may be treated by an organ, tissue or cell type-targeting approach. In particular embodiments, the organ, tissue or cell type may comprise prostate cancer.

Certain embodiments concern methods of obtaining antibodies against an antigen. In preferred embodiments, the antigen comprises one or more targeting peptides. The targeting peptides may be prepared and immobilized on a solid support, serum-containing antibodies is added and antibodies that bind to the targeting peptides may be collected.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4. Selection of peptide library on immunoglobulins from the serum of metastatic prostate cancer patients. Each successive round of panning demonstrates an increase in selectivity as measured by the increase in total number of transducing units for cancer patients relative to the serum of control volunteers. Three metastatic androgen-independents (patients A, B, and D) serum samples and one metastatic androgen-dependent (patient C) serum sample were examined. Standard error of the mean (S.E.M.) from triplicate plating is shown.

FIG. 6A. Distribution of reactivity is shown as the ratio of GST-peptide to GST alone for the four prostate cancer groups and control. Positive reactivity was defined by a ratio of GST-peptide to GST alone equal to or greater than 2.

FIG. 6B. Distribution of reactivity is shown as a percentage of positive reactivity for each group. GST, glutathione S-transferase; A.D., androgen-dependent; A.I., androgen-independent.

FIG. 6C. Correlation between overall survival and serological reactivity against the CNVSDKSC (SEQ ID NO:39) peptide. The same prostate cancer patient population was used to generate the Kaplan-Meier survival curves shown. Log-Rank tests were used to detect significant differences in survival time between patients positively reacting versus non-reacting to the peptide. A significant correlation was observed between poor survival outcome and positive serum reactivity against the peptide CNVSDKSC (SEQ ID NO:39).

FIG. 8. Cross-inhibition of patient serum antibodies by (A) GRP78 or (B) GST-CNVSDKSC (SEQ ID NO:39). Recombinant GRP78 or GST-CNVSDKSC (SEQ ID NO:39) were coated on microtiter well plates and various concentrations of patient serum, anti-GRP78 antibody and anti-CNVSDKSC (SEQ ID NO:39) antibodies were added and analyzed by ELISA. Pre-incubation of the patient serum antibodies with GRP78 or GST-CNVSDKSC (SEQ ID NO:39) inhibited the reaction. The data shows means±SD of triplicate wells.

FIG. 13. Transduction of tumor cells by targeted phage is specific. Tumor cells were incubated with targeted phage. β-gal expression was evaluated after 72 hours. An anti β-gal antibody (Sigma) was used for the staining. (A, B) KS1767 cells with HWGF-β-gal phage, (C, D) MDA-MB-435 cells with RGD-4C-β-gal phage, (E, F) control insertless phage (fd-tet-β-gal). The left side (A, C, E) shows only Texas Red-positive (β-gal infected) cells. The right side (B, D, E) shows the total number of cells in identical fields. Magnification: ×200.

FIG. 14. Quantitative analysis of cell transduction by targeted and control phage. Phage were incubated with tumor cell lines as described in the legend to FIG. 13. (A) An anti-β-gal antibody was used for staining. Gene expression was detected by immunofluorescence and results are expressed in % of β-gal positive cells. In each case, standard error of the mean (SEM) was calculated after counting 10 fields under the microscope in three independent experiments. (B) Inhibition of HWGF-β-gal phage transduction by the synthetic CTTHWGFTLC (SEQ ID NO:69) peptide. (C) Inhibition of RGD-4C-β-gal phage transduction by the synthetic RGD-4C peptide. Unrelated control peptides did not inhibit transduction of the tumor cells by the targeted phage; non-specific transduction levels were determined by using control insertless phage. Shown are mean±SEM obtained from duplicate wells.

FIG. 21. Time course of gene transduction. Cells were plated at 3×10$^5$ cells/well, infected with $10^5$ TU of phage per cell for 4 hours, and sorted based on GFP expression by FACS at seven days post-infection. GFP-positive cells were plated and GFP expression was monitored. Robust GFP expression is shown at days 0, 15, 30, and 45.

FIG. 22. AAP vectors promote AAV integration. Viral rescue experiments. GFP-expressing cells were detected after 48 hours. AAV particles can be detected after adenoviral rescue in AAP-transduced 293 cells but not in control uninfected 293 cells incubated with culture medium.

FIG. 27. Fat resorption induced by fat vasculature-targeted apoptosis. (A) Representative high-fat cafeteria diet-fed obese c57bl/6 mice; (B) and (C) representative regular diet-fed old (~1 year) c57bl/6 mice; or (D) epididymal fat from representative regular diet-fed old c57bl/6 mice from the experiment described in FIG. 10. Whole mice (A), subcutaneous fat (B), peritoneal fat (C) and total epididymal fat (D) from the corresponding indicated treatments were photographed 1 week (A) or 3 weeks (B), (C) and (D) after the beginning of subcutaneous injections. The injected peptides were CKGGRAKDC (SEQ ID NO:81) linked to (KLAKLAK)$_2$ (SEQ ID NO:1) (left column), CARAC (SEQ ID NO:71) linked to (KLAKLAK)$_2$ (SEQ ID NO:1) (middle column), and CKGGRAKDC (SEQ ID NO:81) co-administered with (KLAKLAK)$_2$ (SEQ ID NO:1) (right column).

DESCRIPTION OF ILLUSTRATIVE EMBODIMENTS

Figure 1:
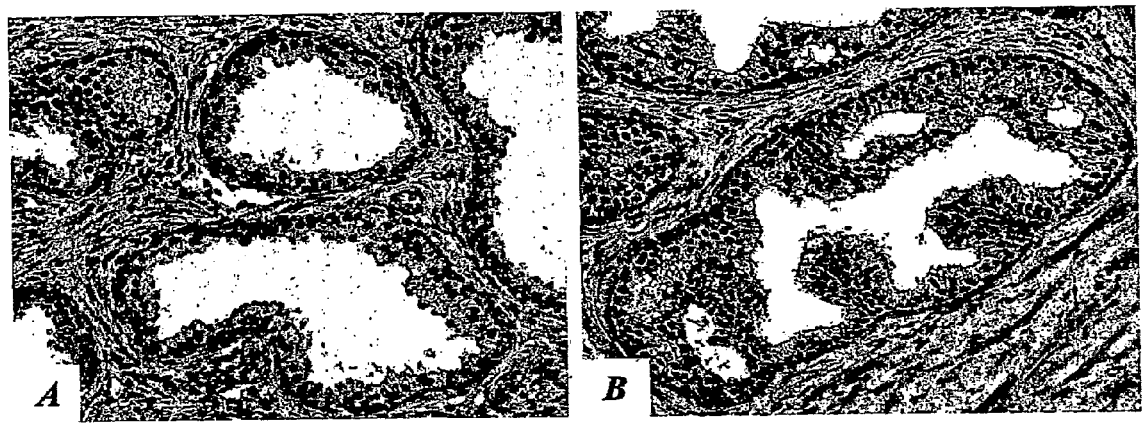
FIG. 1. IHC (immunohistochemistry) localization of IL-11Rα in benign prostate glands. (A) Normal glands from the peripheral zone showed predominant nuclear staining of the basal and luminal cell layers (×200). (B) A similar pattern of staining was observed in normal glands from the central zone (×200).

As used herein in the specification, "a" or "an" may mean one or more. As used herein in the claim(s), in conjunction with the word "comprising," the words "a" or "an" may mean one or more than one. As used herein "another" may mean at least a second or more of an item.

A "targeting peptide" is a peptide comprising a contiguous sequence of amino acids, which is characterized by selective localization to an organ, tissue or cell type. Selective localization may be determined, for example, by methods disclosed below, wherein the putative targeting peptide sequence is incorporated into a protein that is displayed on the outer surface of a phage. Administration to a subject of a library of such phage that have been genetically engineered to express a multitude of such targeting peptides of different amino acid sequence is followed by collection of one or more organs, tissues or cell types from the subject and identification of phage found in that organ, tissue or cell type. A phage expressing a targeting peptide sequence is considered to be selectively localized to a tissue or organ if it exhibits greater binding in that tissue or organ compared to a control tissue or organ. Preferably, selective localization of a targeting peptide should result in a two-fold or higher enrichment of the phage in the target organ, tissue or cell type, compared to a control organ, tissue or cell type. Selective localization resulting in at least a three-fold, four-fold, five-fold, six-fold, seven-fold, eight-fold, nine-fold, ten-fold or higher enrichment in the target organ compared to a control organ, tissue or cell type is more preferred. Alternatively, a phage expressing a targeting peptide sequence that exhibits selective localization preferably shows an increased enrichment in the target organ compared to a control organ when phage recovered from the target organ are reinjected into a second host for another round of screening. Further enrichment may be exhibited following a third round of screening. Another alternative means to determine selective localization is that phage expressing the putative target peptide preferably exhibit a two-fold, more preferably a three-fold or higher enrichment in the target organ compared to control phage that express a non-specific peptide or that have not been genetically engineered to express any putative target peptides. Another means to determine selective localization is that localization to the target organ of phage expressing the target peptide is at least partially blocked by the co-administration of a synthetic peptide containing the target peptide sequence. "Targeting peptide" and "homing peptide" are used synonymously herein.

A "phage display library" means a collection of phage that have been genetically engineered to express a set of putative targeting peptides on their outer surface. In preferred embodiments, DNA sequences encoding the putative targeting peptides are inserted in frame into a gene encoding a phage capsule protein. In other preferred embodiments, the putative targeting peptide sequences are in part random mixtures of all twenty amino acids and in part non-random. In certain preferred embodiments the putative targeting peptides of the phage display library exhibit one or more cysteine residues at fixed locations within the targeting peptide sequence. Cysteines may be used, for example, to create a cyclic peptide.

A "macromolecular complex" refers to a collection of molecules that may be random, ordered or partially ordered in their arrangement. The term encompasses biological organisms such as bacteriophage, viruses, bacteria, unicellular pathogenic organisms, multicellular pathogenic organisms and prokaryotic or eukaryotic cells. The term also encompasses non-living assemblages of molecules, such as liposomes, microcapsules, microparticles, magnetic beads and microdevices. The only requirement is that the complex contains more than one molecule. The molecules may be identical, or may differ from each other.

A "receptor" for a targeting peptide includes but is not limited to any molecule or macromolecular complex that binds to a targeting peptide. Non-limiting examples of receptors include peptides, proteins, glycoproteins, lipoproteins, epitopes, lipids, carbohydrates, multi-molecular structures, a specific conformation of one or more molecules and a morphoanatomic entity. In preferred embodiments, a "receptor" is a naturally occurring molecule or complex of molecules that is present on the lumenal surface of cells forming blood vessels within a target organ, tissue or cell type.

A "subject" refers generally to a mammal. In certain preferred embodiments, the subject is a mouse or rabbit. In even more preferred embodiments, the subject is a human.

Prostate Cancer Detection and Diagnosis

A particular problem in cancer detection and diagnosis occurs with prostate cancer. Carcinoma of the prostate (PCA) is the most frequently diagnosed cancer among men in the United States. Although relatively few prostate tumors progress to clinical significance during the lifetime of the patient, those which are progressive in nature are likely to have metastasized by the time of detection. Survival rates for individuals with metastatic prostate cancer are quite low. Between these extremes are patients with prostate tumors that will metastasize but have not yet done so, for whom surgical prostate removal is curative. Determination of which group a patient falls within is critical in determining optimal treatment and patient survival.

Serum prostate specific antigen (PSA) is widely used as a biomarker to detect and monitor therapeutic response in prostate cancer patients (Badalament et al., 1996; O'Dowd et al., 1997). Although PSA has been widely used since 1988 as a clinical marker of prostate cancer (Partin and Oesterling, 1994), screening programs utilizing PSA alone or in combination with digital rectal examination (DRE) have not been successful in improving the survival rate for men with prostate cancer (Partin and Oesterling, 1994). PSA is produced by normal and benign as well as malignant prostatic tissue, resulting in a high false-positive rate for prostate cancer detection (Partin and Oesterling, 1994). While an effective indicator of prostate cancer when serum levels are relatively high, PSA serum levels are more ambiguous indicators of prostate cancer when only modestly elevated. The specificity of the PSA assay for prostate cancer detection at low serum PSA levels remains a problem.

Other markers that have been used for prostate cancer detection include prostatic acid phosphatase (PAP) (Brawn et al., 1996), prostate secreted protein (PSP) (Huang et al., 1993), prostate specific membrane antigen (PSMA) Murphy et al., 1995), human kallekrein 2 (HK2) (Piironen et al., 1996), prostate specific transglutaminase (pTGase) and interleukin 8 (IL-8) (Veltri et al., 1999). None of these has yet been demonstrated to provide a more sensitive and discriminating test for prostate cancer than PSA.

In addition to these protein markers for prostate cancer, genetic changes reported to be associated with prostate cancer, include allelic loss (Bova, et al., 1993); DNA hypermethylation (Isaacs et al., 1994); point mutations or deletions of the retinoblastoma (Rb), p53 and KAI1 genes (Isaacs et al., 1991); aneuploidy and aneusomy of chromosomes detected by fluorescence in situ hybridization (FISH) (Macoska et al., 1994) and differential expression of HER2/neu oncogene receptor (An et al., 1998). None of these has been reported to exhibit sufficient sensitivity and specificity to be useful as general screening tools for asymptomatic prostate cancer.

In current clinical practice, the serum PSA assay and digital rectal exam (DRE) is used to indicate which patients should have a prostate biopsy (Orozco et al., 1998). Histological examination of the biopsied tissue is used to make the diagnosis of prostate cancer. It is estimated that over a half million prostate biopsies are performed annually in the United States (Orozco et al., 1998). A need exists for a serological test that is sensitive enough to detect small and early stage prostate tumors, that also has sufficient specificity to exclude a greater portion of patients with noncancerous conditions such as BPH.

There remain deficiencies in the prior art with respect to the identification of markers linked with the progression of prostate cancer and the development of diagnostic methods to monitor disease progression. The identification of novel, prostate selective or specific markers that are differentially expressed in metastatic and/or non-metastatic prostate cancer, compared to non-malignant prostate tissue, would represent a major, unexpected advance for the diagnosis, prognosis and treatment of prostate cancer. As discussed below, one approach to identifying novel prostate cancer markers involves the phage dislay technique. The skilled artisan will realize that although various embodiments of the invention are discussed in terms of prostate cancer, the disclosed methods and/or compositions may be of use to identify markers (targeting peptides) for other types of cancer within the scope of the invention.

Phage Display

Recently, an in vivo selection system was developed using phage display libraries to identify organ, tissue or cell type-targeting peptides in a mouse model system. Phage display libraries expressing transgenic peptides on the surface of bacteriophage were initially developed to map epitope binding sites of immunoglobulins (Smith, G P and Scott, J K, 1985. *Science*, 228:1315-1317, Smith, G P and Scott, J K, 1993. *Meth. Enzymol.* 21:228-257). Such libraries can be generated by inserting random oligonucleotides into cDNAs encoding a phage surface protein, generating collections of phage particles displaying unique peptides in as many as $10^9$ permutations. (Pasqualini, R. and Ruoslahti, E. 1996, *Nature*, 380: 364-366; Arap et al, 1998a; Arap et al., 1998b, Curr. Opin. Oncol. 10:560-565).

Intravenous administration of phage display libraries to mice was followed by the recovery of phage from individual organs (Pasqualini and Ruoslahti, 1996). Phage were recovered that were capable of selective homing to the vascular beds of different mouse organs, tissues or cell types, based on the specific targeting peptide sequences expressed on the outer surface of the phage (Pasqualini and Ruoslahti, 1996). A variety of organ and tumor-homing peptides have been identified by this method (Rajotte et al., 1998, *J. Clin. Invest.* 102:430-437; Rajotte et al, 1999, *J. Biol. Chem.* 274:11593-11598; Koivunen et al., 1999a, *Nature Biotechnol.* 17: 768-774; Burg M, et al., 1999a, *Cancer Res.* 58:2869-2874; Pasqualini, 1999, *Quart. J. Nucl. Med* 43:159-162). Each of those targeting peptides bound to different receptors that were selectively expressed on the vasculature of the mouse target tissue (Pasqualini, 1999; Pasqualini et al., 2000; Folkman J. *Nature Biotechnol.* 15:510, 1997; Folkman J. *Nature Med* 1:27-31, 1995). In addition to identifying individual targeting peptides selective for an organ, tissue or cell type (Pasqualini and Ruoslahti, 1996; Arap et al, 1998a; Koivunen et al., *Methods Mol. Biol.* 129: 3-17, 1999b), this system has been used to identify endothelial cell surface markers that are expressed in mice in vivo (Rajotte and Ruoslahti, 1999).

Attachment of therapeutic agents to targeting peptides resulted in the selective delivery of the agent to a desired organ, tissue or cell type in the mouse model system. Targeted delivery of chemotherapeutic agents and proapoptotic peptides to receptors located in tumor angiogenic vasculature resulted in an increase in therapeutic efficacy and a decrease in systemic toxicity in tumor bearing mouse models (Arap et al., 1998a, 1998b; Ellerby et al., *Nature Med* 9:1032-1038, 1999).

The methods described herein for identification of targeting peptides involve the in vivo administration of phage display libraries. Various methods of phage display and methods for producing diverse populations of peptides are well known in the art. For example, U.S. Pat. Nos. 5,223,409; 5,622,699 and 6,068,829 disclose methods for preparing a phage library. The phage display technique involves genetically manipulating bacteriophage so that small peptides can be expressed on their surface (Smith and Scott, 1985, 1993). The past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that serve as leads to the development of peptidomimetic drugs or imaging agents (Arap et al., 1998a). In addition to peptides, larger protein domains such as single-chain antibodies can also be displayed on the surface of phage particles (Arap et al., 1998a).

Targeting peptides selective for a given organ, tissue or cell type can be isolated by "biopanning" (Pasqualini and Ruoslahti, 1996; Pasqualini, 1999). In brief, a library of phage containing putative targeting peptides is administered to an animal or human and samples of organs, tissues or cell types containing phage are collected. In preferred embodiments utilizing filamentous phage, the phage may be propagated in vitro between rounds of biopanning in pilus-positive bacteria. The bacteria are not lysed by the phage but rather secrete multiple copies of phage that display a particular insert. Phage that bind to a target molecule can be eluted from the target organ, tissue or cell type and then amplified by growing them in host bacteria. If desired, the amplified phage can be administered to a host and samples of organs, tissues or cell types again collected. Multiple rounds of biopanning can be performed until a population of selective binders is obtained. The amino acid sequence of the peptides is determined by sequencing the DNA corresponding to the targeting peptide insert in the phage genome. The identified targeting peptide can then be produced as a synthetic peptide by standard protein chemistry techniques (Arap et al., 1998a, Smith and Scott, 1985). This approach allows circulating targeting peptides to be detected in an unbiased functional assay, without any preconceived notions about the nature of their target. Once a candidate target is identified as the receptor of a targeting peptide, it can be isolated, purified and cloned by using standard biochemical methods (Pasqualini, 1999; Rajotte and Ruoslahti, 1999).

In certain embodiments, a subtraction protocol may be used with biopanning to further reduce background phage binding. The purpose of subtraction is to remove phage from the library that bind to cells other than the cell of interest, or that bind to inactivated cells. In alternative embodiments, the phage library may be prescreened against a subject who does not possess the targeted cell, tissue or organ. For example, prostate and/or prostate cancer binding peptides may be identified after prescreening a library against female subjects. After subtraction, the library may be screened against the cell, tissue or organ of interest. In another alternative embodiment, an unstimulated, quiescent cell type, tissue or organ may be screened against the library and binding phage removed. The cell line, tissue or organ is then activated, for example by administration of a hormone, growth factor, cytokine or chemokine and the activated cell type, tissue or organ screened against the subtracted phage library. Other methods of subtraction protocols are known and may be used in the practice of the present invention, for example as disclosed in U.S. Pat. Nos. 5,840,841, 5,705,610, 5,670,312 and 5,492,807.

Choice of Phage Display System.

Previous in vivo selection studies performed in mice preferentially employed libraries of random peptides expressed as fusion proteins with the gene III capsule protein in the fUSE5 vector (Pasqualini and Ruoslahti, 1996). The number and diversity of individual clones present in a given library is a significant factor for the success of in vivo selection. It is preferred to use primary libraries, which are less likely to have an over-representation of defective phage clones (Koivunen et al., 1999b). The preparation of a library should be optimized to between $10^8$-$10^9$ transducing units (T.U.)/ml. In certain embodiments, a bulk amplification strategy is applied between each round of selection.

Phage libraries displaying linear, cyclic, or double cyclic peptides may be used within the scope of the present invention. However, phage libraries displaying 3 to 10 random residues in a cyclic insert ($CX_{3-10}C$) are preferred, since single cyclic peptides tend to have a higher affinity for the target organ than linear peptides. Libraries displaying double-cyclic peptides (such as $CX_3CX_3CX_3C$; Rojotte et al., 1998) have been successfully used. However, the production of the cognate synthetic peptides, although possible, can be complex due to the multiple conformers with different disulfide bridge arrangements.

Identification of Homing Peptides and Receptors by in vivo Phage Display in Mice.

In vivo selection of peptides from phage-display peptide libraries administered to mice has been used to identify targeting peptides selective for normal mouse brain, kidney, lung, skin, pancreas, retina, intestine, uterus, prostate, and adrenal gland (Pasqualini and Ruoslahti, 1996; Pasqualini, 1999; Rajotte et al., 1998). These results show that the vascular endothelium of normal organs is sufficiently heterogeneous to allow differential targeting with peptide probes (Pasqualini and Ruoslahti, 1996; Rajotte et al., 1998). A panel of peptide motifs that target the blood vessels of tumor xenografts in nude mice has been assembled (Arap et al., 1998a; reviewed in Pasqualini, 1999). These motifs include the sequences RGD-4C, NGR, and GSL. The RGD-4C peptide has previously been identified as selectively binding αv integrins and has been reported to home to the vasculature of tumor xenografts in nude mice (Arap et al., 1998a, 1998b; Pasqualini et al., *Nature Biotechnol* 15: 542-546, 1997).

The receptors for the tumor homing RGD-4C targeting peptide has been identified as αv integrins (Pasqualini et al., 1997). The αv integrins play an important role in angiogenesis. The αvβ3 and αvβ5 integrins are absent or expressed at low levels in normal endothelial cells and are induced in angiogenic vasculature of tumors (Brooks P C, Clark R A, Cheresh D A. *Science,* 264: 569-571, 1994a; Hammes H P, Brownlee M, Jonczyk A, Sutter A, and Preissner K T. *Nature Med.* 2: 529-533, 1996.). Aminopeptidase N/CD13 has recently been identified as an angiogenic receptor for the NGR motif (Burg, M. A., et al. *Cancer Res.* 59, 2869-2874, 1999.). Aminopeptidase N/CD13 is strongly expressed not only in the angiogenic blood vessels of prostate cancer in TRAMP mice but also in the normal epithelial prostate tissue.

Tumor-homing phage co-localize with their receptors in the angiogenic vasculature of tumors but not in non-angiogenic blood vessels in normal tissues (Arap et al., 1998b). Immunohistochemical evidence shows that vascular targeting phage bind to human tumor blood vessels in tissue sections (Pasqualini et al., 2000) but not to normal blood vessels. A negative control phage with no insert (fd phage) did not bind to normal or tumor tissue sections. The expression of the angiogenic receptors was evaluated in cell lines, in non-proliferating blood vessels and in activated blood vessels of tumors and other angiogenic tissues such as corpus luteum. Flow cytometry and immunohistochemistry showed that these receptors are expressed in a number of tumor cells and in activated HUVECs (data not shown). The angiogenic receptors were not detected in the vasculature of normal organs of mouse or human tissues.

The distribution of these receptors was analyzed by immunohistochemistry in tumor cells, tumor vasculature, and normal vasculature. Alpha v integrins, CD13, aminopeptidase A, NG2, and MMP-2/MMP-9—the known receptors in tumor blood vessels—are specifically expressed in angiogenic endothelial cells and pericytes of both human and murine origin. Angiogenic neovasculature expresses markers that are either expressed at very low levels or not at all in non-proliferating endothelial cells (not shown).

The markers of angiogenic endothelium include receptors for vascular growth factors, such as specific subtypes of VEGF and basic FGF receptors, and αv integrins, among many others (Mustonen T and Alitalo K. *J. Cell Biol.* 129: 895-898, 1995.). Thus far, identification and isolation of novel molecules characteristic of angiogenic vasculature has been slow, mainly because endothelial cells undergo dramatic phenotypic changes when grown in culture (Watson et al., *Science,* 268:447-448, 1995).

Many of these tumor vascular markers are proteases and some of the markers also serve as viral receptors. Alpha v integrins are receptors for adenoviruses (Wickham et al., *Cancer Immunol. Immunother.* 45:149-151, 1997c) and CD13 is a receptor for coronaviruses (Look et al. N. *J. Clin. Invest.* 83:1299-1307, 1989.). MMP-2 and MMP-9 are receptors for echoviruses (Koivunen et al., 1999a). Aminopeptidase A also appears to be a viral receptor. Bacteriophage may use the same cellular receptors as eukaryotic viruses. These findings suggest that receptors isolated by in vivo phage display will have cell internalization capability, a key feature for utilizing the identified peptide motifs as targeted gene therapy carriers.

Targeted Delivery

Peptides that home to tumor vasculature have been coupled to cytotoxic drugs or proapoptotic peptides to yield compounds that were more effective and less toxic than the parental compounds in experimental models of mice bearing tumor xenografts (Arap et al., 1998a; Ellerby et al, 1999). The insertion of the RGD-4C peptide into a surface protein of an adenovirus has produced an adenoviral vector that may be of use for tumor targeted gene therapy (Arap et al., 1998b). A need exists for improved gene therapy vectors capable of targeted delivery in human subjects, particularly for improved vectors that exhibit prolonged expression of therapeutic genes in the transfected cells.

BRASIL

In preferred embodiments, separation of phage bound to the cells of a target organ, tissue or cell type from unbound phage is achieved using the BRASIL technique (PCT Patent Application PCT/US01/28124 entitled, "Biopanning and Rapid Analysis of Selective Interactive Ligands (BRASIL)" by Arap et al., filed Sep. 7, 2001, incorporated herein by reference in its entirety). In BRASIL (Biopanning and Rapid Analysis of Soluble Interactive ligands), an organ, tissue or cell type is gently separated into cells or small clumps of cells that are suspended in an aqueous phase. The aqueous phase is layered over an organic phase of appropriate density and centrifuged. Cells attached to bound phage are pelleted at the bottom of the centrifuge tube, while unbound phage remain in the aqueous phase. This allows a more efficient separation of bound from unbound phage, while maintaining the binding interaction between phage and cell. BRASIL may be performed in an in vivo protocol, in which organs, tissues or cell types are exposed to a phage display library by intravenous administration, or by an ex vivo protocol, where the cells are exposed to the phage library in the aqueous phase before centrifugation. A non-limiting exemplary application of the BRASIL technique is disclosed in the Examples below.

Preparation of Large Scale Primary Libraries

In certain embodiments, primary phage libraries are amplified before injection into a human subject. A phage library is prepared by ligating targeting peptide-encoding sequences into a phage vector, such as fUSE5. The vector is transformed into pilus negative host *E. coli* such as strain MC1061. The bacteria are grown overnight and then aliquots are frozen to provide stock for library production. Use of pilus negative bacteria avoids the bias in libraries that arises from differential infection of pilus positive bacteria by different targeting peptide sequences.

To freeze, bacteria are pelleted from two thirds of a primary library culture (5 liters) at 4000×g for 10 min. Bacteria are resuspended and washed twice with 500 ml of 10% glycerol in water, then frozen in an ethanol/dry ice bath and stored at −80° C.

For amplification, 1.5 ml of frozen bacteria are inoculated into 5 liters of LB medium with 20 µg/ml tetracycline and grown overnight. Thirty minutes after inoculation, a serial dilution is plated on LB/tet plates to verify the viability of the culture. If the number of viable bacteria is less than 5-10 times the number of individual clones in the library ($1-2\times10^8$) the culture is discarded.

After growing the bacterial culture overnight, phage are precipitated. About ¼ to ⅓ of the bacterial culture is kept growing overnight in 5 liters of fresh medium and the cycle is repeated up to 5 times. Phage are pooled from all cycles and used for injection into human subjects.

Human Subjects

The methods used for phage display biopanning in the mouse model system require substantial improvements for use with humans. Techniques for biopanning in human subjects are disclosed in PCT Patent Application PCT/US01/28044, filed Sep. 7, 2001, the entire text of which is incorporated herein by reference. In general, humans suitable for use with phage display are either brain dead or terminal wean patients. The amount of phage library (preferably primary library) required for administration must be significantly increased, preferably to $10^{14}$ TU or higher, preferably administered intravenously in approximately 200 ml of Ringer lactate solution over about a 10 minute period.

The amount of phage required for use in humans has required substantial improvement of the mouse protocol, increasing the amount of phage available for injection by five orders of magnitude. To produce such large phage libraries, the transformed bacterial pellets recovered from up to 500 to 1000 transformations are amplified up to 10 times in the bacterial host, recovering the phage from each round of amplification and adding LB Tet medium to the bacterial pellet for collection of additional phage. The phage inserts remain stable under these conditions and phage may be pooled to form the large phage display library required for humans.

Samples of various organs and tissues are collected starting approximately 15 minutes after injection of the phage library. Samples are processed as described below and phage collected from each organ, tissue or cell type of interest for DNA sequencing to determine the amino acid sequences of targeting peptides.

With humans, the opportunities for enrichment by multiple rounds of biopanning are severely restricted, compared to the mouse model system. A substantial improvement in the biopanning technique involves polyorgan targeting.

Polyorgan Targeting

In the standard protocol for phage display biopanning, phage from a single organ are collected, amplified and injected into a new host, where tissue from the same organ is collected for phage rescue and a new round of biopanning. This protocol is feasible in animal subjects. However, the limited availability and expense of processing samples from humans requires an improvement in the protocol.

It is possible to pool phage collected from multiple organs after a first round of biopanning and inject the pooled sample into a new subject, where each of the multiple organs may be collected again for phage rescue. The polyorgan targeting protocol may be repeated for as many rounds of biopanning as desired. In this manner, it is possible to significantly reduce the number of subjects required for isolation of targeting peptides for multiple organs, while still achieving substantial enrichment of the organ-homing phage.

In preferred embodiments, phage are recovered from human organs, tissues or cell types after injection of a phage display library into a human subject. In certain embodiments, phage may be recovered by exposing a sample of the organ, tissue or cell type to a pilus positive bacterium, such as *E. coli* K91. In alternative embodiments, phage may be recovered by amplifying the phage inserts, ligating the inserts to phage DNA and producing new phage from the ligated DNA.

Proteins and Peptides

In certain embodiments, the present invention concerns novel compositions comprising at least one protein or peptide. As used herein, a protein or peptide generally refers, but is not limited to, a protein of greater than about 200 amino acids up to a full length sequence translated from a gene; a polypeptide of about 100 to 200 amino acids; and/or a peptide of from about 3 to about 100 amino acids. For convenience, the terms "protein," "polypeptide" and "peptide are used interchangeably herein.

In certain embodiments the size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| bAad | 3-Aminoadipic acid | Hyl | Hydroxylysine |
| bAla | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| bAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for known genes may be amplified and/or expressed using the techniques disclosed herein or as would be know to those of ordinary skill in the art. Alternatively, various commercial preparations of proteins, polypeptides and peptides are known to those of skill in the art.

Peptide Mimetics

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993), incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and even improved characteristics.

Fusion Proteins

Other embodiments of the present invention concern fusion proteins. These molecules generally have all or a substantial portion of a targeting peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In preferred embodiments, the fusion proteins of the instant invention comprise a targeting peptide linked to a therapeutic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually and protein or peptide could be incorporated into a fusion protein comprising a targeting peptide. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

Protein Purification

In certain embodiments a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography, reverse phase chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Synthetic Peptides

Because of their relatively small size, the targeting peptides of the invention can be synthesized in solution or on a solid support in accordance with conventional techniques. Various automatic synthesizers are commercially available and can be used in accordance with known protocols. See, for example, Stewart and Young, Solid Phase Peptide Synthesis, 2d ed. Pierce Chemical Co., 1984; Tam et al., J. Am. Chem. Soc., 105:6442, 1983; Merrifield, *Science,* 232: 341-347, 1986; and Barany and Merrifield, *The Peptides*, Gross and Meienhofer, eds., Academic Press, New York, pp. 1-284, 1979, each incorporated herein by reference. Short peptide sequences, usually from about 6 up to about 35 to 50 amino acids, can be readily synthesized by such methods. Alternatively, recombinant DNA technology may be employed wherein a nucleotide sequence which encodes a peptide of the invention is inserted into an expression vector, transformed or transfected into an appropriate host cell, and cultivated under conditions suitable for expression.

Antibodies

In certain embodiments, it may be desirable to make antibodies against the identified targeting peptides or their receptors. The appropriate targeting peptide or receptor, or portions thereof, may be coupled, bonded, bound, conjugated, or chemically-linked to one or more agents via linkers, polylinkers, or derivatized amino acids. This may be performed such that a bispecific or multivalent composition or vaccine is produced. It is further envisioned that the methods used in the preparation of these compositions are familiar to those of skill in the art and should be suitable for administration to humans, i.e., pharmaceutically acceptable. Preferred agents are the carriers are keyhole limpet hemocyanin (KLH) or bovine serum albumin (BSA).

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlow and Lane, *Antibodies: A Laboratory Manual*, Cold Spring Harbor Laboratory, 1988; incorporated herein by reference).

In various embodiments of the invention, circulating antibodies from one or more individuals with a disease state may be obtained and screened against phage display libraries. Targeting peptides that bind to the circulating antibodies may act as mimeotopes of a native antigen, such as a receptor protein located on an endothelial cell surface of a target tissue. For example, circulating antibodies in an individual with prostate cancer may bind to antigens specifically or selectively localized in prostate tumors. As discussed in more detail below, targeting peptides against such antibodies may be identified by phage display. Such targeting peptides may be used to identify the native antigen recognized by the antibodies, for example by using known techniques such as immunoaffinity purification, Western blotting, electrophoresis followed by band excision and protein/peptide sequencing and/or computerized homology searches. The skilled artisan will realize that antibodies against disease specific or selective antigens may be of use for various applications, such as detection, diagnosis and/or prognosis of a disease state, imaging of diseased tissues and/or targeted delivery of therapeutic agents.

Imaging Agents and Radioisotopes

In certain embodiments, the claimed peptides or proteins of the present invention may be attached to imaging agents of use for imaging and diagnosis of various diseased organs, tissues or cell types. For example, a prostate cancer selective targeting peptide may be attached to an imaging agent, provided to a subject and the precise boundaries of the cancer tissue may be determined by standard imaging techniques, such as CT scanning, MRI, PET scanning, etc. Alternatively, the presence or absence and location in the body of metastatic prostate cancer may be determined by imaging using one or more targeting peptides that are selective for metastatic prostate cancer. Targeting peptides that bind to normal as well as cancerous prostate tissues may still be of use, as such peptides would not be expected to be selectively localized anywhere besides the prostate in disease-free individuals. Naturally, the distribution of a prostate or prostate cancer selective targeting peptide may be compared to the distribution of one or more non-selective peptides to provide even greater discrimination for detection and/or localization of diseased tissues.

Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides of the present invention may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides according to the invention may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups that are often used to bind radioisotopes that exist as metallic ions to peptides are diethylenetriaminepenta-acetic acid (DTPA) and ethylene diaminetetra-acetic acid (EDTA). Also contemplated for use are fluorescent labels, including rhodamine, fluorescein isothiocyanate and renographin.

In certain embodiments, the claimed proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Cross-linkers

The targeting peptides, ligands, receptor proteins and other molecules of interest may be attached to surfaces or to therapeutic agents and other molecules using a variety of known cross-linking agents. Methods for covalent or non-covalen attachment of proteins or peptides are well known in the art. Such methods may include, but are not limited to, use of chemical cross-linkers, photoactivated cross-linkers and/or bifunctional cross-linking reagents. Exemplary methods for cross-linking molecules are disclosed in U.S. Pat. No. 5,603,872 and U.S. Pat. No. 5,401,511, incorporated herein by reference. Non-limiting examples of cross-linking reagents of potential use include glutaraldehyde, bifunctional oxirane, ethylene glycol diglycidyl ether, carbodiimides such as 1-ethyl-3-(3-dimethylaminopropyl) carbodiimide or dicyclohexylcarbodiimide, bisimidates, dinitrobenzene, N-hydroxysuccinimide ester of suberic acid, disuccinimidyl tartarate, dimethyl-3,3'-dithio-bispropionimidate, azidoglyoxal, N-succinimidyl-3-(2-pyridyldithio)propionate and 4-(bromoadminoethyl)-2-nitrophenylazide.

Homobifunctional reagents that carry two identical functional groups are highly efficient in inducing cross-linking. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied.

In certain embodiments, it may be appropriate to link one or more targeting peptides to a liposome or other membrane-bounded particle. For example, targeting peptides cross-linked to liposomes, microspheres or other such devices may be used to deliver larger volumes of a therapeutic agent to a target organ, tissue or cell type. Various ligands can be covalently bound to liposomal surfaces through the cross-liking of amine residues. Liposomes containing phosphatidylethanolamine (PE) may be prepared by established procedures. The inclusion of PE provides an active functional amine residue on the liposomal surface.

In another non-limiting example, heterobifunctional cross-linking reagents and methods of use are disclosed in U.S. Pat. No. 5,889,155, incorporated herein by reference. The cross-linking reagents combine a nucleophilic hydrazide residue with an electrophilic maleimide residue, allowing coupling in one example, of aldehydes to free thiols. The cross-linking reagent can be modified to cross-link various functional groups.

Other techniques of general use for proteins or peptides that are known in the art have not been specifically disclosed herein, but may be used in the practice of the claimed subject matter.

Nucleic Acids

In certain embodiments, nucleic acids may encode a targeting peptide, a receptor protein, a fusion protein or other protein or peptide. The nucleic acid may be derived from genomic DNA, complementary DNA (cDNA) or synthetic DNA. Where incorporation into an expression vector is desired, the nucleic acid may also comprise a natural intron or an intron derived from another gene. Such engineered molecules are sometime referred to as "mini-genes." In various embodiments of the invention, targeting peptides may be incorporated into gene therapy vectors via nucleic acids.

A "nucleic acid" as used herein includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded protein or peptide.

It is contemplated that targeting peptides, fusion proteins and receptors may be encoded by any nucleic acid sequence that encodes the appropriate amino acid sequence. The design and production of nucleic acids encoding a desired amino acid sequence is well known to those of skill in the art, using standardized codon tables (see Table 2 below). In preferred embodiments, the codons selected for encoding each amino acid may be modified to optimize expression of the nucleic acid in the host cell of interest. Codon preferences for various species of host cell are well known in the art.

TABLE 2

| Amino Acid | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In addition to nucleic acids encoding the desired peptide or protein, the present invention encompasses complementary nucleic acids that hybridize under high stringency conditions with such coding nucleic acid sequences. High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture.

Nucleic acids for use in the disclosed methods and compositions may be produced by any method known in the art, such as chemical synthesis (e.g. Applied Biosystems Model 3900, Foster City, Calif.), purchase from commercial sources (e.g. Midland Certified Reagents, Midland, Tex.) and/or standard gene cloning methods. A number of nucleic acid vectors, such as expression vectors and/or gene therapy vectors, may be commercially obtained (e.g., American Type Culture Collection, Rockville, Md.; Promega Corp., Madison, Wis.; Stratagene, La Jolla, Calif.).

Vectors for Cloning, Gene Transfer and Expression

In certain embodiments expression vectors are employed to express the targeting peptide or fusion protein, which can then be purified and used. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are known.

Regulatory Elements

The terms "expression construct" or "expression vector" are meant to include any type of genetic construct containing a nucleic acid coding for a gene product in which part or all of the nucleic acid coding sequence is capable of being transcribed. In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent and under the control of a promoter that transcriptionally active in human cells. Generally speaking, such a promoter might include either a human or viral promoter.

In various embodiments, the human cytomegalovirus (CMV) immediate early gene promoter, the SV40 early promoter, the Rouse sarcoma virus long terminal repeat, rat insulin promoter, and glyceraldehyde-3-phosphate dehydrogenase promoter can be used to obtain high-level expression of the coding sequence of interest. The use of other viral or mammalian cellular or bacterial phage promoters that are known in the art to achieve expression of a coding sequence of interest is contemplated as well, provided that the levels of expression are sufficient for a given purpose.

Where a cDNA insert is employed, one will typically include a polyadenylation signal to effect proper polyadenylation of the gene transcript. The nature of the polyadenylation signal is not believed to be crucial to the successful practice of the invention, and any such sequence may be employed, such as human growth hormone and SV40 polyadenylation signals. Also contemplated as an element of the expression construct is a terminator. These elements can serve to enhance message levels and to minimize read through from the construct into other sequences.

Selectable Markers

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a dug selection marker aids in cloning and in the selection of transformants. For example, genes that confer resistance to neomycin, puromycin, hygromycin, DHFR, GPT, zeocin, and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Ridgeway, 1988; Nicolas and Rubinstein, In: *Vectors: A survey of molecular cloning vectors and their uses*, Rodriguez and Denhardt, eds., Stoneham: Butterworth, pp. 494-513, 1988; Baichwal and Sugden, Baichwal, In: *Gene Transfer*, Kucherlapati R, ed., New York, Plenum Press, pp. 117-148, 1986. 1986; Temin, In: Gene Transfer, Kucherlapati, R. ed., New York, Plenum Press, pp. 149-188, 1986). Preferred gene therapy vectors are generally viral vectors.

In using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

DNA viruses used as gene vectors include the papovaviruses (e.g., simian virus 40, bovine papilloma virus, and polyoma) (Ridgeway, pp 467-492, 1988; Baichwal and Sugden, 1986) and adenoviruses (Ridgeway, 1988; Baichwal and Sugden, 1986).

An exemplary method for in vivo delivery involves the use of an adenovirus expression vector. Although adenovirus vectors have a low capacity for integration into genomic DNA, this feature is counterbalanced by the high efficiency of gene transfer afforded by these vectors. "Adenovirus expression vector" is meant to include, but is not limited to, constructs containing adenovirus sequences sufficient to (a) support packaging of the construct and (b) to express an antisense or a sense polynucleotide that has been cloned therein.

Generation and propagation of adenovirus vectors that are replication deficient depend on a helper cell line, such as the 293 cell line, which was transformed from human embryonic kidney cells by Ad5 DNA fragments and constitutively expresses E1 proteins (Graham et al., *J. Gen. Virol.*, 36:59-72, 1977). Since the E3 region is dispensable from the adenovirus genome (Jones and Shenk, *Cell*, 13:181-188, 1978), adenovirus vectors, with the help of 293 cells, carry foreign DNA in either the E1, the E3, or both regions (Graham and Prevec, In: *Methods in Molecular Biology: Gene Transfer and Expression Protocol*, E. J. Murray, ed., Humana Press, Clifton, N.J., 7:109-128, 1991).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. Racher et al., (*Biotechnol. Tech.* 9:169-174, 1995) disclosed methods for culturing 293 cells and propagating adenovirus.

Adenovirus vectors have been used in eukaryotic gene expression (Levrero et al., *Gene*, 101:195-202, 1991; Gomez-Foix et al., *J. Biol. Chem.*, 267:25129-25134, 1992) and vaccine development (Grunhaus and Horwitz, 1992; Graham and Prevec, 1991). Animal studies have suggested that recombinant adenovirus could be used for gene therapy (Stratford-Perricaudet and Perricaudet, In: *Human Gene Transfer*, O. Cohen-Haguenauer et al, eds. John Libbey Eurotext, France, pp. 51-61, 1991; Stratford-Perricaudet et al., *Hum. Gene Ther.* 1:241-256, 1990; Rich et al., *Hum. Gene. Ther.* 4:461-476, 1993). Studies in administering recombinant adenovirus to different tissues include trachea instillation (Rosenfeld et al., *Science,* 252: 431-434, 1991; Rosenfeld et al., *Cell*, 68: 143-155, 1992), muscle injection (Ragot et al., *Nature,* 361: 647-650, 1993), peripheral intravenous injections (Herz and Gerard, *Proc. Natl. Acad. Sci. USA,* 90:2812-2816, 1993) and stereotactic innoculation into the brain (Le Gal La Salle et al., *Science,* 259:988-990, 1993).

In preferred embodiments, gene therapy vectors are based upon adeno-associated virus (AAV), discussed in more detail in the Examples below.

Other gene transfer vectors may be constructed from retroviruses. (Coffin, In: *Virology*, Fields et al., eds., Raven Press, New York, pp. 1437-1500, 1990.) The retroviral genome contains three genes, gag, pol, and env. that code for capsid proteins, polymerase enzyme, and envelope components, respectively. A sequence found upstream from the gag gene contains a signal for packaging of the genome into virions. Two long terminal repeat (LTR) sequences are present at the 5′ and 3′ ends of the viral genome. These contain strong promoter and enhancer sequences, and also are required for integration in the host cell genome (Coffin, 1990).

In order to construct a retroviral vector, a nucleic acid encoding protein of interest is inserted into the viral genome in the place of certain viral sequences to produce a virus that is replication-defective. In order to produce virions, a packaging cell line containing the gag, pol, and env genes, but without the LTR and packaging components, is constructed (Mann et al., *Cell,* 33:153-159, 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., *Virology,* 67:242-248, 1975).

Other viral vectors may be employed as expression constructs. Vectors derived from viruses such as vaccinia virus (Ridgeway, 1988; Baichwal and Sugden, 1986; Coupar et al., *Gene* 68:1-10, 1988), adeno-associated virus (AAV) (Ridgeway, 1988; Baichwal and Sugden, 1986; Hermonat and Muzycska, *Proc. Natl. Acad. Sci. USA,* 81: 6466-6470, 1984), and herpes viruses may be employed. They offer several attractive features for various mammalian cells (Friedmann, *Science,* 244:1275-1281, 1989; Ridgeway, 1988; Baichwal and Sugden, 1986; Coupar et al., 1988; Horwich et al., *J. Virol.,* 64:642-650, 1990).

Several non-viral methods for the transfer of expression constructs into cultured mammalian cells also are contemplated by the present invention. These include calcium phosphate precipitation (Graham and van der Eb, *Virology,* 52:456-467, 1973; Chen and Okayama, *Mol. Cell Biol.,* 7:2745-2752, 1987; Rippe et al., *Mol. Cell Biol.* 10: 689-695, 1990; DEAE dextran (Gopal, et al. *Mol. Cell. Biol.,* 5:1188-1190, 1985), electroporation (Tur-Kaspa et al., *Mol. Cell Biol.,* 6:716-718, 1986; Potter et al., *Proc. Natl. Acad. Sci. USA,* 81: 7161-7165, 1984), direct microinjection, DNA-loaded liposomes and lipofectamine-DNA complexes, cell sonication, gene bombardment using high velocity microprojectiles, and receptor-mediated transfection (Wu and Wu, *J. Biol. Chem.* 262:4429-4432, 1987; Wu and Wu, *Biochemistry,* 27:887-892, 1988). Some of these techniques may be successfully adapted for in vivo or ex vivo use.

In a further embodiment of the invention, the expression construct may be entrapped in a liposome. Liposome-mediated nucleic acid delivery and expression of foreign DNA in vitro has been very successful. Wong et al., (*Gene,* 10:87-94, 1980) demonstrated the feasibility of liposome-mediated delivery and expression of foreign DNA in cultured chick embryo, HeLa, and hepatoma cells. Nicolau et al., (*Methods Enzymol.,* 149:157-176, 1987) accomplished successful liposome-mediated gene transfer in rats after intravenous injection.

Pharmaceutical Compositions

Where clinical applications are contemplated, it may be necessary to prepare pharmaceutical compositions—expression vectors, virus stocks, proteins, antibodies and drugs—in a form appropriate for the intended application. Generally, this will entail preparing compositions that are essentially free of impurities that could be harmful to humans or animals.

One generally will desire to employ appropriate salts and buffers to render delivery vectors stable and allow for uptake by target cells. Aqueous compositions of the present invention may comprise an effective amount of a protein, peptide, fusion protein, recombinant phage and/or expression vector, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the proteins or peptides of the present invention, its use in therapeutic compositions is contemplated. Supplementary active ingredients also can be incorporated into the compositions.

The active compositions of the present invention may include classic pharmaceutical preparations. Administration of these compositions according to the present invention are via any common route so long as the target tissue is available via that route. This includes oral, nasal, buccal, rectal, vaginal or topical. Alternatively, administration may be by orthotopic, intradermal, subcutaneous, intramuscular, intraperitoneal, intraarterial or intravenous injection. Such compositions normally would be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Therapeutic Agents

In certain embodiments, therapeutic agents may be attached to a targeting peptide or fusion protein for selective delivery to, for example, non-metastatic and/or metastatic prostate cancer. Agents or factors suitable for use may include any chemical compound that induces apoptosis, cell death, cell stasis and/or anti-angiogenesis or otherwise affects the survival and/or growth rate of a cancer cell.

Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-Like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Tsujimoto et al., 1985). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

Non-limiting examples of pro-apoptosis agents contemplated within the scope of the present invention include gramicidin, magainin, mellitin, defensin, cecropin, (KLAK- LAK)$_2$ (SEQ ID NO:1), KLAKKLA)$_2$ (SEQ ID NO:2), (KAAKKAA)$_2$ (SEQ ID NO:3) or (KLGKKLG)$_3$ (SEQ ID NO:4).

Angiogenic Inhibitors

In certain embodiments the present invention may concern administration of targeting peptides attached to anti-angiogenic agents, such as angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

Proliferation of tumors cells relies heavily on extensive tumor vascularization, which accompanies cancer progression. Thus, inhibition of new blood vessel formation with anti-angiogenic agents and targeted destruction of existing blood vessels have been introduced as an effective and relatively non-toxic approach to tumor treatment. (Arap et al., *Science* 279:377-380, 1998a; Arap et al., *Curr. Opin. Oncol.* 10:560-565, 1998b; Ellerby et al., *Nature Med.* 5:1032-1038, 1999). A variety of anti-angiogenic agents and/or blood vessel inhibitors are known. (E.g., Folkman, In: *Cancer: Principles and Practice*, eds. DeVita et al., pp. 3075-3085, Lippincott-Raven, New York, 1997; Eliceiri and Cheresh, *Curr. Opin. Cell. Biol.* 13, 563-568, 2001).

Cytotoxic Agents

A wide variety of anticancer agents are well known in the art and any such agent may be coupled to a cancer targeting peptide for use within the scope of the present invention. Exemplary cancer chemotherapeutic (cytotoxic) agents of potential use include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of (DTIC), transplatinum, vinblastine and methotrexate, vincristine, or any analog or derivative variant of the foregoing. Most chemotherapeutic agents fall into the categories of alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics" and "Remington: The Science and Practice of Pharmacy," 20th edition, Gennaro, Lippincott, 2000, each incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Of course, all of these dosages and agents described herein are exemplary rather than limiting, and other doses or agents may be used by a skilled artisan for a specific patient or application. Any dosage in-between these points, or range derivable therein is also expected to be of use in the invention.

Alkylating Agents

Alkylating agents are drugs that directly interact with genomic DNA to prevent cells from proliferating. This category of chemotherapeutic drugs represents agents that affect all phases of the cell cycle, that is, they are not phase-specific. An alkylating agent, may include, but is not limited to, nitrogen mustard, ethylenimene, methylmelamine, alkyl sulfonate, nitrosourea or triazines. They include but are not limited to: busulfan, chlorambucil, cisplatin, cyclophosphamide (cytoxan), dacarbazine, ifosfamide, mechlorethamine (mustargen), and melphalan.

Antimetabolites

Antimetabolites disrupt DNA and RNA synthesis. Unlike alkylating agents, they specifically influence the cell cycle during S phase. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

Natural Products

Natural products generally refer to compounds originally isolated from a natural source, and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

Mitotic inhibitors include plant alkaloids and other natural agents that can inhibit either protein synthesis required for cell division or mitosis. They operate during a specific phase during the cell cycle. Mitotic inhibitors include, for example, docetaxel, etoposide (VP16), teniposide, paclitaxel, taxol, vinblastine, vincristine, and vinorelbine.

Taxoids are a class of related compounds isolated from the bark of the ash tree, *Taxus brevifolia*. Taxoids include but are not limited to compounds such as docetaxel and paclitaxel. Paclitaxel binds to tubulin (at a site distinct from that used by the vinca alkaloids) and promotes the assembly of microtubules.

Antibiotics

Certain antibiotics have both antimicrobial and cytotoxic activity. These drugs also interfere with DNA by chemically inhibiting enzymes and mitosis or altering cellular membranes. These agents are not phase specific so they work in all phases of the cell cycle. Examples of cytotoxic antibiotics include, but are not limited to, bleomycin, dactinomycin, daunorubicin, doxorubicin (Adriamycin); plicamycin (mithramycin) and idarubicin.

Miscellaneous Agents

Miscellaneous cytotoxic agents that do not fall into the previous categories include, but are not limited to, platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are not limiting and it is contemplated that any known cytotoxic, cytostatic or cytocidal agent may be attached to targeting peptides and administered to a targeted organ, tissue or cell type within the scope of the invention.

Cytokines and Chemokines

In certain embodiments, it may be desirable to couple specific bioactive agents to one or more targeting peptides for targeted delivery to an organ, tissue or cell type. Such agents include, but are not limited to, cytokines and/or chemokines.

The term "cytokine" is a generic term for proteins released by one cell population that act on another cell as intercellular mediators. Examples of cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-alpha. and -beta; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha and TGF-.beta.; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18, LIP, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines.

Dosages

The skilled artisan is directed to "Remington: The Science and Practice of Pharmacy," 20th edition, Gennaro, lippincott (2000). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA Office of Biologics standards.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Biopanning with Phage Display Libraries Using Human Patients

Certain of the methods and compositions of the present invention concern identification of targeting peptides for human organs, tissues or cell types by in vivo biopanning. Generally, protocols used in animal subjects, such as mice, are not suited for humans. Further, ethical considerations play a large role in human protocols. The following novel methods are preferred for use with humans, although the skilled artisan will realize that variations on the methods and compositions disclosed herein may be used within the scope of the present invention.

Human Preparation

Patients were selected for the protocol according to inclusion and exclusion criteria Inclusion criteria include: (1) patient legally declared brain dead or terminal wean patient; (2) approval of attending and/or treating physicians; and (3) approved written informed consent form signed by the patient's legally responsible family member. Exclusion criteria were: (1) the absence of a responsible family member; (2) HIV positive patient; (3) patient with active tuberculosis infection; (4) acute or chronic hepatitis B or C infections; or (5) patient was a potential organ transplant donor. In preferred embodiments, the patient was not on antibiotics for at least the previous 6 hrs, preferably the last 24 hrs, in order to avoid detrimental effects on the bacterial hosts used to propagate the phage used for the peptide display library.

After informed consent and before the patient was prepared for the procedure, relatives of the patient were asked to leave the room the patient was in. The patient had a well running IV line (preferably central) with nothing but saline running through the channel of application of the phage library. Personnel required for the procedure were notified (i.e., intervention radiologist, internist, surgeon, nurse, possibly neurologist or neuroradiologist). Materials needed for biopsies were collected: bone marrow aspiration needle, lumbar puncture kit, skin biopsy kit, materials for taking biopsies of any organ, tissue or cell type used for targeted peptide identification, such as liver, fat and tumor, materials for transabdominal prostate biopsy, 50 ml syringe with 40 ml saline for blood sample, 10 ml tube containing heparin and 10 ml serum collection tube to draw blood sample for lab tests. Before phage library injection, blood samples were drawn for routine screening of liver function, bicarbonate, electrolytes and blood count, unless test results from the day of the injection were available.

In the laboratory, 120 large dishes with LB-tet/kan agar as well as 200 regular LB tet/kan plates (100 mm) were prepared (tetracycline concentration=40 μg/ml, kanamycin concentration=50 μg/ml). E. coli K91 kan were grown in 10 independent tubes, each containing 10 ml TB medium plus supplements. Growth of bacteria was started approx. 15-60 min prior to beginning the biopsies. About $10^{14}$ TU of the (preferably primary) phage library were diluted in 200 ml ringer lactate at room temperature and aspirated under clean but not necessarily sterile conditions into four 50 ml syringes. LB-tet/kan dishes or plates were warmed in a 37° C. incubator. One liter of LB medium containing 0.2 μg/ml tet and 100 μg/ml kan was warmed in the waterbath at 37° C. One liter LB medium containing 40 μg/ml tet and 100 μg/ml kan was warmed to 37° C. and 8 more liters were prepared at room temperature. Thirty glass grinders A and B size as well as suitable glass tubes were autoclaved. Three 50 ml Falcon tubes were prepared for each of the organs for which biopsies were to be taken. Tubes were filled with 10 ml DMEM-PI—DMEM containing PMSF (1 mM), aprotinin (20 µg/ml) and leupeptin (1 µg/ml)—and put on ice approximately 15 minutes before tissue collection. For each of the 4 teams taking over in the lab after the tissue samples were collected, one autoclaved set of surgicals (i.e., at least one forceps and one pair of scissors and a scalpel) were prepared in order to trim, divide or mince organ samples.

Phage Library Injection

All drugs running through the intended port of application of the phage library were discontinued during library injection. If possible without compromising the patient's hemodynamic stability, all IV drugs running through different ports were discontinued during library injection as well. A running saline infusion ensured that the IV line for the library injection was open and was left running during the injection.

The 200 ml library solution was manually injected over a period of 10 minutes while monitoring and protocoling the patient's vital functions such as breathing (if not mechanically ventilated), heart rate and blood pressure. The injection was stopped any time the running saline infusion stopped dripping, indicating obstruction of the line. Fifteen minutes after beginning the injection, tissue sample collection (biopsies) was initiated. Biopsy sites included bone marrow aspirate, liver, prostate, skin, skeletal muscle, tumor (if applicable), adipose tissue, blood (as positive control), blood (for red/white blood cells) and cerebral-spinal fluid (CSF).

The samples were taken under very clean if not sterile conditions to reduce contamination with bacteria. To the extent possible, the different samples were taken simultaneously. For small samples, triplicate biopsies were preferred. The time elapsed between beginning of injection and the collection of a particular tissue sample was recorded. Tissue samples were placed in the prepared 50 ml tubes containing DMEM-PI and stored on ice. For bone marrow, a regular diagnostic sample (undiluted into a syringe with heparin) was taken in addition to the samples diluted in 40 ml saline to confirm aspiration of bone marrow as opposed to blood. If needed, all IV drugs, including antibiotics, were continued after removal of tissue samples.

All organ samples that were not taken in triplicate were divided under clean conditions to obtain three different pieces of tissue. The three samples of each organ were handled as follows. One piece was stored at −80° C. as a backup. One piece was forwarded to the histology/pathology department to cut cryosections (or to make smears for bone marrow) and perform HE staining (Pappenheim staining for bone marrow) as well as phage staining to confirm that the samples contained the organ of interest. In some cases the histology sample was divided in two—one for regular HE staining and one for LCM (laser capture microscopy) or LPC (laser pressure catapulting). The last of the three original pieces was processed for bacterial infection to recover phage.

After freezing of backup tissue and saving material for pathology, samples for phage rescue were weighed. Samples were kept on ice at all times. Sample was transferred to 1 ml DMEM-PI in a glass tube and homogenized with a grinder. Some organs such as bone marrow, blood, or CSF do not require homogenization, whereas other organs like muscle need to be minced before they can be efficiently homogenized. Lysis of erythrocytes for blood samples was preferred. Homogenized samples were transferred to autoclaved 2 ml Eppendorf tubes.

Tissue samples were washed 3 times with ice cold DM-PI containing 1% BSA by mixing the tissue with DMEM-PI and vortexing for 30 seconds. After centrifugation at 4,000 rpm for 3 min, supernatant was carefully discarded, leaving the tissue pellet undisturbed. A small amount of medium was left on the surface of the pellet. Samples were vortexed again for 30 seconds before adding more medium to facilitate resuspension of the tissue. After adding 1.5 ml of DMEM-PI plus BSA the samples were centrifuged again. When processing multiple samples, the tissues were kept on ice at all times.

After 3 washes, the pellet was briefly vortexed and the dissolved pellet was warmed briefly to 37° C. before adding bacteria. The washed tissue samples were incubated with 1.5 ml of competent K91-kan bacteria ($OD_{600}$ 0.2 in 1:10 dil.) for one hour at room temperature, then transferred to Falcon tubes containing 10 ml of LB medium with 0.2 µg/ml tetracycline. After 20 min at RT, multiple aliquots were plated on LB tet/kan plates or dishes containing 40 µg/ml of tetracycline and 100 µg/ml kanamycin. The following quantities (per organ sample) were plated: 2 dishes with 3 ml; 2 dishes with 1 ml; 3 dishes with 300 µl; 3 dishes with 100 µl; 3 dishes with 30 µl.

The beads that were used for plating were passed on to two subsequent 10 cm LB tet/kan plates to recover every potentially phage infected bacterial clone that might be trapped on the bead surface. Dishes were incubated overnight at 37° C.

The remaining 2-3 ml of infected culture (including the homogenized tissue) was transferred to 10 ml of LB medium containing 40 µg/ml tetracycline and 100 µg/ml kanamycin (LB tet/kan) and shaken at 37° C. for 2 hr. This approximately 12 ml culture was transferred to 1 liter LB tet/kan and grown overnight in a 37° C. shaker.

The next day, phage were rescued from the bulk amplified bacterial culture-according to standard protocols and saved for a potential second round of in vivo selection. From the plates/dishes in the incubator, 1500 well separated colonies were picked for each organ plated and transferred to 96 well plates containing 20 µl PBS/well for sequencing. This assumed a readout of about 2 out of 3 picked colonies to obtain 1000 sequences.

After picking 1500 colonies, the remainder of colonies on the dishes/plates were grown in 1000 ml LB tet/kan overnight in the 37° C. shaker. Then phage were harvested as before for a second round of selection. Alternatively, the plates were stored in the refrigerator and 1000-2000 individual colonies grown at a time. Alternatively, the remainder of colonies were transferred to PBS and stored frozen to infect and amplify as needed.

Numerous non-limiting examples of human organ, tissue or cell type selective targeting peptides have been identified by in vivo biopanning using the present methods, as disclosed below.

Example 2

Mapping the Human Vasculature by In vivo Phage Display

The in vivo selection method discussed above was used to screen a phage library in a human subject. A pattern recognition analysis program was used to survey 47,160 tripeptide motifs within peptides that localized to the human bone marrow, fat, skeletal muscle, prostate, or skin. The results of this large-scale screening indicated that the distribution of circulating peptide motifs to different organs is non-random. High-throughput analysis of peptide motifs enriched in individual tissues revealed similarities to sequences present in candidate ligands for differentially expressed vascular receptors.

These data represent a major step towards the construction of a ligand-receptor map of human vasculature and may have broad implications for the development of targeted therapies.

Many therapeutic targets may be expressed in very restricted—but highly specific and accessible—locations in the vascular endothelium. Potential targets for intervention may be overlooked in high-throughput DNA sequencing or in gene arrays because these approaches do not usually take into account cellular location and anatomical, and functional context. The human in vivo phage display screening methods disclosed herein are uniquely suited to identification of naturally occurring ligand-receptor pairs that may provide the basis for highly selective therapies against various disease states.

Materials and Methods

A 48 year-old male Caucasian patient who had been diagnosed with Waldenström macroglobulinemia (a B cell malignancy) was previously treated by splenectomy, systemic chemotherapy (fludarabine, mitoxantrone, and dexamethasone), and immunotherapy (anti-CD20 monoclonal antibody). In the few months prior to his admission, the disease became refractory to treatment and clinical progression occurred with retroperitoneal lymphadenopathy, pancytopenia, and marked bone marrow infiltration by tumor cells. The patient was admitted with massive intracranial bleeding secondary to thrombocytopenia. Despite prompt craniotomy and surgical evacuation of a cerebral hematoma, the patient remained comatose with progressive and irreversible loss of brainstem function until the patient met the formal criteria for brain-based determination of death, as evaluated by an independent clinical neurologist. Because of his advanced cancer, the patient was rejected as transplant organ donor. After surrogate written informed consent was obtained from the legal next of kin, in vivo phage display was performed.

In Vivo Phage Display

A large-scale preparation of a $CX_7C$ (C, cysteine; X, any amino acid residue) phage display random peptide library was optimized to create the highest possible insert diversity (Pasqualini et al., 2000). The diversity of the library was about $2 \times 10^8$ and its final titer was about $10^{12}$ transducing units (TU)/ml. For biopanning with human subjects, use of a large-scale phage display library (diversity about $2 \times 10^8$) is advantageous compared to the smaller scale libraries used in mouse studies. Short-term intravenous infusion of the phage library (a total dose of $10^{14}$ phage TU suspended in 100 ml of saline) into the patient was followed by multiple representative tissue biopsies. Prostate and liver samples were obtained by needle biopsy under ultrasonographic guidance. Skin, fat tissue, and skeletal muscle samples were obtained by surgical excision. Bone marrow needle aspirates and core biopsies were also obtained. Histopathological diagnosis was determined by examination of frozen sections processed from tissues obtained at the bedside.

Triplicate samples were processed for host bacterial infection, phage recovery, and histopathological analysis. In brief, tissues were weighed, ground with a glass Dounce homogenizer, suspended in 1 ml of Dulbecco Modified Eagle's medium (DMEM) containing proteinase inhibitors (DMEM-prin; 1 mM PMSP, 20 µg/ml aprotinin, and 1 µg/ml leupeptin), vortexed, and washed three times with DMEM-prin. The human tissue homogenates were incubated with 1 ml of host bacteria (log phase E. coli K91kan; $OD_{600}$~2). Aliquots of the bacterial culture were plated onto Luria-Bertani agar plates containing 40 µg/ml tetracycline and 100 µg/ml of kanamycin. Plates were incubated overnight at 37° C. Bacterial colonies were processed for sequencing of phage inserts recovered from each tissue and from unselected phage library. Human samples were handled with universal blood and body fluid precautions.

Statistical Analysis

A high-throughput character pattern recognition program (M.D. Anderson Cancer Center, Biostatistics, Houston, Tex.) was developed to automate the analysis of the peptide motifs derived from phage screenings. By using SAS (version 8, SAS Institute) and Perl (version 5.0), the program conducts an exhaustive amino acid residue sequence count and tracks the relative frequencies of N distinct tripeptide motifs representing all possible $n_3$ overlapping tripeptide motifs in both directions ($N<<n_3$). This was applied for phage recovered from each target tissue and for the unselected $CX_7C$ random phage display peptide library.

With "p" defined as the probability of observing a particular tripeptide motif under total randomness, and $q=1-p$, the probability of observing K sequences characterized as a particular tripeptide motif out of $n_3$ total tripeptide motif sequences is binomial ($n_3$, p). That probability may be approximated by the formula: $p_K = \Phi[(k+1)/\sqrt{n_3 pq}] - \Phi[k/\sqrt{n_3 pq}]$, where $\Phi$ is the cumulative Gaussian probability. The value $p_K$ may be treated as a P-value in testing for total randomness of observing exactly K sequences of a particular tripeptide motif. However, this test requires exact knowledge of the true value of p, which it is difficult to obtain in practice.

In order to identify the motifs that were enriched in the screening, the count for each tripeptide motif within each tissue was compared with the count for that tripeptide motif within the unselected library. Starting from a $CX_7C$ peptide insert, counts were recorded for all overlapping interior tripeptide motifs, subject only to reflection and single-voting restrictions. No peptide was allowed to contribute more than once for a single tripeptide motif (or a reflected tripeptide motif). Each peptide contributed five tripeptide motifs. Tripeptide motif counts were conditioned on the total number for all motifs being held fixed within a tissue. The significance of association of a given allocation of counts was assessed by Fisher's exact test (one-tailed). Results were considered statistically significant at $P<0.05$. In summary, to test for randomness of distribution, the relative frequencies of a particular tripeptide motif from each target was compared to the frequencies of the motifs from the unselected library. This approach is a large-scale contingency table association test.

Results

Phage localizing to human prostate tissue exhibited targeting peptide sequences as disclosed in Table 3, minus the terminal cysteine residues on each end of the peptides.

TABLE 3

| Human Prostate Targeting Peptides | | | |
|---|---|---|---|
| GRRAGGS | (SEQ ID NO:5) | LLAGGVL | (SEQ ID NO:18) |
| TRRAGGG | (SEQ ID NO:6) | LVVSAGG | (SEQ ID NO:19) |
| SRAGGLG | (SEQ ID NO:7) | RTQAGGV | (SEQ ID NO:20) |
| SYAGGLG | (SEQ ID NO:8) | AGGFGEQ | (SEQ ID NO:21) |
| DVAGGLG | (SEQ ID NO:9) | AGGLIDV | (SEQ ID NO:22) |
| GAGGLGA | (SEQ ID NO:10) | AGGSTWT | (SEQ ID NO:23) |
| GAGGWGV | (SEQ ID NO:11) | AGGDWWW | (SEQ ID NO:24) |
| AGGTFKP | (SEQ ID NO:12) | AGGGLLM | (SEQ ID NO:25) |
| LGEVAGG | (SEQ ID NO:13) | VAAGGGL | (SEQ ID NO:26) |
| GSNDAGG | (SEQ ID NO:14) | LYGAGGS | (SEQ ID NO:27) |

TABLE 3-continued

Human Prostate Targeting Peptides

| | | | |
|---|---|---|---|
| YRGIAGG | (SEQ ID NO:15) | CALAGGC | (SEQ ID NO:28) |
| AGGVAGG | (SEQ ID NO:16) | IGAGGVH | (SEQ ID NO:29) |
| GGLAGGF | (SEQ ID NO:17) | | |

To determine the distribution of the peptide inserts homing to specific sites after intravenous administration, the relative frequencies of every tripeptide motif from prostate tissue were compared to the frequencies from the unselected library. The 1,018 phage inserts recovered from representative samples of prostate and from the unselected library were analyzed. Tripeptide motifs were chosen for the phage insert analysis because three amino acid residues appear to provide the minimal framework for structural formation and protein-protein interaction (Vendruscolo et al., 2001). Examples of biochemical recognition units and binding of tripeptide ligand motifs to receptors include RGD (Ruoslahti, 1996), LDV (Ruoslahti, 1996), and LLG (Koivunen et al., 2001) to integrins, NGR (Pasqualini et al., 2000) to aminopeptidase N/CD13, and GFE (Rajotte and Ruoslahti, 1999) to membrane dipeptidase.

Each phage insert analyzed contained seven amino acid residues and contributed five potential tripeptide motifs. Comparisons of the motif frequencies in prostate tissue are shown in Table 4. The AGG (SEQ ID NO:30) motif was found only in prostate homing phage, while the other tripeptide motifs were all found in at least one other tissue. Table 4 lists motifs occurring in peptides isolated from prostate but not from the unselected phage library (Fisher's exact test, one-tailed; P<0.05).

TABLE 4

Peptide Motifs Isolated from Prostate by In Vivo Phage Display in Humans

| Motif | Motif Frequency | P-value |
|---|---|---|
| AGG (SEQ ID NO:30) | 2.5 | 0.0340 |
| EGR (SEQ ID NO:31) | 1.0 | 0.0185 |
| GER (SEQ ID NO:32) | 0.9 | 0.0382 |
| GVL (SEQ ID NO:33) | 2.3 | 0.0079 |

The ClustalW program European Molecular Biology Laboratory; EMBL) was used to analyze the original cyclic phage peptide inserts of seven amino acid residues containing the tripeptide motifs. The analysis revealed five to six residue motifs that were shared among multiple peptides isolated from prostate (Table 5), including RRAGGS (SEQ ID NO:34) and RRAGG (SEQ ID NO:35). On-line databases were searched for each of the motifs (including BLAST, SWISSPROT, PROSITE, PRODOM, and BLOCKS) through the NCBI website http://www.ncbi.nlm.nih.gov/blast/html/blastcgihelp). These motifs are likely to represent sequences present in circulating ligands (either secreted proteins or surface receptors in circulating cells) that home to vascular receptors in prostate. Candidate human proteins potentially mimicked by the selected peptide motifs are presented in Table 5.

TABLE 5

Examples of human proteins potentially mimicked by peptide motifs

| Extended motif | Human protein | Protein description | Accession number |
|---|---|---|---|
| Prostate | | | |
| RRAGGS (SEQ ID NO:34) | Interleukin 11 | cytokine | NP_000632 |
| RRAGG (SEQ ID NO.35) | Smad6 | Smad family member | AAB94137 |

Table 5 shows sequences corresponding to regions of 100% sequence identity between the peptide selected and the candidate protein. The identified homologous proteins may represent natural ligands for the human receptors that bound targeting phage. For example, interleukin 11 has been reported to interact with receptors within endothelium and prostate epithelium (Mahboubi et al., 2000). IL-11 may be mimicked by a targeting peptide recovered from the prostate (Table 5). These results were confirmed by in situ staining, using polyclonal antibodies against IL-11 receptor alpha IL-11 is a cytokine that is apparently mimicked by the peptide motif RRAGGS (SEQ ID NO:34), a human prostate targeting peptide. This suggests that the IL-11 receptor alpha (IL-11Rα) should be overexpressed in prostate blood vessels. Studies with cultured cells have indicated that IL-11 interacts with receptors in endothelium and prostate epithelium (Mahboubi et al., 2000; Campbell et al., 2001). However, expression of IL-11Rα in prostate blood vessels has not previously been examined.

Immunostaining of prostate thin sections with antibodies against IL-11Rα showed that IL-11Rα is present in the luminal prostate epithelium and in prostate blood vessels (not shown). This result validates the human biopanning results and shows that the presence of cell surface receptors identified by targeting peptide binding can be confirmed by antibodies against the receptor protein.

A considerable advantage of the present method is that the selected targeting peptides bind to native receptors, as they are expressed in vivo. Even if a ligand-receptor interaction is mediated through a conformational (rather than a linear) epitope, it is still possible to select binders in the screening. As it is difficult to ensure that transmembrane proteins expressed by recombinant systems (such as in protein arrays) maintain the correct structure and folding after purification in vitro, peptides selected in vivo are likely to be more suitable to clinical applications, such as identification of novel inhibitors or activators of native receptor proteins.

The skilled artisan will realize that the prostate-targeting peptide sequences identified in the present Example will be of use for numerous applications within the scope of the present invention, including but not limited to targeted delivery of therapeutic agents or gene therapy, in vivo imaging of normal or diseased organs, tissues or cell types, identification of receptors and receptor ligands in organs, tissues or cell types, and therapeutic treatment of human diseases, such as benign prostatic hyperplasia (BPH) and/or prostate cancer.

Example 3

The IL-11 Receptor as a Therapeutic and Diagnostic Target in Cancer

The preceding Example identified prostate-targeting motifs (RRAGGS, SEQ ID NO:34 and RRAGG, SEQ ID NO:35) in normal human prostate tissue. The homology of the RRAGGS (SEQ ID NO:34) motif with human IL-11 suggests that the native prostate receptor for binding of RRAGGS (SEQ ID NO:34) may be the IL-11 receptor. The present Example determined whether the IL-11 receptor could be targeted in prostate cancer, including metastatic prostate cancer.

To test the tissue specificity of the IL-11 peptide mimic, a phage overlay assay was developed to evaluate receptor-ligand interactions in tissue sections, using the motif RRAGGS (SEQ ID NO:34) (Arap et al., Nature Med. 8:121-127, 2002). Phage overlay on human tissue sections showed that the prostate-homing phage displaying an IL-11 peptide mimic specifically bound to the endothelium and epithelium of normal prostate, but not to control organs, such as skin (data not shown). In contrast, a control phage that localized to skin tissue, displaying the motif HGGVG (SEQ ID NO:36), did not bind to prostate tissue (not shown). However, the control phage specifically recognized blood vessels in the skin (not shown).

The immunostaining pattern obtained with an antibody against human IL-11Rα (IL-11 receptor alpha) on normal prostate tissue was indistinguishable from that of a CGRRAGGSC (SEQ ID NO:37)-displaying phage overlay (not shown). In contrast, a control antibody showed no staining in prostate tissue (not shown). These findings were recapitulated in multiple tissue sections obtained from several different patients (Arap et al., 2002).

Using a ligand-receptor binding assay in vitro, the interaction of the CGRRAGGSC (SEQ ID NO:37)-displaying phage with immobilized IL-11Rα was demonstrated at the protein-protein level (not shown). Recombinant IL-11Rα, vascular endothelial growth factor receptor-1 (VEGFR1) or leptin receptor (OB-R) were incubated with phage displaying the CGRRAGGSC (SEQ ID NO:37) peptide. VEGFR1 was used as a representative vascular receptor, while OB-R was used because it shares a co-receptor with IL-11Rα. An unrelated phage clone displaying the peptide CRVDFSKGC (SEQ ID NO:38) and insertless fd-tet phage were used as controls. Only the IL-11Rα receptor protein exhibited a significant amount of binding to CGRRAGGSC (SEQ ID NO:37)-phage (not shown). Neither OB-R nor VEGFR1 showed binding to CGRRAGGSC (SEQ ID NO:37)-phage above control levels (not shown). Neither of the control phage exhibited selective binding to IL-11Rα (not shown). Binding of CGRRAGGSC (SEQ ID NO:37)-phage to IL-11Rα was specific, since it was inhibited by the native IL-11 ligand in a concentration-dependent manner (not shown). Close to 100% inhibition of CGRRAGGSC (SEQ ID NO:37)-phage binding was observed at a peptide concentration of about 0.1 nM (not shown). These observations with normal prostate tissues were followed by an examination of the expression of IL-11Rα in tumors, as discussed in the present Example. IL-11R expression was found to be upregulated in human prostate cancer (see below).

Characteristics of IL-11 Receptor

IL-11Rα is a member of the gp130-dependent family of proteins, along with receptors for IL6, oncostatin M, leukemia inhibitory factor, and cilliary neurotrophic factor (Du and Williams, Blood 89:3897-3908, 1997). IL-11 initiates signaling via binding to the unique IL-11Rα chain, The complex of IL-11 and IL-11Rα then binds to and induces clustering of gp130, leading to the activation of associated Janus kinases (JAKs) and translocation to the nucleus of the signal transducers and activators of transcription (STAT) proteins 3 and 1 (Lutticken et al., Science 263:89, 1994; Campbell et al., Am. J. Pathol. 158:25-32, 2001). STAT3 has been reported to be constitutively activated in prostate cancer (Ni et al., J. Urol. 167:1859-62, 2002). IL-11Rα expression was reported to be increased in primary prostatic carcinoma compared to non-malignant prostate tissue (Campbell et al., 2001). No previous reports have characterized IL-11Rα expression in metastatic cancer.

Other signaling systems that may be activated by IL-11Rα include MAP kinase, and the ribosomal S6 protein kinase pp90rsk, src-family tyrosine kinases including p60src and p62yes, and phosphatidylinositol-3 kinase. IL-11Rα has been characterized on human solid tumors such as breast, colon, ovary, and melanoma (Douglas et al., Oncogene 14:661-69, 1997; Gupta et al., Proc. Am. Assn. Cancer Res. 38:554, 1997; Paglia et al., J. Interf. Cytokine Res., 15:455-460, 1995; Campbell et al, Gynecol. Oncol. 80:121-27, 2001), although its functional role and prognostic significance were unknown.

Distribution of IL-11Rα in Primary and Metastatic Prostate Cancer

Immunohistochemical (IHC) analysis was performed to examine the distribution of IL-11Rα in primary prostate cancer and metastatic prostate cancer. The present Example represents the first report of IL-11Rα distribution in metastatic cancer of any kind. Normal tissues from different areas in the prostate were also examined. Tissues from 99 archival formalin-fixed paraffin-embedded human primary and metastatic prostate cancers and the corresponding adjacent non-neoplastic tissues were obtained from 90 patients and evaluated. Samples consisted of 81 primary adenocarcinomas (71 androgen-dependent [AD] obtained from radical prostatectomy without prior treatment, and 10 androgen-independent [AI] obtained either from radical prostatectomy, cystoprostatectomy, or pelvic exenteration) and 18 lymph node and bone metastases and were selected to reflect: 1) stages in prostate cancer progression; 2) different Gleason scores; 3) hormonal dependence: AD and AI tumours; and 4) zonal origin: peripheral zone and transition zone. Additional blocks from the same specimens, including benign prostatic tissue from peripheral zone, transition zone, and central zone, and the seminal vesicle/ejaculatory duct, were included when available.

The samples were stained within two weeks of cutting to minimize loss of immunoreactivity. Four-μm sections were conventionally deparaffinized and rehydrated, blocked for endogenous peroxidases, antigen-retrieved in a microwave oven by treatment with EDTA solution (pH 8.0; Zymed, San Francisco, Calif.), and biotin and protein blocked (both from DAKO Corp., Carpinteria, Calif.). Incubation with anti-human IL-11Rα K-20 (1:15 for 45 minutes at room temperature; Santa Cruz Biotechnology, Santa Cruz, Calif.) followed. The LSAB+kit (DAKO) was used for immunostaining and development. All sections from each specimen were from the same staining run to avoid interassay variability.

Competition experiments with the antigenic peptide (5:1 w/w absorption; Santa Cruz) were performed to confirm specificity. Paraffin sections of the HeLa cell line were used as immunopositive controls. Negative controls included omission of the primary antibody, and substitution of primary antibody with non-immune goat serum at equivalent immunoglobulin concentration. Endothelial cells were immunostained by JC/70A (anti-CD31, DAKO) monoclonal antibody. IL-11Rα staining was evaluated both in tumour and non-tumour tissues, including pathologic conditions as benign prostatic hyperplasia (BPH) and transitional metaplasia, and high-grade prostatic intraepithelial neoplasia (PIN).

Positive cases were defined by the presence of cytoplasmic staining, as seen in the positive controls. Intensity in benign and malignant tissues was scored as 0 (negative), 1+ (weak), 2+ (moderate), or 3+ (strong). IL-11Rα expression in benign glands was generally observed in the basal cell compartment with/without staining of the luminal cells. We evaluated benign glands from 1+ (no/weak luminal cell staining) to 3+, taking into account then the highest intensity of staining in the luminal compartment, and compared this score with the most prevalent one observed in the cancerous tissue from the corresponding area Due to heterogeneity in intensity among and within tumour samples, a total immunostaining score was calculated as the sum of the products of percentage of cells (in 10% units) per intensity level (up to a maximum score of 300) to evaluate differences in expression among cancerous specimens. All analyses were done with S-PLUS 2000 (Math Soft, Inc.).

TABLE 6

Clinical and histopathological characteristics and IL11Rα expression

| Specimen | Number of cases | Median score (range)* | p |
|---|---|---|---|
| Normal prostate | | | |
| Peripheral zone | 62 | 1+ (1-2) | NS§ |
| Transition zone | 51 | 1+ (1-2) | |
| Central zone | 40 | 1+ (1-2) | |
| Seminal vesicle/ | 43/3 | 2+ (2-3)/ | . . . |
| Ejaculatory Duct | | 2+ (2) | |
| Benign pathologic conditions | | | |
| Benign prostatic hyperplasia | 15 | 1+ (1-2) | . . . |
| Stromal nodule | 2 | 1+ (1-2) | . . . |
| Atrophy | 10 | 2+ (1-2) | . . . |
| Transitional metaplasia | 18 | 2+ (1-2) | . . . |
| Prostatic intraepithelial neoplasia (PIN) | 23 | 2+ (1-3) | . . . |
| Primary prostate cancer | | | |
| Androgen-dependent | 71 | 2+ (1-3)/ | . . . |
| | | 180 (50-290) | |
| Zonal origin | | | |
| Peripheral zone | 55 | 190 (50-290) | 0.0003‖ |
| Transition zone | 16 | 135 (50-250) | |
| Gleason score† | | | |
| ≦7 (3 + 4) | 26 | 150 (50-260) | 0.004¶ |
| ≧7 (4 + 3) | 38 | 200 (100-290) | |
| Pathological stage† | | | |
| $pT_2$-$pT_{3a}$ | 42 | 175 (50-290) | 0.046¶ |
| $pT_{3b}$-$pT_{any}pN_1$ | 22 | 210 (100-280) | |
| PSA (ng/mL)† | | | |
| <10 | 48 | 180 (50-280) | NS¶ |
| ≧10 | 14 | 200 (100-290) | |
| Androgen-independent | 10 | 250 (80-300) | . . . |

TABLE 6-continued

Clinical and histopathological characteristics and IL11Rα expression

| Specimen | Number of cases | Median score (range)* | p |
|---|---|---|---|
| Metastatic prostate cancer | | | |
| Lymph nodes | | | |
| Androgen-dependent | 4 | 235 (200-290) | NS‖ |
| Androgen-independent | 8 | 235 (190-300) | |
| Bone | 6 | 270 (140-290) | . . . |

NS = non-significant.
*Categories 1+-3+ were used for evaluation of benign prostatic tissues and comparison to prostatic intraepithelial neoplasia and primary prostate cancer. A combined intensity per percentage of immunostained tumour cells scoring system was used to evaluate differences in expression among cancerous specimens (see text).
†Only the predominant tumour focus in each case was considered (64/71 cases).
§Wilcoxon signed rank test.
‖Mann-Whitney rank sum test.
¶Spearman correlation test.

No differences were observed in IL-11Rα expression between normal glands in the different prostatic areas (Table 6). Some background, distinct to a frequent stromal staining, was observed in the epithelium of seminal vesicles and ejaculatory ducts. Expression in PIN and AD samples examined was significantly higher than in their benign counterparts from the same areas (p<0.0001 in both cases, Wilcoxon signed rank test), but no differences were observed between PIN and AD (p=0.5, signed rank test). Among primary AD specimens, IL-11Rα immunoreactivity was increased in cancers from the peripheral vs. transition zone (=0.0003), in Gleason≧7 (4+3) vs. Gleason≦7 (3+4)=0.004), and, more marginally, in $pT_{3b}$-$pT_{any}pN_1$ tumours vs. $pT_2$-$pT_{3a}$ (p=0.046) (Table 6).

Primary AI specimens showed a more homogeneous pattern of staining, with more than 80% cells displaying moderate/strong intensity in 80% of the samples. However, no significant increase in expression was observed in AI vs. AD cases matched by Gleason score (p=0.15, rank-sum test), likely because of the small number of samples. Expression in 6 regional (4 AD and 2 μl) and 6 distant lymph node metastases (6 AI) was also intense in a high percentage of tumour cells. Cancer cells displayed a homogeneous moderate to strong intensity of staining in 5 out of 6 specimens from bone metastases (all AI). Both osteoblasts and osteoclasts stained moderately, and were used as internal positive controls. Interestingly, blood vessels in bone and lymph node metastases and in primary cases with previous treatment, showed an occasionally striking IL11Rα immunoreactivity that was confirmed by CD31 staining on consecutive slides, as opposed to a more random pattern in the other benign and malignant tissues analysed.

Figure 2:
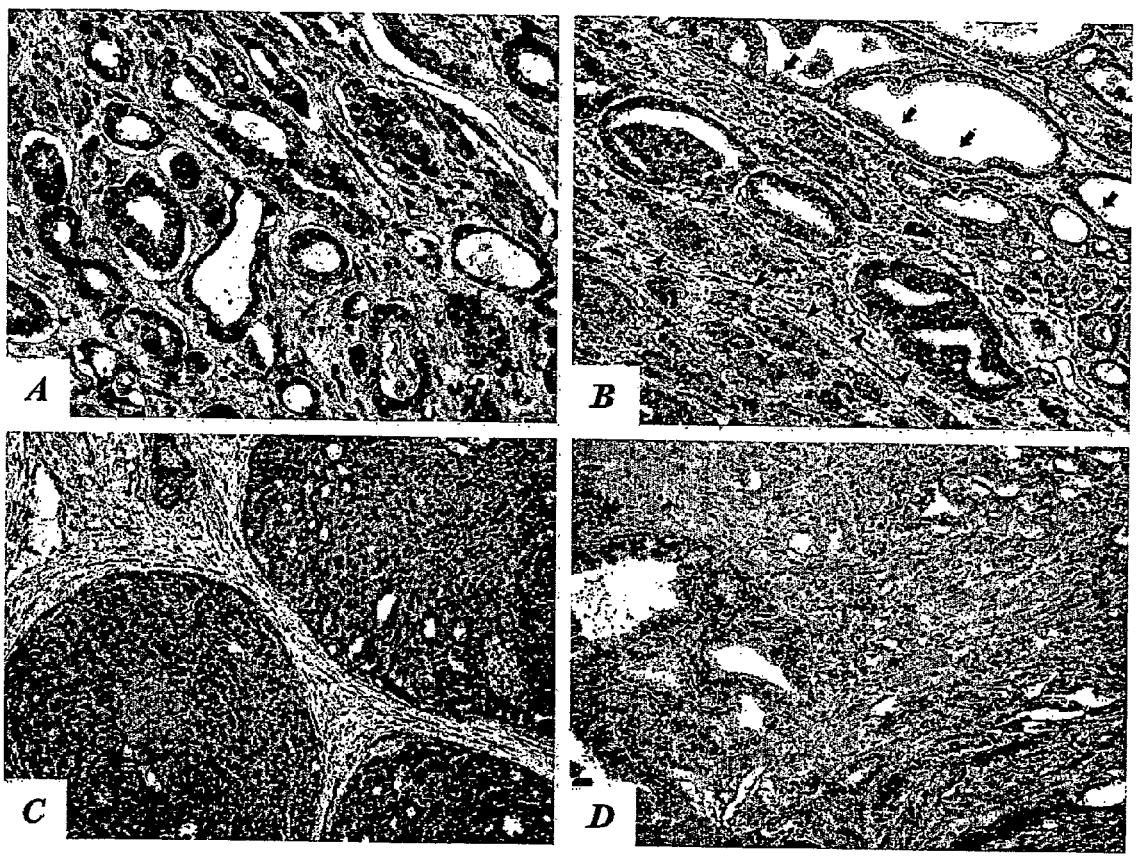
FIG. 2. IHC staining of IL-11Rα expression in primary androgen dependent prostate cancer of low, intermediate, and high Gleason scores (FIG. 2A-C, respectively). (A) Gleason score 6 prostate adenocarcinoma showed homogeneous 2+ staining (×200). (B) Prostate carcinoma (arrowheads) showing 1+ and 2+ heterogeneous staining. Note negative staining in the luminal cells of the contiguous benign glands (black arrows) (×100). (C) Strong 3+ positive staining in high-grade prostatic adenocarcinoma (×100). (D) Negative control including benign glands from the peripheral zone and a few neoplastic acini (×100).

The results show that IL-11Rα expression correlates with tumor progression (FIG. 1 and FIG. 2). FIG. 1 shows localization of IL-11Rα in benign prostate glands. Normal prostate glands in the peripheral (FIG. 1A) or central (FIG. 1B) zones showed predominantly nuclear staining of the basal and luminal cell layers.

FIG. 2 illustrates IHC staining for IL-11Rα in primary androgen dependent prostate cancer of low (FIG. 2A), intermediate (FIG. 2B) and high (FIG. 2C) Gleason grade prostate tumors. FIG. 2A shows IL-11Rα distribution in a Gleason score 6 prostate adenocarcinoma (homogeneous 2+ staining).

FIG. 2B shows IL-11Rα distribution in prostate carcinoma (arrowheads) (1+ and 2+ staining). The prostate carcinoma exhibited elevated staining for IL-11Rα compared to adjacent luminal cells of benign prostate (arrows). Strong (3+) staining for IL-11Rα was observed in high-grade prostate adenocarcinoma (FIG. 2C). FIG. 2D shows that benign prostate glands from the peripheral zone, containing a few neoplastic acini, exhibited little or no staining for IL-11Rα compared to prostate cancer.

Figure 3:
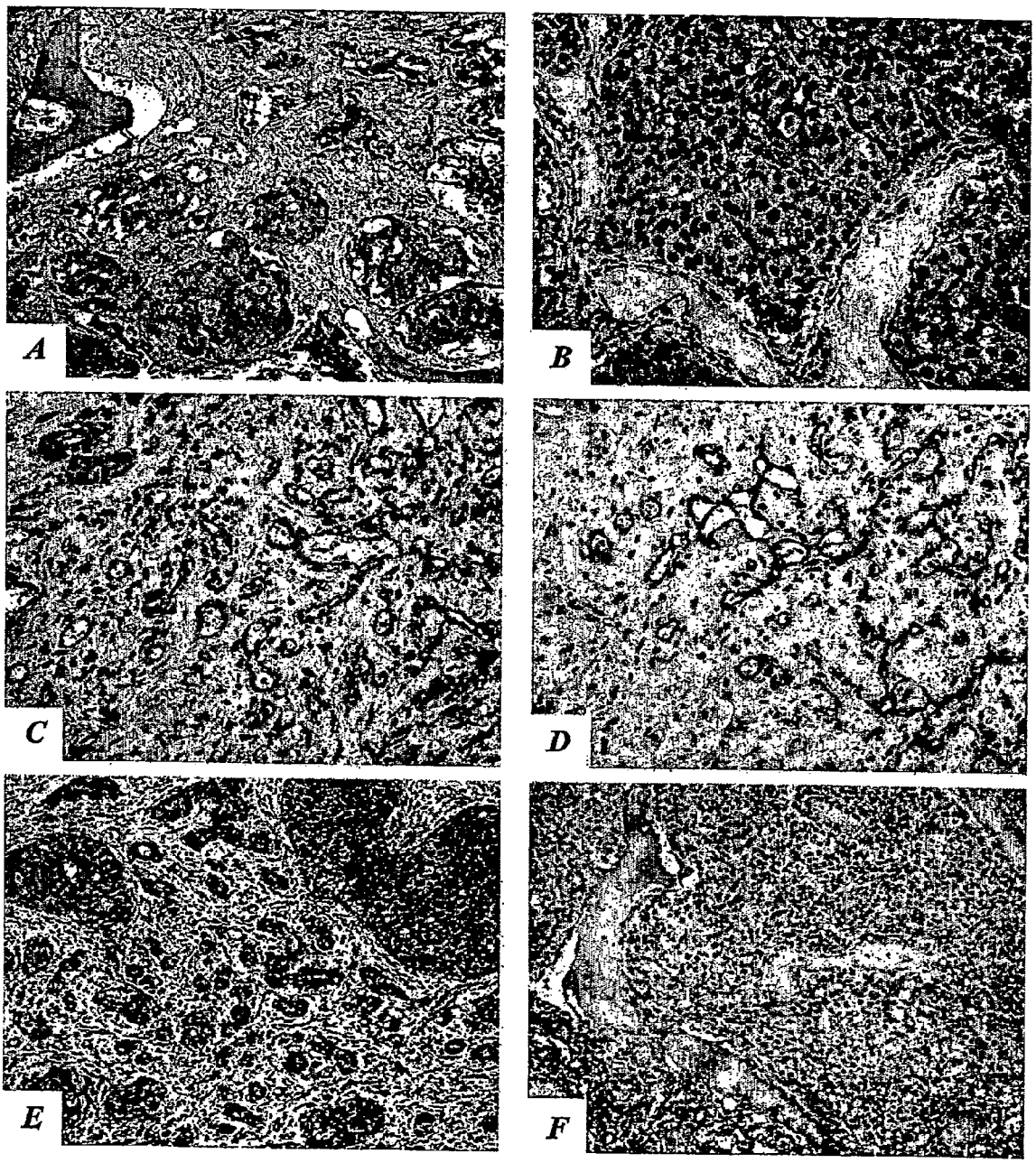
FIG. 3. Immunodetection of IL-11Rα in advanced, androgen independent, prostate cancer. (A) Homogeneous 3+ expression of IL-11Rα in prostate cancer metastatic to the bone (×100). (B) A higher power view of a bone metastasis showing 2+ and 3+ expression of the receptor in the tumor cells (×200). (C) Positive staining in the small vessels around the tumor nodules in the bone matrix (×200). (D) CD31 staining of the previous area confirming endothelial cell reactivity (×200) (E) High-grade, androgen-independent primary tumor showing strong (3+) and homogeneous expression of IL-11Rα (×100). (F) Negative control from the same area as (B) (×100).
Figure 33:
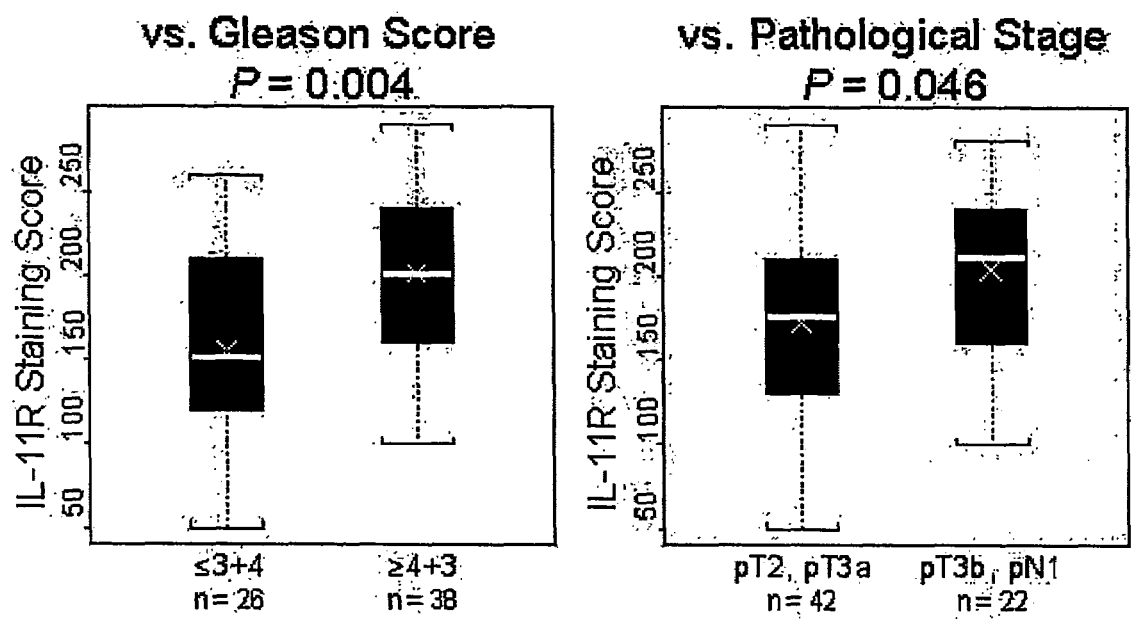
FIG. 33. Distribution of IL-11Rα expression in primary androgen-dependent prostate carcinoma by immunohistochemical score, according to Gleason grade and pathological stage.

IL-11Rα expression was strongly up-regulated in metastatic prostate cancer (FIG. 3). FIG. 3A shows strong homogenous (3+) staining in prostate cancer that had metastasized to bone. A higher power magnification of the same sample shows 2+ and 3+ staining in tumor cells (FIG. 3B). FIG. 3C shows that small blood vessels around tumor nodules in the bone matrix also exhibited strong staining for IL11Rα. CD31 staining of the same sample (FIG. 3D) confirmed the endothelial cell reactivity of the IL-11Rα IHC staining. A high-grade, androgen-independent primary prostate tumor also exhibited strong (3+) staining for IL-11Rα (FIG. 3E). A negative control of benign prostate tissue from the same area as FIG. 3B exhibited little or no staining for IL-11Rα (FIG. 3F). FIG. 33 shows the distribution of IL-11Rα expression in primary androgen-dependent prostate carcinoma by immunohistochemical score, according to Gleason grade and pathological stage.

IL-11Rα expression was examined in blood vessels of prostate tissue samples. Although staining was observed in some prostate blood vessels, it was not observed in others. A sub-group of cases displayed a stronger and more consistent staining in blood vessels. The majority of such cases were androgen-independent, including both primary and metastatic androgen-independent tumors (17 of 24 AI cases). Blood vessel staining in AI tumors could result from either a shift in hormonal dependence or exposure to previous treatment. No common modality of treatment was observed in such cases, with the exception of hormone ablation. A few cases had been treated with radiotherapy and the rest with different type of chemotherapy. In some cases the systemic treatments had been administered a long time before sample analysis for IL-11Rα expression. It is concluded that androgen independence is correlated with high levels of IL-11Rα expression in blood vessels. The skilled artisan will realize that IL-11Rα staining may be of use to distinguish androgen-dependent from androgen-independent cases and therefore to assist in tailoring therapeutic treatment to the status of the tumor as androgen-dependent or androgen-independent.

It is concluded that expression of IL-11Rα is of use as a specific marker for metastatic prostate cancer in bone tissue. The skilled artisan will realize that IL-11Rα staining may be used for detection, diagnosis and/or imaging of metastatic prostate cancer in bone and/or other tissues, such as lymph nodes.

Clinical Significance

Approximately half of presently hospitalized cancer patients will die of their disease despite optimal management Given such a high failure rate, estimates of potentially curative treatment based on the risk of recurrence remain difficult to extrapolate for an individual cancer patient. There is a clear need for improved biomarkers of cellular growth potential and targets in cancer. Based on the present results, expression of IL-11Rα in prostate cancer appears to be one such biomarker.

The molecular observations reported herein may be confirmed in a clinical context by following patient outcome in prostatic cancers with varying levels of IL-11Rα expression, using known methods. For example, probabilities of survival for each group of patients may be analyzed by the Kaplan-Meier method. Log-Rank test may be used to determine statistical differences between groups. A Cox proportional hazards model may be used to analyze the effect of single and multiple risk factors in association with survival. Martingale residual plots may be used to assess the proportional hazard assumption. Results may be considered statistically significant at $P<0.05$.

Such observations may be validated in archived pathological material. Group stratification of cancer patients based on a panel of one or more such markers would allow less aggressive tumors to be effectively eradicated, while patients with more aggressive tumors could be offered experimental therapies earlier in their clinical progression. Without reliable ways of predicting which tumors will progress, many cases are treated aggressively on the chance of cure, but often at the price of potentially devastating treatment-associated side effects. There is a clear need for markers of cellular growth potential, such as IL-11Rα, as diagnostic and therapeutic targets in cancer patients. The skilled artisan will realize that expression of IL-11Rα may be useful in other types of tumors besides prostate cancer, so long as IL-11Rα is correlated with tumor growth and/or metastatic potential. Exemplary tumors in which IL-11Rα may be of use for detection, diagnosis and/or prognosis of cancer include prostate, breast, colon, ovary and melanoma.

Example 4

Biopanning Circulating Immunoglobulins in Human Prostate Cancer Patients

A phage display library was screened against a pool of circulating antibodies obtained from a human prostate cancer patient. The biopanning procedure resulted in the identification of a novel marker for prostate cancer that is diagnostic for disease progression in metastatic prostate cancer. In this embodiment, the antibody pool provides a structural sampling of ligands targeted to naturally occuring receptors, some of which may constitute novel disease markers. Biopanning against an antibody pool may be used to identify disease markers and to further characterize the molecular events underlying the disease state.

The present Example shows the feasibility of this approach by identifying a novel marker for prostate cancer. The results further show that this marker has prognostic value for predicting which individuals with prostate cancer are likely to have an unfavorable clinical outcome, resulting in death of the patient. As discussed above, there is a great need in the field of prostate cancer for a reliable method to separate those individuals whose prostate cancer will prove lethal (and therefore are candidates for more agressive therapeutic intervention) from individuals who will not die from prostate cancer. The present Example represents a significant advance in prostate cancer prognosis and illustrates the utility of the claimed methods and compositions.

The skilled artisan will realize that although the present Example deals with prostate cancer, the methods and compositions disclosed are suitable for use with any disease state or condition in which the host immune system is likely to produce antibodies against a molecular marker associated with the disease or condition.

The repertoire of circulating antibodies from the serum of prostate cancer patients with advanced disease was used to screen a phage display library. Certain peptides binding to those antibodies correspond to tumor antigens expressed in bone metastasis of prostate cancer. A panel of prostate cancer serum samples from patients with recorded clinical outcome was screened by an ELISA assay against those peptides. The results show that reactivity against one particular peptide ("peptide C") can be used to identify patients with metastatic androgen-independent prostate cancer. Moreover, patients with detectable levels of circulating antibodies against peptide C exhibited decreased survival compared to individuals without such antibodies.

Methods

Sera was selected from patients diagnosed with androgen-dependent and androgen-independent prostate cancer. A CX6C peptide library was screened against this pool of IgGs in a two-step procedure. First, the peptide library was pre-cleared against a pool of purified IgGs from normal serum samples using Protein G affinity chromatography. This step removed peptides from the phage display library that bound to immunoglobulins from patients without prostate cancer. Next, the pre-cleared peptide library was screened against the pool of purified IgGs from the serum of prostate cancer patients. This step selected peptides binding specifically to IgGs elicited against prostate cancer.

Human Sera and Tissue Samples

Human plasma samples were prospectively collected from 91 patients with locally advanced, metastatic androgen-dependent and metastatic androgen-independent adenocarcinoma of the prostate. In each case, the patient was evaluated in reference to tumor staging (locally advanced or metastatic disease) and hormone responsiveness of the disease (androgen-dependent or androgen-independent). Criteria for enrollment consisted of a combination of the TNM classification and histological grading. Patients diagnosed with adenocarcinoma of the prostate with stage T1c or T2 with Gleason score less than or equal to 7 and serum PSA<10 ng/ml were considered to have clinically organ-confined prostate cancer. Study entry in the locally advanced group required appropriate primary tumor staging (stage $T_{1c}$ or $T_2$ with Gleason score greater than 7; or clinical stage $T_{2b-2c}$ with Gleason score equal to or greater than 7 and serum PSA>10 ng/ml; or clinical stage $T_3$) and no regional ($N_0$) or distant ($M_0$) metastases. Study entry in the metastatic group required evidence of regional ($N_1$) and/or distant ($M_1$) metastases in radionuclide bone scan, chest radiography, or computed tomography of the abdomen and pelvis. Androgen-independence was defined as serum testosterone lower than 50 ng/dl and serially rising serum PSA; index patients 1, 2, and 4 were androgen-independent, while index patient 3 was androgen-dependent at the time their serum samples were obtained.

For biopanning, sera was examined from three metastatic androgen-independent and one metastatic androgen-dependent prostate cancer patients. Plasma from 34 healthy individual donors (eleven males) was obtained from the Blood Bank at the University of Texas M. D. Anderson Cancer Center (UTMDACC). Archived tissue paraffin blocks were obtained from the Department of Pathology at UTMDACC. The blood samples were initially allowed to clot at room temperature and then centrifuged to separate the cellular component from the supernatant. Aliquots of supernatant were promptly frozen and stored at −80° C. until assayed.

Biopanning.

A 6-mer cyclic peptide ($CX_6C$) phage display library was used for the biopanning. To select peptides specific to the serum antibodies of cancer patients, a pre-clearing stage was employed to remove non-specific peptides by pre-absorbing the peptide library onto purified IgGs from pooled normal serum (five healthy male individuals). The pre-cleared peptide library was screened onto the purified IgGs from the serum of prostate cancer patients. In brief, $10^9$ transducing units (T.U.) of a $CX_6C$ cyclic peptide phage library were incubated with IgG antibodies from 50 μl of normal serum immobilized on 50 μl of protein G (Gibco BRL) for 1 hour at 4° C. This was followed by affinity selection on the immobilized IgG antibodies from prostate cancer patient serum for 2 hours at 4° C. Phage peptides specifically bound to IgGs elicited against prostate cancer were eluted with 100 μl of 0.1 M glycine buffer, pH 2.2, neutralized by the addition of 10 μl 1M Tris pH 9.0, and used to infect E. coli strain K91. Ten-fold serial dilutions of the infected solution were spread onto agar plates containing 40 μg/ml of tetracycline and grown overnight. Two hundred colonies were picked, amplified, and precipitated for a subsequent round of panning. A total of three rounds were performed. Individual phage clones were picked for PCR and the insert DNA was sequenced.

Enzyme-linked Immunosorbent Assay and Peptide Inhibition Study.

A 20 μg/ml solution of purified GST or GST-fusion proteins in 0.1M $NaHCO_3$ was used to coat maxisorp multi-well plates (Nalge Nunc International Corporation) and incubated overnight at 4° C. The plates were blocked in a blocking buffer (4% milk, 2% casein, and 0.05% Tween-20) for 3-4 hours. A series of 100-fold dilutions (1:100-1:1200) of sera from prostate cancer patients or healthy individuals was added and incubated for 1.5 hours and then washed five times with washing buffer (1% milk, 0.5% casein, and 0.025% Tween-20), followed by incubation at 4° C. with anti-human alkaline phosphatase-conjugated antibodies (Gibco). The plates were then washed six times in washing buffer and developed using p-NPP (Sigma) as a substrate. An automatic ELISA plate reader (BIO-TEK instrument) recorded the results at OD405 nm.

Antibody Biotinylation.

GST-fusion proteins containing the peptide sequence from patient C were coated on multi-well plates. After incubating the plates with the patient's serum, the plates were washed. The bound IgG antibodies were eluted with 50 μl of 0.1 M glycine buffer, pH 2.2, by addition of 10 μl 1 M Tris pH 9.0, and dialyzed in PBS overnight followed by concentration of the antibody using Centricon-30 (Millipore) filters. The purified antibody (500 μg) was coupled to biotin according to the manufacturer's instructions (Vector). The biotinylated antibody was analyzed by SDS-gel electrophoresis.

Immunohistological Staining.

Paraffin sections (4 μm) were stained with purified biotinylated antibodies and peptide antibodies by immunoperoxidase detection using the Dako antigen retrieval kit and DAB (diaminobenzidine) as a substrate. All of the sections were counter-stained with hematoxylin. Purified IgGs were coupled to biotin and resolved by SDS-PAGE. The biotinylated immunopurified antibodies were used at a dilution of 1:60. Peptide C antibodies and purified pre-immune antibodies were used at 0.01 μg/μl. For the inhibition staining, peptide C antibodies were pre-incubated for 30 minutes at room temperature with the corresponding GST-peptide C (500 μg) prior to staining. For the GRP78 immunostaining, anti-GRP78 antibody (C-20) was used at 1:350 (Santa Cruz Biotechnology, Santa Cruz, Calif.). Peptide antibodies were generated in rabbits and purified using a T-gel immunoglobulin purification kit and protein G column (Pierce).

Protein Purification, Mass Spectrometry, and Immunoprecipitation

DU-145 prostate cancer cells (American Type Culture Collection), which express the native antigen (data not shown), were used for protein purification. Cells were grown to 70% confluence, harvested in PBS, and treated with TM buffer (100 mM Tris-Cl, 2 mM $MgCl_2$, 1% Triton-X100). Cells were sheared to separate nuclei from cytoplasm and other organelles. The cytosolic/membrane fraction was centrifuged. The supernatant was collected, resolved on 4-20% gradient SDS-PAGE, probed by rabbit anti-peptide antibodies on Western blots and detected by enhanced chemiluminescence (ECL; Pharmacia). The band containing the protein recognized by the anti-serum was excised and used for protein sequencing. Mass spectrometry analysis was compared to databases containing known protein sequences by BLAST homology search.

For immunoprecipitation, 200 µl of protein G agarose beads (Pierce) were coupled to anti-GRP78 or rabbit anti-peptide antibodies, and the recombinant GRP78 (Stressgen) was added at 150 µg, and incubated for 4 hours. As a negative control, protein G agarose beads alone were used. The immunoprecipitates were recovered by centrifugation, rinsed with wash buffer (0.05% Tween-20 in PBS), and resolved by SDS-PAGE.

A Western blot was probed with either anti-CNVSDKSC (SEQ ID NO:39) or anti-GRP78 antibodies (each at 1:200 dilution) and detected by ECL. For detection of GRP78 in the normal prostate and bone metastasis, whole lysates from frozen tissue samples were prepared by grinding the tissue in a dounce homogenizer in a 2 ml of Tissue Protein Extraction Reagent (Pierce) per sample with protease inhibitors (10 µg/ml of leupeptin and aprotonin). The homogenate was incubated on ice for 10 minutes prior to repeated grinding. The homogenate was spun at 610 g for 5 minutes and the supernatant was removed and protein concentration was measured using the Protein DC Assay (BIO-RAD). 20 µg of protein from the normal prostate and bone metastasis lysates were resolved on a 4-20% SDS-PAGE, probed by anti-GRP78 antibody on Western blots and detected by ECL.

Cross-inhibition Assays

Microtiter 96-well plates were coated with 10 µg/ml recombinant GRP78 (Stressgen) or GST attached to CNVSDKSC (SEQ ID NO:39) in 100 mM $NaHCO_3$ overnight at 4° C., washed and then blocked with blocking buffer (2% milk, 1% casein, 0.05% Tween-20 in PBS) for 2 hours at 37° C. To determine the inhibitory activities of GRP78 or GST-CNVSDKSC (SEQ ID NO:39), patient serum (1:50), anti-GRP78 (1:1000), and anti-GST-CNVSDKSC (1:20) were incubated with GRP78 (50-100 µg) or GST-CNVSDKSC (SEQ ID NO:39) (100-300 µg). The mixtures were incubated for 1 hour at 37° C. prior to adding to the coated wells. After 1 hour of incubation at room temperature the wells were washed several times with PBST buffer (0.05% Tween-20 in PBS). Secondary antibodies conjugated to horseradish peroxidase were added at 1:5000 dilution, incubated for 30 minutes at room temperature and washed five times with PBST buffer. Finally, the substrate 3,3',5,5'-Tetramethylbenzidine CIMB; Calbiochem) was added and incubated for 15 minutes at room temperature before stopping the reaction by addition of 0.5M $H_2SO_4$. Absorbance at 450 nm was determined in an automated ELISA reader (Bio-Tek).

Statistical Analysis.

Probabilities of survival for each group were estimated using the Kaplan-Meier method. A log-rank test was implemented in order to detect significant differences between the groups. Reactivity was considered to be detected if the ratio between GST-peptide and GST alone was greater or equal to two by the ELISA data. A Log-Rank test was used to determine statistical differences between groups. A statistical CART analysis (Classification And Regression Tree) was used to identify the best cut-off point for determining reactivity to GRP78. In this method, the censored survival data were transformed into a single uncensored data value (the so-called "null martingale residual"), which was used as input into a standard regression tree algorithm. A cut-off point of 0.95 was determined by this program Results After three rounds of selection, a striking enrichment (log scale) was observed in three out of the four serum samples examined (FIG. 4). In the fourth patient sample, no enrichment was observed and this patient was not studied further. Individual phage clones from the second and third rounds of selection from serum samples A, B, and C were sequenced. The peptide motifs CHQKPWEC (SEQ ID NO:40) from patient A and CKDRFERC (SEQ ID NO:41) from patient B represented 100% of the clones analyzed from those patients. In patient C, the peptide CNVSDKSC (SEQ ID NO:39) appeared in 55% of the clones analyzed. The remaining clones identified in patient C were CNWTDKTC (SEQ ID NO:43), representing 33.3% of the clones in round II and 7% of the clones in round III, CNITQKSC (SEQ ID NO:44), representing 33.3% of the clones in round II and 0% in round III, and CNKTDKGC (SEQ ID NO:45), representing 16.7% of the clones in round II and 0% in round III.

Figure 5:
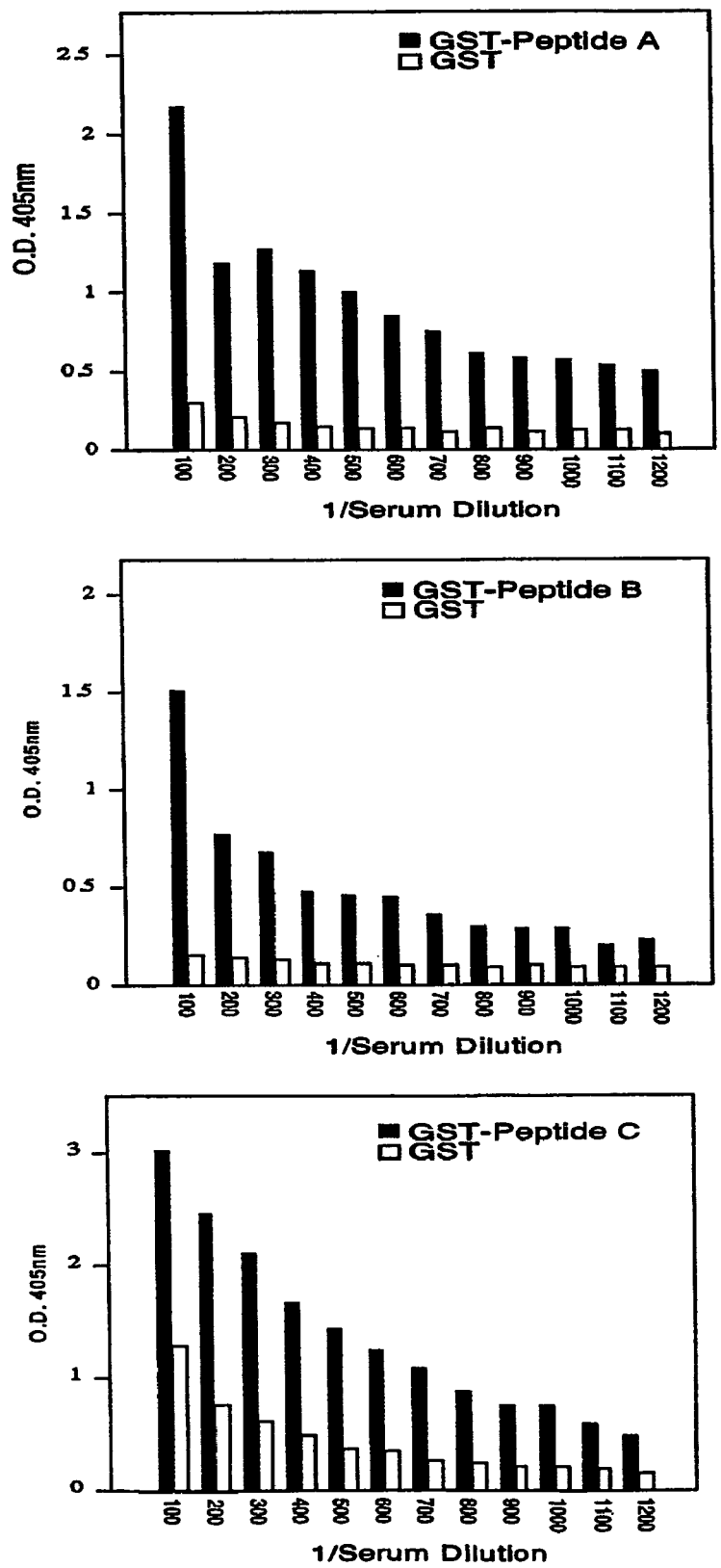
FIG. 5. Selection of peptide library on immunoglobulins from the serum of metastatic prostate cancer patients. A series of 100-fold dilutions (1:100-1:1200) was performed for each patient's serum to test specific binding of cancer antibodies to immobilized GST-fusion proteins by ELISA.

ELISA was performed to assess if the peptides could be specifically recognized by the antibodies present in the serum of the patients selected for the screenings. Peptides A (CHQKPWEC, SEQ ID NO:40), B (CKDRFERC, SEQ ID NO:41), and C (CNVSDKSC, SEQ ID NO:39) were produced as GST-fusion proteins and immobilized onto microtiter wells, along with GST alone as a negative control. For each sample tested, a series of 100-fold dilutions was performed. Little reactivity occurred with the GST control, whereas strong reactivity occurred with the GST-fusion peptides (FIG. 5). The reactivity of each serum against peptides A, B and C was inhibited by the corresponding synthetic peptides (data not shown).

Figure 6:
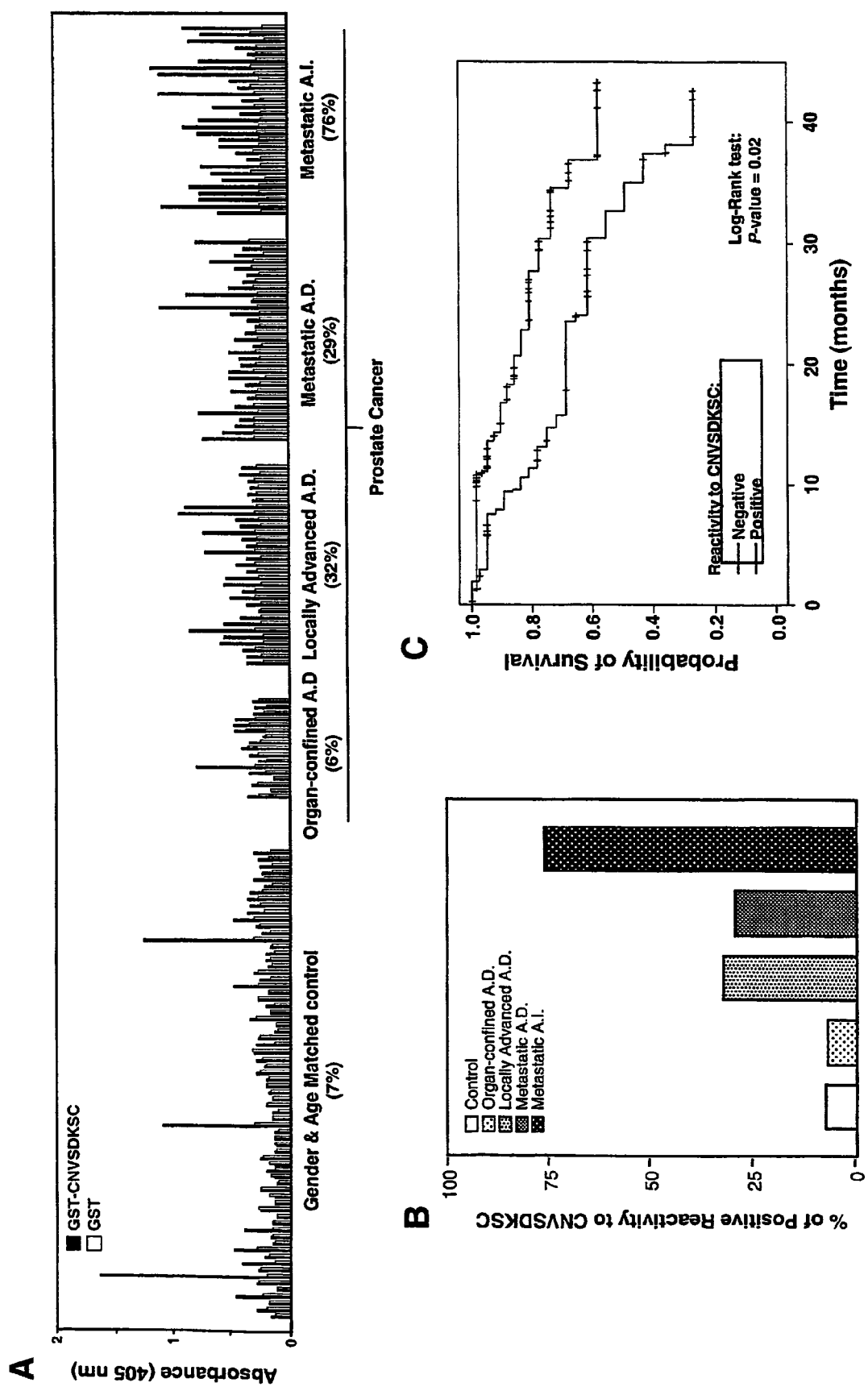
FIG. 6. Reactivity between the serum from prostate cancer patients or control men and the selected peptide is stage-specific. Serum samples derived from a large panel of prostate cancer patients (n=108) were divided into four groups: organ-confined (n=17), locally advanced (n=31), and metastatic androgen-dependent (n=31), and metastatic androgen-independent (n=29). Serum samples derived from 71 age-matched blood-donor men served as a negative control group. Serial dilutions were performed for each serum to determine optimal reactivity by ELISA.

Characterization of the Peptide CNVSDKSC (SEQ ID NO:39) and Clinical Correlations Having shown selective binding of GST-CNVSDKSC (SEQ ID NO:39) fusion peptides to prostate cancer patient serum, the reactivity profile against the peptide CNVSDKSC (SEQ ID NO:39) was assessed in a population of 108 sera obtained from clinically annotated prostate cancer patients and 71 age-matched healthy men (negative control). Among the control serum samples tested, a small percentage of positive reactivity (7%) was detected with the selected peptide (FIGS. 6A and 6B). In contrast, positive serum reactivity from the 108 sera samples from prostate cancer patients correlated positively with the natural progression of the disease (FIGS. 6A and 6B). Thus, positive serum reactivity against CNVSDKSC (SEQ ID NO:39) correlated with late-stage prostate cancer and androgen-independence. For example, only 6% of the organ-confined patients' sera reacted against the peptide CNVSDKSC (SEQ ID NO:39), whereas patients with androgen-dependent tumors reacted against the peptide in 29% of the samples (FIG. 6B). Most notably, 76% of the samples obtained from patients with metastatic androgen-independent prostate cancer reacted to the sequence CNVSDKSC (SEQ ID NO:39) (FIG. 6B).

Kaplan-Meier curve estimates (Kaplan and Meier, *J. Am. Statist. Assoc.* 53:457-481, 1958) were applied to compare survival between the positive reactive and negative reactive groups (FIG. 6C). Reactivity against the peptide CNVSDKSC (SEQ ID NO:39) (n=42) was associated with a significantly shorter patient survival (FIG. 6C, Log-Rank test, P=0.02). The median survival in the positive reactivity group was reached after 32.7 months while the median survival in the non-reactivity group was not reached (FIG. 6C). The data show a strong correlation between positive reactivity against the peptide CNVSDKSC (SEQ ID NO:39), development of metastatic androgen-independent prostate cancer (the most advanced stage of the disease), and decreased survival.

Identification of the Corresponding Native Tumor-Associated Antigen.

Figure 7:
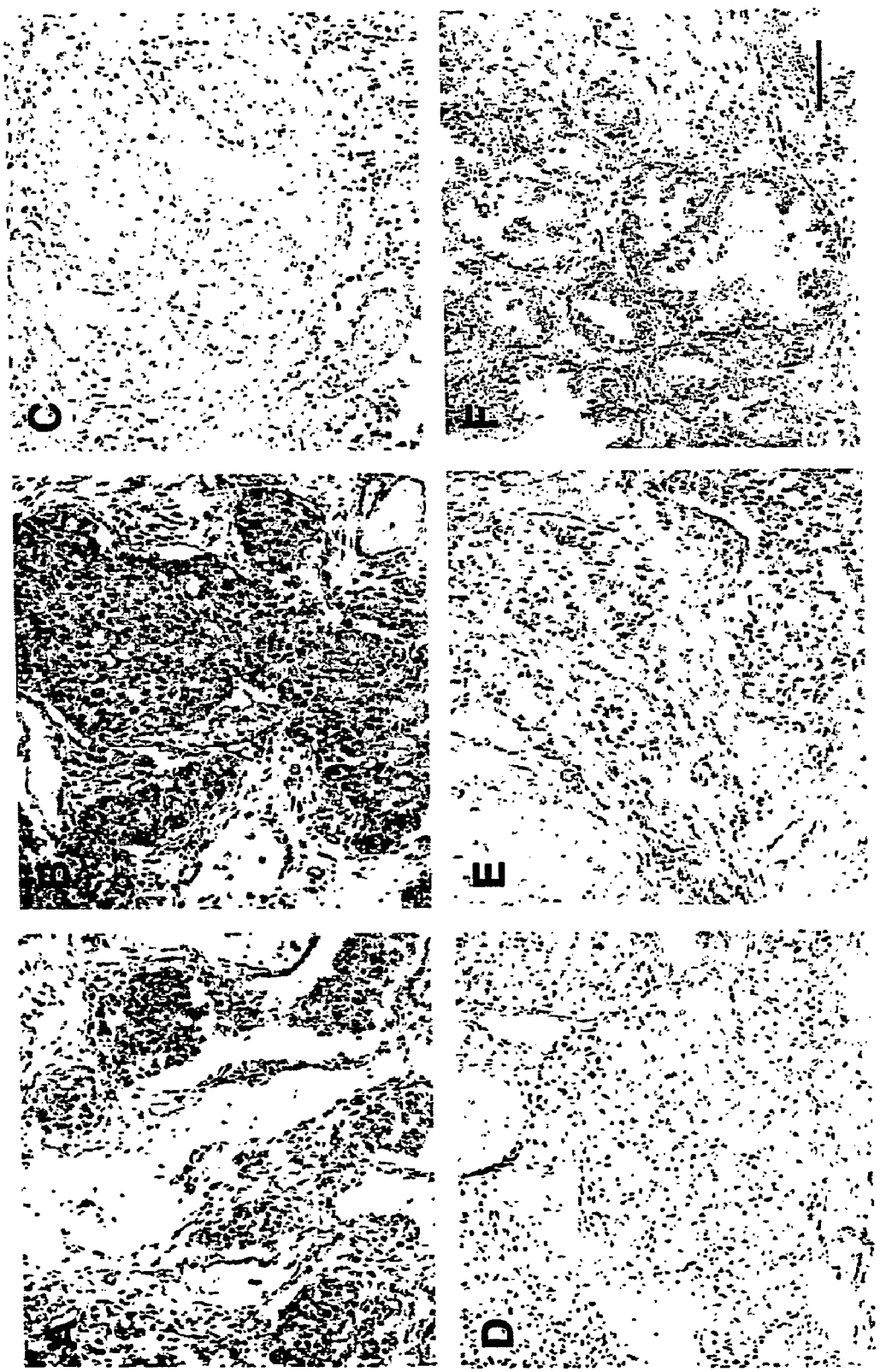
FIG. 7. Immunohistological analysis of tumors from a prostate cancer patient. Immunostaining of sections from prostate cancer metastatic to the bone marrow of the patient whose screening yielded CNVSDKSC (SEQ ID NO:39) and of normal prostate are shown. (A) Strong staining was observed on metastatic tumor with the autologous immunopurified IgGs. (B) Strong staining was also observed with a rabbit polyclonal antibody raised against the synthetic form of the CNVSDKSC (SEQ ID NO:39) soluble peptide. (C) No staining was observed with the rabbit pre-immune serum. (D) No staining was observed with secondary antibody alone. (E) A recombinant CNVSDKSC (SEQ ID NO:39) fusion protein inhibited staining under the same conditions used in FIG. 7B. (F) Weak staining was observed in normal prostate with the same rabbit polyclonal antibody used in FIG. 7B. Scale bar is 50 μm.

Antibodies against the peptide sequence CNVSDKSC (SEQ ID NO:39) were used to determine whether they could specifically recognize tumor-associated targets in tissue sections by immunohistochemistry. Normal prostate tissue and metastatic prostate cancer from bone marrow in samples obtained from patient C were subject to IHC staining using autologous immunopurified IgGs or a rabbit polyclonal antibody against CNVSDKSC (SEQ ID NO:39). Strong staining was observed using immuno-purified antibodies from the autologous patient serum (FIG. 7A). Specific immunostaining was also observed using a rabbit polyclonal antibody raised against the synthetic peptide CNVSDKSC (SEQ ID NO:39) (FIG. 7B). No immunostaining was observed with the pre-immune antibodies (FIG. 7C) or a secondary antibody alone (FIG. 7D). The immunohistochemical signal observed in FIG. 7B was mostly inhibited by a fusion protein containing the sequence CNVSDKSC (SEQ ID NO:39) demonstrating the specificity of the staining protocol (FIG. 7E). Normal prostate from the same individual only exhibited weak staining using the antibody against CNVSDKSC (SEQ ID NO:39) (FIG. 7F).

The target antigen mimicked by the peptide sequence CNVSDKSC (SEQ ID NO:39) was identified by standard biochemical techniques. An extract of the DU145 prostate cell line, containing cytosolic and cell membrane fractions, was prepared as disclosed above and reacted with anti-CNVSDKSC (SEQ ID NO:39) polyclonal antibody, prepared by injecting rabbits with CNVSDKSC (SEQ ID NO:39) conjugated to KLH. A single 80 KDa protein was identified by Western blotting (not shown).

The 80 kDa band was excised for protein sequencing. Five peptide sequences were obtained from the protein excised from SDS gels. All five peptides matched portions of the 78 kDa glucose regulated protein (Table 6, GRP78, SEQ ID NO:42, GenBank Accession Numbers CAB71335 and XM 044202). The locations of the five sequenced peptides within GRP78 are indicated in Table 7 in bold font. A commercial antibody against GRP78 (Santa Cruz Biotechnology, Santa Cruz, Calif.) reacted on Western blotting with the purified 80 kDa peptide C antigen from DU145 cells (not shown). The original peptide C sequence (SEQ ID NO:39) is not found within the GRP78 sequence (SEQ ID NO:42), indicating that the epitope recognized in vivo by anti-peptide C antibodies is formed from discontiguous regions of the GRP78 protein.

TABLE 7

Sequence of Human GRP78 (SEQ ID NO:42)

MKLSLVAAMLLLLSAARAEEEDKKEDVGTVVGIDLGTTYSCVGVFKNGRV

EIIANDQGNRITPSYVAFTPEGERLIGDAAKNQLTSNPENTVFDAKRLIG

RTWNDPSVQQDIKFLPFKVVEKKTKPYIQVDIGGGQTKTFAPEEISAMVL

TKMKETAEAYLGKKVTHAVVTVPAYFNDAQRQATKDAGTIAGLNVMRIIN

EPTAAAIAYGLDKREGEKNILVFDLGGGTFDVSLLTIDNGVFEVVATNGD

THLGGEDFDQRVMEHFIKLYKKKTGKDVRKDNRAVQKLRREVEKAKRALS

SQHQARIEIESFYEGEDFSETLTRAKFEELNMDLFRSTMKPVQKVLEDSD

TABLE 7-continued

Sequence of Human GRP78 (SEQ ID NO:42)

LKKSDIDEIVLVGGSTRIPKIQQLVKEFFNGKEPSRGINPDEAVAYGAAV

QAGVLSGDQDTGDLVLLDVCPLTLGIETVGGVMTKLIPRNTVVPTKKSQI

FSTASDNQPTVTIKVYEGERPLTKDNHLLGTFDLTGIPPAPRGVPQIEVT

FEIDVNGILRVTAEDKGTGNKNKITITNDQNRLTPEEIERMVNDAEKFAE

EDKKLKERIDTRNELESYAYSLKNQIGDKEKLGGKLSSEDKETMEKAVEE

KIEWLESHQDADIEDFKAKKKELEEIVQPIISKLYGSAGPPPTGEEDTAE

KDEL

The molecular mimicry between the selected peptide and GRP78 was shown by reciprocal co-immunoprecipitation with either anti-GRP78 antibody or anti-peptide CNVSDKSC (SEQ ID NO:39) antibody (not shown). Whole lysates were made from frozen tissue samples of normal prostate and bone metastasis. Equivalent amounts of protein (20 ug) were resolved on 4-20% SDS-PAGE and probed with an anti-GRP78 antibody on Western blots. GRP78 was weakly expressed in normal prostate tissue, whereas it was highly expressed in the bone metastasis from a patient with prostate cancer (not shown). Recombinant GRP78 or the GST-CNVSDKSC (SEQ ID NO:39) fusion protein were capable of blocking binding to the 80 kDa protein of the patient's serum antibodies, the anti-GRP78 antibody, and polyclonal antibodies raised against the peptide CNVSDKSC (SEQ ID NO:39) (FIG. 8). Collectively, these data demonstrate that GRP78 is the endogenous antigen against which circulating antibodies are present in a high percentage of metastatic prostate cancer patients.

Prognosis and Predictive Value of Serum Reactivity to GRP78.

GRP78 functions in antigen presentation Melnick & Argon, Immunol. Today 16:243-50 1995). Its stress-responsive promoter is strongly induced in response to glucose deprivation, acidosis, and chronic hypoxia Lee, Trends Biochem. Sci. 26:504-510, 2001). Since such conditions are generally present in poorly vascularized solid tumors, it was determined whether GRP78 is a general biomarker of the tumor microenvironment or whether its expression is specific to prostate cancer.

Figure 9:
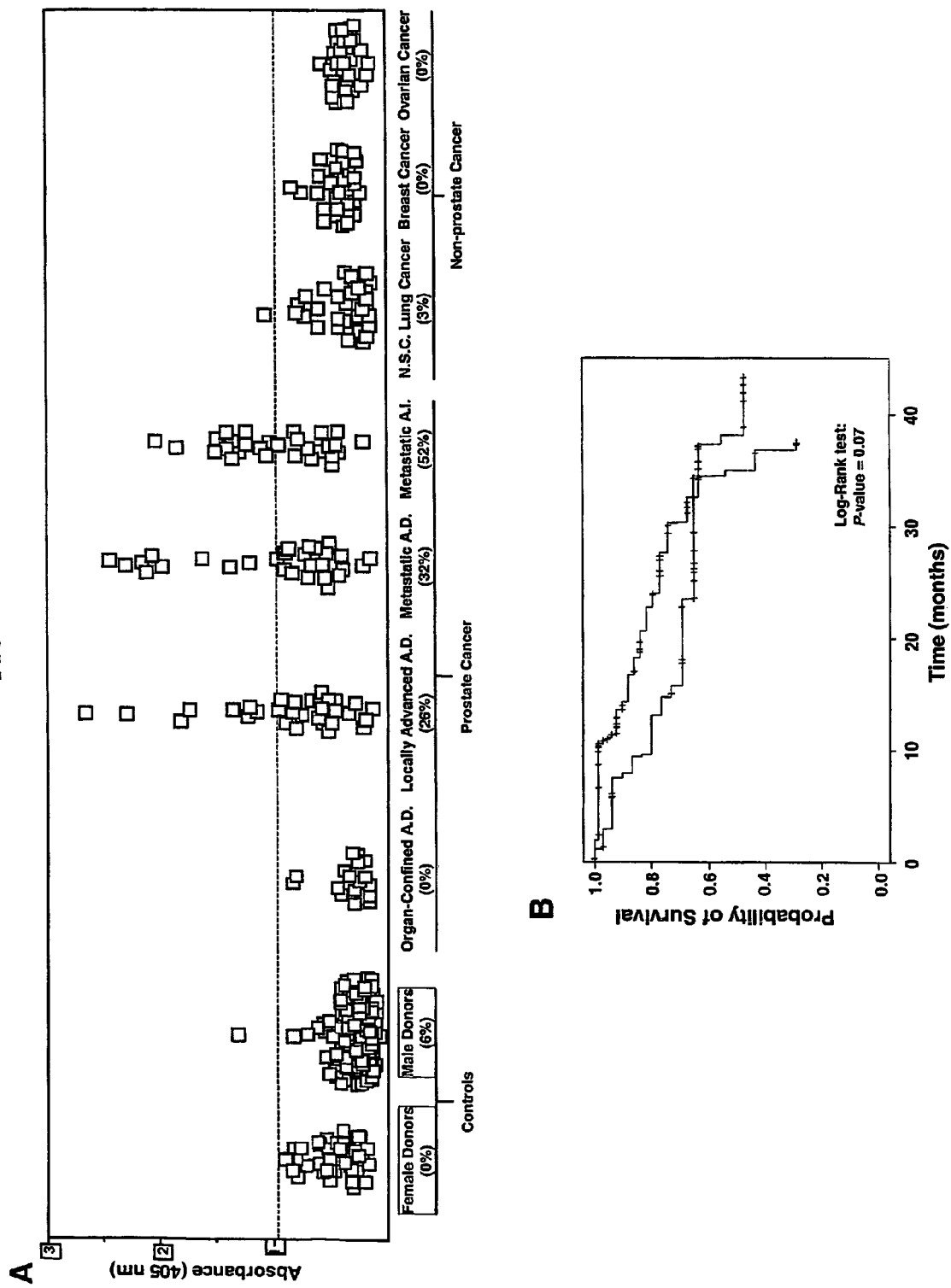
FIG. 9. Reactivity against GRP78 is a serum marker of prostate cancer. (A) Microtiter wells were coated with recombinant GRP78 and triplicates of serum samples were added at a 1:50 dilution. Serum samples from the same prostate cancer population presented in FIG. 6 were examined. For this assay, male (n=155) and female (n=48) donors served as negative controls. Positive reactivity by ELISA was defined as an Absorbance equal to or greater than 0.95 as determined by a statistical method "CART". To test whether reactivity against GRP78 was restricted to prostate cancer, three additional non-prostate cancer tumor types are shown as controls: metastatic non-small cell (N.S.C.) lung cancer (n=31), metastatic breast cancer (n=32) and advanced ovarian cancer (32). Percentages of positive reactivity are shown. (B) CART test for comparative survival of GRP78 reactive (lower line) versus non-reactive (upper line) individuals with prostate cancer.

The reactivity of serum samples obtained from prostate cancer patients and controls was evaluated against GRP78. Using a cut-off point of 0.95 absorbance as determined by the "CART" (Classification And Regression Tree) statistical method, a 26-52% positive reactivity was observed in a population of patients with advanced prostate cancer in contrast to only 6% in age-matched control men and 0% in the organ-confined group (FIG. 9A). GRP78 reactivity was also examined in the serum of three groups of non-prostate cancer patients (FIG. 9A). Significantly less reactivity against GRP78 was observed in serum from patients with metastatic non-small cell lung cancer (P<0.001), metastatic breast cancer (P<0.001) and advanced ovarian cancer (P<0.001) (FIG. 9A).

A survival curve was applied to compare the overall survival between the positive reactivity and non-reactivity groups (n=108) for GRP78 (FIG. 9B). Positive reactivity to GRP78 was associated with a shorter survival outcome (Log-Rank test, P=0.07) (FIG. 9B, lower line). Taken together, these data strongly suggest that reactivity against GRP78 is a preferential serological marker of prostate cancer relative to other malignant tumors.

Expression of GRP78 in Bone Metastasis and Normal Prostate Tissue.

Figure 10:
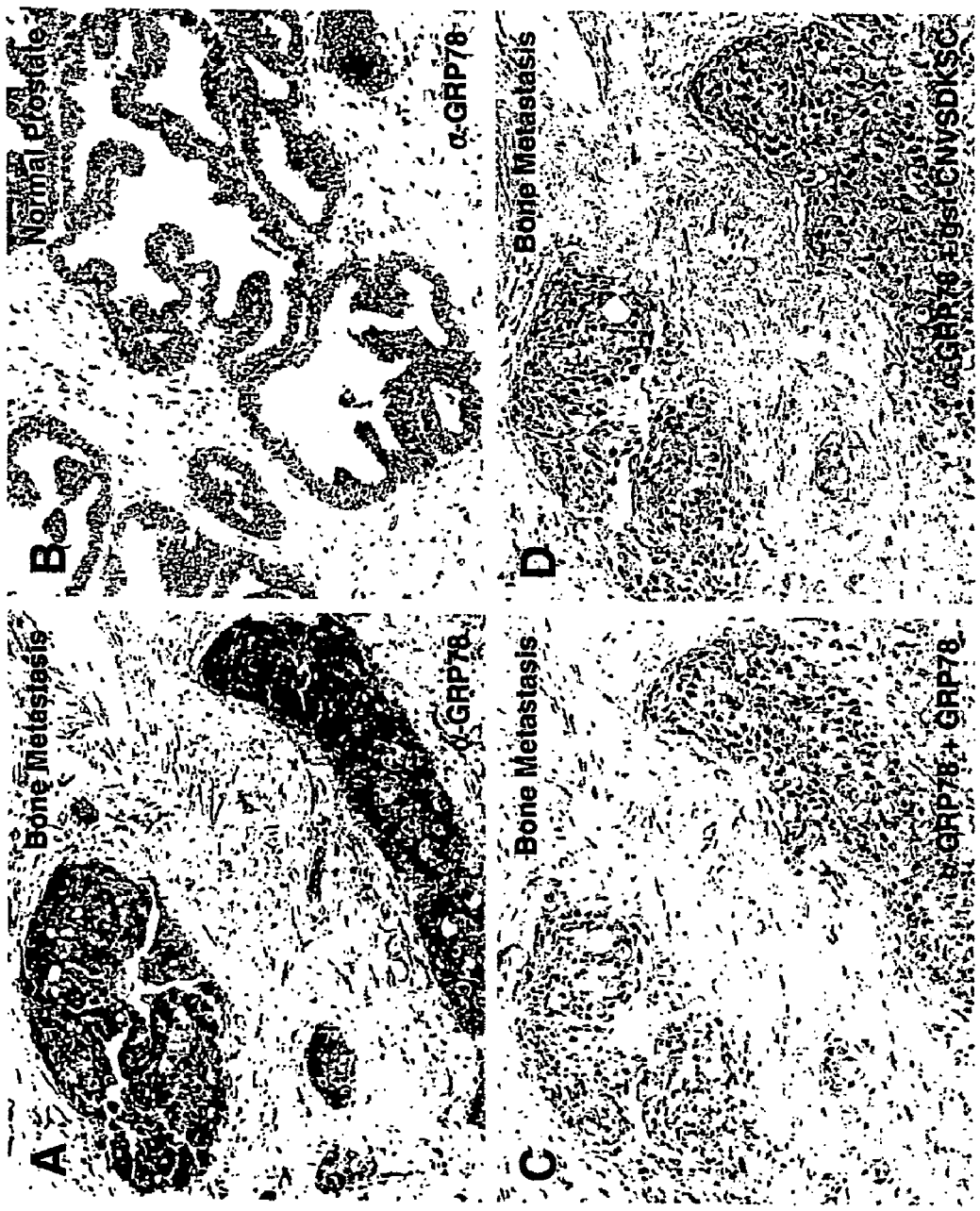
FIG. 10. Expression pattern of GRP78 by immunohistochemistry. Immunostaining of normal prostate tissue and bone metastasis by anti-GRP78 antibody and anti-CNVS-DKSC (SEQ ID NO:39) antibodies are shown. (A) Strong staining was observed in bone metastasis. (B) Weak staining was observed in the normal prostate. (C) Recombinant GRP78 can inhibit staining. (D) Recombinant GST-CNVS-DKSC (SEQ ID NO:39) also inhibits staining. The magnification=100×.

The presence of circulating antibodies against GRP78 was associated with the most aggressive stage of prostate cancer (metastatic androgen-independent disease). The expression of GRP78 was examined by immunohistochemical analysis in normal prostate tissue and bone marrow metastasis from a prostate cancer. The GRP78 antigen was highly expressed in bone marrow metastasis as shown by strong immunostaining (FIG. 10A), whereas weak staining was observed in normal prostate tissue (FIG. 10B). These results confirm the Western analysis using the same tissue samples noted above (FIG. 7F). To show specificity, staining was inhibited using recombinant GRP78 (FIG. 10C) or the peptide fusion protein GST-CNVS-DKSC (SEQ ID NO:39) (FIG. 10D). These data demonstrate that GRP78 is highly expressed in prostate cancer metastases to bone marrow and weakly expressed in normal prostate tissue.

Discussion

The present Example shows that it is possible to identify molecular markers of disease progression and survival without prior knowledge of the antigens related to the disease. In cases where the tumor antigen is unknown, disease-specific antigens identified by this approach could be employed to define common or unique features in the immune response of individuals to the same disease, i.e., to fingerprint the immune response against a given antigen. The approach presented here is based on selection of immunoglobulin-binding peptides that mimic tumor-related antigens from phage libraries. Serum samples from human prostate cancer were screened and an antibody-binding peptide ligand was validated by using a large panel of patient serum samples. The corresponding tumor antigen eliciting the immune response was identified as GRP78, a molecular marker of use for detection, diagnosis and/or prognosis of metastatic prostate cancer. The GRP78 protein is highly expressed in bone marrow metastasis and the high prevalence of circulating antibodies against GRP78 is associated with metastatic androgen-independent disease and poor prognosis.

GRP78 (also known as Hsp70 protein 5) expression is induced by cellular stress and hypoxia, conditions associated with prostate cancer. Recently, this protein has been shown to be abundant in malignant prostate tumor by two-dimensional electrophoresis and mass spectrometry (Alaiya et al., *Cell Mol. Life Sci.* 58:307-11, 2001). In addition to GRP78, other heat shock proteins, such as 90, 72, and 27, are highly expressed in malignant prostate tissue (Thomas et al., *Br. J. Urol.* 77:367-72, 1996). GRP78 associates with the major histocompatibility complex (MHC) class I on the cell surface and its presence on the cell surface is not dependent on MHC class I expression (Triantafilou et al., *Hum. Immol.* 62:764-70, 2001). Cancer-derived HSP-peptide complexes are being used as HSP vaccine in human cancer (Tamura et al., *Science* 278:117-120, 1997). A recent study showed that the expression of heat shock proteins could independently determine the clinical outcome of individual prostate cancers (Tamura et al., 1997).

Although phage peptide libraries have been used to identify various pathological and disease-related agents in patients including Lyme disease, hepatitis, HIV-1, and autoimmune diseases, this is the first report in which sera from prostate cancer patients have been used to identify new markers for this cancer.

Example 5

Biopanning Circulating Antibodies in Prostate Cancer: Antibody Progression Corresponds to Disease Progression The present Example illustrates a further embodiment of the invention, using phage display library screening to examine the progression in circulating antibodies accompanying disease progression in prostate cancer.

The methods used were similar to those described in Example 4. A subtraction protocol was used, in which IgG from a normal individual was coupled to protein G chromatography beads. A cyclic $CX_6C$ phage display library, prepared as described above, was exposed to the normal IgG's. Phage that did not bind to the normal IgG pool were collected and used for the next step. Antibodies from patient M (prostate cancer patient) were attached to fresh protein G chromatograpy beads. The phage display library that had been preexposed to normal IgG's was exposed to the IgG pool from patient M. After thorough washing of the column, the phage that bound to the prostate cancer IgG (but did not bind to normal IgG) was eluted and amplified. This procedure was followed for three rounds of screening and targeting peptides against patient M's antibodies were obtained.

Serum samples from the same patient were obtained from archival specimens and used to obtain targeting peptides. Patient M's serum from 1994 (early stage cancer), 1998 (intermediate stage) and 2000 (late stage) were used to obtain antibody targeting peptides as described above. These peptides were shown in Table 8. The numbers in parentheses indicate the number of phage exhibiting the sequence out of the total number of clones obtained.

TABLE 8

Peptides identified after three rounds of panning on purified immunoglobulins from the serum of prostate cancer patient M.

| 1994 Serum | 1998 Serum | 2000 Serum |
| --- | --- | --- |
| CTFAGSSC (6/22) (SEQ ID NO:46) | CTFAGSSC (12/20) (SEQ ID NO:46) | CTFAGSSC (26/29) (SEQ ID NO:46) |
| CNSAFAGC (1/22) (SEQ ID NO:47) | CSKKFVTC (3/20) (SEQ ID NO:62) | CNSAFAGC (1/29) (SEQ ID NO:47) |
| CSYTFAGC (1/22) (SEQ ID NO:48) | CNSAFAGC (1/20) (SEQ ID NO:47) | CFPKRVTC (1/29) (SEQ ID NO:66) |
| CSTFAGSC (1/22) (SEQ ID NO:49) | CKNKHTTC (1/20) (SEQ ID NO:63) | CPRSAKNC (1/29) (SEQ ID NO:67) |
| CRDGYHHC (1/22) (SEQ ID NO:50) | CFETFAGC (1/20) (SEQ ID NO:64) | |
| CSASDLSC (2/22) (SEQ ID NO:51) | CNNMYAGC (1/20) (SEQ ID NO:65) | |
| CQNQYPEC (1/22) (SEQ ID NO:52) | CQNQYPEC (1/20) (SEQ ID NO:52) | |
| CRASAMVC (1/22) (SEQ ID NO:53) | | |
| CIDMTHQC (1/22) (SEQ ID NO:54) | | |
| CISSPSNC (1/22) (SEQ ID NQ:55) | | |

TABLE 8-continued

Peptides identified after three rounds of panning on purified immunoglobulins from the serum of prostate cancer patient M.

| 1994 Serum | 1998 Serum | 2000 Serum |
|---|---|---|
| CNQSMWSC (1/22) (SEQ ID NO:56) | | |
| CQFENGTC (1/22) (SEQ ID NO:57) | | |
| CAVKSVTC (1/22) (SEQ ID NO:58) | | |
| CNGFMGYC (1/22) (SEQ ID NO:59) | | |
| CLTSENAC (1/22) (SEQ ID NO:60) | | |
| CRASAMVC (1/22) (SEQ ID NO:61) | | |

It is apparent that one sequence, CTFAGSSC (SEQ ID NO:46) was the predominant antibody-binding peptide in all three samples. Further, the frequency of this targeting peptide as a fraction of the total pool of targeting peptides increased with time, suggesting that the antibody that bound this peptide also became more prevalent with tumor progression. It is also apparent that the diversity of targeting peptides binding to circulating antibodies decreased with disease progression, indicating that there was a corresponding decrease in antibody diversity.

It is not unusual for tumor cells to shed antigens into the circulation. Leukocytes may also be exposed to tumor antigens in situ. It is therefore expected that cancer patients in general will exhibit cirfculating antibodies against tumor antigens. Phage display libraries may be screened against cancer patient samples to identify targeting peptides that bind to antibodies against tumor specific or tumor associated antigens. The identified targeting peptides may be used, for example, to purify anti-tumor antibodies using affinity chromatograpy or other well-known techniques. The purified anti-tumor antibodies can be used in diagnostic kits to identify individuals with cancer. Alternatively, they could be attached to various therapeutic moieties, such as chemotherapeutic agents, radioisotopes, anti-angiogenic agents or pro-apoptosis agents and used for cancer therapy. The targeting peptides against anti-tumor antibodies may also be used to identify novel tumor specific or tumor-associated antigens, of diagnostic or therapeutic use. Phage display antibody libraries may also be constructed and screened against tumor targeting peptides. By this method, it is possible to isolate and purify large quantities of antibodies specific for tumor antigens.

The skilled artisan will realize that the CTFAGSSC (SEQ ID NO:46) peptide could be used for ELISA or other immunoassays to screen the blood of individuals at risk for prostate cancer. The presence of an antibody that bound to SEQ ID NO:46 in the serum of a patient would be indicative of prostate cancer. The peptide may also be used to prepare monoclonal or polyclonal antibodies that are of use for tumor diagnosis, imaging or therapy.

Example 6

Targeted Phage-Based Vectors for Systemic Gene Delivery

Certain embodiments of the present invention concern gene therapy vectors for treatment of various cell, tissue or organ-localized disease states, such as prostate cancer. Targeting peptides may be incorporated into or attached to therapeutic vectors and administered to patients with the disease, decreasing the systemic toxicity of the therapeutic agent and increasing its targeting to the diseased tissue, thereby increasing efficacy. In particular embodiments, the gene therapy vectors of use include, but are not limited to, modified adeno-associated virus (AAV) vectors, referred to herein as adeno-associated phage (AAP) vectors. The AAP vector enables systemic and local gene delivery and robust long-term transgene expression. The vector specifically homes to receptors that have been well characterized for selective expression on the vascular endothelium. The AAP vector can deliver genes to angiogenic or tissue-specific receptors. It results in markedly increased transduction stability and duration of gene expression The development of vectors for systemic targeted delivery is required for successful gene therapy. Commonly used approaches rely on ablating the native tropism of viral vectors and/or retargeting them to alternative receptors. Thus far, a major drawback of these approaches has been that the expression of the receptors is not restricted to the target tissues.

Many malignant, cardiovascular, and inflammatory diseases have a marked angiogenic component. In cancer, tumor vasculature is a suitable target for intervention because the vascular endothelium is composed of non-malignant cells that are genetically stable but epigenetically diverse (St. Croix, B. et al., *Science* 289:1197-1202, 2000; Kolonin et al., *Curr. Opin. Chem. Biol.* 5:308-313, 2001). In vivo phage display has been used to isolate probes that home selectively to different vascular beds and target receptors expressed only on certain blood vessels. Both tissue-specific and angiogenesis-related vascular ligand-receptor pairs have been identified with this technology. Targeted delivery of cytotoxic drugs (Arap et al., *Science* 279:377-380, 1998a), proapoptotic peptides (Ellerby et al. *Nat. Med.* 5:1032-1038, 1999), fluorophores (Hong & Clayman, *Cancer Res.* 60:6551-6556, 2000) or cytokines (Curnis et al, *Nat. Biotechnol.* 18:1185-1190, 2000) to the vasculature generally improved selectivity and/or therapeutic windows in animal models. Vascular receptors are attractive targets for systemic delivery of gene therapy. Such receptors are readily accessible through the circulation and often can mediate internalization of ligands by cells (Kolonin et al., 2001).

While incorporation of vascular homing peptides derived from in vivo phage display screenings into viral vectors has been attempted, this strategy has proven quite challenging because the structure of the capsid and the targeting properties of the peptides can be adversely affected (Wickham, *Gene Ther.* 7:110-114, 2000). However, gene expression in mammalian cells is possible if phage vectors are processed in the correct trafficking pathway (Poul & Marks, *J. Mol. Biol.* 288:203-211, 1999).

In theory, phage vectors have several advantages over mammalian viruses conventionally used for gene therapy. Receptors for prokaryotic viruses such as untargeted (wild-type) phage are not expressed on mammalian cells. Receptor-mediated internalization by mammalian cells does occur if re-targeted phage vectors display certain peptide ligands (Larocca et al., *Faseb J.* 13:727-734, 1999). There is substantial evidence suggesting that phage can be safely administered to patients, as bacteriophage were given to humans during the pre-antibiotic era with no adverse effects (Barrow & Soothill, *Trends Microbiol.* 5:268-271, 1997). Because homing phage have been pre-selected to home to vascular receptors in an in vivo screening, there is no need for further targeting modifications. The localization of gene expression in vivo recapitulates previous observations using immunohistochemistry for phage localization (Rajotte et al., 1998; Rajotte & Ruoslahti, 1999; Pasqualini et al., 1997). The parental tumor-homing phage used in the present Example are known to target receptors expressed in the activated blood vessels of multiple types of human and murine tumors, including carcinomas, melanomas, and sarcomas in mouse models (Pasqualini et al., 1997; Arap et al., 1998; Koivunen et al., 1999a). The lung-homing phage and its corresponding receptor expressed in the lung vasculature have also been well characterized in mice (Rajotte et al., 1998; Rajotte & Ruoslahti, 1999).

Based on the rationale outlined above, targeted systemic gene delivery to the vascular endothelium may be accomplished with phage particles homing to cell surface receptors on blood vessels while meeting receptor requirements for selective tissue expression and vector accessibility. The results presented herein demonstrate the feasibility of this approach.

A new generation of targeted phage-based vectors is provided that enables systemic gene delivery and robust long-term transgene expression. A novel chimeric phage-based vector containing the inverted terminal repeat (ITR) sequences from adeno-associated virus (AAV) has been designed, constructed, and evaluated. As demonstrated below, these vectors (i) specifically home to receptors that have been well characterized for selective expression on the vascular endothelium, (ii) can deliver genes to angiogenic or tissue-specific blood vessels, and (iii) markedly increase transduction stability and duration of gene expression. These data indicate that targeted phage-based vectors and their derivatives are of use for clinical applications, such as targeted delivery to prostate cancer.

Materials and Methods

Reagents, Cells, and Tissue Culture

All of the restriction enzymes (New England Biolabs, Beverly, Mass.), T4 DNA ligase (Roche, Indianapolis, Ind.), topotecan (Sigma Chemical Company, St. Louis, Mo.), and cisplatin (Sigma) were obtained commercially. The fMCS1 plasmid was obtained from Dr. George P. Smith (University of Missouri, Mo.). DNA sequence analysis was performed with the Big Dye® terminator sequence kit (Perkin Elmer/ABI Systems, Norwalk, Conn.). All peptides used in this Example were synthesized at greater than 95% purity, cyclized, and analyzed by HPLC and mass spectrometry (AnaSpec, San Jose, Calif.). Targeting peptides used in this Example included the GFE (CGFECVRQCPERC, SEQ ID NO:68); HWGF (CTTHWGFTLC, SEQ ID NO:69) and RGD-4C (CDCRGDCFC, SEQ ID NO:70) peptides.

The human cell lines used were Kaposi's sarcoma (KS1767), 293 embryonic kidney (ATCC; Manassas, Va.), and MDA-MB-435 breast carcinoma. Cell lines were maintained in minimal essential medium (MEM; Irvine Scientific, Santa Ana, Calif.) supplemented with 10% fetal calf serum (FCS; Gibco-BRL, Rockville, Md.) plus sodium pyruvate, L-glutamine, and penicillin/streptomycin (Gibco-BRL).

Construction of Phage-based Targeted Expression Vectors

Figure 11:
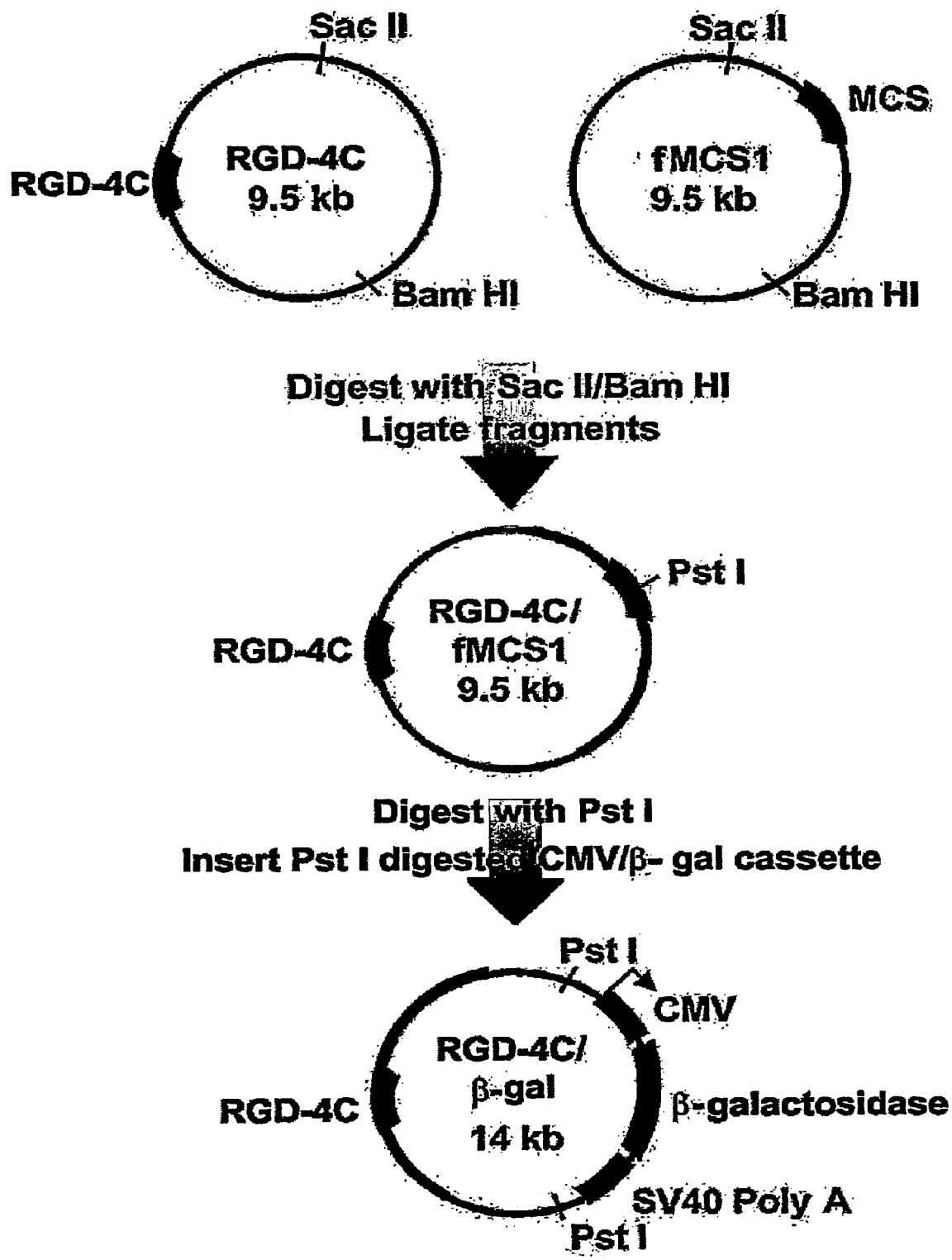
FIG. 11. Scheme of the construction of phage with a targeting domain and a mammalian reporter gene cassette. Replicative forms of the phage-derived RGD-4C and the fd-tet derived fMCS1 DNA were digested with Sac II and Bam HI. Ligation of the FMCS1 fragment with the RGD-4C plasmid fragment resulted in a chimeric RGD-4C-fMCS1 phage vector with a multicloning site containing a Pst I site. The Pst I-digested β-gal gene cassette was cloned into the Pst I site of the chimeric vector RGD-4C-fMCS1. The mammalian transgene cassette contains a CMV promoter, a β-galactosidase (β-gal) gene, and an SV40 polyadenylation signal (SV40 polyA). The other targeted and control phage vectors presented in this study were constructed by the same general strategy.

The FUSE5-based filamentous phage display vector was modified by inserting into an intergenic region of the phage genome a β-galactosidase (β-gal) coding sequence under the control of a CMV promoter. Targeted RGD4C-β-gal phage vector was engineered in a two-step process that included the generation of an intermediate construct (termed RGD-4C-fMCS1) and subsequent production of RGD-4C-β-gal. The overall construction scheme is illustrated in FIG. 11. RGD-4C-fMCS1 contained the oligonucleotide insert encoding the RGD-4C targeting peptide, inserted into the Sfi I site of the gene III minor coat protein of the FUSE5 phage, and a fragment of the fMCS1 plasmid that had a multicloning site (MCS) for insertion of transgenes. RGD-4C phage-derived fUSE5 DNA and fd-tet phage-derived fMCS1 DNA were purified from lysates of host bacteria (*E. coli* MC1061). The intermediate RGD-4C-fMCS1 vector was constructed by ligating a 5.4-kb BamHI/SacII fragment of the RGD-4C plasmid to the 4.1 kb BamHI/SacII fragment of the fMCS1 plasmid. Next, a 14 kb RGD-4C-β-gal phage plasmid was obtained by insertion of a 4.5 kb PstI CMV-β-gal fragment derived from pCMVβ (Clontech, Palo Alto, Calif.) into the PstI site of RGD-4C-fMCS1. This strategy allowed cloning of the CMV-β-gal cassette in either forward or reverse orientation.

Orientations of resulting vectors were differentiated by EcoRV restriction analysis and by DNA sequencing. Targeted phage vectors were designated fRGD4C-β-gal (forward) and rRGD4C-β-gal (reverse). Other targeting (HWGF-βgal, GFE-β-gal) phage and insertless control (fd-βgal) phage were constructed through the same strategy. The targeting phage were designed to target integrins (RGD-4C) and the MMP-2 and MMP-9 matrix metalloproteinases (HWGF), expressed in angiogenic vasculature. The GFE phage were designed to target membrane dipeptidase (MDP) expressed in lung vasculature.

Figure 32:
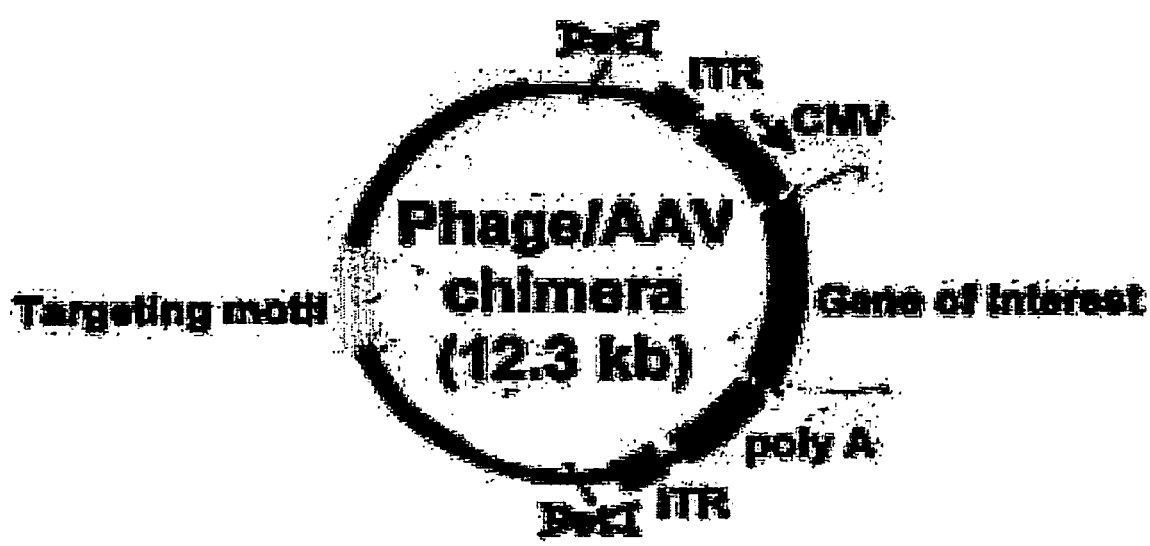
FIG. 32. AAP construction. The AAP vector was constructed as disclosed in Example 6.

A targeted phage/AAV chimeric vector was created by cloning a 2.8 kb fragment of pAAV-eGFP (enhanced GFP; Stratagene) from ITR (inverted terminal repeat) to ITR into the PstI site of RGD-fMSC. Briefly, pAAV was digested with PacI to release a 2.8 kb fragment, which was blunted with DNA polymerase and cloned into the blunted PstI site of RGD-fMSC (thus destroying the PstI restriction site). The final AAP vector construct is illustrated in FIG. 32. The 12.3 kb DNA contains a targeting motif inserted into gene III, a gene of interest (e.g., β-gal) inserted between the AAV ITR elements under control of a CMV promoter and with a poly A terminator. The locations of the deleted Pst I sites are also shown (crossed out). In each of the constructs, correct orientation of insert was verified by restriction analysis. Single clones in each orientation were sequenced. Unless otherwise stated, the forward vectors were used.

Phage DNA Transfection into Mammalian Cells

The double-stranded DNAs of the replicative forms of targeted (RGD-4C-β-gal, HWGF-β-gal, GFE-β-gal) and insertless control (fd-β-gal) constructs were prepared by using the Plasmid Maxi kit (Qiagen). The single-stranded DNAs of the infective forms of the phage vectors were extracted from the phage capsid proteins by using the Strataclean resin (Stratagene), followed by two ethanol precipitations. DNA was quantified by spectrophotometry with 1.0 $A_{260}$ equal to 40 µg/ml for single-stranded DNA or 50 µg/ml for double-stranded DNA. The 293 recipient cells were transfected with 5 µg of either double-stranded or single-stranded phage DNA into $5 \times 10^5$ cells by using the SuperFect® reagent (Qiagen) according to the manufacture's protocol. Both the gene expression and enzyme activity of β-gal were evaluated at least 48 hours post-transfection. Cells were incubated with the X-gal substrate for 3 hours at 37° C. and enzyme activity was visualized by using an in situ β-galactosidase staining kit (Stratagene) according to the manufacturer's instructions.

Vector Production, Purification, and Titration

Phage vectors were isolated and purified from the culture supernatant as disclosed (Pasqualini et al., in *Phage Display: A Laboratory Manual* (Barbas et al., eds.), chap. 22, pp. 1-24, Cold Spring Harbor Laboratory Press, Cold Spring Harbor, N.Y., 2000). Phage were re-suspended in Tris-buffered saline (pH 7.4) and re-centrifuged to remove residual bacteria and debris. The resulting supernatant containing the phage in suspension was filtered through a 0.45 µm filter and titered according to standard protocols (Pasqualini et al., 2000).

Targeted phage vector transduction and specific inhibition by using synthetic peptides. MDA-MB-435 breast cancer and KS1767 Karposi's sarcoma cells were cultured on 8-well chamber glass slides. The culture media was replaced by 200 µl of MEM with 2% FCS and $5 \times 10^{10}$ TU of RGD-4C-β-gal, HWGF-β-gal, or fd-β-gal phage vectors (at $10^5$ transducing units/cell in each case). Both cell lines express high levels of the integrin and MMP receptors for those targeting peptides. Phage were incubated with cells for 3 hr at 37° C., followed by a medium change to MEM plus 10% FCS. The cells were incubated for 72 hr at 37° C. to allow for β-gal gene expression.

In the peptide inhibition studies, MDA-MB-435 cells were cultured on 12-well plates and then incubated with 10 µg of RGD-4C peptide or control peptides (CARAC, SEQ ID NO:71 or CKDRFERC, SEQ ID NO:41) in normal growth media for 30 minutes. KS1767 cells were grown on 12-well plates and then incubated with 40 µg CTTHWGFTLC (SEQ ID NO:69) or control peptides in normal growth media for 30 minutes. The growth media were replaced by 500 µl of MEM containing 2% FCS and $5 \times 10^{10}$ transducing units (TU) of either RGD-4C-β-gal, HWGF-β-gal, or control fd-β-gal phage. Phage vectors were incubated on peptide-treated cells (three hours at 37° C., 5% $CO_2$) followed by a media change to MEM plus 10% FCS. Transduced cells were maintained in a cell incubator for 72 hours (37° C., 5% $CO_2$).

In the cell culture transduction assay, β-gal expression was analyzed by immunofluorescence. For quantification of expression in cell culture, the transduced cells were washed with PBS and permeabilized with 0.2% Triton X-100 for five minutes on ice, followed by blocking with 1% BSA in PBS. An anti-β-gal antibody (Sigma) diluted to 1:2,000 in blocking solution was then incubated with the cells overnight. Next, a Texas Red-conjugated secondary antibody (Caltag, Burlingame, Calif.) diluted to 1:600 in PBS was incubated with the cells for 1 hour. The degree of β-gal gene expression was determined by counting fluorescent cells in at least ten fields under an inverted microscope (Nikon, Japan). Quantification of the β-gal activity in cell culture was measured as relative light units (RLU) in a luminometer and then normalized to the amount of protein in micrograms, as determined by the Lowry method in a protein assay kit (Bio-Rad Protein Assay®; Hercules, Calif.). Subsequently, blue cells were counted under an inverted microscope (Nikon).

In the peptide inhibition assays, β-gal activity in cell lysates was detected by the Galacto-Star® chemiluminescent reporter gene system (Tropix, Bedford, Mass.) according to the manufacturer's protocol. In other peptide inhibition assays, 293 cells were plated at $3 \times 10^5$ cells/well and incubated with either 1 mg/ml of RGD-4C peptide or unrelated control peptides (CARAC, SEQ ID NO:71 or CKDRFERC, SEQ ID NO:41). After 30 minutes, cells were washed and $10^5$ TU of phage per cell were added for 4 hours in serum free media After the 4 hours, 10% FCS supplemented medium was added. Cells were analyzed for GFP gene expression at 72 hours post infection. For GFP detection, cells were analyzed by fluorescence activated cell sorting (FACS) in a FAC-Scan (Becton-Dickinson, San Jose, Calif.) or counted and photographed under a fluorescence microscope (Nikon).

For time course of gene expression assays, cells were plated at $3 \times 10^5$ cells/well and infected with $10^5$ TU of phage per cell for 4 hours in serum-free media. After 4 hours, 10% FCS supplemented medium was added. Cells were visualized 72 hours post-infection and sorted by FACS for GFP expression 7 days after infection. GFP-positive cells were plated in T75 tissue culture flasks and serial assays of GFP expression as described above were made weekly for the next 60 days.

Genotoxic Agents.

Semi-confluent MDA-MB-435 cells were infected with $10^5$ TU of phage per cell for 4 hours in serum free media, after which fresh medium supplemented with FCS was added (no phage were washed out or removed). In some experiments, a phage admixture of forward and reverse clones at $10^{10}$ TU (forward/reverse molar ratio=1) was tested. Next, cells were incubated for 36 hours followed by the addition of genotoxic drugs (topotecan, 10 µM; cisplatin, 10 µM) or administration of UV radiation (15 $J/m^2$) with a cross-linker apparatus (UV Stratalinker Model 2400; Stratagene). At 72 hours post-infection, the cells were analyzed for transduction of a reporter gene (β-gal or GFP), and gene expression was normalized per cell number relative to controls.

In vivo Transduction of Tumor Xenografts and Normal Lung in Mouse Models.

Female 4-month old nude mice and female 4-month old immunocompetent C57Bl/6 mice (Harlan Sprague Dawley, San Diego, Calif.) were used in this study. Avertin (0.015 ml/g) was used as an anesthetic. Tumor xenografts derived from human Kaposi's sarcoma KS1767 cells were established by injecting tumor cells ($10^6$ cells per mouse in 200 µl of serum-free MEM) into the mammary fat pad of nude mice. Tumor-bearing mice with matched tumor sizes were used for systemic gene transfer experiments 20 to 40 days afterwards when tumors reached 0.5 to 1.5 cm in diameter.

In tumor transduction experiments, RGD-4C-β-gal, HWGF-β-gal, and fd-β-gal phage ($10^9$ TU/mouse) were injected intravenously (tail vein) into female nude mice carrying subcutaneous tumor xenografts. One week after vector administration of the targeted or control phage, tumors and control organs (liver, brain) were surgically harvested under deep anesthesia and the mice euthanized. β-gal expression in the tumor and control tissues was detected by an anti-β-gal antibody by using a peroxidase-based immunodetection kit (Vector Labs, Burlingame, Calif.).

In lung transduction studies, GFE-β-gal phage and fd-β-gal control phage ($10^9$ TU/mouse) were injected intravenously into female C57Bl/6 mice. Lungs and livers were harvested two weeks after vector administration. For in vivo experiments involving tissue extracts, β-gal activity in the lung and control tissues were detected by a chemiluminescent assay system (Tropix). Several assays for β-galactosidase were used in different studies to ensure that the results were not assay-dependent and were reproduced with distinct methods.

AAP Vector for Delivery of Therapeutic Genes to Tumors

The efficacy of the AAP vector to deliver therapeutic genes to Karposi's sarcoma tumors in nude mice was evaluated. The most frequently used system of gene delivery consists of transferring the Herpes simplex virus type 1 (HSV-1) thymidine kinase (TX) gene into tumor cells, followed by treatment with Ganciclovir (GCV). This guanosine analogue is specifically monophosphorilated by the viral kinase and then converted by cellular enzymes into the triphosphate derivative, which, upon incorporation into elongating DNA, induce cell death, by premature chain termination. To determine whether AAP vector could be used for systemic gene therapy delivery, the β-gal cassette was replaced with a "suicide" gene (thymidine kinase—TK). The resulting RGD-4C-AAP-TK vector was injected intravenously in nude mice bearing human KS1767 Kaposi's sarcoma xenografts. Targeting, internalization and transduction of the therapeutic AAP vector into the tumor cells, followed by treatment with GCV should result in cell death.

Molecular Characterization of AAP Vectors

Viral rescue experiments were performed in AAP-transduced 293 cells by infecting them with Ad5 (MOI of 10 particles/cell). After 48 hours the cells were processed to obtain a crude viral lysate, then heat inactivated to remove contaminating adenovirus. The resulting material was next used to infect 293 cells and 8431 cells. GFP-expressing cells were detected after 48 hours. PCR analysis was performed by analysis of genomic DNA extracted from AAP-transduced 293 cells and from control cells. Genomic DNA (200 µg/reaction) was reacted with GFP specific primers (GFP-N, bp 143-164; GFP-C, bp 654-676). After 30 PCR cycles, the presence of a diagnostic 490 bp band is evaluated. To ensure specific amplification, pCMV-GFP DNA was used as a positive control and pCMV DNA was used as a negative control. Southern Blot analysis was performed with Eco RI-digested genomic DNA extracted from AAP-transduced 293 cells and controls. The digests were electrophoresed and hybridized with a $^{32}$P-labeled cDNA fragment containing an AAV-specific probe. The presence of a diagnostic 2.3 kb band was evaluated.

Results

Targeted Phage Vectors Designed to Drive Gene Expression in Eukaryotic Cells.

The fUSE5-based filamentous phage display vector (Smith & Scott, 1993) was modified by inserting the β-galactosidase (β-gal)-encoding gene under the control of a CMV promoter into an intergenomic region of the phage genome to construct a fUSE5-β-gal backbone vector. Next, DNA olignonucleotide sequences encoding the targeting peptides CDCRGDCFC (SEQ ID NO:70, "RGD-4C"), CTTHWGFTLC (SEQ ID NO:69, "HWGF") or CGFECVRQCPERC (SEQ ID NO:68, "GFE") were inserted into the Sfi I site of the gene III minor coat protein (pIII) of the phage. Phage produced in this manner display 3-5 copies of the targeting peptides per viral particle.

The resulting viral constructs (RGD-4C-β-gal, HWGF-β-gal, and GFE-β-gal) were used for production of targeted phage particles that display each of the targeting peptides and carry a CMV-β-gal transgene (FIG. 11). RGD-4C-β-gal and HWGF-β-gal were designed to target αv integrins and matrix metalloproteinases (MMP-2 and MMP-9), respectively, expressed in angiogenic vasculature. GFE-β-gal was designed to target membrane dipeptidase (MDP) expressed in lung vasculature. The strategy depicted in FIG. 11 was used to construct the other targeting and control vectors.

Phage DNA Context Permits Transgene Expression in Mammalian Cells

Figure 12:
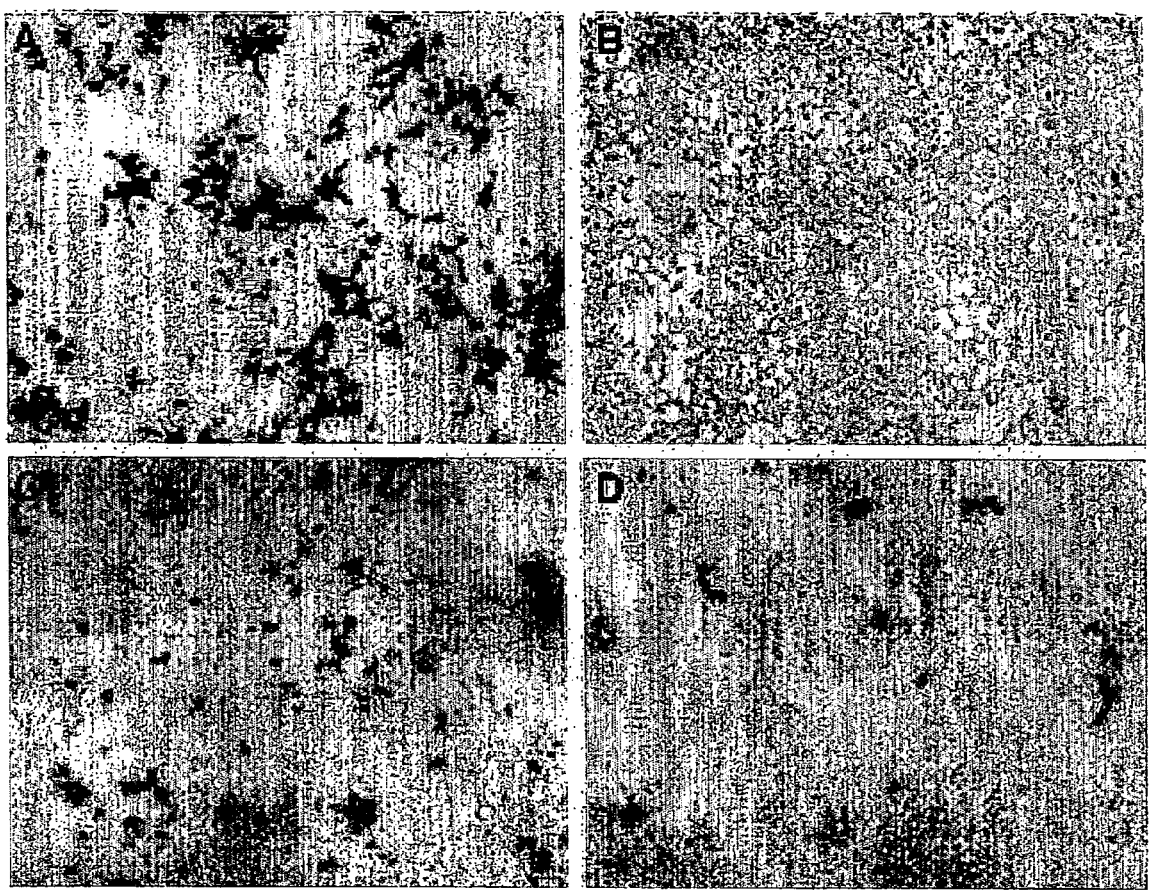
FIG. 12. Transgene expression in mammalian cells after transfection of single-stranded phage DNA into 293 cells. β-gal expression was analyzed by an X-gal staining after 24 hours. (A) Positive control plasmid pCMVβ-gal. (B) Negative control plasmid without the reporter gene cassette. (C) Single-stranded DNA extracted from phage with a forward orientation of the transgene cassette. (D) Single-stranded DNA extracted from phage with a reverse orientation of the transgene cassette.

To determine whether the inserted β-gal cassette was functional, embryonic human kidney cells were transfected with the infective forms of the phage DNA, constructed to contain the reporter transgene in either forward or reverse orientation. A CMV-driven mammalian expression vector was used as a positive control (FIG. 12A) and an empty vector as a negative control (FIG. 12B) for β-gal expression. Transfer of the modified single-stranded DNA of the phage infective form promoted transgene expression in mammalian cells. Furthermore, the orientation of the transgene cassette did not significantly influence the level of gene expression (FIG. 12C vs. FIG. 12D). All subsequent experiments used the vector with the β-gal expression cassette in the forward orientation. Given that single-stranded DNA does not support gene expression in mammalian cells and that the infective forms of the phage genome are single-stranded, these results strongly suggest that the single-stranded phage genome must be first converted to double-stranded DNA in recipient cells before allowing gene expression.

Consistent with this hypothesis, DNA from replicative forms of the phage, which are double-stranded, expressed the β-gal transgene several fold more efficiently at levels comparable to the mammalian expression vector used as the positive control (data not shown).

Receptor-mediated Internalization and Specific Transduction of Recipient Cells by Targeted Phage Vectors in vitro.

Having shown that the transgene constructs were functional, transduction of human cell lines expressing the receptors targeted by RGD-4C-β-gal and HWGF-β-gal phage vectors was examined. The untargeted fUSE5-derived control phage vector (fd-β-gal) was used as a negative control. RGD-4C-β-gal phage (FIG. 13C-D) and HWGF-β-gal phage (FIG. 13A-B) were incubated with breast cancer (FIG. 13C-D) and Kaposi's sarcoma (FIG. 13A-B) cells (MDA-MB-435 and KS1767 lines), respectively. Both cell lines express high levels of the RGD-4C-receptors αvβ3 and αvβ5 integrins and of the HWGF receptors MMP-2 and MMP-9.

β-gal transduction was observed of 14±2% (mean±standard error of the mean; SEM) of MDA-MB-435 cells incubated with RGD-4C-β-gal phage and 12±2% (mean±SEM) of the KS1767 cells incubated with HGWF-β-gal (FIG. 14A). Comparable transduction results were also obtained by incubating HWGF-β-gal on MDA-MB-435 cells and RGD-4C-β-gal on KS1767 cells (data not shown). Control phage (fd-β-gal) were not internalized when incubated with either cell line and only minimal β-gal transduction (~0.1% of the tumor cells) could be detected (FIG. 14A).

To demonstrate specificity, transduction with RGD-4C-β-gal and HWGF-β-gal phage was blocked by pre-incubating the target cells with the corresponding synthetic peptides (FIG. 14B-C). In each case, almost complete inhibition of transduction was observed, of greater than 99% with RGD-4C peptide (FIG. 14C) and greater than 90% with CTTHWGFTLC (SEQ ID NO:69) peptide (FIG. 14B) in a dose-dependent manner. Pre-incubation with nonspecific negative control peptides had no significant effects on transduction of the recipient cells (FIG. 14 B-C). These data show that transduction of mammalian cells by internalized phage vectors in vitro is substantial, specific, and mediated by ligand-receptor mechanisms.

Targeted Transduction of Tissue-specific and Tumor Vasculature Upon Systemic Administration in vivo To determine whether the targeted RGD-4Cβ-gal and HWGF-β-gal phage vectors could selectively transduce tumors upon systemic administration, each vector was administered intravenously into nude mice bearing human KS1767 Kaposi's sarcoma xenografts. KS1767 cells are suitable because they form well-vascularized tumors and the receptor expression profiles in tumor cells and tumor-associated blood vessels has been characterized (Pasqualini et al., 1997; Arap et al., 1998a, 1998b; Koivunen et al., 1999a). The αv integrins and gelatinases (MMP-2 and -9) receptors for the targeting peptides are highly expressed on the KS1767-derived tumor xenografts and their angiogenic vasculature. Phage displaying RGD-4C and HWGF peptides target KS1767 tumors efficiently and specifically in vivo. Tumor targeted phage were not detected in control tissues studied, including brain, kidney, pancreas, adrenal, skin, muscle, intestine, lymph nodes, uterus, prostate, and fat (Pasqualini et al., 1997; Arap et al., 1998a, 1998b; Koivunen et al., 1999a).

Tumors and control organs were surgically harvested one week after administration of the vectors. Tumor and control organs (liver and brain) were immunostained with an anti-β-gal antibody. The RGD-4C-β-gal (FIGS. 15A, D and G), HWGF-β-gal (FIGS. 15B, E, and H), and control fd-β-gal (FIGS. 15C, F, and I) vectors were analyzed.

Figure 15:
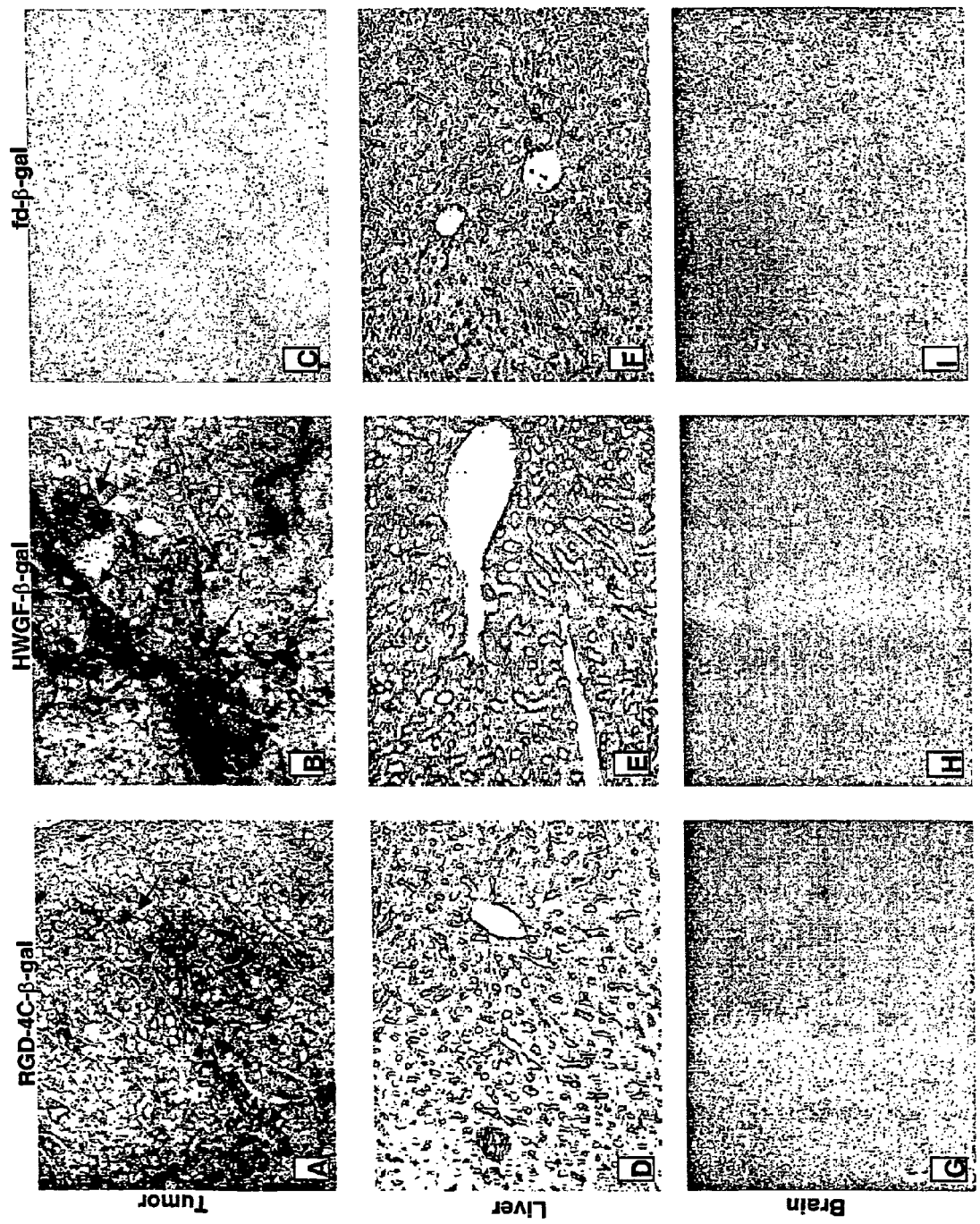
FIG. 15. Specific transduction in vivo by tumor-targeting phage. Immunohistochemical analysis of β-gal expression after systemic administration of targeted or control phage into tumor-bearing mice was performed. RGD-4C-β-gal (A, D, and G), HWGF-β-gal (B, E, and H), or control phage (C, F, and I) were injected intravenously into mice bearing KS1767-derived Kaposi's sarcoma xenografts. At seven days post-administration, tumors and control organs were removed, fixed in 4% paraformaldehyde, embedded in paraffin, and sectioned. An antibody anti-β-gal (Sigma) was used for staining. Liver (D, E, and F) and brain (G, H, and I) are shown as control organs. Magnification: ×400. Arrows point to anti-β-gal immunoreactivity.
Figure 16:
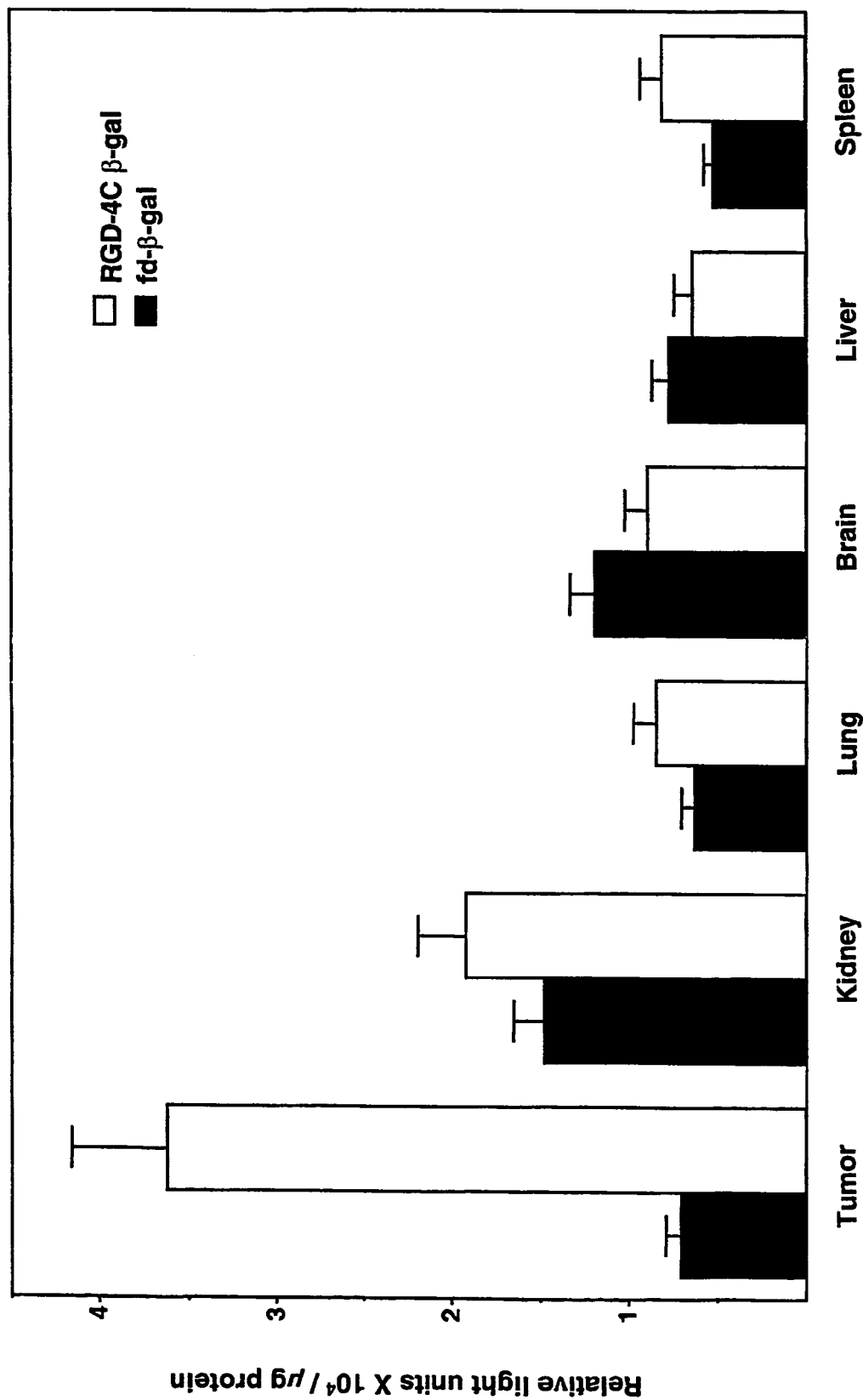
FIG. 16. Tumor-selective targeting by RGD-4C β-Gal phage, compared to control insertless phage. The ability of different tissues to be infected by the tumor targeting versus control phage was examined for tumor, kidney, lung, brain, liver and spleen tissues. Although a comparatively high level of RGD-4C phage were localized to kidney, the difference between tumor-targeting and control phage distribution was not significant. Only tumor tissue showed a significant enhancement of phage localization for the RGD-4C phage compared to control phage.

Strong β-gal immunostaining was observed in tumor tissues (FIGS. 15A and B), with negligible immunostaining observed in control liver and brain organs (FIGS. 15D, E, G and H). In contrast, tissues recovered from mice that received untargeted negative control fd-β-gal phage vector did not show detectable β-gal expression in either the tumor (FIG. 15C) or the control organs (FIGS. 15F and I). In each case, β-gal reactivity matched the corresponding immunostaining pattern of phage targeting to the vascular endothelium of blood vessels in tumors (Pasqualini et al., 1997; Arap et al., 1998; Koivunen et al., 1999). A non-β-gal-containing phage produced no staining in the liver (data not shown). Measuring β-gal activity produced results consistent with the immunohistochemistry data used for detection of targeted gene transduction (FIG. 16).

Figure 17:
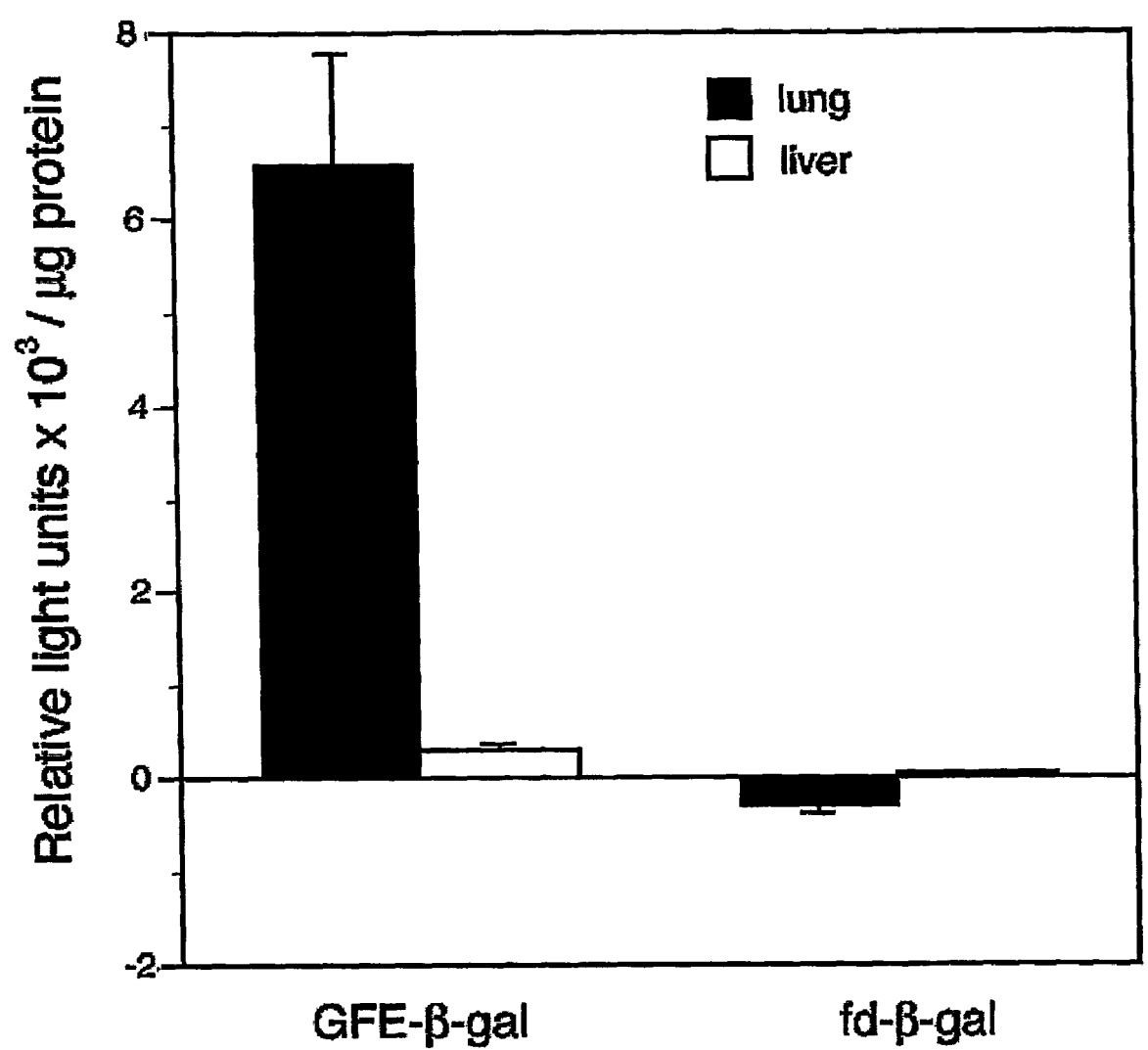
FIG. 17. Specific transduction in vivo by lung-targeting phage. Lung (targeted organ) and liver (control organ) were evaluated for β-gal expression after systemic administration of GFE-phage or control phage into C57Bl/6 immunocompetent mice. At 14 days post-administration lungs and livers were removed and processed as described in the text. β-gal enzymatic activity in the tissue cell lysates was measured by chemiluminescence. Shown are mean±SEM (n=5 mice per group).

Targeted gene delivery was also evaluated in vivo by using GFE-β-gal, a phage vector targeted to MDP in the vascular endothelium of lung blood vessels (Rajotte & Ruoslahti, 1998). The lung-homing GFE-β-gal vector was injected intravenously into immunocompetent C57Bl/6 mice. Substantial β-gal activity was seen in the lungs of mice injected with GFE-β-gal phage but not in the lungs of mice injected with fd-β-gal control (FIG. 17). In contrast, the β-gal activity in the liver of mice injected with the GE-β-gal phage was similar to that of background β-gal activity from mice injected with control phage (FIG. 17). Taken together, these results show in vivo systemic gene delivery and transduction targeted to and mediated by vascular receptors selectively expressed in tumors, and in normal organs.

Increase in Transduction by Genetic Trans-complementation.

Figure 18:
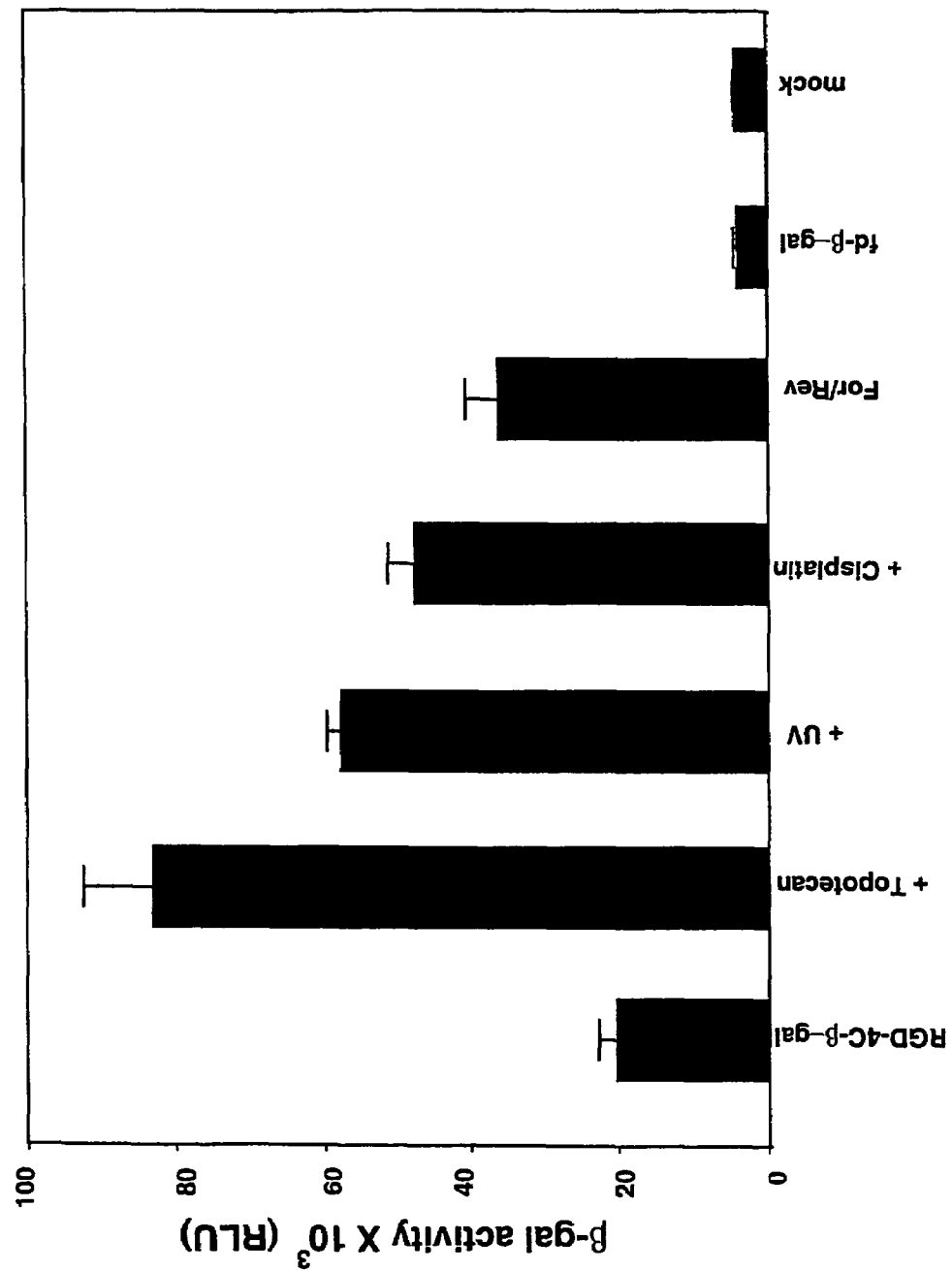
FIG. 18. Enhancement of transduction by genotoxic agents or genetic trans-complementation. Semi-confluent MDA-MB-435 cells were infected with $10^5$ TU of phage per cell for four hours. Next, the cells were incubated for 36 hours followed by addition of genotoxic drugs (topotecan, 10 μM; cisplatin, 10 μM) or application of physical agents such as ultraviolet radiation (UV; 15 J/m$^2$). A phage mixture of RGD-4C-βgal forward and reverse clones (molar ratio=1; termed For/Rev) at the same number of phage TU of RGD-4C-βgal phage was also tested. At 72 hours post-infection, the cells were analyzed for expression of a reporter transgene. Shown are mean±SEM (n=3) normalized green fluorescent protein (GFP) expression relative to controls.
Figure 19:
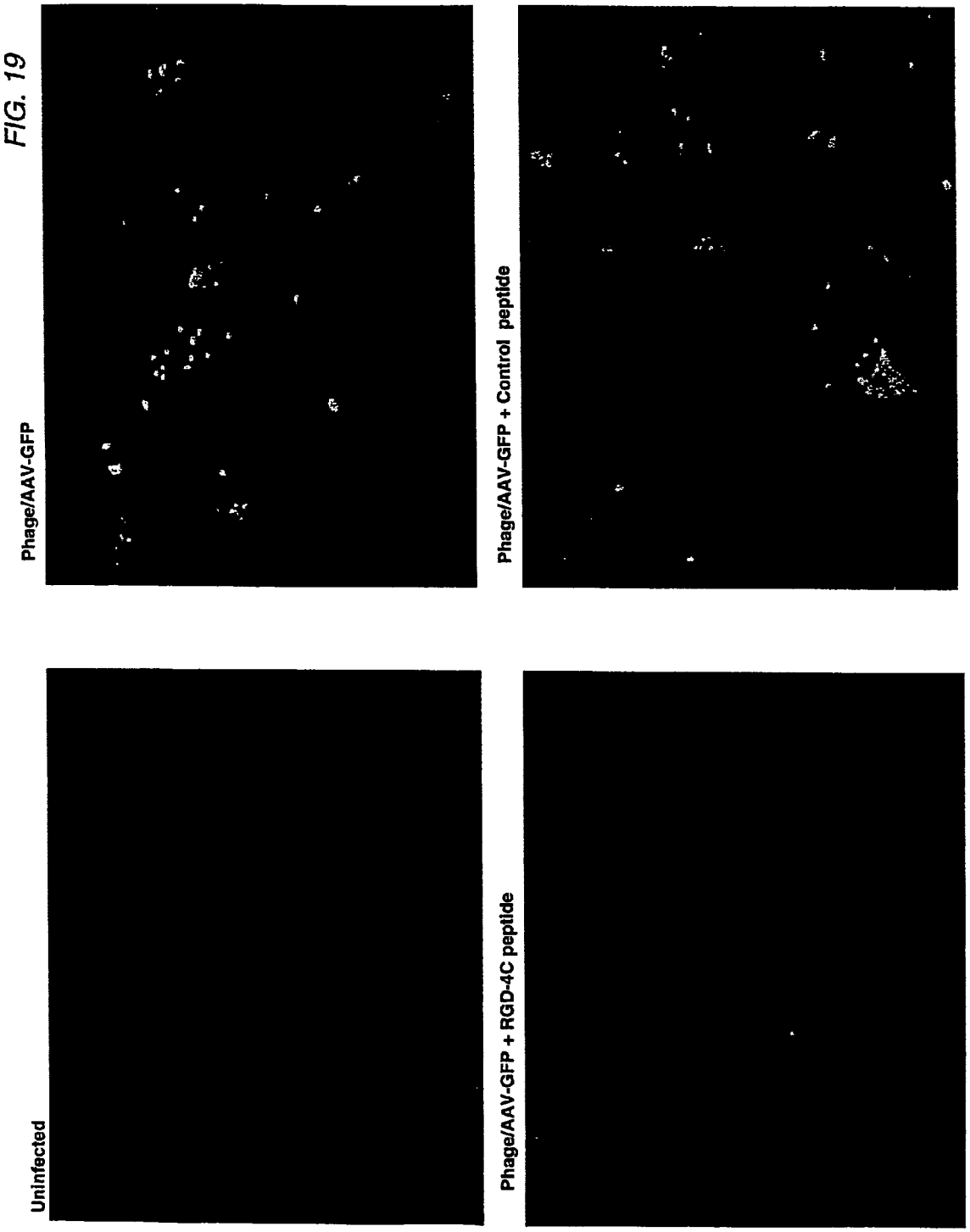
FIG. 19. AAP vectors markedly improve gene transduction stability. Vectors were constructed by cloning a full-length 2.8 kb fragment of pAAV-eGFP (Green Fluorescent Protein, Stratagene) from inverted terminal repeat (ITR) to ITR into the blunted PstI site of the construct presented in FIG. 11. An engineered chimeric vector composed of an RGD-4C targeted phage and AAV genetic cis-elements was incubated with cells and analyzed for GFP gene expression 72 hours after infection as indicated. Either synthetic RGD-4C peptide or control unrelated peptide (CKDRFERC, SEQ ID NO:41) was pre-incubated with cells to confirm specificity of targeted gene transduction.

Because the genome from the infective form of M13-derived phage is single-stranded, conversion to double-stranded DNA is required to allow gene expression. It was hypothesized that genotoxic agents that promote DNA repair would enhance the transduction of genes carried by single-stranded phage vectors. To test this hypothesis, cells infected by targeted phage vectors were challenged with genotoxic agents such as ultraviolet (UV) radiation and cancer chemotherapy drugs (topotecan and cisplatin). This approach consistently resulted in gene transduction several fold higher than various controls (FIG. 18). Interestingly, an equal mixture of forward and reverse single-stranded phage clones showed a two-fold increase in gene expression relative to the same molar concentrations of either forward or reverse phage (FIG. 18). It is postulated that the presence of both sense and anti-sense of the reporter gene allowed hybridization of the strands to occur. Such facilitation in gene expression is consistent with the requirement for double-stranded DNA. The enhancement of gene expression by DNA lesions or genetic trans-complementation indicates that conversion to double-stranded DNA is a rate-limiting step in developing of effective phage vectors. These data also suggest the possibility of synergism if cytotoxic agents commonly utilized in clinical applications are used in combination with phage-derived vectors.

Phage/AAV Chimeric Vectors Markedly Improve Gene Transduction Stability.

Figure 20:
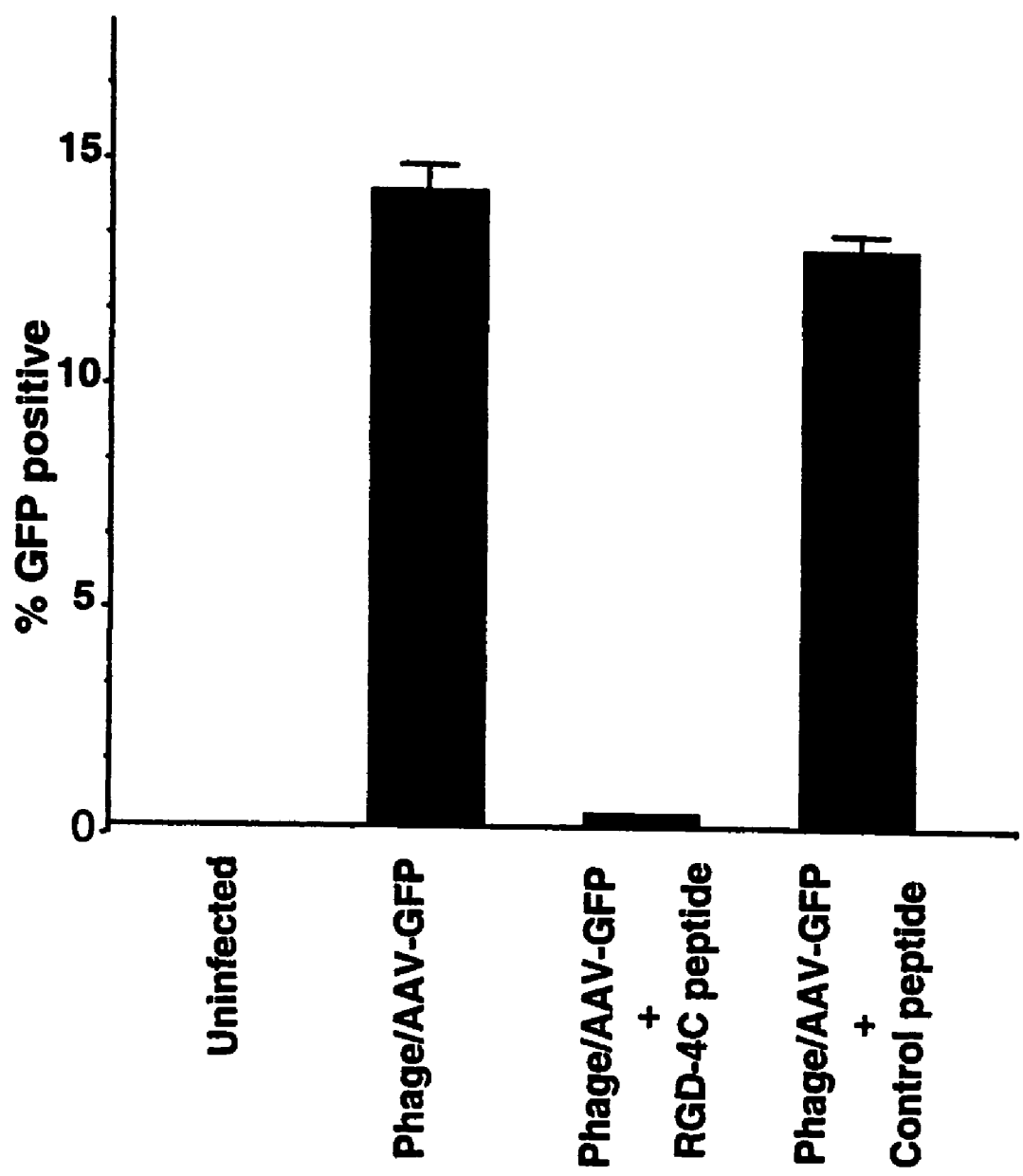
FIG. 20. GRP expression in cells infected with an AAV-GFP vector, in the presence or absence of RGD-4C peptide or control peptide. For GFP detection, cells in each experiment were analyzed by fluorescence activated cell sorting (FACS) and photographed under a fluorescence microscope.

To solve the DNA conversion problem described above, it was determined whether the incorporation of genetic cis-elements derived from AAV (a single-stranded mammalian virus) into targeted phage-based constructs would affect gene transduction. First, chimeric vectors composed of a targeted phage and an AAV genome from inverted terminal repeat (ITR) to ITR was designed and engineered. Vectors were constructed by cloning a full-length 2.8 kb fragment of pAAV-eGFP (Green Fluorescent Protein, Stratagene) from inverted terminal repeat (ITR) to ITR into the blunted PstI site of the construct presented in FIG. 11. The targeting properties of the resulting chimeric vectors were not altered by insertion of AAV genetic elements. Specific inhibition by the corresponding synthetic peptide was again observed (FIG. 20) indicating that the phage targeting features were intact.

Having established that the tropism of the targeted vector was preserved, the effects of AAV genome insertion on transgene expression was assessed. While the levels of gene expression remained unchanged (data not shown), the duration of gene transduction was markedly prolonged relative to the parental targeted phage. Robust long-term expression of the reporter gene was observed beyond eight weeks (FIG. 21). This finding is in clear contrast to the one-week transgene expression usually observed with the parental targeted phage vector in vitro (Table 9). Table 9 represents relative reporter gene expression in 293 cells transfected with targeted phage versus AAP, using triplicate wells for each time point. Results represent averaged independent determinations by two different investigators. Expression in the standard targeted phage vector disappeared after 10 days, while some expression was observed in AAP vectors for at least 60 days.

TABLE 9

Transgene expression in vitro

| | Post-infection day # | | | | | | | | | |
|---|---|---|---|---|---|---|---|---|---|---|
| | 0 | 5 | 0 | 0 | 5 | 0 | 5 | 0 | 5 | 0 |
| Targeted phage | + | | | | | | | | | |
| AAP | + | + | + | + | + | + | + | + | | |

Tumor targeted transgene expression was also observed in vivo after systemic AAP administration in mice bearing MDA-MB-435 xenografts. Such transduction was specific because it was blocked by co-administration of cognate—but not unrelated control—synthetic peptides (not shown).

The combination of genotoxic agents plus insertion of AAV cis-elements appears to be at least additive if not synergistic (data not shown). Gene expression in cells transduced with targeted phage/AAV chimeric vectors has been systematically followed for up to 60 days (Table 8). Expression of GFP has been detected for as long as 90 days (not shown). To rule out the possibility of genetic complementation by trans-acting factors (for example, E4 or f6) in the permissive 293 cell line, the transduction of HepG2 (liver carcinoma-derived) and MDA-MB-435 cells was examined. Similar levels and duration of gene expression were observed (data not shown).

To characterize the AAP chimeric vectors, studies were performed to detect AAV elements in cells transduced with AAP vectors and to demonstrate excision, amplification, and integration (FIG. 22). Adenoviral rescue (FIG. 22), PCR (not shown) and Southern Blot analysis (not shown) demonstrate that (i) AAV particles can be generated using the supernatant from cells infected with AAP; and (ii) AAV elements integrate within the genome in cells transduced with targeted AAP, but not control phage vectors (targeted or untargeted).

These data indicate that phage/AAV chimeric (AAP) vectors may be readily constructed and used with no apparent losses in their targeted acquired tropism and with substantial enhancement in the long-term stability of the genes transduced.

Delivery of Therapeutic Genes into Tumors

An AAP vector designed to contain a "suicide" TK gene was constructed as described above and injected into nude mice containing Karposi's sarcoma human tumors. Seven (7) days after vector injection, mice received daily intraperitoneal injections of GCV (5 mg/Kg/day) for 7 days. Tumors in animals injected with RGD-4C-TK-AAP vector, followed by GCV treatment, showed significant growth reduction, comparing to tumors in the control animals which were injected with insertless fd-AAP-TK vector prior to GCV treatment. These results demonstrate the feasibility of using AAP vectors for targeted delivery of therapeutic genes to tumors and other tissues for which selective and/or specific targeting peptide sequences have been identified. The skilled artisan will realize that the AAP vector described herein is not limited to targeted delivery to tumor tissues, but may be used for targeted gene therapy of a wide variety of organs, tissues or cell types.

Discussion

The present Example shows for the first time that systemic gene delivery can be achieved by genetically adapting targeted phage clones selected from screenings of phage display random peptide libraries. The characteristics of an efficient phage-based gene therapy vector include: [1] selectivity towards target tissues; [2] receptor-mediated cell internalization; and [3] long-term duration of gene transduction upon delivery. Each of these characteristics was exhibited by the AAP vectors disclosed herein.

Targeting peptides can be integrated into conventional gene therapy vectors or even used as bi-functional molecular adaptors (Larocca et al., 1999; Wickham, 2000; Grifman et al., Mol. Ther. 6:964-975, 2001; Trepel et al., Hum. Gene Ther. 11:1971-81, 2000). These strategies have proven to be technically challenging and not necessarily efficient. Issues of specificity and efficiency have been addressed by taking advantage of peptide ligands selected from phage libraries in vitro and in vivo. The targeting phage obtained in screenings performed in vivo are often selected using a 3-minute circulation timeframe. Thus, it is unlikely that the phage exits the circulation. The selection strategy is designed to favor vascular targeting and the isolation of phage that target markers that are accessible to circulating ligands (i.e., expressed in cells forming vascular endothelium).

Given that selection has already occurred for those particular clones, it is likely that such phage would meet criteria for tissue targeting. Here, it was demonstrated that the null-tropism of wild-type phage towards mammalian cells can be modified to target and deliver genes to receptors expressed on the vascular endothelium of normal organs (such as the lung) and tumors. Thus, the phage vectors introduced by this study have a number of potential advantages. Their targeting to selective vascular beds is based on receptor expression patterns that are known and characterized. The receptors are accessible to circulating probes. These ligand-receptor pairs provide internalization of the vector into targeted cells.

While it has been shown that phage can promote gene expression in vitro, gene transduction in vivo after systemic administration of a targeted phage vector has not as yet been reported. A major limitation in the practical use of phage vectors has been poor levels of transduction achieved in vivo. A possible cause of this is the low efficiency of conversion from single-stranded to double-stranded DNA occurring in mammalian cells. To solve this problem two independent strategies were applied: (i) enhancement of gene transduction by genotoxic agents (cytotoxic drugs and UV radiation) which cause strand breaks and promote DNA repair; and (ii) genetic incorporation of AAV cis-elements into targeted phage vectors. The strategies are not mutually exclusive and may be used together to further improve the efficiency of gene therapy in vivo.

The term adeno-associated phage (AAP) is used for the new class of vectors for gene delivery described here. The biological features of AAP are distinct from either targeted phage or AAV. While the enhanced duration of gene transduction by AAP is similar to the long-term expression patterns associated with AAV transduction, the receptor-mediated targeting is characteristic of phage clones selected in screenings. Thus, AAP are endowed with several advantages as a gene therapy vector. AAP are easy to produce in high titers in host bacteria. No helper viruses or trans-acting factors are needed. The native tropism of AAV for human cells is eliminated because there is no AAV capsid formation. The AAP vectors are presumed targeted because they incorporate peptides that have been isolated in vivo and are defined by their ability to home to selective vascular beds. Gene transduction stability was compared between a targeted phage and AAP vectors. Targeted gene delivery specific to the ligand-receptor pair to which the phage is directed is possible, and gene expression is maintained for over two months (possibly because of DNA integration).

The results reported herein demonstrate that the targeting properties are preserved in the hybrid AAP (a feature conferred by the phage) and that gene expression elicited by such vectors is robust (a feature conferred by the AAV elements). Data with the AAP in vivo appear to confirm these contentions (not shown).

In summary, genetically modified phage have potential to be adapted as targeted gene delivery vectors to mammalian cells after systemic administration. Based on the favorable targeting properties and long-term duration of gene transduction of AAP, these vectors are of use as superior gene delivery tools.

The skilled artisan will realize that the AAP vectors are not limited to the targeting peptides used in the present Example, but rather may take advantage of any of the targeting peptides known in the art or disclosed herein, such as the prostate cancer targeting peptides described above. Such AAP gene therapy vectors, designed to contained cytostatic, cytotoxic, pro-apoptotic, anti-angiogenic or other therapeutic genes may be selectively and/or specifically targeted to tissues, such as cancer tissues, prostate cancer tissues, and/or metastatic prostate cancer tissues to provide a high efficacy of tumor treatment, while exhibiting little or no systemic toxicity.

Example 7

Identification of Mouse Adipose Targeting Peptides

The present Example concerns compositions and uses of novel adipose targeting peptides and receptors. In certain embodiments, the peptides and receptor targets may be of use for targeted delivery of therapeutic agents to tumors and/or normal adipose tissues.

Adipose Targeting Peptides

A substractive phage display protocol (see Example 8 below) was used to isolate fat targeting peptides from a genetically obese mouse (Zhang et al., Nature, 372:425-432, 1994; Pelleymounter et al., Science 269:540-543, 1994). Phage that had been subjected to biopanning in obese mice were post-cleared in a normal mouse. The fat-targeting peptides isolated included TRNTGNI (SEQ ID NO:72), FDGQDRS (SEQ ID NO:73); WGPKRL (SEQ ID NO:74); WGESRL (SEQ ID NO:75); VMGSVTG (SEQ ID NO:76), KGGRAKD (SEQ ID NO:77), RGEVLWS (SEQ ID NO:78), TREVHRS (SEQ ID NO:79) and HGQGVRP (SEQ ID NO:80).

Homology searches identified several candidate proteins as the endogenous analogs of the fat targeting peptides, including stem cell growth factor (SCGF) (KGGRAKD, SEQ ID NO:77), attractin (mahogany) (RGEVLWS, SEQ ID NO:78), angiopoietin-related adipose factor (FIAF) (TREVHRS, SEQ ID NO:79), adipophilin (ADRP) (VMGSVTG, SEQ ID NO:76), Flt-1 or procollagen type XVII (TRNTGNI, SEQ ID NO:72) and fibrillin 2 or transferrin-like protein p97 (HGQGVRP, SEQ ID NO:80)

Validation of Adipose Targeting Peptides

Figure 23:
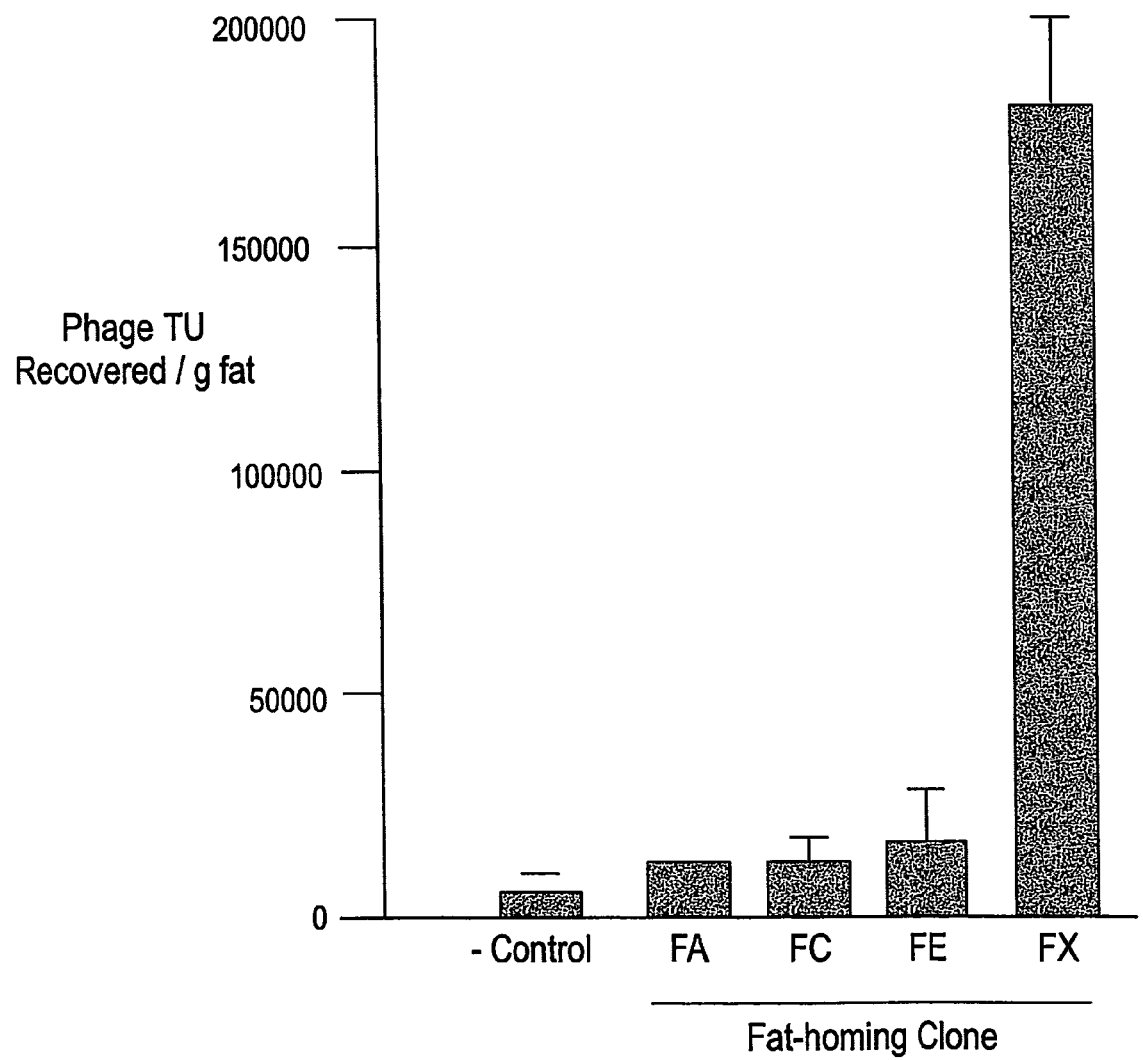
FIG. 23. Validation of adipose homing peptides. Phage bearing targeting peptides were injected into obese mice and their recovery from adipose tissue was compared to control fd-tet phage without targeting sequences.

The fat homing peptides were validated by in vivo homing, as shown in FIG. 23. The fat homing clones selected were: FA—KGGRAKD (SEQ ID NO:77), FC—RGEVLWS (SEQ ID NO:78), FE—TREVHRS (SEQ ID NO:79) and FX—VMGSVTG (SEQ ID NO:76). As seen in FIG. 23, all of these clones exhibited some elevation of homing to adipose tissue, with clone FX showing several orders of magnitude higher adipose localization than control fd-tet phage. Clone FX also exhibited substantially higher localization than the other selected fat homing clones. However, by analogy with the placental homing peptides disclosed above, the skilled artisan will realize that fat homing clones exhibiting lower levels of adipose tissue localization may still be of use for targeted delivery of therapeutic agents.

The skilled artisan will realize that targeting peptides selective for angiogenic vasculature in adipose tissue could be of use for weight reduction or for preventing weight gain. By attaching anti-angiogenic or toxic moieties to an adipose targeting peptide, the blood vessels supplying new fat tissue could be selectively inhibited, preventing the growth of new deposits of fat and potentially killing existing fat deposits.

Example 8

CKGGRAKDC (SEQ ID NO:81) Homes to White Fat in ob/ob Mice

Materials and Methods
Experimental Animals

C57BL/6 mice were purchased from Harlan Teklad. Leptin-deficient (ob/ob) (stock 000632) and leptin receptor-deficient (stock 000642) mice were purchased from Jackson Laboratories (Bar Harbor, Me.). Anesthesia was performed with Avertin (0.015 ml/g) administered intraperitoneally (Arap, et al., 1998; Pasqualini & Rouslahti, 1996).

In vivo Phage Library Screening

In vivo phage-display screening of the $CX_7C$ library (C, cysteine; X, any amino acid) (Pasqualini et al., 2000; Arap et al., Nature Med. 8:121-127, 2002) for fat-homing peptides was performed (Pasqualini & Rouslahti 1996, Pasqualini et al., 2000). In each biopanning round, an adult ob/ob mouse was injected intravenously (tail vein) with $10^{10}$ transducing units (TU) of the library. Phage (~300 TU/g in round 1 increased to ~$10^4$ TU/g in round 3) were recovered after 5 min of circulation by grinding subcutaneous white fat with a glass Dounce homogenizer, suspending the homogenate in 4° C. Dulbecco's Modified Eagle's medium (DMEM) containing proteinase inhibitors (DMEM-prin: 1 mM PMSF, 20 µg/ml aprotinin, and 1 µg/ml leupeptin) and washing with DMEM-prin. The lipid phase was discarded during the washes and only the solid-phase cellular material was used. Washed homogenates were incubated with host bacteria (log phase E. coli K91kan; $OD_{600}$~2). Bacterial cultures were plated onto Luria-Bertani agar plates containing 40 µg/ml tetracycline and 100 µg/ml kanamycin, incubated overnight at 37° C. and selected clones were bulk-amplified and used to precipitate phage for a subsequent round of biopanning. The sub-library amplified after the third round of panning was enriched for fat-specific binders using a subtraction step. A lean C57BL/6 female was injected (tail vein) with $10^9$ TU of phage selected in round 3. After 5 min of circulation, the unbound phage were recovered from plasma and amplified for the fourth and final round of biopanning. In this protocol, phage that bound to tissues other than adipose were removed from the sub-library, increasing the selectivity of the recovered phage for binding to adipose tissue.

Peptide Localization in Tissues

Staining of formalin-fixed, paraffin-embedded mouse tissue sections was performed (Pasqualini & Rouslahti, 1996; Pasqualini et al., 2000). For phage-peptide immunolocalization, $10^{10}$ TU of CKGGRAKDC (SEQ ID NO:81)-phage or a control insertless phage was injected intravenously. Phage immunohistochemistry was performed using a rabbit anti-fd phage antibody (Sigma Chemicals, St. Louis, Mo.) used at 1:1,000 dilution and a secondary horseradish peroxidase (HRP)-conjugated antibody. Apoptosis was detected using standard TUNEL immunohistochemistry and an HRP-conjugated antibody. For in vivo peptide homing validation, stocks of 5-carboxyfluorescein (FITC)-conjugated CKGGRAKDC (SEQ ID NO:81) or CARAC (SEQ ID NO:71) were chemically synthesized, cyclized using the terminal cysteines and HPLC-purified to >90% purity by Anaspec (San Jose, Calif.). Lyophilized peptides were dissolved in DMSO to a concentration of 20 mM. Ten µl of 1 mM peptide-FITC solution in PBS was injected 5 min prior to tissue extraction. For blood vessel localization, 10 µl of 2 mg/ml of rhodamine-conjugated lectin-I (RL-1102, Vector Laboratories, Burlingame, Calif.) was co-injected. All immunohistochemistry and FITC immunofluorescence images were captured using an Olympus IX70 microscope and digital camera setup (Melville, N.Y.).

Anti-obesity Therapy

Stocks of CKGGRAKDC (SEQ ID NO:81) fused to $(KLAKLAK)_2$ (SEQ ID NO:1); $(KLAKLAK)_2$ (SEQ ID NO:1) alone; CARAC (SEQ ID NO:71) fused to $(KLAKLAK)_2$ (SEQ ID NO:1); and CKGGRAKDC (SEQ ID NO:81) peptide were chemically synthesized, cyclized using the terminal cysteines and HPLC-purified to >90% (Anaspec). Lyophilized peptides were dissolved in DMSO to a concentration of 65 mM to make stock solutions. A total of 150 µl of 0.65 mM peptide solution in PBS was subcutaneously injected daily in the back of C57BL/6 males, after body mass was measured each day. High-fat cafeteria diet for obesity induction (TD97366: 25.4% fat, 21.79% protein, 38.41% carbohydrate) was purchased from Harlan Teklad. Mice were pre-fed with TD97366 prior to the initiation of treatment with adipose targeting peptides to induce diet-related obesity. The high-fat diet resulted in an average weight of 50 g before treatment.

Results

In vivo phage display (Pasqualini and Ruoslahti, Nature 380:364-366, 1996; Kolonin et al., Curr. Opin. Chem. Biol. 5:308-313, 2001; Pasqualini et al., In Vivo Phage Display, In Phage Display: A Laboratory Manual, eds. Barbas et al., pp. 1-24. Cold Spring Harbor Laboratory Press, New York, 2000) was used as described above to obtain a peptide targeting the fat vasculature. A phage-display library was screened for peptide motifs that home to the vasculature of subcutaneous white fat in morbidly obese leptin-deficient (ob/ob) mice (Zhang et al. *Nature* 372:425-432, 1994). This model provides a convenient source of adipose tissue. Four rounds of panning were followed by a fat-specific in vivo subtraction to restrict ligands to those binding to adipose-specific endothelial receptors. The DNA encoding the corresponding phage-displayed peptides was then sequenced to obtain the targeting peptide amino acid sequences. Statistical analysis of selected motifs using SAS software (version 8, SAS Institute) revealed that the motif CKGGRAKDC (SEQ ID NO:81) constituted 4.5% of all clones identified in the screen. Intravenous administration of this clone into ob/ob mice showed that CKGGRAKDC (SEQ ID NO:81)-phage accumulated in subcutaneous fat to a higher level than a control insertless phage (data not shown).

Figure 24:
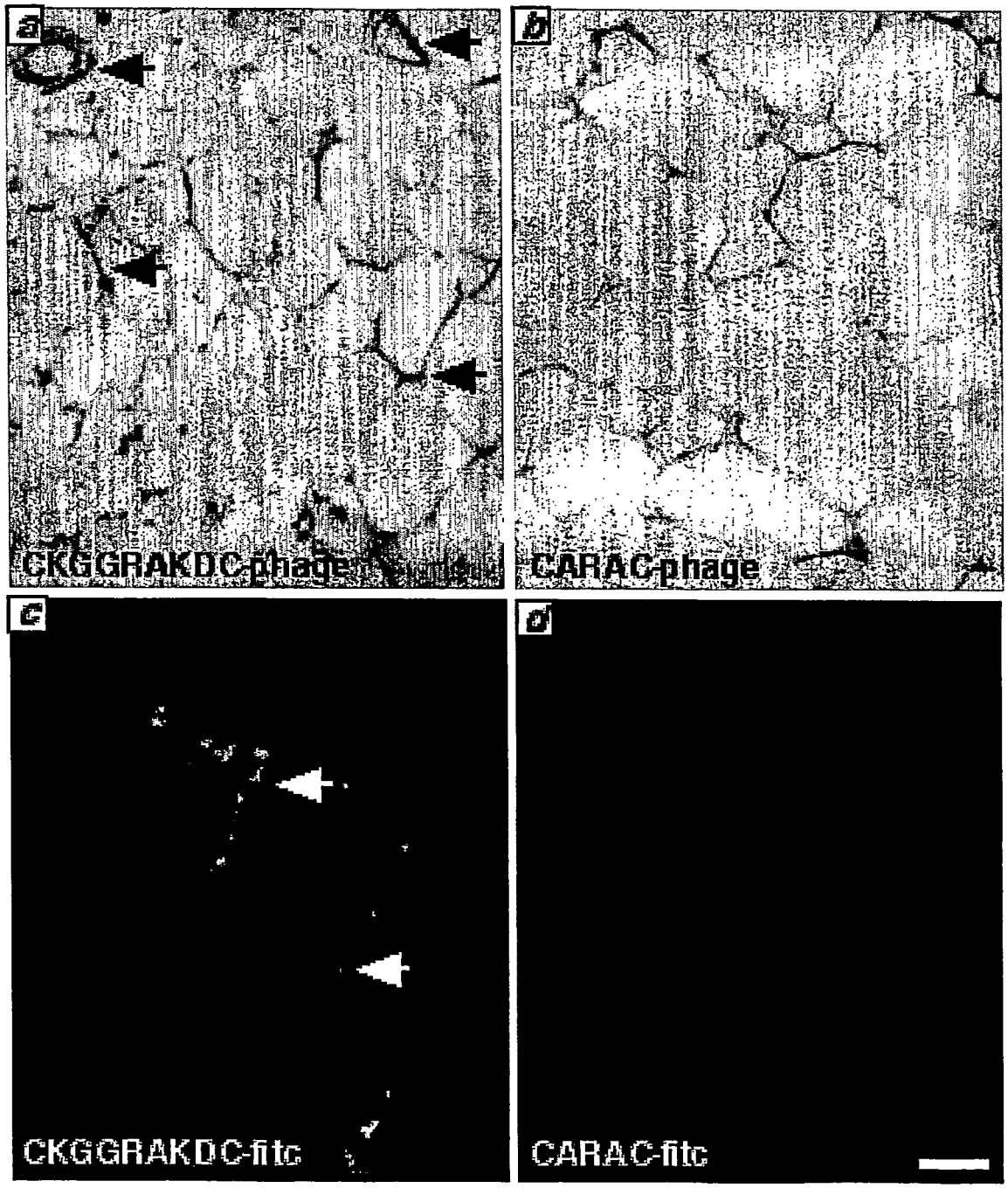
FIG. 24. In vivo fat homing of the CKGGRAKDC (SEQ ID NO:81) motif in genetically obese mice. (A) and (B) Antiphage immunohistochemistry in paraffin sections of subcutaneous white fat from leptin-deficient mice intravenously injected 6 hr prior to tissue processing. (C) and (D) Peptide-FITC immunofluorescence in paraffin sections of subcutaneous white fat from leptin-deficient mice intravenously injected 6 hr prior to tissue processing. Mice were injected with (A) CKGGRAKDC (SEQ ID NO:81) phage, (B) control insertless phage, (C) CKGGRAKDC (SEQ ID NO:81) linked to FITC peptide, or (D) control CARAC (SEQ ID NO:71) linked to FITC peptide. Homing of the CKGGRAKDC (SEQ ID NO:81) peptide to fat blood vessels (arrows) and its uptake by fat endothelium are indicated. Bar: 10 µm.

The tropism of CKGGRAKDC (SEQ ID NO:81)-phage for adipose tissue was confirmed by immunohistochemistry: CKGGRAKDC (SEQ ID NO:81)-phage showed marked localization to the vasculature of subcutaneous and peritoneal white fat (FIG. 24a, arrows), whereas the control phage was undetectable in fat blood vessels (FIG. 24b). To test whether targeting of the CKGGRAKDC (SEQ ID NO:81) motif to the fat vasculature would also occur when the peptide is outside of the context of the phage, the in vivo distribution of intravenously injected CKGGRAKDC (SEQ ID NO:81) peptide fused to fluorescent (FITC) was determined. Immunofluorescence in subcutaneous and peritoneal fat from peptide-injected ob/ob mice showed that CKGGRAKDC (SEQ ID NO:81)-FITC localized to and was internalized by cells of white adipose vasculature (FIG. 24c, arrows), whereas a control CARAC (SEQ ID NO:71)-FITC conjugate was undetectable in adipose tissue (FIG. 24d).

CKGGRAKDC (SEQ ID NO:81) Homes to White Fat in Wild-type Mice

The mutation in leptin that leads to the extreme proliferation of white adipose tissue in mice (Zhang et al., 1994) is not frequently encountered in humans (Ozata et al., *J. Clin. Endocrinol. Metab.* 84:3686-3695. 1999). Thus, this animal model may not be representative of the typical pattern of obesity in humans. To exclude the possibility that CKGGRAKDC (SEQ ID NO:81) homing to fat is limited to ob/ob mice and to demonstrate the general applicability of adipose-targeting peptides for naturally-occurring obesity, the CKGGRAKDC (SEQ ID NO:81) peptide was tested in wild-type mice.

Figure 25:
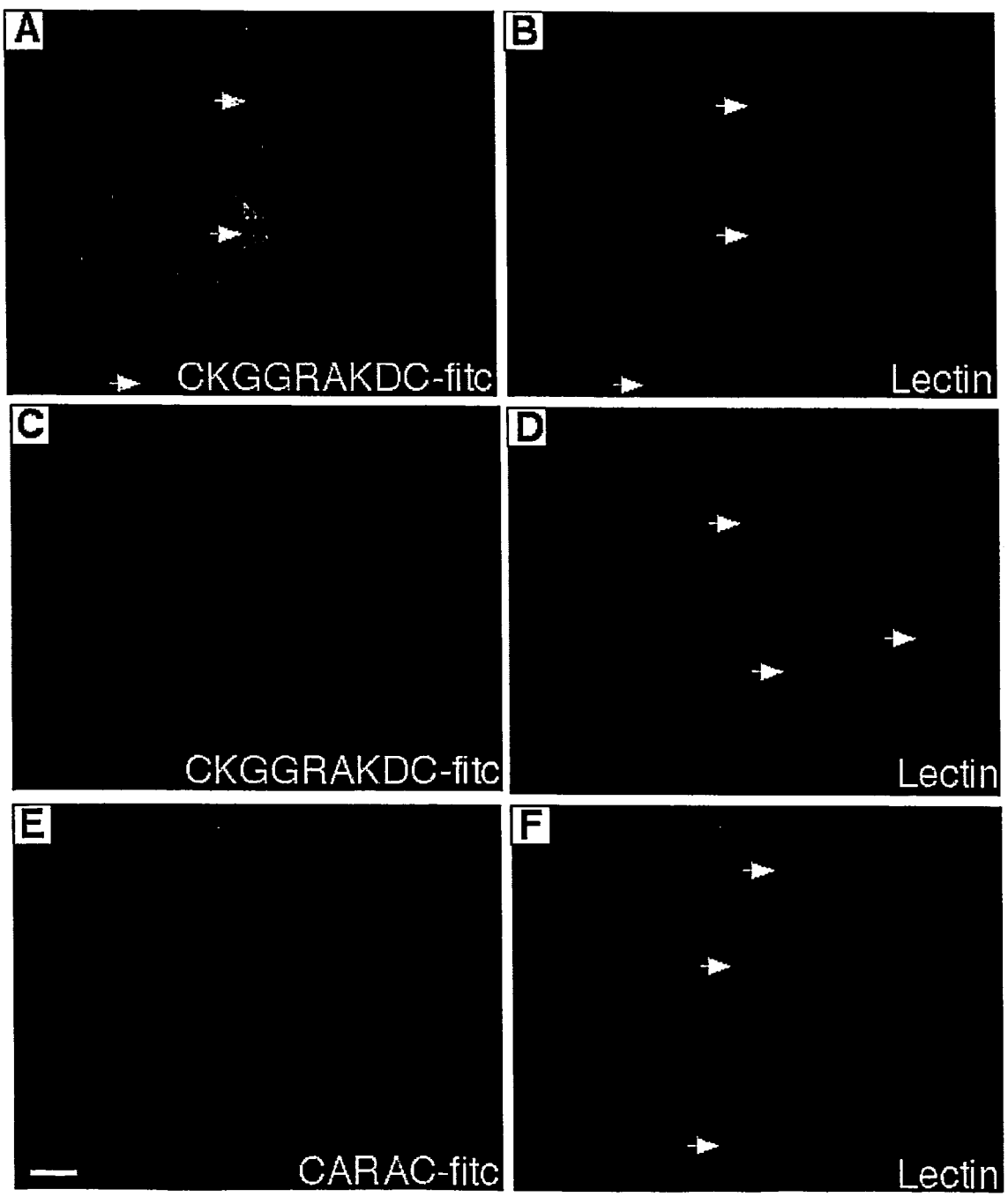
FIG. 25. In vivo fat homing of the CKGGRAKDC (SEQ ID NO:81) motif in wild-type mice. (a), (C) and (E) Peptide-FITC immunofluorescence or (B), (D) and (F) lectin-rhodamine immunofluorescence in blood vessels of (A), (B), (E) and (F) subcutaneous white fat or (C) and (D) pancreas controls detected in paraffin-sectioned tissues from c57bl/6 mice intravenously co-injected 5 min prior to tissue processing. Mice were injected with (A), (B), (C) and (D) CKGGRAKDC (SEQ ID NO:81) linked to FITC peptide and lectin-rhodamine; or (E) and (F) control CARAC (SEQ ID NO:71) linked to FITC peptide and lectin-rhodamine. (B), (D) and (F) Arrows show endothelium marked with lectin. (A) Arrows show homing of the CKGGRAKDC (SEQ ID NO:81) peptide to fat endothelium. Bar: 10 µm.

FIG. 25 shows that the CKGGRAKDC (SEQ ID NO:81)-FITC fusion peptide intravenously injected into C57BL/6 (leptin +/+) mice specifically localized to blood vessels of subcutaneous and peritoneal white fat (FIG. 25A, FIG. 25B). A lectin-rhodamine peptide was used to visualize blood vessel endothelium (arrows, FIG. 25B, FIG. 25D, FIG. 25F). The CKGGRAKDC (SEQ ID NO:81)-FITC fusion peptide co-localized with lectin-rhodamine in adipose tissue (arrows, FIG. 25A and FIG. 25B). No such co-localization was observed in control pancreatic tissue (FIG. 25C and FIG. 25D) or other control organs (data not shown). The control CARAC (SEQ ID NO:71)-FITC peptide was not detectable in white fat vasculature (FIG. 25E and FIG. 25F). These in vivo localization data show that the adipose-targeting CKGGRAKDC (SEQ ID NO:81) peptide targets the white adipose vasculature in genetically normal obese mice as well as in leptin deficient mice, demonstrating the general applicability of adipose targeting using such peptides. The uptake of CKGGRAKDC (SEQ ID NO:81)-FITC by the endothelium of fat tissue suggests that the motif targets a receptor selectively expressed in the adipose vasculature that could provide a mechanism for directed delivery of therapeutic compounds to fat Design and Use of Fat-targeted Pro-apoptotic Peptide It was next determined whether proliferation of adipose tissue could be controlled via targeted destruction of the fat vasculature. The pro-apoptotic peptide KLAKLAKKLAKLAK (SEQ ID NO:1) (Ellerby et al., *Nature Med.* 5:1032-38, 1999), designated (KLAKLAK)$_2$ (SEQ ID NO:1), which disrupts mitochondrial membranes to induce apoptosis, has been targeted to receptors in tumor vasculature via a conjugated homing peptide (Ellerby et al 1999, Arap, et al., *Proc. Natl. Acad. Sci. U.S.A.* 99:1527-1531, 2002). The (KLAKLAK)$_2$ (SEQ ID NO:1) peptide was conjugated to the fat targeting CKGGRAKDC (SEQ ID NO:81) peptide for targeted delivery to fat vasculature in adipose tissue. The D enantiomer of (KLAKLAK)$_2$ (SEQ ID NO:1), which is resistant to proteolysis but still exhibits pro-apoptotic activity, was conjugated to the CKGGRAKDC (SEQ ID NO:81) peptide via a glycinylglycine bridge. The conjugated fat-targeting, pro-apoptotic peptide was administered to mice and the effect on adipose tissue was monitored.

Figure 26:
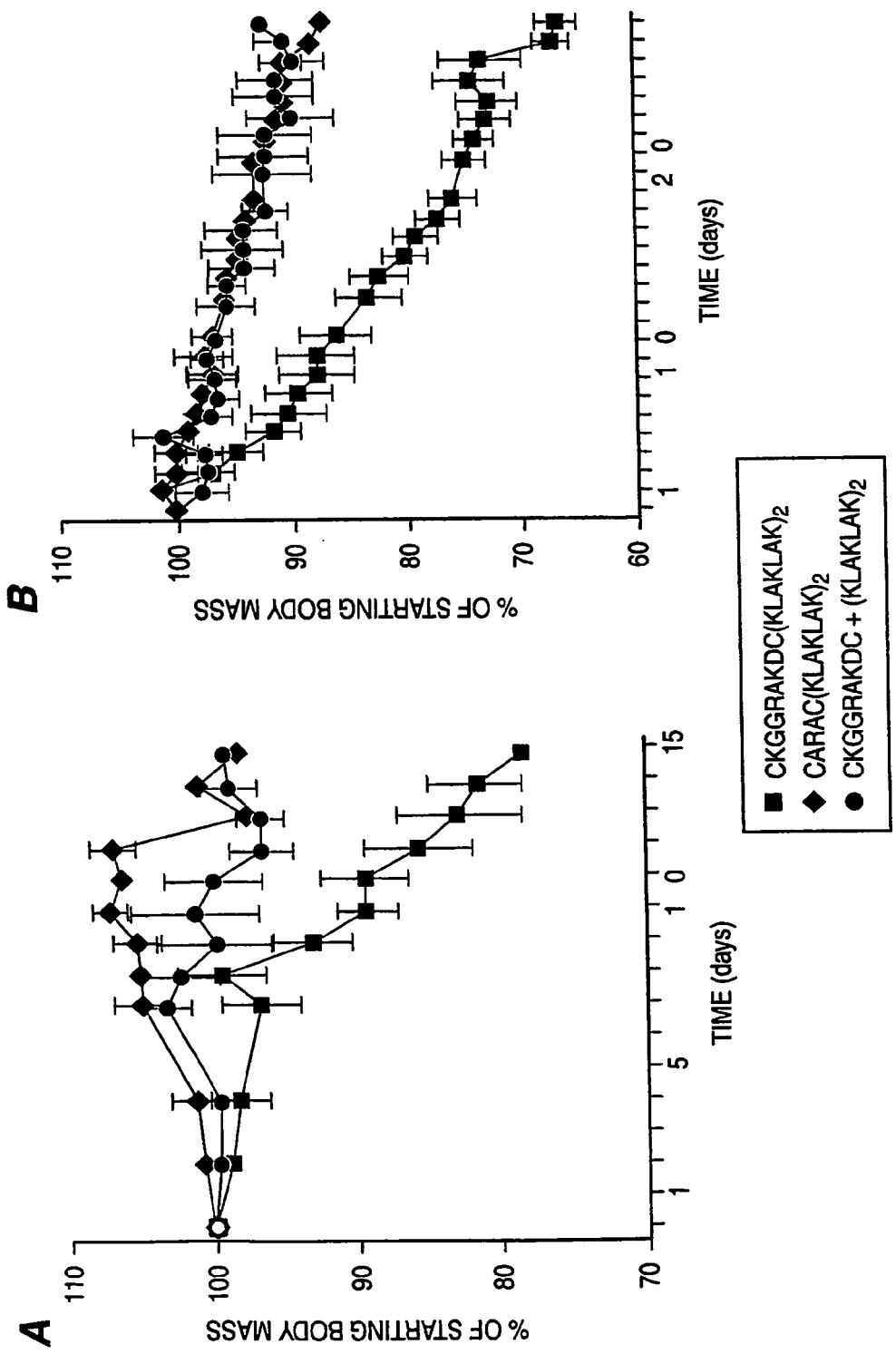
FIG. 26. Treatment of mouse obesity with fat vasculature-targeted apoptosis. Three cohorts (n=3) of (A) high-fat cafeteria diet-fed obese c57bl/6 mice; or (B) regular diet-fed old (~1 year) c57bl/6 mice were each subcutaneously injected daily with equimolar amounts of the indicated peptides. Mouse body mass measurement was taken on days when injections were performed (injections were skipped on days for which body mass measurement is not shown). Error bars are SEM for the measurements in three mice.

A non-genetic mouse obesity model was initially used. A cohort of C57BL/6 (wild-type) mice, in which obesity had been induced by a high-fat cafeteria diet, were subcutaneously injected with CKGGRAKDC (SEQ ID NO:81)-(KLAKLAK)$_2$ (SEQ ID NO:1) peptide and weighed daily over a period of two weeks. Cafeteria dieting continued throughout the experiment. As shown in FIG. 26A, injections of CKGGRAKDC (SEQ ID NO:81) conjugated to (KLAKLAK)$_2$ (SEQ ID NO:1) prevented obesity development and surprisingly caused a rapid decrease in body mass of up to 20%. In contrast, obese mice injected with two negative controls (an equimolar amount of either unconjugated CKGGRAKDC (SEQ ID NO:81) and (KLAKLAK)$_2$ (SEQ ID NO:1) or a control CARAC (SEQ ID NO:71)-(KLAKLAK)$_2$ (SEQ ID NO:1) conjugate) did not show a significant body mass decrease and continued to increase in weight (FIG. 26A).

The effectiveness of the CKGGRAKDC (SEQ ID NO:81)-(KLAKLAK)$_2$ (SEQ ID NO:1) conjugate was also examined in wild-type mice fed on a regular diet (FIG. 26B). C57BL/6 mice that had developed a considerable amount of subcutaneous and peritoneal fat due to old age were subcutaneously injected with the CKGGRAKDC (SEQ ID NO:81)-(KLAKLAK)$_2$ (SEQ ID NO:1) conjugate or control peptides over a period of one month. As in the diet-induced obesity model, targeting of (KLAKLAK)$_2$ (SEQ ID NO:1) to fat by conjugation with CKGGRAKDC (SEQ ID NO:81) resulted in greater than 35% reduction in body mass at a rate of 10% per week (FIG. 10B). No toxicity of the conjugated peptide was detected under these conditions (data not shown). In fact, the CKGGRAKDC (SEQ ID NO:81)-(KLAKLAK)$_2$ (SEQ ID NO:1) treated mice became more active and agile following body mass reduction and appeared healthier than prior to treatment (data not shown). The control untargeted (KLAKLAK)$_2$ (SEQ ID NO:1) treatments resulted in only a slight body mass reduction (FIG. 26B), possibly due to low levels of nonspecific toxicity. The control mice did not exhibit the increased activity and/or agility seen in treated mice (data not shown).

Fat Resorption with CKGGRAKDC (SEQ ID NO:81)-(KLAKLAK)$_2$ (SEQ ID NO:1) is Mediated by Apoptosis In both diet-induced and age-related obesity, the effect of CKGGRAKDC (SEQ ID NO:81)-(KLAKLAK)$_2$ (SEQ ID NO:1) treatment on body mass was due to fat resorption, which was visually apparent by the end of treatment (FIG.

27). Wild-type mice were fed on a high fat cafeteria diet (FIG. 27A). Alternatively, wild-type fed on a regular diet became obese as a consequence of old age (FIG. 27B, FIG. 27C, FIG. 27D). Mice were treated with CKGGRAKDC (SEQ ID NO:81) conjugated to (KLAKLAK)$_2$ (SEQ ID NO:1) (left side of FIG. 27), with CARAC (SEQ ID NO:71) conjugated to (KLAKLAK)$_2$ (SEQ ID NO:1) (middle of figure), or with unconjugated CKGGRAKDC (SEQ ID NO:81) and (KLAKLAK)$_2$ (right side of FIG. 27).

Gross inspection of mouse organs revealed that both subcutaneous (FIG. 27B) and visceral (FIG. 27C) fat exhibited marked resorption upon treatment with CKGGRAKDC (SEQ ID NO:81) conjugated to (KLAKLAK)$_2$ (SEQ ID NO:1) (right side of FIG. 27). Quantification of fat resorption after three weeks of treatment by weighing a specific fat depot (epididymal fat, FIG. 27D) showed a greater than 3-fold reduction in fat mass compared with controls (FIG. 27D, left side of figure compared to middle and right side).

Figure 28:
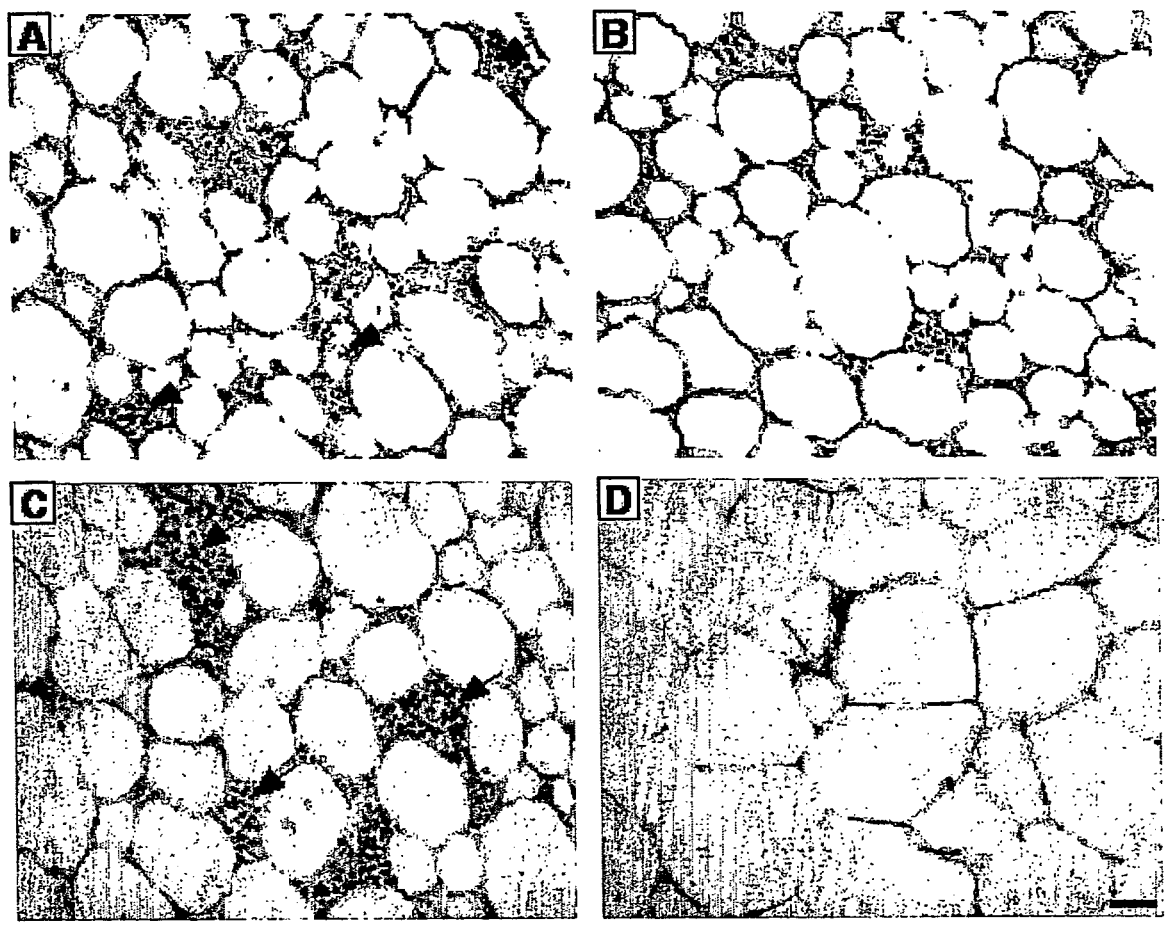
FIG. 28. Destruction of fat blood vessels as a result of targeted apoptosis. (A) Tunnel immunohistochemistry, (B) secondary antibody only negative tunnel staining control and (C) and (D) hematoxylin/eosin staining of white fat of mice. (A), (B) and (C) Mice were treated with CKGGRAKDC (SEQ ID NO:81) linked to (KLAKLAK)$_2$ (SEQ ID NO:1). (D) Mice were treated with CARAC (SEQ ID NO:71) linked to (KLAKLAK)$_2$ (SEQ ID NO:1). Apoptosis (arrows, (A)) and necrosis/lymphocyte infiltration (arrows, (C)) in response to CKGGRAKDC (SEQ ID NO:81) linked to (KLAKLAK)$_2$ (SEQ ID NO:1) treatment are indicated. Bar: 10 µm.

Histopathological analysis of tissues from mice treated with CKGGRAKDC (SEQ ID NO:81) conjugated to (KLAKLAK)$_2$ (SEQ ID NO:1) showed vascular apoptosis (FIG. 28A, arrows) and resulting fat necrosis with lymphocyte infiltration (FIG. 28C, arrows) in adipose tissue. following treatment. In contrast, mice treated with a control fusion peptide comprising CARAC (SEQ ID NO:71) conjugated to (KLAKLAK)$_2$ (SEQ ID NO:1) showed no vascular apoptosis or fat necrosis (FIG. 28D). No abnormalities in other organs treated with CKGGRAKDC (SEQ ID NO:81) conjugated to (KLAKLAK)$_2$ (SEQ ID NO:1) (data not shown).

Injection of CKGGRAKDC (SEQ ID NO:81) conjugated to (KLAKLAK)$_2$ (SEQ ID NO:1) into genetically obese mice, but not into normal obese mice, was occasionally observed to result in mortality within a few days of injection. It is not clear what the mechanism might be for inducing death in genetically obese mice, although development of pulmonary or cardiac fat embolism or rapid drop of serum calcium due to saponification by released lipids are possibilities. However, these results suggest that treatment of grossly obese subjects might result in sufficient adipose cell death and necrosis to adversely affect the health of the subject, indicating that lower dosages and/or use of a time release formulation of the adipose targeting conjugate may be preferred in cases of excessive obesity.

Adipose Receptor Protein for CKGGRAKDC (SEQ ID NO:81)

A band of approximately 35,000 Daltons (35 kDa) was isolated from mouse adipose tissue extract that bound to CKGGRAKCDC (SEQ ID NO:81) conjugated to (KLAKLAK)$_2$ (SEQ ID NO:1) (not shown). There was much less binding of the 35 kDa fraction to the control peptide CARAC (SEQ ID NO:71) conjugated to (KLAKAK)$_2$ (SEQ ID NO:1) (data not shown). The 35 kDa band was analyzed by mass spectrometry, which identified three proteins present in the sample.

The three proteins included predominately a B cell receptor associated protein (prohibitin), apolipoprotein E, and the voltage dependent anion channel (VDAC). Further studies were performed by immunoprecipitation, using either CKGGRAKDC (SEQ ID NO:81) or CARAC (SEQ ID NO:71) conjugated to (KLAKAK)$_2$ (SEQ ID NO:1) and precipitating with commercially available antibodies.

SDS-polyacrylamide gel electrophoresis of the immunoprecipitated protein showed that only the prohibitin receptor protein complex was substantially enriched by binding to CKGGRAKDC (SEQ ID NO:81) (data not shown), with over a ten-fold enrichment in the CKGGRAKDC (SEQ ID NO:81) precipitated fraction compared to the CARAC (SEQ ID NO:71) precipitated fraction (data not shown). The CARAC (SEQ ID NO:71)-(KLAKAK)$_2$ (SEQ ID NO:1) fusion peptide exhibited low levels of non-specific binding to all three proteins (VDAC, prohibitin and apolipoprotein E). It is unknown whether those proteins bound to the CARAC (SEQ ID NO:71) moiety or to (KLAKAK)$_2$ (SEQ ID NO:1).

It is concluded that the adipose tissue endothelial receptor for CKGGRAKDC (SEQ ID NO:81) is prohibitin (Genbank Accession No. NM_008831). Probitin is expressed in mitochrondria of various cell types and in the cell membrane of B lymphocytes, where it is associated with the IgM receptor (McClung et al., Exp. Gerontol. 30:99-124, 1995). Based on these results, it is concluded that pro-apoptosis agents conjugated to targeting peptides that bind to a prohibitin receptor protein complex may be effective to induce adipose cell death and weight loss in obese subjects. The skilled artisan will realize that other prohibitin-binding targeting peptides, antibodies, etc. may be used within the scope of the claimed methods and compositions to control weight and/or to induce weight loss. Further, other known cytocidal, cytotoxic and/or cytostatic agents may be used in place of (KLAKAK)$_2$ (SEQ ID NO:1) to control weight or induce weight loss within the scope of the claimed subject matter.

The results obtained in a mouse model system were confirmed in human tissue sections. Rabbit polyclonal antibodies against prohibitin were commercially purchased (RDI-PROHIBIT, Research Diagnostics, Inc., Flanders, N.J.). Immunohistochemistry on sections of fixed human paraffin-embedded tissues was performed using the LSAB+peroxidase kit from Dako (Carpinteria, Calif.). Comparison of prohibitin expression in mouse versus human white fat tissue showed that prohibitin is highly expressed in blood vessels of both mouse and human white fat tissues (not shown).

Figure 30:
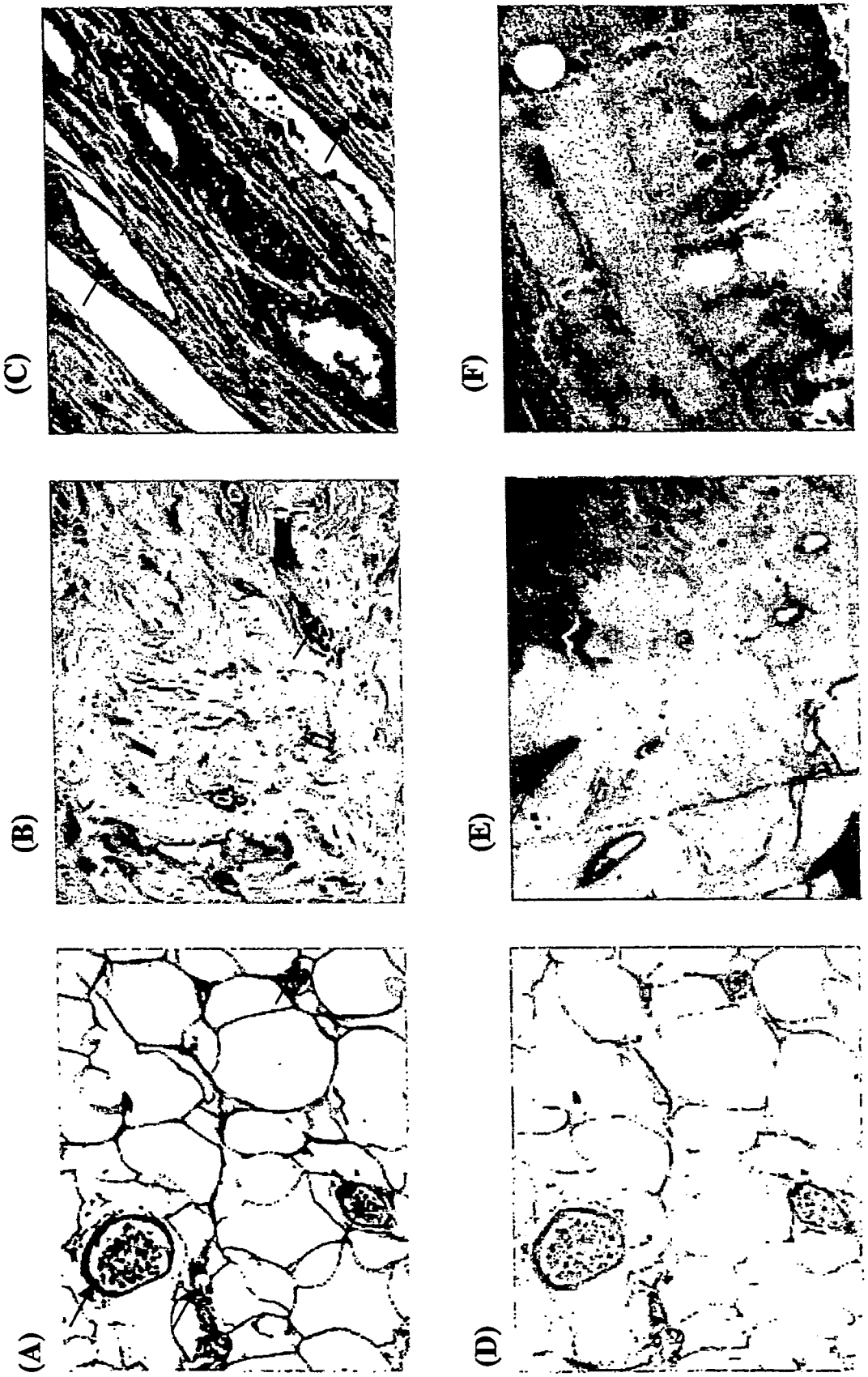
FIG. 30. Expression of prohibitin in human tissues. Prohibitin expression was determined by immunohistochemistry of fixed human paraffin-embedded thin tissue sections with rabbit polyclonal antibodies against prohibitin. Arrows indicate prohibitin staining in normal human tissues of: (A) white fat; (B) skin; (C) prostate; (E) bone; and (F) muscle; and (F) skeletal muscle. A fat staining control is shown in (D).

Prohibitin is expressed in the vascular endothelium of a number of human organs (FIG. 30, arrows), including white fat tissue (FIG. 30A), skin (FIG. 30B), prostate (FIG. 30C) and bone (FIG. 30E). However, the level of prohibitin expression in white fat blood vessels is much higher than in other types of human tissues (FIG. 30).

Figure 29:
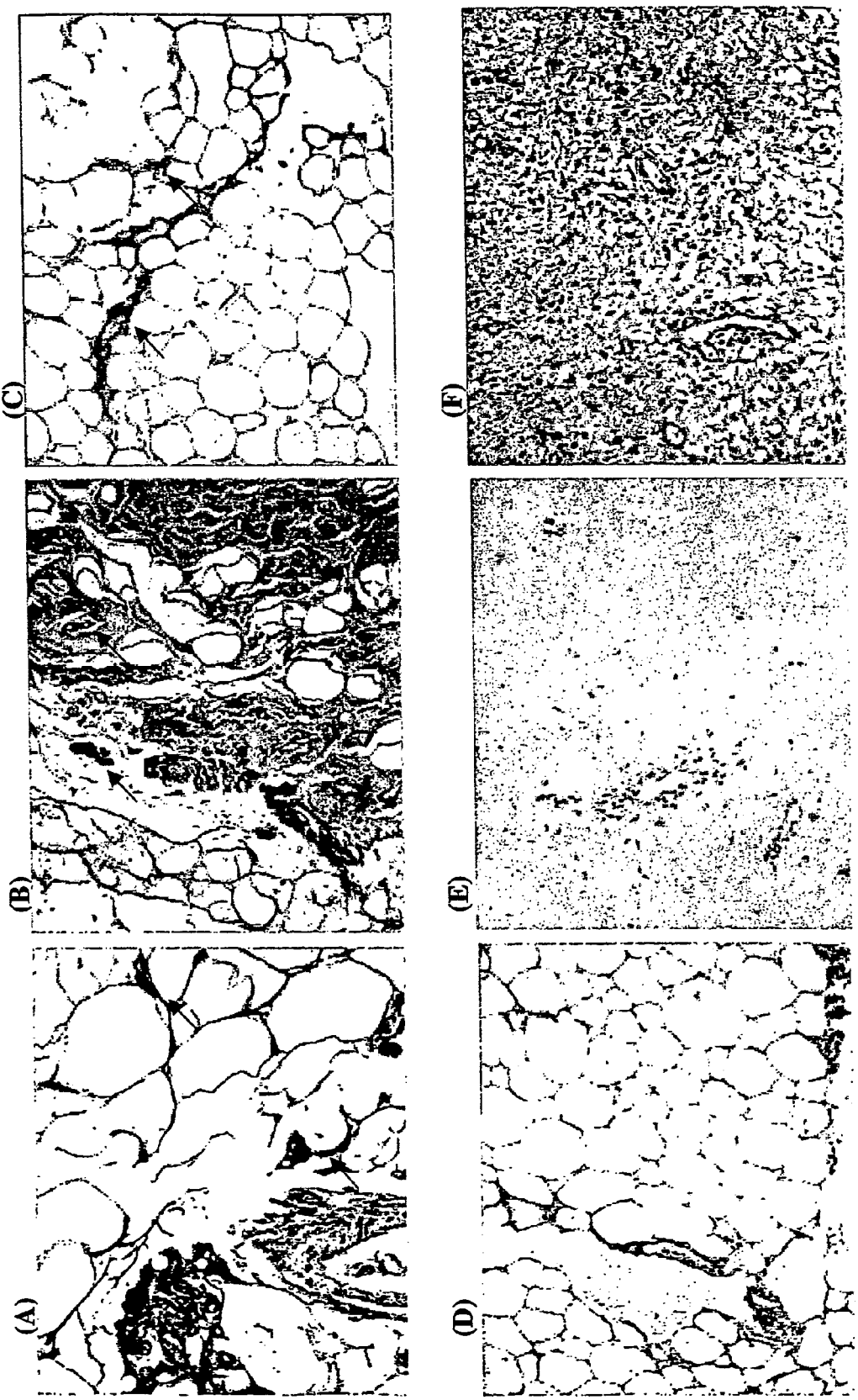
FIG. 29. Expression of prohibitin in human tissues. Prohibitin expression was determined by immunohistochemistry of fixed human paraffin-embedded thin tissue sections with rabbit polyclonal antibodies against prohibitin. Arrows indicate prohibitin staining in: (A) normal human white fat tissue; (B) normal human breast tissue; (C) a low grade human lipoma; (D) a high grade human lipoma; (E) a myxoid liposarcoma; and (F) a dedifferentiated liposarcoma.

Prohibitin expression appears to be inversely correlated with the degree of malignancy in human adipose tissues (FIG. 29). The arrows indicate prohibitin staining in normal human white fat tissue (FIG. 29A), normal human breast tissue (FIG. 29B), a low grade human lipoma (FIG. 29C), a high grade human lipoma (FIG. 29D), a myxoid liposarcoma (FIG. 29E) and a dedifferentiated liposarcoma (FIG. 29F). For each tumor sample, prohibitin expression was also evaluated in a control organ from the same patient (data not shown) to verify that prohibitin was specifically downregulated in the vasculature of the tumor. FIG. 29 shows that prohibitin expression is progressively lost in the blood vessels of fat tissue, parallel to fat transformation into malignant liposarcoma tissues. Thus, prohibitin is a negative indicator of malignancy in adipose tissues, as prohibitin expression is inversely correlated with the degree of malignancy of the tissue.

Figure 31:
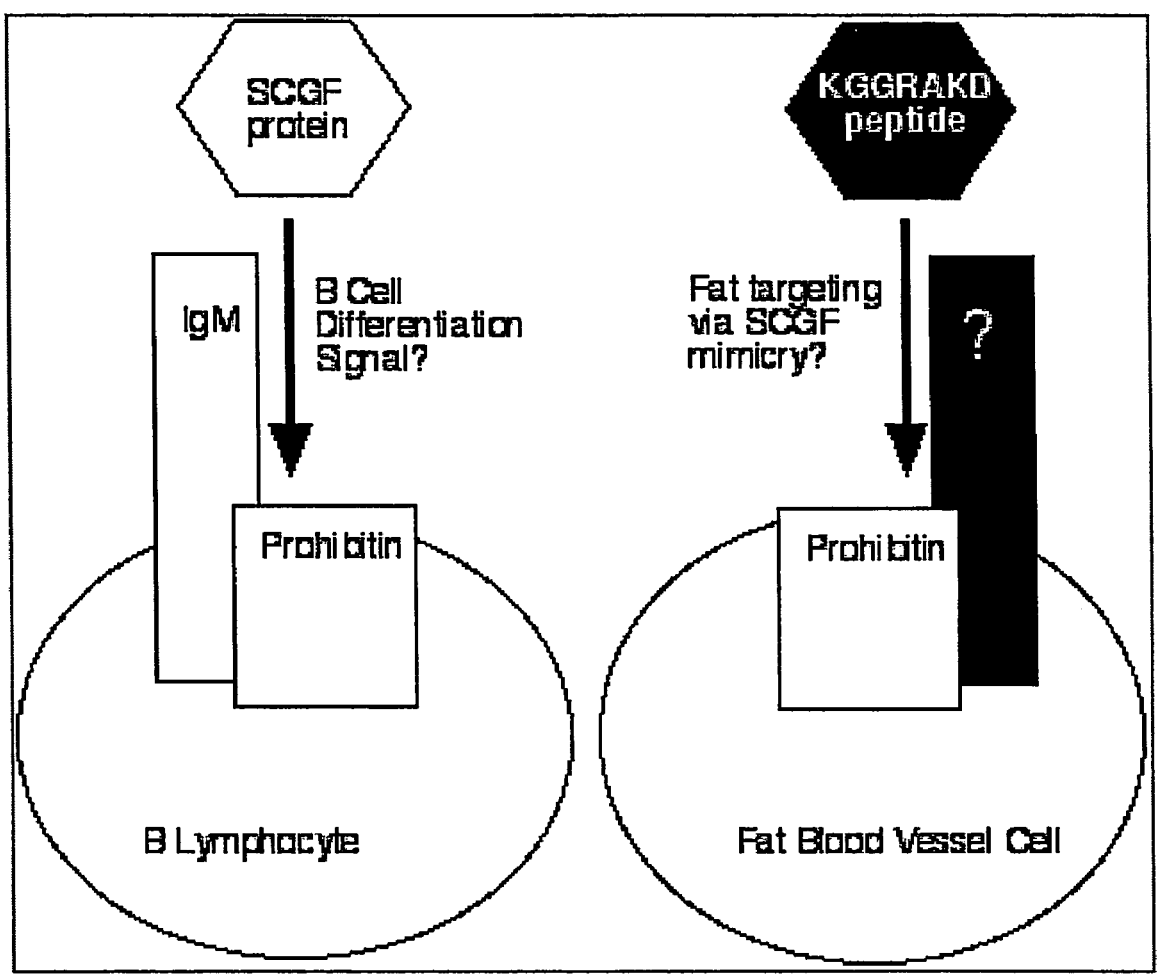
FIG. 31. Model of prohibitin function in fat vasculature.

A model for prohibitin function in fat vasculature is presented in FIG. 31. The KARGG (SEQ ID NO:82) motif, found in reverse orientation in the prohibitin binding peptide CKGGRAKDC (SEQ ID NO:81), shows homology with the human stem cell growth factor (SCGF) protein (FIG. 31), a member of the C-type lectin superfamily. SCGF in combination with VEGF has been reported to cause differentiation of CD34(+) progenitor cells into endothelial cells, with characteristics of vascular endothelium (Gehling et al., Blood, 95:3106-12, 2000). SCGF expression also appears to be associated with B lymphopoiesis (Witte et al., Eur. J. Immunol. 32:1809-17, 1993). It is proposed that binding of SCGF protein to a complex of prohibitin and the IgM receptor protein in B lymphocytes may mediate B cell differentiation (FIG. 31). It is further suggested that binding of CKGGRAKDC (SEQ ID NO:81) to prohibitin in adipose blood vessel cells may potentially mimic an endogenous SCGF dependent signaling pathway, perhaps related to endothelial cell differentiation (FIG. 31).

Example 9

Novel Prostate Tumor Targeting Peptides

DU145 prostate tumor cells were injected subcutaneously into the right fat pad of nude mice. A large phage library ($X_2CX_{14}CX_2$) was prepared as discussed above and $10^9$ phage were injected into male tumor-bearing nude mice. After 24 hr circulation, tumors were removed and phage recovered from the tumors using the bulk method disclosed above. The recovered phage were amplified, titered and reinjected into a new set of tumor bearing nude mice. The biopanning protocol was repeated for a total of three rounds. Ninety-six phage clones recovered from the third round of biopanning were selected for sequencing. Translated sequences were obtained for 76 of the 96 clones.

Targeting peptides recovered from DU145 xenograftic tumors are listed in Table 10. The primary prostate tumor targeting peptides recovered were YRCTLNSPFFWEDMTHECHA (SEQ ID NO:83) and LGCMASMLREFEGATHACTQ (SEQ ID NO:84). The numbers in parentheses indicate the number of times the same targeting peptide sequence was obtained. As indicated in Table 9, the YRCTLNSPFFWEDMTHECHA (SEQ ID NO:83) targeting sequence was recovered in 11 out of 76 colonies, while the LGCMASMLREFEGATHACTQ (SEQ ID NO:84) peptide was recovered in 8 out of 76 colonies. No obvious homologies were observed between the prostate tumor targeting peptides listed in Table 10 and any known protein sequence.

TABLE 10

Prostate Tumor-Targeting Peptides Recovered From DU145 Xenografts

| | | |
|---|---|---|
| YRCTLNSPFFWEDMTHECHA (11) | SEQ ID NO:83 | |
| LGCMASMLREFEGATHACTQ (8) | SEQ ID NO:84 | |
| RGCTEAAGLVIGITTHQCGN (3) | SEQ ID NO:85 | |
| IGCNHPSPLGSTVVPTYCFK (3) | SEQ ID NO:86 | |
| GTCPRQFFHMQEFWPSDCSR (3) | SEQ ID NO:87 | |
| DRCVLVRPEFGRGDARLCHS (2) | SEQ ID NO:88 | |
| EGCSDIMNTAAERVTGDCSY (2) | SEQ ID NO:89 | |
| VFCCGSYCGGVEMLASRCGH (2) | SEQ ID NO:90 | |
| RECGRTVHRYPWGSPESCER (2) | SEQ ID NO:91 | |
| DACSRFLGERVDATAAGCSR (2) | SEQ ID NO:92 | |
| GNCMGLQVSELFMGPYKCRQ (2) | SEQ ID NO:93 | |
| SRCHALRSQSVSTSAGACIS (1) | SEQ ID NO:94 | |
| YSCTRLNGTGLQNPPSACDR (1) | SEQ ID NO:95 | |
| WVCTSASQDTRLKEPGMCIA (1) | SEQ ID NO:96 | |
| MHCTSQTLRGTPSLAPKCSD (1) | SEQ ID NO:97 | |

TABLE 10-continued

Prostate Tumor-Targeting Peptides Recovered From DU145 Xenografts

| | | |
|---|---|---|
| QHCVKGQFPFRESVTITCNS (1) | SEQ ID NO:98 | |
| HTCWGARDVAQPSGTVRCLK (1) | SEQ ID NO:99 | |
| ARCREDTGFMGLGSANICTD (1) | SEQ ID NO:100 | |
| RTCEEVRNRALEELTNFCPY (1) | SEQ ID NO:101 | |
| RTCQVRSNNISPRMALACVT (1) | SEQ ID NO:102 | |
| RSCVNSDTGVLQRGAPSCLF (1) | SEQ ID NO:103 | |
| RGCWRDSTAWHVSYPVECLA (1) | SEQ ID NO:104 | |
| NRCMPGFLDDADSAASPCGS (1) | SEQ ID NO:105 | |
| NQCSSLLTYQGWKRTKDCIP (1) | SEQ ID NO:106 | |
| NDCSAHAQPGWDEVPPMCNQ (1) | SEQ ID NO:107 | |
| NNCPVEGSQQNYSGATWCRA (1) | SEQ ID NO:108 | |
| TTCNKSMSSQPMRDSRECHR (1) | SEQ ID NO:109 | |
| TSCVRTGHDENLLKAAYCSS (1) | SEQ ID NO:110 | |
| TECRGASSGSVSGAATDCRD (1) | SEQ ID NO:111 | |
| TLCPPASMGLGREKPRLCSV (1) | SEQ ID NO:112 | |
| TLCRSLEHEVGLFKPRECPF (1) | SEQ ID NO:113 | |
| LRCPLEVDRPNRDPAFLCSQ (1) | SEQ ID NO:114 | |
| LGCNXGRYWLSTRLSVSCAL (1) | SEQ ID NO:115 | |
| VACDISAVERLPASARSCKT (1) | SEQ ID NO:116 | |
| VVCFMERQMGTDVVSPMCVN (1) | SEQ ID NO:117 | |
| VECVMASASTDGTAAHPCKP (1) | SEQ ID NO:118 | |
| VRCNEAQLQDSGTVPHPCLR (1) | SEQ ID NO:119 | |
| PNCDLDDIVLNPYTAGPCGT (1) | SEQ ID NO:120 | |
| PNCYSGDGEISSHIPVQCLM (1) | SEQ ID NO:121 | |
| PGCVVSPFALSAQGTSVCTI (1) | SEQ ID NO:122 | |
| GDCETNNVTKVGGITRNCVG (1) | SEQ ID NO:123 | |
| GYCLTVVGGAVLTIALLCVT (1) | SEQ ID NO:124 | |
| GPCAATGVNPGDHGAAVCDQ (1) | SEQ ID NO:125 | |
| GDCETNNVTKVGGITRNCVG (1) | SEQ ID NO:126 | |
| KSCGKYGLIVGQPFAEHCPP (1) | SEQ ID NO:127 | |
| KLCYRSSAGSELRPPEKCAY (1) | SEQ ID NO:128 | |
| KICPVTNMWTTPSWAHKCGM (1) | SEQ ID NO:129 | |

To determine the specificity of the prostate tumor targeting peptides, $10^9$ phage carrying the targeting peptide sequences YRCTLNSPFFWEDMTHECHA (SEQ ID NO:83) and LGCMASMLREFEGATHACTQ (SEQ ID NO:84) were injected into nude mice bearing DU145 xenografts. After 24 hour circulation, tissue samples were obtained from tumor and control organs (kidney, brain, lung and spleen). Tissue samples were washed immediately in DMAM and fixed in 10% formalin for 48 hours at room temperature. Thin sections were stained for phage using anti-phage antibody (1:500 dilution) and detected using the DAKO LSAB+ system. The DU145 tumor showed very heavy staining with anti-phage antibodies (data not shown). No staining was observed for control kidney, brain or lung tissues (not shown). A low level of anti-phage staining was observed in normal spleen tissue (not shown). This may be due to the tendency of spleen tissue to trap phage and other foreign particles in general as part of the reticuloendothelial system. In a separate study, samples of the MDA-MB-435 breast carcinoma showed no apparent localization of phage bearing the YRCTLNSPFFWEDMTHECHA (SEQ ID NO:83) sequence.

Competition studies with the YRCTLNSPFFWEDMTHECHA (SEQ ID NO:83) peptide were performed to determine whether it could inhibit localization of phage bearing the same targeting sequence to DU145 tumors. Nude mice bearing the prostate tumor xenograft were simultaneously injected with 300 µg of synthetic YRCTLNSPFFWEDMTHECHA (SEQ ID NO:83) peptide and $10^9$ phage bearing the same targeting peptide sequence. A control tumor-bearing mouse was co-injected with fd insertless phage plus synthetic peptide. After 24 hours of circulation, tumor tissue samples were removed, washed, fixed, sectioned and stained as disclosed above. Co-administration of synthetic peptide with the same targeting sequence inhibited the ability of YRCTLNSPFFWEDMTHECHA (SEQ ID NO:83)-phage to localize to prostate carcinoma tissue (not shown). No staining of prostate carcinoma with control fd-tet phage was observed (not shown)

Receptor Purification

The prostate homing receptor for the B2 clone (YRCTLNSPFFWEDMTHECHA SEQ ID NO:83) was identified. Nude mice bearing DU145 xenografts were prepared and tissue samples from tumor, kidney and liver were removed. The tissue samples were immediately washed with PBS and three parts of homogenization buffer (PBS, 250 mM sucrose, 1 mM EDTA, protease inhibitors) was added to one part of tissue sample (about 4 ml). The tissue with homogenized with an electric grinder, then further homogenized with a dounce homogenizer. After sonication for 1 min on ice, the homogenate was centrifuged at 8000×g for 5 min. The supernatant was removed and the pellet was analyzed for receptor content.

The YRCTLNSPFFWEDMTHECHA (SEQ ID NO:83) peptide was biotinylated and coupled to NeutrAvidin beads (Molecular Probes, Eugene, Oreg.) using standard methods. About 500 µg of biotinylated peptide was incubated with 1 ml of NeutrAvidin beads in binding buffer (0.5 M NaCl in PBS) overnight at 4° C. in a 2 ml column. The column was agitated using a rotator. Uncoupled peptides were removed and the beads washed three times with binding buffer and protease inhibitors. Approximately 1 mg of tissue extract was added to the biotinylated peptide conjugated beads. The material was resuspended in 2 ml of binding buffer and incubated overnight at 4° C. on a rotator. The material was centrifuged and supernatant was removed The beads were washed four times with wash buffer (0.1% Triton X-100 in PBS with protease inhibitors) and the bound material eluted with 8 M guanidine HCl. Eluted proteins were analyzed on a 4-20% SDS-PAGE denaturing gel. Protein (40 µg) from the tumor and kidney were run as controls. Bands that showed apparent enrichment for binding to the YRCTLNSPFFWEDMTHECHA (SEQ ID NO:83) peptide were cut out for protein sequencing.

MALDI analysis of the excised bands identified HSP90 and an unidentified protein. HSP90 is known to be overexpressed in prostate cancer and to be associated with MHC-I on the cell surface. It is concluded that the endogenous receptor for the YRCTLNSPFFWEDMTHECHA (SEQ ID NO:83) peptide is HSP90α (GenBank Accession No. NM005348).

Example 10

Novel Ovarian Cancer Targeting Peptides

Background

Carcinomas that arise from the ovarian surface epithelium represent a great challenge in gynecologic oncology Rosenthal & Jacobs, Semin Oncol, 1998. 25:315-25). Ovarian cancer is the sixth most common cancer in women and the deadliest of all gynecologic malignancies, resulting in about 14,000 deaths annually in the United States. Although the prognosis of ovarian cancer is influenced by many factors capable of predicting clinical outcome, including tumor stage, pathological grade, patient performance status and amount of residual disease following primary debulking surgery, the biological aspects of ovarian cancer are not completely understood, implying that there may be other predictive indicators that could be used. Tumor markers have the potential to contribute to cancer screening, diagnosis, monitoring, and prognosis as well as provide targets for anti-tumor therapy. The most extensively researched tumor marker in ovarian carcinoma is CA125. CA125 levels have been used as indicators of treatment response or progression. In monitoring response to therapy, CA125 is able to reflect progression or regression in over 90% of patients who had elevated preoperative levels. Still, in respect to persistent disease, CA125 only has an accuracy of 60-80% and normal values often do not exclude active disease. Thus, the identification of additional markers with biological relevance would be desirable.

Neoplasms of the ovary represent a diverse group. They can be divided into four major histological classes based on their origin: coelomic epithelial, germ cell, specialized gonadal-stromal, and non-specific mesenchymal. The neoplasms derived from coelomic epithelium are the most common, comprising over 80% of all ovarian tumors. In becoming neoplastic, the coelomic epithelium exhibits a variety of Müllerian type differentiation, such as serous, mucinous, endometroid, and clear cell, which comprise the different histological subtypes.

The molecular and cellular events leading to the development of ovarian cancer are not completely understood and it is unclear whether ovarian cancer follows a stepwise pattern of progression, as no pre-malignant lesion has yet been identified. One proposed theory is that in early stages the cancer is confined to small epithelial inclusion cysts in the ovary. With time, the tumor penetrates through the surface capsule and malignant cells enter the peritoneal cavity. Here, exfoliation and implantation are the primary modes of spread of ovarian cancer. Within the peritoneal cavity, the cells follow the natural pattern of peritoneal fluid circulation, leaving all peritoneal surfaces at risk for tumor cell implantation. Likewise, ovarian cancer may spread by lymphatic dissemination and less commonly by hematogenous route to areas such as the liver and lungs.

The standard staging system for ovarian cancer is based on surgical exploration and clinical examination. Stage I is confined to the ovaries; stage II is confined to the pelvis; stage III has spread throughout the peritoneal cavity; and stage IV is occult distant metastasis, including parenchymal liver and lung metastasis. Currently, the most powerful determinant of prognosis in ovarian cancer is the extent to which the tumor has disseminated from the primary site at the time of diagnosis. If diagnosed and treated while the cancer has not spread outside the ovary, the five-year survival rate is 95%. However, only 25% of all ovarian cancers are found at this early stage due to vague symptomatology and lack of effective screening strategies. Moreover, older women with ovarian cancer tend to have a poorer prognosis than younger ones. The overall primary treatment response rate is 80-90%, however, the clinical complete response rate is only 40-50% and the pathological response rate is even lower, about 20-40%. Thus, even with optimal cytoreduction and chemotherapy, many patients remain at risk for the development of recurrent disease.

Since ovarian malignancy may result in the accumulation of ascites in the peritoneal cavity that contains tumor cells as well as tumor-associated immunoglobulins, probing the antibody repertoire in the ascites of ovarian cancer patients may result in the identification of peptide epitopes resembling tumor antigens. The identified peptide epitopes would correspond to primary sequences found in tumor antigens or mimetopes of such antigens and could potentially serve as markers for the ovarian cancer. Such markers may be of use for the detection, diagnosis and/or prognosis of ovarian and/or other cancers of the female reproductive tract.

The phage display methods disclosed above were used to identify novel tumor markers for ovarian cancer. Random peptide phage library were screened against IgGs isolated from the ascites of ovarian cancer patients to enrich for phage that bind to ovarian cancer patient IgGs and identify ovarian cancer peptide epitopes. Biochemical methods are employed to identify the antigen eliciting the antibody response. The identified peptide epitopes and corresponding antigens are tested to determine whether they are linked to disease progression and survival. To assess the value of each motif and corresponding antigen, banked ascites and serum from ovarian cancer patients are screened by an enzyme linked immunosorbent assay (ELISA) protocol.

Materials and Methods

Experimental samples from patients with ovarian cancer were obtained from the M. D. Anderson Cancer Center Specialized Program of Research Excellence (SPORE) Ovarian Tumor Bank. Control serum samples were obtained from healthy blood-donor age-matched women. Ascites samples were collected into sterile containers and subjected to centrifugation to separate the cell free fraction from the cellular fraction. The fluid was stored in aliquots at −20° C. and the remaining cellular fraction processed to purify the cells involved in the immune response as well as ovarian cancer tumor cells. All blood samples were allowed to clot at room temperature and then centrifuged. They were promptly aliquoted and frozen at −20° C. Protein G beads (Pierce) were used for immunoaffinity purification of IgG from serum and ascites samples. Archived paraffin-embedded tissue blocks and slides (malignant and non-malignant) collected from the Department of Pathology at the M. D. Anderson Cancer Center were also utilized.

Figure 34:
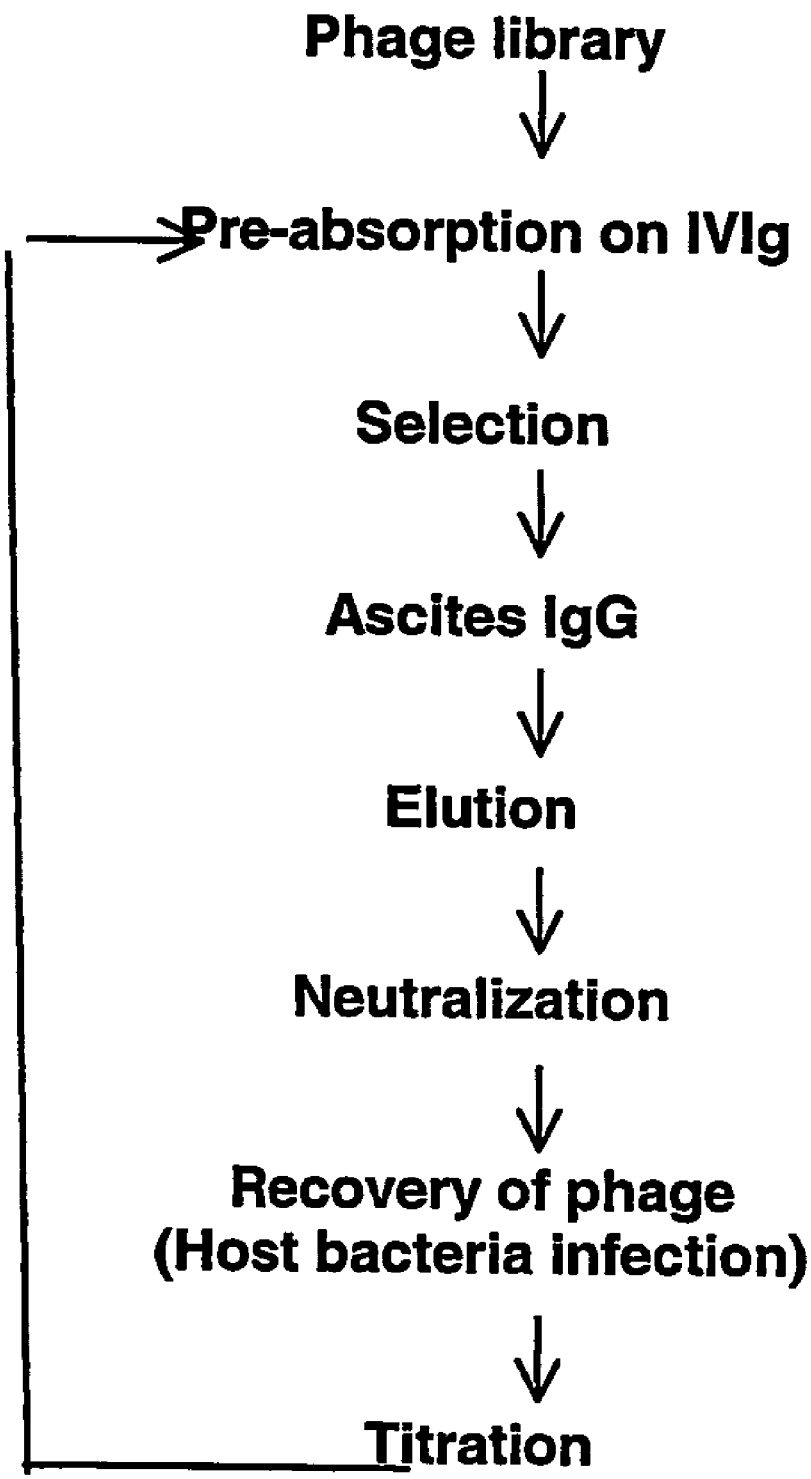
FIG. 34. Screening procedure for biopanning against ovarian cancer ascites.

To identify peptide epitopes specific for the anti-tumor immune response in ovarian cancer, a two-step screening procedure was followed (FIG. 34). The peptide library was initially pre-cleared on IVIg (intravenous immunoglobulins) to remove non-specific peptides. The pre-cleared peptide phage library was then incubated with IgGs isolated from the ascites of ovarian cancer patients. Phage bound to the ovarian cancer IgGs were recovered, amplified, and precipitated for subsequent rounds of biopanning. Following enrichment of a phage population that bound to ovarian cancer patient IgGs, individual phage clones were picked for sequence analysis to evaluate enrichment of the most consistently binding peptide sequences. Phage display biopanning was performed as described above.

Once the selection rounds were completed as determined by enrichment of phage capable of binding cancer patient IgGs over control at least 3 fold, sequencing and evaluation of the DNA phage insert were undertaken. To sequence the FUSE5 ssDNA directly, phage ssDNA was prepared using the StrataClean™ resin (Stratagene). StrataClean bead slurry was placed in a microcentrifuge tube containing phage. The mixture was vortexed strongly for 30 seconds and then incubated at room temperature for one minute. The tubes were centrifuged at 2,000×g for 1 minute. The supernatant containing the ssDNA was placed into a fresh microcentrifuge tube. A total of 3 extractions were performed. The DNA was then precipated with ethanol and used as a template for the sequencing reaction utilizing the primer. Sequencing was done by the chain termination method on an ABI Prism® 3700 (Applied Biosystems/Hitachi. The commercially available computer program, DNA Strider, was used in the analysis of the sequences.

Analysis of the distribution of inserts from the random peptide library used a program based on SAS (version 8; SAS Institute) and Perl (version 5.0). The program is a high-throughput pattern recognition software used to analyze short amino-acid residue sequences. The program conducts an exhaustive amino-acid residue sequence count and keeps track of the relative frequencies of n distinct tripeptide motifs representing all possible n3 overlapping tripeptide motifs in both directions (n<<n3). Counts were recorded for all interior tripeptide motifs, subject only to reflection and single-voting restrictions. No peptide, in the program, is allowed to contribute more than once for a single tripeptide motif (or a reversed tripeptide motif). Tripeptide motifs were chosen for the phage insert analysis because three amino-acid residues seem to provide the minimal framework for structural formation and protein-protein interaction. Each phage insert analyzed contained seven amino-acid residues and contributed to ten potential tripeptide motifs.

The Clustal W software from the European Molecular Biology Laboratory was adopted to analyze the cyclic phage peptides. Clustal W is a general purpose multiple sequence alignment program for DNA or proteins and produces biologically meaningful multiple sequence alignments of divergent sequences. It calculates the best match for the selected sequences, and lines them up so that the identities, similarities and differences can be seen.

Construction and purification of GST-fusion peptides. Peptide coding sequences were amplified using colony PCR with the following forward (5'AGGCTCGAGGATCCTCGGC-CGACGGGGCT-3', SEQ ID NO:130) and reverse (5'-AG-GTCTAGAATTCGCCCCAGCGGCCCC-3', SEQ ID NO:131) primers that contain BamHI and EcoRI sites (shown in bold), respectively. The amplified sequence, containing the peptide coding sequence, was cloned into the BamHI-EcoRI sites of the GST vector, pGEX-2TK (Amersham/Pharmacia), and automated sequencing used for verification of positive clones. Positive clones were transformed into the bacterial expression host strain, BL21 (DE3) pLys (Stratagene), by electroporation. Expression of the GST-fusion proteins was induced with 200 μM isopropylthiogalactoside (IPTG). Expression of the GST-fusion constructs was compared to uninserted pGEX-2TK vector to select for positive clones that produced the greatest amount of fusion proteins. GST-fusion proteins were expressed from selected clones and affinity purified from bacterial lysates by affinity chromatography to immobilized glutathione using glutathione Sepharose 4B resin (Amersham/Pharmacia).

Testing of individual phage clones (binding assays using patient derived or control IgGs). Binding of individual phage clones to cancer patient IgGs was studied by a microtiter assay. Antibodies from the ascites or donor were purified by standard techniques. The antibodies were used to coat MaxiSorp 96-well plates (Nalge Nunc International Corporation) at a concentration of 10-100 μg/ml. Coating of plates was carried out at 4° C. overnight. The plates were blocked with 3% Bovine serum albumin/phosphate buffered saline (BSA/PBS). For the binding reaction, $10^9$ TU of phage was added to the coated and blocked plates. The binding was performed at room temperature for 2 hours. After the binding reaction, the wells were washed four times with 3% BSA/PBS. Addition of K91Kan bacterial culture and incubation at room temperature for 30 min were used to rescue bound phage. The bacteria were diluted in 10 ml of LB culture media supplemented with 0.2 μg/ml tetracycline and incubated for another 30 min at room temperature. Serial dilutions of this bacterial culture were plated on LB plates containing 40 μg/ml tetracycline. Plates were incubated at 37° C. overnight before counting colonies. Binding of control (insertless) phage was also assessed.

Inhibition of binding assays. Both GST fusion proteins and synthetic peptides corresponding the sequence displayed were used for inhibitory studies. Inhibition studies were performed in a similar manner as the binding assays described above with the exception that either GST fusion protein or synthetic peptide corresponding to the phage clone were added to the experiment. Where the peptide is mediating the interaction with the immunoglobulins then an inhibition of phage binding should be observed in a dose dependent manner versus the synthetic peptide. GST alone and a control peptide containing unrelated amino acids were tested at identical concentrations.

Purification of peptide specific antibodies and immunohistochemistry. To test if the antigen is indeed specifically expressed in ovarian cancer and tumor-associated, the specific immunoglobulins capable of reacting with the identified peptide epitopes were purified and immunohistochemical staining performed on tissue sections from the patient in whom the initial screening was performed. GST fusion proteins made from inserting recombinant peptide sequences of interest in an expression vector were coated on MaxiSorp multi-well plates (Nalge Nunc International Corporation). The plates were incubated with the ascites fluid from which the peptide was originally isolated. Following a washing procedure to remove unbound IgGs, bound IgGs were eluted with 0.1 M glycine buffer, pH2.2, neutralized with 1 M Tris-Cl, pH9.0, and dialyzed in PBS overnight. To concentrate the IgG, centricon-30 columns (Millipore) were used. The purified antibody was coupled to biotin according to the manufacturer's instructions (Vector). The biotinylated antibody was analyzed by SDS-gel electrophoresis. Tumor paraffin sections were deparaffinized in xylene, rehydrated in ethanol, and treated with an antigen retrieval reagent (DAKO) in 10 mM sodium citrate, pH 7.5 in a steam bath. Non-specific sites on the tissue were blocked by incubating the deparaffinized slide in a casein blocking buffer. Affinity purified biotinylated ovarian cancer ascites fluid IgGs was applied to the sections. A rinsing step and the addition of strepavidin conjugated to horseradish peroxidase followed. Positive staining cells were visualized by the addition of diamino benzidine and sections with phase contrast microscopy with an Olympus IX70 Inverted microscope. All sections were additionally counterstained with hematoxylin.

Protein homology searches. Database searches may be helpful in the identification of the antigen for a given peptide sequence. Validated peptide epitope(s) were searched in online databases (through the National Center for Biotechnology Information (NCBI; http://www.ncbi.nlm.nih.gov/BLAST/) and candidate tumor antigens were identified by homology with known human proteins.

Analysis of Patients Eliciting an Immune Response Against the Identified Peptide(s).

An ELISA protocol was used to examine the presence of antibodies for the selected markers in a panel of ovarian cancer patients. Normal serum and non-malignant ascites were also tested to help show whether or not the immune response to the marker was associated with evaluated patient characteristics.

ELISA. Peptide sequences of interest were expressed as GST fusion proteins (described above) and used to screen banked ascites and serum to determine the role of the humoral response against these markers. The purified GST-fusion proteins were used to coat a 96-well plate at 100 ng/well at room temperature (RT) or at 4° C. overnight. Following coating, the wells were emptied, rinsed, and non-specific sites were blocked with 200 μl 3% BSA/PBS at RT for 1-2 hours. Cancer patient ascites and/or sera were applied to each coated and blocked well at 1:100 dilution and then incubated at RT for 1 hour. The wells were rinsed 3× with 3% BSA/PBS containing 0.01% Tween 20, and then incubated for 1 hour with 50 μl each of anti-human alkaline phosphatase at 1:2000 dilution. Signals were detected in the presence of p-nitrophenyl phosphate by measuring $OD_{405}$ at specific intervals to follow the course of color development. A positive control was the cancer ascites the peptide was identified from, and a negative control was donor sera and/or BSA.

Results

Figure 35:
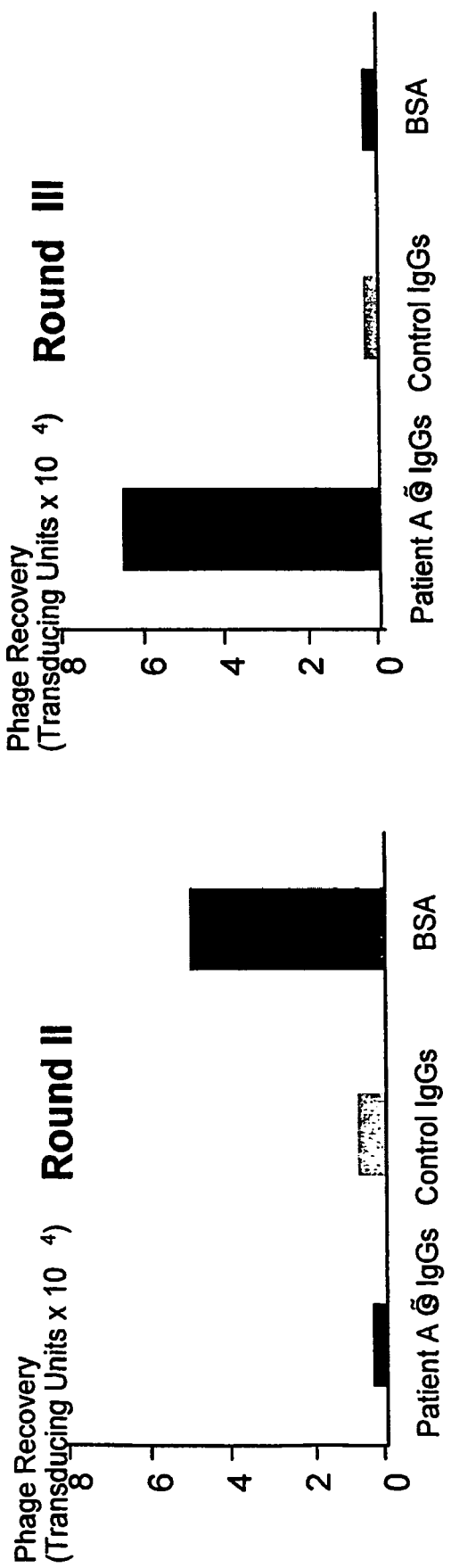
FIG. 35. Specificity of phage binding to ovarian cancer IgG vs. BSA or control IgGs.

FIG. 35 shows the results of biopanning a $CX_7C$ phage display library against ascites taken from an ovarian cancer patient after 2 and 3 rounds of biopanning. As can be seen, after two rounds of biopanning the targeting phage specificity was fairly low, exhibiting higher levels of binding to the BSA and control immunoglobulins. However, after a third round of biopanning the phage exhibited a very high degree of selectivity for binding to the ovarian cancer patient's immunoglobulins, compared to control IgGs or BSA.

Figure 36:
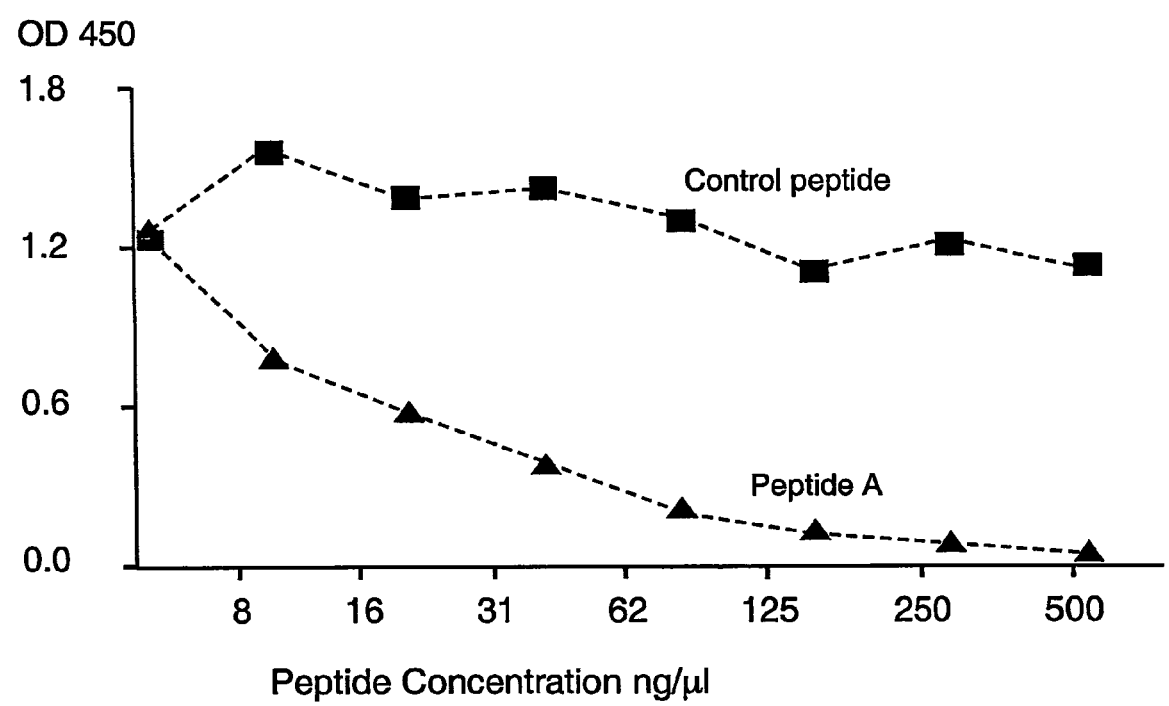
FIG. 36. Validation of ovarian cancer targeting by competition for binding to IgGs isolated from ovarian cancer ascites to immobilized GST fusion peptides versus the corresponding synthetic peptide (CVPELGHEC, SEQ ID NO:132).

The primary peptide sequence recovered against ovarian cancer patient ascites exhibited the targeting sequence CVPELGHEC (SEQ ID NO:132). This peptide represented 86% (73 of 85) of the phage clones that were sequenced. Additional studies were carried out to validate the ovarian ascites targeting specificity of this peptide sequence. FIG. 36 shows that antibodies isolated from the ascites of an ovarian cancer patient bound specifically to the targeting peptide sequence CVPELGHEC (SEQ ID NO:132). Purified ascites immunoglobulins were exposed to microtiter plates containing immobilized GST-CVPELGHEC (SEQ ID NO:132) fusion proteins. Antibody binding to the immobilized fusion protein was competitively inhibited in a dose-dependent fashion by the synthetic CVPELGHEC (SEQ ID NO:132) peptide, but was unaffected by a control peptide (FIG. 36).

Figure 37:
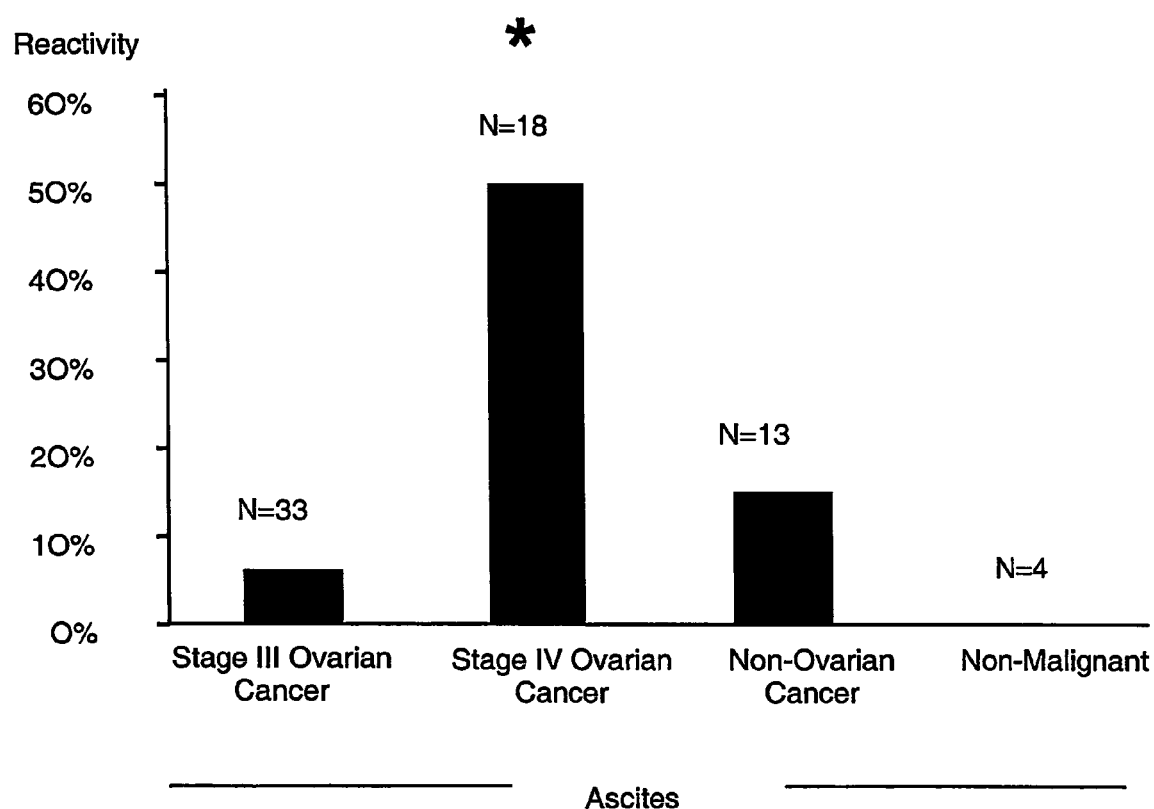
FIG. 37. Reactivity between GST-CVPELGHEC (SEQ ID NO:132) fusion peptide and ascites from patients with different stages of ovarian cancer versus non-ovarian cancer or non-malignant conditions. Positive reactivity is indicated as the ratio between binding to GST-fusion peptide compared to GST alone.

Ascites from patients with different stages of ovarian cancer, non-ovarian cancer or non-malignant conditions was screened against GST-CVPELGHEC (SEQ ID NO:132) fusion proteins using serial dilutions to determine the optimal reactivity of immunoglobulins present in each sample. The results, presented in FIG. 37, show that peptide binding to immunoglobulins is stage dependent, with ascites from Stage IV ovarian cancers showing a higher reactivity than ascites from Stage III ovarian cancer. Some reactivity was also observed with ascites from non-ovarian cancer, but not with ascites from patients with non-malignant conditions (FIG. 37).

These results demonstrate the utility of the CVPELGHEC (SEQ ID NO:132) peptide for the detection, diagnosis, staging and/or prognosis of ovarian cancer. The present of antibodies reactive with the CVPELGHEC (SEQ ID NO:132) peptide in ascites from suspected ovarian cancer patients is indicative of the presence of a high stage ovarian cancer. The skilled artisan will realize that the presence of anti-CVPELGHEC (SEQ ID NO:132) antibodies in patient ascites may also be indicative of the presence of non-ovarian cancers. The artisan will further realize that the CVPELGHEC (SEQ ID NO:132) peptide may be of use as a mimeotope of an ovarian cancer selective endogenous protein. As discussed above, the endogenous mimeotope of the CVPELGHEC (SEQ ID NO:132) peptide may be identified by protein homology searches of the CVPELGHEC (SEQ ID NO:132) peptide against standard databases. Alternatively, as disclosed above, antibodies binding to the CVPELGHEC (SEQ ID NO:132) peptide may be purified by immunoaffinity chromatography and used to identify the endogenous mimeotope. Also alternatively, monoclonal antibodies reactive with the CVPELGHEC (SEQ ID NO:132) peptide may be prepared by standard methods and used to identify the endogenous mimeotope. A preliminary BLAST search against the NCBI database did not reveal any obvious homologies with known protein sequences, indicating that the ovarian cancer targeting peptide may mimic an epitope comprised of two or more portions of the primary sequence of the endogenous mimeotope.

Immunohistochemical analysis against ovarian cancer thin sections from the same patient whose ascites was screened for reactive antibodies demonstrated that an endogenous mimeotope was in fact present in the ovarian tumor (not shown). Autologous immunopurified immunoglobulins used for IHC versus a primary ovarian lesion as well as a metastatic peritoneal nodule showed the presence of strong immunoreactive staining (not shown). Negative controls using secondary antibody alone, or in combination with immunoglobulins obtained from a pool of non-cancer patients showed no IHC staining under identical conditions (not shown). A recombinant GST-CVPELGHEC (SEQ ID NO:132) fusion protein inhibited staining with autologous immunoglobulins. These results demonstrate that IgGs from the ascites of ovarian cancer patients are reactive against an endogenous ovarian cancer antigen that is of use for ovarian cancer detection, diagnosis and/or staging.

All of the COMPOSITIONS, METHODS and APPARATUS disclosed and claimed herein can be made and executed without undue experimentation in light of the present disclosure. While the compositions and methods of this invention have been described in terms of preferred embodiments, it are apparent to those of skill in the art that variations maybe applied to the COMPOSITIONS, METHODS and APPARATUS and in the steps or in the sequence of steps of the methods described herein without departing from the concept, spirit and scope of the invention. More specifically, it are apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Allhoff et al., *World J. Urol.*, 7:12-16, 1989.

An et al., *Molec. Urol.*, 2: 305-309, 1998.

Anand-Apte B, Pepper M S, Voest E, Montesano R, Olsen B, Murphy G, Apte S S and Zetter B. Inhibition of angiogenesis by tissue inhibitor of metallopeinase-3. Invest. Opthamol. Vis. Sci. 38: 817-823, 1997

Arap W, Pasqualini R, and Ruoslahti E. Chemotherapy targeted to tumor vasculature. Curr. Opin. Oncol., 1998b.

Arap, W., Pasqualini R., and Ruoslahti, E. Cancer treatment by targeted drug delivery to tumor vasculature. Science 279:377-380, 1998a.

Arap, W., Pasqualini, R. & Ruoslahti, E. Chemotherapy targeted to tumor vasculature. *Curr Opin Oncol* 10, 560-565, 1998b.

Babian et al., *J. Urol.*, 156:432-437, 1996.

Badalament et al., *J. Urol.*, 156: 1375-1380, 1996.

Baichwal and Sugden, In: *Gene Transer*, Kucherlapati R, ed., New York, Plenum Press, pp. 117-148, 1986.

Bakhshi et al., *Cell* 41:899-906, 1985.

Baldwin, R. W. et al. Monoclonal antibody-defined antigens on tumor cells. Biomembranes 11, 285-312 (1983).

Barany and Merrifield, *The Peptides*, Gross and Meienhofer, eds., Academic Press, New York, pp. 1-284, 1979.

Bartlett, J. S., Kleinschmidt, J., Boucher, R. C. & Samulski, R. J. Targeted adeno-associated virus vector transduction of nonpermissive cells mediated by a bispecific Fab'gamma)2 antibody. Nat Biotechnol 17, 181-186, 1999.

BERGELSON, J. M., CUNNINGHAM, J. A., DROGUETT, G., KURT-JONES, E. A., KRITHIVAS, A., HONG, J. S., HORWITZ, M. S., CROWELL, R. L., and FINBERG, R. W. (1997). Isolation of a common receptor for coxsackie B viruses and adenoviruses 2 and 5. Science 275; 1320-1322.

Bielenberg, D. R., M. F. McCarty, C. D. Bucana, S. H. Yuspa, D. Morgan, J. M. Arbeit, L. M. Ellis, K. R. Cleary, and I. J. Fidler. 1999. Expression of interferon-beta is associated with growth arrest of murine and human epidermal cells. J Invest Dermatol 112:802-9.

Boehm T, Folkman J, Browder T, and O'Reilly M S. Antiangiogenic therapy of experimental cancer does not induce acquired drug resistance. Nature 390:404-407, Boon, T. & Old, L. J. Cancer Tumor antigens. *Curr Opin Immunol* 9, 681-683 (1997).

Bossemeyer, D., Engh, R. A., Kinzel, V., Ponstingl, H. and Huber, R. Phosphotransferase and substrate binding mechanism of the cAMP-dependent protein kinase catalytic subunit from porcine heart as deduced from the 2.0 A structure of the complex with $Mn^{2+}$ adenylyn imidiophosphate and inhibitor peptide PKI(5-24). *EMBO J.* 12:849-859, 1993.

Bova et al., *Cancer Res.*, 53:3869-3873, 1993.

Brawn et al., *The Prostate*, 28: 295-299, 1996.

Brodt et. al, The role of marrow endothelium in the localization of metastatic cancer cells to bone. In Bone Metastasis-mechanisms and pathophysiology, pp 17-23, 1996. (Orr and Singh, eds.)

Brooks P C, Clark R A, Cheresh D A. Requirement of vascular integrin αvβ3 for angiogenesis. Science 264:569-571, 1994a Brooks P C, Stromblad S, Klemle R, Visscher D, Sarkar P H, and Cheresh D A. Anti-integrin αvβ3 blocks human breast cancer growth and angiogenesis in human skin. J. Clin. Invest. 96:1815-1822, 1995.

Brooks, P. C. et al. Localization of matrix metalloproteinase MMP-2 to the surface of invasive cells by interaction with integrin alpha v beta 3. Cell 85, 683-693, 1996.

Brooks, P. C., Montgomery A. M., Rosenfeld, M., Reisfeld, R. A., Hu, T., Klier, G., and Cheresh D. A. Integrin αvβ3 antagonists promote tumor regression by inducing apoptosis of angiogenic blood vessels. Cell 79, 1157-1164, 1994b Brousset, P., S. Chittal, D. Schlaifer, J. Icart, C. Payen, F. Rigal-Huguet, J. J. Voigt, and G. Delsol. 1991. Detection of Epstein-Barr virus messenger RNA in Reed-Sternberg cells of Hodgkin's disease by in situ hybridization with biotinylated probes on specially processed modified acetone methyl benzoate xylene (ModAMeX) sections. Blood 77:1781-6.

Burg M, Pasqualini R, Arap W, Stallcup W, and Ruoslahti E. Identification of NG2 proteoglycan-binding peptides that home to tumor neovasculature. Cancer Res 58:2869-2874, 1999a Burg, M. A., Pasqualini, R., Arap, W., Ruoslahti, E. & Stallcup, W. B. NG2 proteoglycan-binding peptides target tumor neovasculature. Cancer Res 59, 2869-2874, 1999b.

Campbell et al., *Am. J. Pathol.*, 158:25-32, 2001.

Cao Y. O'Reilly M S. Marshall B. Flynn E. Ji R W and Folkman J. Expression of angiostatin cDNA in a murine fibrosarcoma suppresses primary tumor growth and produces long-term dormancy of metastases. J. Clin. Invest. 101:1055-1063, 1998.

Carter, H. B., Piantadosi, S. & Isaacs, J. T. Clinical evidence for and implications of the multistep development of prostate cancer. *J Urol* 143, 742-746 (1990).

Chang, K. L., and L. M. Weiss. 1996. The association of the Epstein-Barr virus with malignant lymphoma. Biomed Pharmacother 50:459-67.

Chen and Okayama, *Mol. Cell Biol.*, 7:2745-2752, 1987.

Chen et al., *J. Cell. Biochem.*, 78:404-416, 2000.

Chinni et al., *Clin. Cancer Res.* 3:1557-64, 1997.

Clark, E. A. and Brugge, J. S. Integrins and signal transduction pathways: the road taken. Science 268:233-238, 1995.

Cleary and Sklar, *Proc. Natl. Acad. Sci. USA* 82:7439-43, 1985.

Coffin, In: *Virology*, Fields et al., eds., Raven Press, New York, pp. 1437-1500, 1990.

Cooner et al., *J. Urol.*, 143:1146-1154, 1990.

Cortese, I. et al. Identification of peptides specific for cerebrospinal fluid antibodies in multiple sclerosis by using phage libraries. *Proc Natl Acad Sci USA* 93, 11063-11067 (1996).

Couch et al., *Am. Rev. Resp. Dis.*, 88:394-403, 1963.

Coupar et al., *Gene*, 68:1-10, 1988.

Cox, D. R. Regression models and life tables. *Journal of the Royal Statistical Society* 74, 187-220 (1972).

Curiel, D. T. Strategies to adapt adenoviral vectors for targeted delivery. Ann N Y Acad Sci 886, 158-171, 1999.

Defilippi, P., Bozzo, C., Volpe, G., Romano, G., Venturino, M., Silengo, L. and Tarone, G. Integrin-mediated signal transduction in human endothelial cells: analysis of tyrosine phosphorylation events. Cell Adh. Commun. 87:75-86, 1994.

Delannet, M., Martin, F., Bossy, B., Cheresh, D. A., Reichardt, L. P. and Duband, J. L. Specific roles of the αvβ1, αvβ3, and αvβ5 integrins in avian neural crest cell adhesion and migration on vitronectin. *Development*. 120:2687-702, 1994.

Delpino et al., *Mol. Membr. Biol.* 15:21-26, 1998.

Dente, L., Vetriani, C., Zucconi, A., Pelicci, G., Lanfrancone, L., Pelicci, P. G. and Cesareni, G. Modified phage peptide libraries as a tool to study specificity of phosphorylation and recognition of tyrosine containing peptides. *J. Mol. Biol.* 269:694-703, 1997.

Derossi, D., Chassaing, G. and Prochiantz, A. Trojan peptides: the penetratin system for intracellular delivery. *Trends Cell Biol.* 8:84-87, 1998.

Derossi, D., Joliot, A. H., Chassaing, G. and Prochiantz, A. The third helix of Antennapedia homeodomain translocates through biological membranes. *J. Biol. Chem.* 269:10444-10450, 1994

DMITRIEV, I., KRASNYKH, V., MILLER, C. R., WANG, M., KASHENTSEV, A. E., MIKHEEVA, G., BELOUSOVA, N., and CURIEL, D. T. (1998). An adenovirus vector with genetically modified fibers demonstrates expanded tropism via utilization of a coxsackie virus and adenovirus receptor-independent cell entry mechanism. J. Virol. 72; 9706-9713.

DOUGLAS, J. T., ROGERS, B. E., ROSENFELD, M. E., MICHAEL, S. I., FENG, M., and CURIEL, D. T. (1996). Targeted gene delivery by tropism-modified adenoviral vectors. Nature Biotechnol. 14; 1574-1578.

Dunn, I. S. Mammalian cell binding and transfection mediated by surface-modified bacteriophage lambda. Biochimie 78, 856-861, 1996.

Dybwad, A., Forre, O., Kjeldsen-Kragh, J., Natvig, J. B. & Sioud, M. Identification of new B cell epitopes in the sera of rheumatoid arthritis patients using a random nanopeptide phage library. *Eur J Immunol* 23, 3189-3193 (1993).

Eisen, T. et al. Continuous low dose Thalidomide: a phase II study in advanced melanoma, renal cell, ovarian and breast cancer. Br J Cancer 82, 812-817, 2000.

Ellerby H M, Arap W, Ellerby L, Kain R, Andrusiak R, Rio G, Krajeswki S, Lombardo C, Rao R, Ruoslahti E, Bredesen D, and Pasqualini R. Anti-cancer Activity of Targeted proapoptotic peptides. Nature Med 9:1032-1038, 1999

Enblad, G., K. Sandvej, E. Lennette, C. Sundstrom, G. Klein, B. Glimelius, and G. Pallesen. 1997. Lack of correlation between EBV serology and presence of EBV in the Hodgkin and Reed-Sternberg cells of patients with Hodgkin's disease. Int J Cancer 72:394-7.

Engelstädter M et al. Targeting human T cells by retroviral vectors displaying antibody domains selected from a phage display library. *Hum Gene Ther.* 2000; 11: 293-303.

Engerman, R. L. and Kern, T. S. (1986) Hyperglycemia as a cause of diabetic retinopathy. *Metabolism* 35(S1), 20-23.

Fearon et al., *Science,* 247:47-56, 1990.

Ferrara, N. and Davis-Smyth, T. (1997) The biology of vascular endothelial growth factor. *Endocr. Rev.,* 18, 4-25.

Filardo, E. J. and Cheresh, D. A. A β turn in the cytoplasmic tail of the integrin αv subunit influences conformation and ligand binding of αvβ3. *J. Biol. Chem.* 269:4641-4647, 1994a.

Filardo, E. J. and Cheresh, D. A. A structural basis for bidirectional integrin signalling. *Princess Takamatsu Symp.* 24:106-117, 1994b.

Filardo, E. J., Brooks, P. C., Deming, S. L., Damsky, C. and Cheresh, D. A. Requirement of the NPXY motif in the integrin β3 subunit cytoplasmic tail for melanoma cell migration in vitro and in vivo. *J. Cell Biol.* 130:441-450, 1995.

Folkman J. Addressing tumor blood vessels. Nature Biotechnol. 15: 510, 1997.

Folkman J. Angiogenesis in cancer, vascular, rheumatoid and other disease. Nature Med 1:27-31, 1995

Folkman, J. Antiangiogenic gene therapy. Proc Natl Acad Sci USA 95, 9064-9066, 1998.

Friedlander M, Brooks P C, Sharffer R W, Kincaid C M, Varner J A, and Cheresh D A. Definition of two angiogenic pathways by distinct αv integrins. Science, 270: 1500-1502, 1995.

Friedlander M, Theesfeld C L, Sugita M, Fruttiger M, Thomas M A, Chang S, Cheresh D A. Involvement of integrins αvβ3 and αvβ5 in ocular neovascular diseases. Proc. Natl. Acad. Sci. USA 93:9764-9769, 1996.

Friedmann, *Science*, 244:1275-1281, 1989.

Frisch S M. And Ruoslahti E. Integrins and anoikis. *Cur. Opin. in Cell Biol.* 9:701-706, 1997.

Puruya et al., *Cancer Res.* 54:6167-75, 1994.

Ghosh-Choudhury et al., *EMBO J.,* 6:1733-1739, 1987.

Gingrich J R, Barrios R J, Morton R A, Boyce B F, DeMayo F J, Finegold M J, Angelopoulou R, Rosen J M and Greenberg N M. Metastatic prostate cancer in a transgenic mouse. Cancer Res. 56:4096-4102, 1996.

Girod A et al. Genetic capsid modifications allow efficient re-targeting of adeno-associated virus type 2. *Nat Med* 1999; 5: 1052-1056.

Gold R. Differenitation between Cellular Apoptosis ad Necrosis by the Combined Use of In Situ Tailing Translation Techniques. Lab. Invest. 71: 219, 1994

Goldman C K et al. Targeted gene delivery to Karposi's sarcoma cells via the fibroblast growth factor receptor. *Cancer Res* 1997; 57: 1447-1451.

GOLDMAN, C. K., ROGERS, B. E., DOUGLAS, J. T., SOSNOWSKI, B. A., YING, W., SIEGAL, G. P., BAIRD, A., CAMPAIN, J. A., and CURIEL, D. T. (1997). Targeted gene delivery to Karposi's sarcoma cells via the fibroblast growth factor receptor. Cancer Res. 57; 1447-1451.

Gomez-Foix et al., *J. Biol. Chem.,* 267:25129-25134, 1992.

Gopal, *Mol. Cell Biol.,* 5:1188-1190, 1985.

Grace, M. J., L. Xie, M. L. Musco, S. Cui, M. Gurnani, R. DiGiacomo, A. Chang, S. Indelicato, J. Syed, R. Johnson, and L. L. Nielsen. 1999. The use of laser scanning cytometry to assess depth of penetration of adenovirus p53 gene therapy in human xenograft biopsies. Am J Pathol 155:1869-78.

Graham and Prevec, In: *Methods in Molecular Biology: Gene Transfer and Expression Protocol*, E. J. Murray, ed., Humana Press, Clifton, N.J., 7:109-128, 1991.

Graham and van der Eb, *Virology,* 52:456-467, 1973.

Graham et al., *J. Gen. Virol.,* 36:59-72, 1977.

Gram, H., Schmitz, R., Zuber, J. F. and Baumann, G. Identification of phosphopeptide ligands for Src-homology 2 (SH2) domain of Grb2 by phage display. *Eur. J. Biochem.* 246:633-637, 1997.

Greenberg N M, DeMayo F, Finegold M J, Medina D, Tilley W D, Aspinall J O, Cunha G R, Donjacour A A, Matusik R J and Rosen J M. Prostate cancer in a transgenic mouse. Proc. Natl. Acad. Sci. USA 92:3439-3443, 1995.

Griscelli P. Li H. Bennaceur-Griscelli A. Soria J. Opolon P. Soria C. Perricaudet M. Yeh P and Lu H. Angiostatin gene transfer: inhibition of tumor growth in vivo by blockage of endothelial cell proliferation associated with a mitosis arrest. Proc. Natl. Acad. Sci. USA 95:6367-72, 1998

Grunhaus and Horwitz, *Seminar in Virology,* 3:237-252, 1992.

Gunge, N., Takata, H., Fukuda, K., Iowa, S. & Miyakawa, I. Relocation of a cytoplasmic yeast linear plasmid to the nucleus is associated with circularization via nonhomologous recombination involving inverted terminal repeats. Mol Gen Genet 263, 846-853 (2000).

Hall, H, Williams, E J., Moore, S E., Walsh, F S., Prochiantz, A. and Doherty, P. Inhibition of FGF-stimulated phosphatidylinositol hydrolysis and neuron outgrowth by a cell-membrane permeable phosphopeptide. *Current Biology,* 6:580-587, 1996.

Hammes H P, Brownlee M, Jonczyk A, Sutter A, and Preissner K T. Subcutaneous injection of a cyclic peptide antagonist of vitronectin receptor-type integrins inhibits retinal neovascularization. Nature Med. 2: 529-533, 1996.

Hanahan, D. and Folkman, J. (1996) Patterns and Emerging Mechanisms of the Angiogenic Switch during Tumorogenesis. *Cell,* 86, 353-364.

Hansen, A. S., Norén, O., Sjöström, H. and Wedelin, O. (1993) A mouse aminopeptidase-N is a marker for antigen presenting cells and apears to be co-expressed with major histocompatibility complex class II molecules. *Eur. J. Immunol.,* 23, 2358-64.

HARLOW, E., and LANE, D. (1988). *Antibodies: A Laboratory Manual* (Cold Spring Harbor Laboratory Press, New York, N.Y.).

Hart S L et al. Cell binding and internalization by filamentous phage displaying a cyclic Arg-Gly-Asp-containing peptide. J. Biol. Chem. 269, 12468-12474, 1994

Hemler, M., Weitzman, J., Pasqualini, R., Kawaguchi, S., Kassner, P. and Berdichevsky, F. Structure, biochemical properties, and biological functions of integrin cytoplasmic domains. In: Integrins: The Biological Problems (ed. Yoshi Takada) CRC Press, Inc., Boca Raton, Fla., USA; pp. 1-35, 1994.

Hendrix R W. Evolution: the long evolutionary reach of viruses. Current Biol. 9:914-917, 1999.

HENRY, L., XIA, D., WILKE, M., DEISENHOFER, J., and GERARD, R. (1994). Characterization of the knob domain of the adenovirus type 5 fiber protein expressed in *E. coli*. J. Virol. 68; 5239-5246.

Herbst, H., E. Steinbrecher, G. Niedobitek, L. S. Young, L. Brooks, N. Muller-Lantzsch, and H. Stein. 1992. Distribution and phenotype of Epstein-Barr virus-harboring cells in Hodgkin's disease. Blood 80:484-91.

Herbst, H., F. Dallenbach, M. Hummel, G. Niedobitek, S. Pileri, N. Muller-Lantzsch, and H. Stein. 1991. Epstein-Barr virus latent membrane protein expression in Hodgkin and Reed-Sternberg cells. Proc Natl Acad Sci USA 88:4766-70.

Hermonat and Muzycska, *Proc. Natl. Acad. Sci. USA,* 81:6466-6470, 1984.

Herndier B G, Werner A, Arnstein P, Abbey N W, Demartis P, Cohen R L, Shuman M A and Levy, J A Characterization of a human Kaposi's sarcoma cell line that induces angiogenic tumors in animals. AIDS 8:575-581, 1996.

Hersdorffer et al., *DNA Cell Biol.,* 9:713-723, 1990.

Herz and Gerard, *Proc. Natl Acad. Sci. USA,* 90:2812-2816, 1993.

HEYWOOD, S. P., and HOOPER, N. M. (1995). Development and application of a fluorometric assay for mammalian membrane dipeptidase. Anal. Biochem. 226; 10-14.

HONG, S. S., GALAUP, A., PEYTAVI, R., CHAZAL, N., and BOULANGER, P. A. (1999). Enhancement of adenovirus-mediated gene delivery by use of an oligopeptide with dual binding specificity. Hum. Gene Ther. 10; 2577-2586.

HONG, S. S., KARYAN, L., TOURNIER, J., CURIEL, D. T., and BOULANGER, P. A. (1997). Adenovirus type 5 fiber knob binds to MHC class I alpha-2 domain at the surface of human epithelial and B lymphoblastoid cells. EMBO J. 16; 2294-2306.

Horwich, et al., *J. Virol.*, 64:642-650, 1990.

Huang et al., *Prostate*, 23: 201-212, 1993.

Hughes et al., *Cancer Res.* 49:4452-54, 1989

Hynes, R. O. Integrins: versatility, modulation and signaling in cell adhesion. *Cell* 69:11-25, 1992.

Isaacs et al., *Cancer Res.*, 51:4716-4720, 1991.

Isaacs et al., *Sem. Oncol.*, 21:1-18, 1994.

Ivanenkov, V., Felici, F. & Menon, A. G. Uptake and intracellular fate of phage display vectors in mammalian cells. Biochim Biophys Acta 1448, 450-462, 1999a.

Ivanenkov, V. V., Felici, F. & Menon, A. G. Targeted delivery of multivalent phage display vectors into mammalian cells. Biochim Biophys Acta 1448, 463-472, 1999b.

*J. Natl. Cancer Inst.* 90:273-286, 1998.

Jacobson et al., *JAMA*, 274:1445-1449, 1995.

Jarrett, A. F., A. A. Armstrong, and E. Alexander. 1996. Epidemiology of EBV and Hodgkin's lymphoma Ann Oncol 7:5-10.

Jarrett, R. F., and J. MacKenzie. 1999. Epstein-Barr virus and other candidate viruses in the pathogenesis of Hodgkin's disease. Semin Hematol 36:260-9.

Johnson et al., "Peptide Turn Mimetics" in *BIOTECHNOLOGY AND PHARMACY*, Pezzuto et al., Eds., Chapman and Hall, New York (1993).

Joliot, A. H. Triller, A., Volovitch, M. Pemelle, C., and Prochiantz, A. alpha-2,8-Polysialic acid is the neuronal surface receptor of antennapedia homeobox peptide. *New Biol.* 3:1121-1131, 1991a.

Joliot, A. H., Pemelle, C., Deagostini-Bazin, H. and Prochiantz, A. Antennapedia homeobox peptide regulates neural morphogenesis *Proc. Natl. Acad. Sci. U.S.A.* 88:1864-1868, 1991b.

Jones and Shenk, *Cell*, 13:181-188, 1978.

Kaplan, E. L. a. M., P. Nonparametric estimation from incomplete observations. *Journal of the American Statistical Association* 53, 457-481 (1958).

Karlsson et al., *EMBO J.*, 5:2377-2385, 1986.

Kasono, K. et al. Selective gene delivery to head and neck cancer cells via an integrin targeted adenoviral vector. Clin Cancer Res 5, 2571-2579, 1999.

Kassner, P. D., Burg, M. A., Baird, A. & Larocca, D. Genetic selection of phage engineered for receptor-mediated gene transfer to mammalian cells. Biochem Biophys Res Commun 264, 921-928, 1999.

Kerr et al., *Br. J. Cancer* 26:239-257, 1972.

Kiang et al., *Chin. J. Physiol.* 40:213-219, 1997

Klemke, R. L., Yebra, M., Bayna, E. M. and Cheresh, D. A. Receptor tyrosine kinase signaling required for integrin αvβ5-directed cell motility but not adhesion on vitronectin. *J. Cell Biol.* 127:859-866, 1994.

Koivunen et al., Tumor targeting with a selective gelatinase inhibitor. Nature Biotechnol 17:768-774, 1999a Koivunen et al., Selection of peptides binding to the □5□1 integrin from phage display library. J. Biol. Chem. 268: 20205-20210, 1993.

Koivunen et al. Phage display libraries displaying cyclic peptides with different ring sizes: ligand specificities of the RGD-directed integrins. BioTechnology 13:265-270, 1995.

Koivunen et al. Integrin-binding peptides derived from phage display libraries. *Methods Mol Biol* 129, 3-17 (1999b).

Koivunen et al., *J. Cell Biol.* 153:905-16, 2001.

Kolanus, W. and Seed, B. Integrins and inside-out signal transduction: converging signals from PKC and PIP3. *Curr. Opin. Cell Biol.* 9:725-731, 1997.

Kolonin M G. Finley R L Jr. Targeting cyclin-dependent kinases in *Drosophila* with peptide aptamers. Proc. of the Natl. Acad. of Sci. USA. 95:14266-71, 1998.

Kolonin et al., *Curr. Opin. Chem. Biol.* 5:308-13, 2001.

Kong H L and Crystal R G. Gene therapy strategies for tumor antiangiogenesis.

Kouzmitcheva G. A. et al. Identifying diagnostic peptides for lyme disease through epitope discovery. *Clin Diagn Lab Immunol* 8, 150-60 (2001).

KOZARSKY, K., JOOSS, K., DUNAHEE, M., STRAUSS, J. F., and WILSON, J. M. (1996). Effective treatment of familial hypercholesterolaemia in the mouse model using adenovirus-mediated transfer of the VLDL receptor gene. Nat. Genet. 13; 54-62.

KRASNYKH, V., DMITRIEV, I., MIKHEEV, A. G., MILLER, C. R., BELOUSOVA, N., and CURIEL, D. T. (1998). Characterization of an adenovirus vector containing a heterologous peptide epitope in the HI loop of the fiber knob. J. Virol. 72; 1844-1852.

KRASNYKH, V., MIKHEEVA, G. V., DOUGLAS, J. T., and CURIEL, D. T. (1996). Generation of recombinant adenovirus vectors with modified fibers for altering viral tropism. J. Virol. 70; 6839-6846.

Lane T. Shah J. Clinical features and management of benign prostatic hyperplasia. Hospital Medicine. 60(10):705-9, 1999.

Larocca D et al. Gene transfer to mammalian cells using genetically targeted filamentous bacteriophage. *FASEB J* 1999; 13:727-734.

Larocca, D., Witte, A., Johnson, W., Pierce, G. F. & Baird, A. Targeting bacteriophage to mammalian cell surface receptors for gene delivery. Hum Gene Ther 9, 2393-2399, 1998.

Le Gal La Salle et al., *Science*, 259:988-990, 1993.

Le Roux, I., Joliot, A. H., Bloch-Gallego, E., Prochiantz, A. and Volovitch, M. Neurotrophic activity of the Antennapedia homeodomain depends on its specific DNA-binding properties. *Proc. Natl. Acad. Sci. U.S.A.* 90:9120-9124, 1993

Levrero et al., *Gene*, 101:195-202, 1991.

Lewis, J. M., Cheresh, D. A. and Schwartz, M. A. Protein kinase C regulates αvβ5-dependent cytoskeletal associations and focal adhesion kinase phosphorylation. *J. Cell Biol.* 134: 1323-1332, 1996.

Lin, T. H., Aplin, A. E., Shen, Y., Chen Q., Schaller, M. D., Romer L., Aukhil, I. and Juliano, R. L. Integrin-mediated activation of MAP kinase is independent of FAK: evidence for dual integrin signalling pathways in fibroblast. *J. Cell Biol.* 136:1385-1395, 1997.

Longhurst, C. M. and Jennings, L. K Integrin-mediated signal transduction. *Cell Mol. Life Sci.* 54:514-526, 1998.

Look A T, Ashmun R A, Shapiro L H and Peiper S C. Human myeloid plasma membrane glycoprotein CD13 (gp150) is identical to aminopeptidase N. J. Clin. Invest. 83:1299-1307, 1989.

LOUIS, N., FENDER, P., BARGE, A., KITS, P., and CHROBOCZEK, J. (1994). Cell-binding domain of adenovirus serotype 2 fiber. J. Virol. 68; 4104-4106.

Lunardi, C. et al. Systemic sclerosis immunoglobulin G autoantibodies bind the human cytomegalovirus late protein UL94 and induce apoptosis in human endothelial cells [In Process Citation]. Nat Med 6, 1183-1186 (2000).

Lynch, C. M. et al. Adeno-associated virus vectors for vascular gene delivery. Circ Res 80, 497-505, 1997.

Lyons, S. F., and D. N. Liebowitz. 1998. The roles of human viruses in the pathogenesis of lymphoma. Semin Oncol 25:461-75.

MacGregor, G. R. & Caskey, C. T. Construction of plasmids that express *E. coli* beta-galactosidase in mammalian cells. Nucleic Acids Res 17, 2365, 1989.

Macoska et al., *Cancer Res.*, 54:3824-3830, 1994.

Mahboubi et al, *J. Immunol.* 164:3837-3846, 2000.

Mann et al., *Cell,* 33:153-159, 1983.

Markowitz et al., *J. Virol.,* 62:1120-1124, 1988.

Martin F et al. Retrovirus targeting by tropism restriction to melanoma cells. *J Virol* 1999; 73: 6923-6929.

Martiny-Baron G, and Marme D. VEGF-mediated tumor angiogenesis: a new target for cancer therapy. Curr. Opin. Biotechnol. 6:675-680, 1995.

Mennuni, C. et al. Selection of phage-displayed peptides mimicking type 1 diabetes-specific epitopes. *J Autoimmun* 9, 431-436 (1996).

Merrifield, *Science,* 232: 341-347, 1986

MICHAEL, S. I., HONG, J. S., CURIEL, D. T., and ENGLER, J. A. (1995). Addition of a short peptide ligand to the adenovirus fiber protein. Gene Ther. 2; 660-668.

Miki et al., *Science,* 266:66-71, 1994.

Mikolajczyk S D. Millar L S. Wang T J. Rittenhouse H G. Marks L S. Song W. Wheeler T M. Slawin K M. A precursor form of prostate-specific antigen is more highly elevated in prostate cancer compared with benign transition zone prostate tissue. Cancer Research. 60(3):756-9, 2000.

Miller C R et al. Differential susceptibility of primary and established human glioma cells to adenovirus infection: targeting via the epidermal growth factor receptor achieves fiber receptor independent gene transfer. *Cancer Res* 1998; 58: 5738-5748.

Motti, C. et al. Recognition by human sera and immunogenicity of HBsAg mimotopes selected from an M13 phage display library. *Gene* 146, 191-198 (1994).

Mulligan, *Science,* 260:926-932, 1993.

Murphy et al., *Cancer,* 78: 809-818, 1996.

Mustonen T and Alitalo K. Endothelial receptor tyrosine linases involved in angiogenesis. J. Cell Biol. 129:895-898, 1995.

Muzyczka N. Adeno-associated virus (AAV) vectors: will they work? J. Clin. Invest. 94:1351, 1994

Nicolas and Rubinstein, In: *Vectors: A survey of molecular cloning vectors and their uses,* Rodriguez and Denhardt, eds., Stoneham: Butterworth, pp. 494-513, 1988.

Nicolau et al., *Methods Enzymol.,* 149:157-176, 1987.

O'Dowd et al., *J. Urol.,* 158:687-698, 1997.

Old, L. J. Cancer immunology: the search for specificity—G. H. A. Clowes Memorial lecture. *Cancer Res* 41, 361-375 (1981).

Olofsson, B. Jeltsch, M., Eriksson, U. and Alitalo, K. (1999) Current Biology of VEGF-B and VEGF-C. *Curr Op Biotechnol,* 10, 528-535.

Olofsson, B., Pajusola, K., Kaipainen, A., Euler, G., Joukov, V., Saksela, O., Orpana, A., Pettersson, R. F., Alitalo, K. and Eriksson, U. (1996) Vascular Endothelial Growth factor B, a novel growth factor for endothelial cells. *Proc Natl Acad Sci USA,* 93, 2576-2581.

Orozco et al., *Urology,* 51:186-195, 1998.

Owens, G. P., R. A. Williamson, M. P. Burgoon, O. Ghausi, D. R. Burton, and D. H. Gilden. 2000. Cloning the antibody response in humans with chronic inflammatory disease: immunopanning of subacute sclerosing panencephalitis (SSPE) brain sections with antibody phage libraries prepared from SSPE brain enriches for antibody recognizing measles virus antigens in situ. J Virol 74:1533-7.

Pallesen, G., S. J. Hamilton-Dutoit, M. Rowe, and L. S. Young. 1991. Expression of Epstein-Barr virus latent gene products in tumour cells of Hodglin's disease [see comments]. Lancet 337:320-2.

Partin and Oesterling, *J. Urol.,* 152:1358-1368, 1994.

Paskind et al., *Virology,* 67:242-248, 1975.

Pasqualini R and Ruoslahti E. Organ targeting in vivo using phage display peptide libraries. Nature 380:364-366, 1996.

Pasqualini R, Koivunen E, and Ruoslahti E. A peptide isolated from phage display libraries is a structural and functional mimic of an RGD-binding site on integrins. J. Cell Biol. 130:1189-1196, 1995.

Pasqualini R, Koivunen E, and Ruoslahti E. αv integrins as receptors for tumor targeting by circulating ligands. Nature Biotechnol 15:542-546, 1997

Pasqualini, R. and Hemler, M. E. Contrasting roles for integrin b1 and b5 cytoplasmic domains in subcellular localization, cell proliferation, and cell migration. *J. Cell Biol.* 125:447-60, 1994.

Pasqualini, R. Vascular Targeting with Phage Display Peptide Libraries. The Quart. J. Nucl. Med. 43:159-162, 1999.

Pasqualini, R., Arap W., Koivunen, E., Kain, R., Lahdenranta, J., Shapiro, L., Sakamoto, M., Stryn, A. and Ruoslahti, E. Aminopeptidase N is a receptor for tumor-homing peptides and a target for inhibiting angiogenesis. Cancer Res. 60: 722-727, 2000.

Pelleymounter et al. Effects of the obese gene product on body weight regulation in ob/ob mice. Science 269: 540-543, 1994.

Pereboeva, L. A., A. V. Pereboev, and G. E. Morris. 1998. Identification of antigenic sites on three hepatitis C virus proteins using phage-displayed peptide libraries. J Med Virol 56:105-11.

Pereboeva, L. A., A. V. Pereboev, L. P. Wang, and G. E. Morris. 2000. Hepatitis C epitopes from phage-displayed cDNA libraries and improved diagnosis with a chimeric antigen. J Med Virol 60:144-51.

Piironen et al., *Clin. Chem.* 42:1034-1041, 1996.

Potter et al., *Proc. Nat. Acad. Sci. USA,* 81:7161-7165, 1984.

Poul, M. A. & Marks, J. D. Targeted gene delivery to mammalian cells by filamentous bacteriophage. J Mol Biol 288, 203-211, 1999.

Prezzi, C. et al. Selection of antigenic and immunogenic mimics of hepatitis C virus using sera from patients. *J Immunol* 156, 4504-4513 (1996).

Prezzi, C., M. Nuzzo, A. Meola, P. Delmastro, G. Galfre, R. Cortese, A. Nicosia, and P. Monaci. 1996. Selection of antigenic and immunogenic mimics of hepatitis C virus using sera from patients. J Immunol 156:4504-13.

PRICE, J. E., POLYZOS, A., ZHANG, R. D., and DANIELS, L. M. (1990). Tumorigenicity and metastasis of human breast carcinoma cells lines in nude mice. Cancer Res. 50; 717-721.

Puntoriero, G. et al. Towards a solution for hepatitis C virus hypervariability: mimotopes of the hypervariable region 1 can induce antibodies cross-reacting with a large number of viral variants. *Embo J* 17, 3521-3533 (1998).

Racher et al., *Biotechnology Techniques,* 9:169-174, 1995.

Ragot et al., *Nature,* 361:647-650, 1993.

Rajotte D and Ruoslahti E. Membrane dipeptidase is the receptor for a lung-targeting peptide identified by in vivo phage display. J Biol Chem 274:11593-11598, 1999

Rajotte D, Arap W, Hagedorn M, Koivunen E, Pasqualini R, and Ruoslahti E. Molecular heterogeneity of the vascular endothelium revealed by in vivo phage display. J Clin Invest 102:430-437, 1998

Rak J W, St. Croix B D, and Kerbel R S. Consequences of angiogenesis for tumor progression, metastasis and cancer. Anticancer Drugs 6:3-18, 1995.

Razzaque, A., Y. Francillon, P. N. Jilly, and F. Varricchio. 1996. Detection of human herpesvirus 6 sequences in lymphoma tissues by immunohistochemistry and polymerase chain reactions. Cancer Lett 106:221-6.

Remington's Pharmaceutical Sciences, 15th ed., pp. 1035-1038 and 1570-1580.

Renan, *Radiother. Oncol.,* 19:197-218, 1990.

Renata Pasqualini, W. A., Daniel Rajotte, and Erkid Ruoslahti. in *Phage Display: A Laboratory manual* (ed. Carlos F. Barbas III, D. R. B., Jamie K. Scott, and Gregg J. Silverman) 22.21-22.24 (Cold Spring Harbor Laboratory Press, New York, 2001).

Rich et al., *Hum. Gene Ther.,* 4:461-476, 1993.

Ridgeway, In: *Vectors: A Survey of Molecular Cloning Vectors and Their Uses,* Rodriguez et al., eds., Stoneham: Butterworth, pp. 467-492, 1988.

Rippe et al., *Mol. Cell Biol.,* 10:689-695, 1990.

ROELVINK, P. W., LEE, G. M., EINFELD, D. A., KOVESDI, I., and WICKHAM, T. J. (1999). Identification of a conserved receptor-binding site on the fiber proteins of CAR-recognizing adenoviridae. Science 286; 1568-1571.

ROMANCZUK, H., GALER, C. E., ZABNER, J., BARSOMIAN, G., WADSWORTH, S. C., and O'RIORDAN, C. R. (1999). Modification of an adenoviral vector with biologically selected peptides: a novel strategy for gene delivery to cells of choice. Hum. Gene Ther. 10; 2615-2626.

Rosenfeld et al., *Cell,* 68:143-155, 1992.

Rosenfeld et al., *Science,* 252:431-434, 1991.

Rowley, M. J. et al. Prediction of the immunodominant epitope of the pyruvate dehydrogenase complex E2 in primary biliary cirrhosis using phage display. *J Immunol* 164, 3413-3419 (2000).

Ruoslahti E. RGD and other sequence recognition sequences for integrins. Annu. Rev. Cell Dev. Biol. 12:697-715, 1996

Sahin, U. et al. Human neoplasms elicit multiple specific immune responses in the autologous host. *Proc Natl Acad Sci USA* 92, 11810-11813 (1995).

Sahin, U., Tureci, O. & Pfreundschuh, M. Serological identification of human tumor antigens. *Curr Opin Immunol* 9, 709-716 (1997).

Scala, G. et al. Selection of HIV-specific immunogenic epitopes by screening random peptide libraries with HIV-1-positive sera. *J Immunol* 162, 6155-6161 (1999).

Schlingemann R O, Rietveld F J, de Waal R M, Ferrone S, Ruiter D J. Expression of the high molecular weight melanoma-associated antigen by pericytes during angiogenesis in tumors and in healing wounds. Am. J. Pathol. 136:1393-1405, 1990.

Schmitz, R., Baumann, G. and Gram, H. Catalytic specificity of phosphotyrosine kinase Blk, Lyn, c-Src and Syk as assessed by phage display *J. Mol. Biol.* 260: 664-677, 1996.

Shattil, S. J. and Ginsberg, M. H. Perspectives series: cell adhesion in vascular biology. Integrin signaling in vascular biology. *J. Clin. Invest.* 100: 1-5, 1997.

Short S M, Talbott G A and Juliano R L. Integrin-mediated Signaling Events in Human Endothelial Cells. Mol. Biol. Cell 9: 1969-1980, 1998

Sidransky et al., *Science,* 252:706-709, 1991.

Sidransky et al., *Cancer Res.,* 52:2984-2986, 1992.

Silverstein, *JCI* 74:1625-1633, 1984

Slamon et al., *Science,* 244:707-712, 1989.

Smith G. P. Surface presentation of protein epitopes using bacteriophage expression system. *Curr Opin Biotechnol* 2, 668-73 (1991).

Smith G P, and Scott J K. Libraries of peptides and proteins displayed in filamentous phage. Meth. Enzymol. 21:228-257, 1993.

Smith G P, and Scott J K. Searching for peptide ligands with an epitope library. Science 228:1315-1317, 1985

Smith, D. B., and K. S. Johnson. 1988. Single-step purification of polypeptides expressed in *Escherichia coli* as fusions with glutathione S-transferase. Gene 67:31-40.

Smith, G. P. 1985. Filamentous fusion phage: novel expression vectors that display cloned antigens on the virion surface. Science 228:1315-7.

Smith, G. P. Surface presentation of protein epitopes using bacteriophage expression systems. *Curr. Opin. Biotechnol.* 2:668-673, 1991.

Solowska J, Edelman J M, Albelda S M and Buck C A. (1991) Cytoplasmic and transmembrane domains of integrin β1 and β3 subunits are functionally interchangeable. J. Cell Biol. 114: 1079-1088.

Staratschek-Jox, A., S. Kotkowski, G. Belge, T. Rudiger, J. Bullerdiek, V. Diehl, and J. Wolf. 2000. Detection of Epstein-Barr virus in Hodgkin-Reed-Sternberg cells: no evidence for the persistence of integrated viral fragments in Latent membrane protein-1 (LMP-1)-negative classical Hodgkin's disease. Am J Pathol 156:209-16.

Sternberg, N. & Hoess, R. H. Display of peptides and proteins on the surface of bacteriophage lambda. Proc Natl Acad Sci USA 92, 1609-1613, 1995.

Stewart and Young, *Solid Phase Peptide Synthesis,* 2d. ed., Pierce Chemical Co., 1984.

Stoeckle et al., *Mol. Cell Biol.* 8:2675-80, 1988.

Stratford-Perricaudet and Perricaudet, In: *Human Gene Transfer,* O. Cohen-Haguenauer et al., eds., John Libbey Eurotext, France, pp. 51-61, 1991.

Stratford-Perricaudet et al, *Hum. Gene. Ther.,* 1:241-256, 1990.

Tam et al., *J. Am. Chem. Soc.,* 105:6442, 1983.

Tanaka T, Cao Y, Folkman J and Fine H A. Viral vector-targeted antiangiogenic gene therapy utilizing an angiostatin complementary DNA. Cancer Res. 58:3362-3369, 1998.

Taparowsky et al., *Nature,* 300:762-764, 1982.

Temin, In: *Gene Transfer,* Kucherlapati R, ed., New York, Plenum Press, pp. 149-188, 1986.

Theodore, L., Derossi, D., Chassaing, G., Llirbat, B., Kubes, M., Jordan, P., Chneiweiss, H, Godement, P., and Prochiantz, A. Intraneuronal delivery of protein kinase C pseudosubstrate leads to growth cone collapse. *J. Neurosci.* 15:7158-7167, 1995.

Tischer, E., Mitchell, R., Hartman, T., Silvia, M., Gospodarowicz, D., Fiddes, J. C. and Abraham, J. (1991) the human Gene for Vascular Endothelial Growth Factor. *J. Biol. Chem.,* 226, 11947-11954.

Top et al., *J. Infect. Dis.,* 124:155-160, 1971.

Triantafilou et al., *Hum. Immunol.* 62:764-770, 2001.

Tsujimoto et al., *Nature* 315:340-343, 1985.

Tureci, O., Sahin, U. & Pfreundschuh, M. Serological analysis of human tumor antigens: molecular definition and implications. *Mol Med Today* 3, 342-349 (1997).

Tur-Kaspa et al., *Mol. Cell Biol.,* 6:716-718, 1986.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 5,021,236
U.S. Pat. No. 5,206,347
U.S. Pat. No. 5,223,409
U.S. Pat. No. 5,401,511
U.S. Pat. No. 5,492,807
U.S. Pat. No. 5,603,872

U.S. Pat. No. 5,622,699
U.S. Pat. No. 5,670,312
U.S. Pat. No. 5,705,610
U.S. Pat. No. 5,840,841
U.S. Pat. No. 5,889,155
U.S. Pat. No. 6,068,829

Varmus et al., Cell, 25:23-36, 1981.

Veikkola, T. and Alitalo, K. (1999) VEGFs, receptors and angiogenesis. Seminar Cancer Bio.l, 9, 211-220.

Veltri et al., Urology, 53:139-147, 1999.

Vendruscolo et al., Nature 409:641-45, 2001.

VIGNE, E., MAHFOUZ, I., DEDIEU, J. F., BRIE, A., PERRICAUDET, M., and YEH, P. (1999). RGD inclusion in the hexon monomer provides adenovirns type 5-based vectors with a fiber knob-independent pathway for infection. J. Virol. 73; 5156-5161.

Vu, T. H. et al. MMP-9/gelatinase B is a key regulator of growth plate angiogenesis and apoptosis of hypertrophic chondrocytes. Cell 93, 411-422, 1998.

Vuori K. Ruoslahti E. Association of insulin receptor substrate-1 with integrins. Science 266:1576-1578, 1994

WATKINS, S. J., MESYANZHINOV, V. V., KUROCHKINA, L. P., and HAWKINS, R. E. (1997). The adenobody approach to viral targeting—specific and enhanced adenoviral gene delivery. Gene Ther. 4; 1004-1012.

Watson C A, Camera-Benson L, Palmer-Croker R and Pober J S. Variability among human umbilical vein endothelial cell cultures. Science 268: 447-448, 1995.

Weiss, L. M., J. G. Strickler, R. A. Warnke, D. T. Purtilo, and J. Sklar. 1987. Epstein-Barr viral DNA in tissues of Hodgkin's disease. Am J Pathol 129:86-91

Weiss, L. M., Y. Y. Chen, X. F. Liu, and D. Shibata. 1991. Epstein-Barr virus and Hodgkin's disease. A correlative in situ hybridization and polymerase chain reaction study. Am J Pathol 139:1259-65.

Weitzman M D, Wilson J M and Eck S L. Adenovirus vectors in cancer gene therapy. In: Gene Therapy and Vector Systems 2: 17-25, 1997.

Wells, J. A. and Lowman, H. B. Rapid evolution of peptide and protein binding properties in vitro. Curr. Opin. Biotechnol. 3:355-362, 1992.

Wickham T J. Haskard D. Segal D. Kovesdi I. Targeting endothelium for gene therapy via receptors up-regulated during angiogenesis and inflammation. Cancer Immunol. Immunother. 45:149-151, 1997c.

Wickham, T. J. Targeting adenovirus. Gene Ther 7, 110-114, 2000.

WICKHAM, T. J., CARRION, M. E., and KOVESDI, I. (1995). Targeting of adenovirus penton base to new receptors through replacement of its RGD motif with other receptor-specific peptide motifs. Gene Ther. 2; 750-756.

WICKHAM, T. J., LEE, G., TITUS, J., SCONOCCHIA, G., BAKACS, T., KOVESDI, I., and SEGAL, D. (1997a). Targeted adenovirus-mediated gene delivery to T-cells via CD3. J. Virol. 71; 7663-7669.

WICKHAM, T. J., MATHIAS, P., CHERESH, D. A., and NEMEROW, G. R. (1993). Integrins alpha v beta 3 and alpha v beta 5 promote adenovirus internalization but not attachment. Cell 73; 309-319.

WICKHAM, T. J., ROELVINK, P. W., BROUGH, D. E., and KOVESDI, I. (1996b). Adenovirus targeted to heparan-containing receptors increases its gene delivery efficiency to multiple cell types. Nature Biotechnol. 14; 1570-1573.

WICKHAM, T. J., SEGAL, D. M., ROELVINK, P. W., CARRION, M. E., LIZONOVA, A., LEE, G. M., and KOVESDI, I. (1996a). Targeted adenovirus gene transfer to endothelial and smooth muscle cells by using bispecific antibodies. J. Virol. 70; 6831-6838.

WICKHAM, T. J., TZENG, E., SHEARS II, L. L., ROELVINK, P. E., LI, Y., LEE, G. M., BROUGH, D. E., LIZONOVA, A., and KOVESDI, L (1997b). Increased in vitro and in vivo gene transfer by adenovirus vectors containing chimeric fiber proteins. J. Virol. 71; 8221-8229.

Wong et al., Gene, 10:87-94, 1980.

Wu and Wu, Biochemistry, 27: 887-892, 1988.

Wu and Wu, J. Biol. Chem., 262: 4429-4432, 1987.

Zetter B R. Angiogenesis and tumor metastasis. Ann Rev Med 49:407-424, 1998

Zhang et al., Nature 372: 425-432, 1994.

Zhang J and Russell S. Vectors for cancer gene therapy. Cancer Met. Rev. 3:385-401, 1996.

ZHANG, W. (1999). Development and application of adenoviral vectors for gene therapy of cancer. Cancer Gene Ther. 6; 113-138.

Zini, S., Fournie-Zaluski, M. C., Chauvel, E., Roques, B., Corvol, P. and Cortes-Llorens, C. (1996) Identification of metabolic pathways of brain angiotensin II and III using specific aminopeptidase inhibitors: predominant role of angiotensin III in the control of vasopressin release. Proc Natl Acad Sci USA, 93, 11968-11973.

Zlotta et al., J. Urol., 157:1315-1321, 1997.

What is claimed is:

1. A method of delivering an agent to a prostate cancer tissue comprising:
   a) obtaining a peptide that selectively binds to prostate cancer tissue, wherein the peptide is less than 100 amino acids in length and includes a prostate cancer targeting motif having the amino acid sequence of any of SEQ ID NO:5 through SEQ ID NO:29, SEQ ID NO:34, SEQ ID NO:35, or SEQ ID NO:37, wherein the peptide is attached or fused to an agent that one desires to target to a prostate cancer tissue; and
   b) exposing the peptide to a population of cells suspected of containing prostate cancer cells.

2. The method of claim 1, wherein the population of cells is in a human subject.

3. The method of claim 1, wherein the population of cells is a thin section of a tissue.

4. The method of claim 1, further comprising detecting prostate cancer cells in said population.

5. The method of claim 1, further comprising diagnosing prostate cancer.

6. The method of claim 1, further comprising providing a prognosis for an individual with prostate cancer.

7. The method of claim 1, further comprising categorizing the prostate cancer as androgen-dependent or androgen-independent.

8. The method of claim 7, wherein said categorizing is based on the expression of IL-11Rα in the blood vessels of said prostate cancer.

9. The method of claim 1, wherein the peptide comprises the amino acid sequence selected from SEQ ID NO:34 or SEQ ID NO:37.

10. The method of claim 1, wherein the agent is a therapeutic agent or an imaging agent.

11. The method of claim 10, wherein the agent is a polypeptide and the peptide and agent form a fusion protein.

12. The method of claim 10, wherein the agent and peptide are administered to an individual having or suspected of having prostate cancer to treat or image the cancer.

13. The method of claim 10, wherein the agent is a therapeutic agent.

14. The method of claim 13, wherein the therapeutic agent is a drug, a chemotherapeutic agent, a radioisotope, a pro-apoptosis agent, an anti-angiogenic agent, a survival factor, an anti-apoptotic agent, an enzyme, a hormone, a hormone antagonist, a cytokine, a cytotoxic agent, a cytocidal agent, a cytostatic agent, a growth factor, a peptide, a protein, an antibiotic, an antibody, a Fab fragment of an antibody, a hormone antagonist, a nucleic acid, an antigen, a virus, a bacteriophage, a bacterium, a liposome, a microparticle, a magnetic bead, a microdevice, a yeast cell, a mammalian cell, a cell or an expression vector.

15. The method of claim 14, wherein the agent is a pro-apoptosis agent is selected from the group consisting of gramicidin, magainin, mellitin, defensin, cecropin, (KLAKLAK)2 (SEQ ID NO:1), (KLAKKLA)2 (SEQ ID NO:2), (KAAKKAA)2 (SEQ ID NO:3) and (KLGKKLG)3 (SEQ ID NO:4).

16. The method of claim 15, wherein the pro-apoptosis agent (KLAKLAK)2 (SEQ ID NO:1).

17. The method of claim 14, wherein the agent is an anti-angiogenic agent selected from the group consisting of thrombospondin, angiostatin5, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-B, thrombospondin, 2-methoxyoestradiol, proliferin-related protein, carboxiamidotriazole, CM 101, Marimastat, pentosan polysuiphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline.

18. The method of claim 14, wherein the agent is a cytokine selected from the group consisting of interleukin 1 (IL-1), IL-2, IL-5, IL-10, IL-11, IL-12, IL-18, interferon-$\gamma$ (IF-$\gamma$), IF-$\alpha$, IF-$\beta$, tumor necrosis factor-$\alpha$ (TNF-$\gamma$), or GM-CSF (granulocyte macrophage colony stimulating factor).

19. The method of claim 10, wherein the agent is an imaging agent.

20. The method of claim 19, wherein the imaging agent is a radioisotope, a paramagnetic ion, or an enzyme.

21. The method of claim 20, wherein the imaging agent is a paramagnetic ion selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), lanthanum (III), gold (III), lead (II), and bismuth (III).

22. The method of claim 20, wherein the imaging agent is a radioisotope selected from the group consisting of astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$.

23. The method of claim 20, wherein the imaging agent is an enzyme selected from the group consisting of urease, alkaline phosphatase, hydrogen peroxidase and glucose oxidase.

24. The method of claim 1, wherein the agent is a virus or phage.

25. The method of claim 24, wherein the agent is a bacteriophage.

26. The method of claim 24, wherein the agent is an adenovirus.

27. The method of claim 24, wherein the agent is an adeno-associated phage.

28. The method of claim 1, wherein the peptide is 25 amino acids or less in size.

29. The method of claim 28, wherein the peptide is 10 amino acids or less in size.

* * * * *

UNITED STATES PATENT AND TRADEMARK OFFICE
CERTIFICATE OF CORRECTION

PATENT NO. : 7,671,010 B2  Page 1 of 1
APPLICATION NO. : 10/530168
DATED : March 2, 2010
INVENTOR(S) : Wadih Arap et al.

It is certified that error appears in the above-identified patent and that said Letters Patent is hereby corrected as shown below:

In claim 17, column 151, line 4, delete "polysuiphate" and insert --polysulphate-- therefor.

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,671,010 B2 | Page 1 of 1 |
| APPLICATION NO. | : 10/530168 | |
| DATED | : March 2, 2010 | |
| INVENTOR(S) | : Arap et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 547 days.

Signed and Sealed this

Seventh Day of December, 2010

David J. Kappos
*Director of the United States Patent and Trademark Office*

SEQUENCE LISTING

```
<160> NUMBER OF SEQ ID NOS: 132

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 1

Lys Leu Ala Lys Leu Ala Lys Lys Leu Ala Lys Leu Ala Lys
  1               5                  10

<210> SEQ ID NO 2
```

```
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Lys Leu Ala Lys Lys Leu Ala Lys Leu Ala Lys Lys Leu Ala
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Lys Ala Ala Lys Lys Ala Ala Lys Ala Ala Lys Lys Ala Ala
 1               5                  10

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Lys Leu Gly Lys Lys Leu Gly Lys Leu Gly Lys Lys Leu Gly Lys Leu
 1               5                  10                  15

Gly Lys Lys Leu Gly
             20

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Gly Arg Arg Ala Gly Gly Ser
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Thr Arg Arg Ala Gly Gly Gly
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide
```

```
<400> SEQUENCE: 7

Ser Arg Ala Gly Gly Leu Gly
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Ser Tyr Ala Gly Gly Leu Gly
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Asp Val Ala Gly Gly Leu Gly
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Gly Ala Gly Gly Leu Gly Ala
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Gly Ala Gly Gly Trp Gly Val
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Ala Gly Gly Thr Phe Lys Pro
  1               5

<210> SEQ ID NO 13
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Leu Gly Glu Val Ala Gly Gly
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Gly Ser Asn Asp Ala Gly Gly
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Tyr Arg Gly Ile Ala Gly Gly
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Ala Gly Gly Val Ala Gly Gly
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Gly Gly Leu Ala Gly Gly Phe
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Leu Leu Ala Gly Gly Val Leu
```

```
                1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Leu Val Val Ser Ala Gly Gly
  1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Arg Thr Gln Ala Gly Gly Val
  1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Ala Gly Gly Phe Gly Glu Gln
  1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Ala Gly Gly Leu Ile Asp Val
  1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Ala Gly Gly Ser Thr Trp Thr
  1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
              Peptide

<400> SEQUENCE: 24

Ala Gly Gly Asp Trp Trp Trp
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 25

Ala Gly Gly Gly Leu Leu Met
 1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 26

Val Ala Ala Gly Gly Gly Leu
 1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 27

Leu Tyr Gly Ala Gly Gly Ser
 1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 28

Cys Ala Leu Ala Gly Gly Cys
 1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 29

Ile Gly Ala Gly Gly Val His
 1               5

<210> SEQ ID NO 30
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Ala Gly Gly
  1

<210> SEQ ID NO 31
<211> LENGTH: 3
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Glu Gly Arg
  1

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Gly Glu Arg
  1

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Gly Val Leu
  1

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Arg Arg Ala Gly Gly Ser
  1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35
```

-continued

```
Arg Arg Ala Gly Gly
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 36

His Gly Gly Val Gly
 1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 37

Cys Gly Arg Arg Ala Gly Gly Ser Cys
 1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 38

Cys Arg Val Asp Phe Ser Lys Gly Cys
 1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 39

Cys Asn Val Ser Asp Lys Ser Cys
 1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 40

Cys His Gln Lys Pro Trp Glu Cys
 1               5

<210> SEQ ID NO 41
<211> LENGTH: 8
<212> TYPE: PRT
<213> ORGANISM: Artificial Sequence
<220> FEATURE:
```

-continued

<223> OTHER INFORMATION: Description of Artificial Sequence: Synthetic
      Peptide

<400> SEQUENCE: 41

Cys Lys Asp Arg Phe Glu Arg Cys
 1               5

<210> SEQ ID NO 42
<211> LENGTH: 654
<212> TYPE: PRT
<213> ORGANISM: Homo sapiens

<400> SEQUENCE: 42

Met Lys Leu Ser Leu Val Ala Ala Met Leu Leu Leu Leu Ser Ala Ala
 1               5                  10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
        50                  55                  60

Tyr Val Ala Phe Thr Pro Glu Gly Glu Arg Leu Ile Gly Asp Ala Ala
 65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

```
Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
                420                 425                 430

Met Thr Lys Leu Ile Pro Arg Asn Thr Val Val Pro Thr Lys Lys Ser
            435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
                500                 505                 510

Ala Glu Asp Lys Gly Thr Gly Asn Lys Asn Lys Ile Thr Ile Thr Asn
            515                 520                 525

Asp Gln Asn Arg Leu Thr Pro Glu Glu Ile Glu Arg Met Val Asn Asp
            530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
            595                 600                 605

Gln Asp Ala Asp Ile Glu Asp Phe Lys Ala Lys Lys Lys Glu Leu Glu
            610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 43

Cys Asn Trp Thr Asp Lys Thr Cys
  1               5

<210> SEQ ID NO 44
<211> LENGTH: 8
<212> TYPE: PRT
<213> ORGANISM: Artificial Sequence
```

```
<220> FEATURE:
<223> OTHER INFORMATION: Description of Artificial Sequence:  Synthetic
      Peptide

<400> SEQUENCE: 44

Cys Asn Ile Thr Gln Lys Ser Cys
  1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 45

Cys Asn Lys Thr Asp Lys Gly Cys
  1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 46

Cys Thr Phe Ala Gly Ser Ser Cys
  1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 47

Cys Asn Ser Ala Phe Ala Gly Cys
  1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 48

Cys Ser Tyr Thr Phe Ala Gly Cys
  1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 49

Cys Ser Thr Phe Ala Gly Ser Cys
  1               5
```

```
<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 50

Cys Arg Asp Gly Tyr His His Cys
  1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 51

Cys Ser Ala Ser Asp Leu Ser Cys
  1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 52

Cys Gln Asn Gln Tyr Pro Glu Cys
  1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 53

Cys Arg Ala Ser Ala Met Val Cys
  1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 54

Cys Ile Asp Met Thr His Gln Cys
  1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 55

Cys Ile Ser Ser Pro Ser Asn Cys
 1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 56

Cys Asn Gln Ser Met Trp Ser Cys
 1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 57

Cys Gln Phe Glu Asn Gly Thr Cys
 1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 58

Cys Ala Val Lys Ser Val Thr Cys
 1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 59

Cys Asn Gly Phe Met Gly Tyr Cys
 1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 60

Cys Leu Thr Ser Glu Asn Ala Cys
 1               5

<210> SEQ ID NO 61
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 61

Cys Arg Ala Ser Ala Met Val Cys
 1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 62

Cys Ser Lys Lys Phe Val Thr Cys
 1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 63

Cys Lys Asn Lys His Thr Thr Cys
 1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 64

Cys Phe Glu Thr Phe Ala Gly Cys
 1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 65

Cys Asn Asn Met Tyr Ala Gly Cys
 1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 66

Cys Phe Pro Lys Arg Val Thr Cys
 1               5
```

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 67

Cys Pro Arg Ser Ala Lys Asn Cys
 1               5

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 68

Cys Gly Phe Glu Cys Val Arg Gln Cys Pro Glu Arg Cys
 1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 69

Cys Thr Thr His Trp Gly Phe Thr Leu Cys
 1               5                   10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 70

Cys Asp Cys Arg Gly Asp Cys Phe Cys
 1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 71

Cys Ala Arg Ala Cys
 1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

```
<400> SEQUENCE: 72

Thr Arg Asn Thr Gly Asn Ile
 1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 73

Phe Asp Gly Gln Asp Arg Ser
 1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 74

Trp Gly Pro Lys Arg Leu
 1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 75

Trp Gly Glu Ser Arg Leu
 1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 76

Val Met Gly Ser Val Thr Gly
 1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 77

Lys Gly Gly Arg Ala Lys Asp
 1               5

<210> SEQ ID NO 78
<211> LENGTH: 7
```

```
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 78

Arg Gly Glu Val Leu Trp Ser
  1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 79

Thr Arg Glu Val His Arg Ser
  1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 80

His Gly Gln Gly Val Arg Pro
  1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 81

Cys Lys Gly Gly Arg Ala Lys Asp Cys
  1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 82

Lys Ala Arg Gly Gly
  1               5

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 83

Tyr Arg Cys Thr Leu Asn Ser Pro Phe Phe Trp Glu Asp Met Thr His
```

```
                1               5                  10                  15

Glu Cys His Ala
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 84

Leu Gly Cys Met Ala Ser Met Leu Arg Glu Phe Glu Gly Ala Thr His
  1               5                  10                  15

Ala Cys Thr Gln
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 85

Arg Gly Cys Thr Glu Ala Ala Gly Leu Val Ile Gly Ile Thr Thr His
  1               5                  10                  15

Gln Cys Gly Asn
            20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 86

Ile Gly Cys Asn His Pro Ser Pro Leu Gly Ser Thr Val Val Pro Thr
  1               5                  10                  15

Tyr Cys Phe Lys
            20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 87

Gly Thr Cys Pro Arg Gln Phe Phe His Met Gln Glu Phe Trp Pro Ser
  1               5                  10                  15

Asp Cys Ser Arg
            20

<210> SEQ ID NO 88
<211> LENGTH: 20
<212> TYPE: PRT
<213> ORGANISM: Artificial Sequence
<220> FEATURE:
```

```
<223> OTHER INFORMATION: Description of Artificial Sequence:  Synthetic
      Peptide

<400> SEQUENCE: 88

Asp Arg Cys Val Leu Val Arg Pro Glu Phe Gly Arg Gly Asp Ala Arg
 1               5                  10                  15

Leu Cys His Ser
            20

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 89

Glu Gly Cys Ser Asp Ile Met Asn Thr Ala Ala Glu Arg Val Thr Gly
 1               5                  10                  15

Asp Cys Ser Tyr
            20

<210> SEQ ID NO 90
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 90

Val Phe Cys Cys Gly Ser Tyr Cys Gly Gly Val Glu Met Leu Ala Ser
 1               5                  10                  15

Arg Cys Gly His
            20

<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 91

Arg Glu Cys Gly Arg Thr Val His Arg Tyr Pro Trp Gly Ser Pro Glu
 1               5                  10                  15

Ser Cys Glu Arg
            20

<210> SEQ ID NO 92
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 92

Asp Ala Cys Ser Arg Phe Leu Gly Glu Arg Val Asp Ala Thr Ala Ala
 1               5                  10                  15

Gly Cys Ser Arg
            20
```

```
<210> SEQ ID NO 93
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 93

Gly Asn Cys Met Gly Leu Gln Val Ser Glu Leu Phe Met Gly Pro Tyr
 1               5                  10                  15

Lys Cys Arg Gln
            20

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 94

Ser Arg Cys His Ala Leu Arg Ser Gln Ser Val Ser Thr Ser Ala Gly
 1               5                  10                  15

Ala Cys Ile Ser
            20

<210> SEQ ID NO 95
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 95

Tyr Ser Cys Thr Arg Leu Asn Gly Thr Gly Leu Gln Asn Pro Pro Ser
 1               5                  10                  15

Ala Cys Asp Arg
            20

<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 96

Trp Val Cys Thr Ser Ala Ser Gln Asp Thr Arg Leu Lys Glu Pro Gly
 1               5                  10                  15

Met Cys Ile Ala
            20

<210> SEQ ID NO 97
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 97
```

```
Met His Cys Thr Ser Gln Thr Leu Arg Gly Thr Pro Ser Leu Ala Pro
1               5                   10                  15

Lys Cys Ser Asp
            20

<210> SEQ ID NO 98
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 98

Gln His Cys Val Lys Gly Gln Phe Pro Phe Arg Glu Ser Val Thr Ile
1               5                   10                  15

Thr Cys Asn Ser
            20

<210> SEQ ID NO 99
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 99

His Thr Cys Trp Gly Ala Arg Asp Val Ala Gln Pro Ser Gly Thr Val
1               5                   10                  15

Arg Cys Leu Lys
            20

<210> SEQ ID NO 100
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 100

Ala Arg Cys Arg Glu Asp Thr Gly Phe Met Gly Leu Gly Ser Ala Asn
1               5                   10                  15

Ile Cys Thr Asp
            20

<210> SEQ ID NO 101
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 101

Arg Thr Cys Glu Glu Val Arg Asn Arg Ala Leu Glu Glu Leu Thr Asn
1               5                   10                  15

Phe Cys Pro Tyr
            20

<210> SEQ ID NO 102
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      Peptide

<400> SEQUENCE: 102

Arg Thr Cys Gln Val Arg Ser Asn Asn Ile Ser Pro Arg Met Ala Leu
 1               5                  10                  15

Ala Cys Val Thr
         20

<210> SEQ ID NO 103
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 103

Arg Ser Cys Val Asn Ser Asp Thr Gly Val Leu Gln Arg Gly Ala Pro
 1               5                  10                  15

Ser Cys Leu Phe
         20

<210> SEQ ID NO 104
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 104

Arg Gly Cys Trp Arg Asp Ser Thr Ala Trp His Val Ser Tyr Pro Val
 1               5                  10                  15

Glu Cys Leu Ala
         20

<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 105

Asn Arg Cys Met Pro Gly Phe Leu Asp Asp Ala Asp Ser Ala Ala Ser
 1               5                  10                  15

Pro Cys Gly Ser
         20

<210> SEQ ID NO 106
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 106

Asn Gln Cys Ser Ser Leu Leu Thr Tyr Gln Gly Trp Lys Arg Thr Lys
 1               5                  10                  15

Asp Cys Ile Pro
         20
```

<210> SEQ ID NO 107
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 107

Asn Asp Cys Ser Ala His Ala Gln Pro Gly Trp Asp Glu Val Pro Pro
 1               5                  10                  15

Met Cys Asn Gln
            20

<210> SEQ ID NO 108
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 108

Asn Asn Cys Pro Val Glu Gly Ser Gln Gln Asn Tyr Ser Gly Ala Thr
 1               5                  10                  15

Trp Cys Arg Ala
            20

<210> SEQ ID NO 109
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 109

Thr Thr Cys Asn Lys Ser Met Ser Ser Gln Pro Met Arg Asp Ser Arg
 1               5                  10                  15

Glu Cys His Arg
            20

<210> SEQ ID NO 110
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 110

Thr Ser Cys Val Arg Thr Gly His Asp Glu Asn Leu Leu Lys Ala Ala
 1               5                  10                  15

Tyr Cys Ser Ser
            20

<210> SEQ ID NO 111
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 111

Thr Glu Cys Arg Gly Ala Ser Ser Gly Ser Val Ser Gly Ala Ala Thr
1               5                   10                  15

Asp Cys Arg Asp
            20

<210> SEQ ID NO 112
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 112

Thr Leu Cys Pro Pro Ala Ser Met Gly Leu Gly Arg Glu Lys Pro Arg
1               5                   10                  15

Leu Cys Ser Val
            20

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 113

Thr Leu Cys Arg Ser Leu Glu His Glu Val Gly Leu Phe Lys Pro Arg
1               5                   10                  15

Glu Cys Pro Phe
            20

<210> SEQ ID NO 114
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 114

Leu Arg Cys Pro Leu Glu Val Asp Arg Pro Asn Arg Asp Pro Ala Phe
1               5                   10                  15

Leu Cys Ser Gln
            20

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 115

Leu Gly Cys Asn Lys Gly Arg Tyr Trp Leu Ser Thr Arg Leu Ser Val
1               5                   10                  15

Ser Cys Ala Leu
            20

<210> SEQ ID NO 116
<211> LENGTH: 20
<212> TYPE: PRT

```
<213> ORGANISM: Artificial Sequence
<220> FEATURE:
<223> OTHER INFORMATION: Description of Artificial Sequence:  Synthetic
      Peptide

<400> SEQUENCE: 116

Val Ala Cys Asp Ile Ser Ala Val Glu Arg Leu Pro Ala Ser Ala Arg
 1               5                  10                  15

Ser Cys Lys Thr
            20

<210> SEQ ID NO 117
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 117

Val Val Cys Phe Met Glu Arg Gln Met Gly Thr Asp Val Val Ser Pro
 1               5                  10                  15

Met Cys Val Asn
            20

<210> SEQ ID NO 118
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 118

Val Glu Cys Val Met Ala Ser Ala Ser Thr Asp Gly Thr Ala Ala His
 1               5                  10                  15

Pro Cys Lys Pro
            20

<210> SEQ ID NO 119
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 119

Val Arg Cys Asn Glu Ala Gln Leu Gln Asp Ser Gly Thr Val Pro His
 1               5                  10                  15

Pro Cys Leu Arg
            20

<210> SEQ ID NO 120
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 120

Pro Asn Cys Asp Leu Asp Asp Ile Val Leu Asn Pro Tyr Thr Ala Gly
 1               5                  10                  15

Pro Cys Gly Thr
```

```
<210> SEQ ID NO 121
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 121

Pro Asn Cys Tyr Ser Gly Asp Gly Glu Ile Ser Ser His Ile Pro Val
  1               5                  10                  15

Gln Cys Leu Met
             20

<210> SEQ ID NO 122
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 122

Pro Gly Cys Val Val Ser Pro Phe Ala Leu Ser Ala Gln Gly Thr Ser
  1               5                  10                  15

Val Cys Thr Ile
             20

<210> SEQ ID NO 123
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 123

Gly Asp Cys Glu Thr Asn Asn Val Thr Lys Val Gly Gly Ile Thr Arg
  1               5                  10                  15

Asn Cys Val Gly
             20

<210> SEQ ID NO 124
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 124

Gly Tyr Cys Leu Thr Val Val Gly Gly Ala Val Leu Thr Ile Ala Leu
  1               5                  10                  15

Leu Cys Val Thr
             20

<210> SEQ ID NO 125
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 125

Gly Pro Cys Ala Ala Thr Gly Val Asn Pro Gly Asp His Gly Ala Ala
1               5                   10                  15

Val Cys Asp Gln
            20

<210> SEQ ID NO 126
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 126

Gly Asp Cys Glu Thr Asn Asn Val Thr Lys Val Gly Gly Ile Thr Arg
1               5                   10                  15

Asn Cys Val Gly
            20

<210> SEQ ID NO 127
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 127

Lys Ser Cys Gly Lys Tyr Gly Leu Ile Val Gly Gln Pro Phe Ala Glu
1               5                   10                  15

His Cys Pro Pro
            20

<210> SEQ ID NO 128
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 128

Lys Leu Cys Tyr Arg Ser Ser Ala Gly Ser Glu Leu Arg Pro Pro Glu
1               5                   10                  15

Lys Cys Ala Tyr
            20

<210> SEQ ID NO 129
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 129

Lys Ile Cys Pro Val Thr Asn Met Trp Thr Thr Pro Ser Trp Ala His
1               5                   10                  15

Lys Cys Gly Met
            20

<210> SEQ ID NO 130
<211> LENGTH: 29
```

-continued

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 130
aggctcgagg atcctcggcc gacggggct                                         29

<210> SEQ ID NO 131
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 131
aggtctagaa ttcgccccag cggcccc                                           27

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 132

Cys Val Pro Glu Leu Gly His Glu Cys
 1               5
```